US010047369B2

(12) United States Patent
Belknap et al.

(10) Patent No.: US 10,047,369 B2
(45) Date of Patent: Aug. 14, 2018

(54) CITRUS DERIVED TRANSCRIPTION AND TRANSLATION REGULATORY ELEMENTS FOR TISSUE SPECIFIC EXPRESSION

(71) Applicant: The United States of America, as represented by the Secretary of Agriculture, Washington, DC (US)

(72) Inventors: William R. Belknap, Albany, CA (US); Kent F. McCue, El Cerrito, CA (US); Roger L. Thilmony, El Cerrito, CA (US); Eddie W. Stover, Fort Pierce, FL (US); James G. Thomson, El Cerrito, CA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 74 days.

(21) Appl. No.: 15/381,442

(22) Filed: Dec. 16, 2016

(65) Prior Publication Data

US 2018/0171347 A1 Jun. 21, 2018

(51) Int. Cl.
*C12N 15/82* (2006.01)
*C12N 15/113* (2010.01)
*A01H 1/02* (2006.01)

(52) U.S. Cl.
CPC ........... *C12N 15/8227* (2013.01); *A01H 1/02* (2013.01); *C12N 15/113* (2013.01); *C12N 15/8225* (2013.01); *C12N 15/8226* (2013.01); *C12N 15/8235* (2013.01)

(58) Field of Classification Search
None
See application file for complete search history.

(56) References Cited

PUBLICATIONS

Belknap et al. A family of small cyclic amphipathic peptides (SCAmpPs) genes in citrus. BMC Genomics. 2015. 16(303): 1-11.*

Belknap, William R. et al., A family of small cyclic amphipathic peptides (SCAmpPs) genes in citrus, BMC Genomics 16:303 (2015).

Wu, G. Albert et al., Sequencing of diverse mandarin, pummelo and orange genomes reveals complex history of admixture during citrus domestication; Nat Biotechnol, (2014), 32(7): 656-662.

Wu, G. Albert et al., The draft genome of sweet orange (*Citrus sinensis*), Nature Genetics, (2013), 45(1):59-68.

* cited by examiner

*Primary Examiner* — Ashley K Buran
(74) *Attorney, Agent, or Firm* — David L. Marks; John D. Fado; Gail E. Poulos

(57) ABSTRACT

Expression vectors and expression cassettes containing a tissue specific 5' transcription regulatory element, optionally linked to a translation regulatory element, optionally linked to an intron transcription regulatory element, operably linked to a heterologous polynucleotide encoding a protein or RNA of interest are described. The 5' transcription regulatory elements control expression in root tissue cells, phloem tissue cells, or fruit and/or abscission zone tissue cells. These sequences are obtained from *citrus* plants. Methods of use of these expression vectors and expression cassettes are described, as well as genetically altered plants and parts thereof that contain these expression vectors and/or cassettes.

20 Claims, 3 Drawing Sheets

FIG. 1

Intron

ATGGAAACAACCAGCGCAG GTTTTTAGGCCAGCTTTACTTTCATTTGAATATCATTCATAATTCTTATTTTAATACATGCATTTGTTAATA SEQ ID NO: 34

M E T T S A SEQ ID NO: 35

Linker GUS

TATTTTTAATATAAAATTTACAG GTAATGATGGATCCCCGGGTGGTCAGTCCCTTATGTTACGTCCTGTAGAAACCCCAACCCGTGAAAT SEQ ID NO: 34

G N D G S P G G Q S L M L R P V E T P T R E SEQ ID NO: 35

5' UTR Intron

TTCTAATTTGAAGAATATGGAAACTCCTTATCCAG GTTCTTAGGCCATGTTCAGCTGAATGTCACTTATAATTTTTATTTTAA SEQ ID NO: 36

M E T P Y P SEQ ID NO: 37

Linker GUS

TATATGTATTTATGAATACAATTGTTGTTATGATTTTTTCAG GTAAGAACGGATCCCCGGGTGGTCAGTCCCTTATGTTACG SEQ ID NO: 36

G K N G S P G G Q S L M L R SEQ ID NO: 37

FIG. 2B

302z No Intron

5' UTR Linker GUS

TTCTAATTTGAAGAATATGGGATCCCCGGGTGGTCAGTCCCTTATGTTACG SEQ ID NO: 38

M G S P G G Q S L M L R SEQ ID NO: 39

FIG. 2C

302z No Intron No ATG

5' UTR Linker GUS

TTCTAATTTGAAGAAGGATCCCCGGGTGGTCAGTCCCTTATGTTACG SEQ ID NO: 40

M L R 289s
5' UTR
Intron
Linker
GUS
M G T P C A
G Y T S S P G G Q S L M L R
SEQ ID NO: 41
SEQ ID NO: 42
SEQ ID NO: 41
SEQ ID NO: 42

289s No Intron
5' UTR
Linker
GUS
M G S P G G Q S L M L R
SEQ ID NO: 43
SEQ ID NO: 44

289s No Intron No ATG
5' UTR
Linker
GUS
M L R
SEQ ID NO: 45

SEQUENCE LISTING

<160> NUMBER OF SEQ ID NOS: 45

<210> SEQ ID NO 1
<211> LENGTH: 17467
<212> TYPE: DNA
<213> ORGANISM: Artificial Sequence
<220> FEATURE:
<223> OTHER INFORMATION: plasmid

<400> SEQUENCE: 1
ccgggctggt tgccctcgcc gctgggctgg cggccgtcta tggccctgca aacgcgccag 60
aaacgccgtc gaagccgtgt gcgagacacc gcggccgccg gcgttgtgga tacctcgcgg 120
aaaacttggc cctcactgac agatgagggg cggacgttga cacttgaggg gccgactcac 180
ccggcgcggc gttgacagat gaggggcagg ctcgatttcg gccggcgacg tggagctggc 240
cagcctcgca aatcggcgaa aacgcctgat tttacgcgag tttcccacag atgatgtgga 300
caagcctggg gataagtgcc ctgcggtatt gacacttgag ggcgcgact actgacagat 360 gaggggcgcg atccttgaca cttgaggggc agagtgctga cagatgaggg gcgcacctat 420
tgacatttga ggggctgtcc acaggcagaa aatccagcat ttgcaagggt ttccgcccgt 480
ttttcggcca ccgctaacct gtcttttaac ctgcttttaa accaatattt ataaaccttg 540
tttttaacca gggctgcgcc ctgtgcgcgt gaccgcgcac gccgaagggg ggtgcccccc 600
cttctcgaac cctcccggcc cgctaacgcg ggcctcccat ccccccaggg gctgcgcccc 660
tcggccgcga acggcctcac cccaaaaatg gcagcgctgg cagtccttgc cattgccggg 720
atcggggcag taacgggatg ggcgatcagc ccgagcgcga cgcccggaag cattgacgtg 780
ccgcaggtgc tggcatcgac attcagcgac caggtgccgg gcagtgaggg cggcggcctg 840
ggtggcggcc tgcccttcac ttcggccgtc ggggcattca cggacttcat ggcggggccg 900
gcaattttta ccttgggcat tcttggcata gtggtcgcgg gtgccgtgct cgtgttcggg 960
ggtgcgataa acccagcgaa ccatttgagg tgataggtaa gattataccg aggtatgaaa 1020
acgagaattg gacctttaca gaattactct atgaagcgcc atatttaaaa agctaccaag 1080
acgaagagga tgaagaggat gaggaggcag attgccttga atatattgac aatactgata 1140
agataatata tcttttatat agaagatatc gccgtatgta aggatttcag ggggcaaggc 1200
ataggcagcg cgcttatcaa tatatctata gaatgggcaa agcataaaaa cttgcatgga 1260
ctaatgcttg aaacccagga caataacctt atagcttgta aattctatca taattgggta 1320
atgactccaa cttattgata gtgttttatg ttcagataat gcccgatgac tttgtcatgc 1380
agctccaccg attttgagaa cgacagcgac ttccgtccca gccgtgccag gtgctgcctc 1440
agattcaggt tatgccgctc aattcgctgc gtatatcgct tgctgattac gtgcagcttt 1500
cccttcaggc gggattcata cagcggccag ccatccgtca tccatatcac cacgtcaaag 1560
ggtgacagca ggctcataag acgccccagc gtcgccatag tgcgttcacc gaatacgtgc 1620
gcaacaaccg tcttccggag actgtcatac gcgtaaaaca gccagcgctg gcgcgattta 1680
gccccgacat agccccactg ttcgtccatt tccgcgcaga cgatgacgtc actgcccggc 1740
tgtatgcgcg aggttacata tgcggtgtga aataccgcac agatgcgtaa ggagaaaata 1800
ccgcatcagg cgctcttccg cttcctcgct cactgactcg ctgcgctcgg tcgttcggct 1860
gcggcgagcg gtatcagctc actcaaaggc ggtaatacgg ttatccacag aatcagggga 1920
taacgcagga aagaacatgt gagcaaaagg ccagcaaaag gccaggaacc gtaaaaaggc 1980
cgcgttgctg gcgtttttcc ataggctccg cccccctgac gagcatcaca aaaatcgacg 2040

-continued

```
ctcaagtcag aggtggcgaa acccgacagg actataaaga taccaggcgt ttccccctgg   2100
aagctccctc gtgcgctctc ctgttccgac cctgccgctt accggatacc tgtccgcctt   2160
tctcccttcg ggaagcgtgg cgctttctca tagctcacgc tgtaggtatc tcagttcggt   2220
gtaggtcgtt cgctccaagc tgggctgtgt gcacgaaccc cccgttcagc ccgaccgctg   2280
cgccttatcc ggtaactatc gtcttgagtc caacccggta agacacgact tatcgccact   2340
ggcagcagcc agttaccgac tgcggcctga gtttttaag tgacgtaaaa tcgtgttgag   2400
gccaacgccc ataatgcggg ctgttgcccg gcatccaacg ccattcatgg ccatatcaat   2460
gattttctgg tgcgtaccgg gttgagaagc ggtgtaagtg aactgcagtt gccatgtttt   2520
acggcagtga gagcagagat agcgctgatg tccggcggtg cttttgccgt tacgcaccac   2580
cccgtcagta gctgaacagg agggacagct gatagacaca gaagccactg gagcacctca   2640
aaaacaccat catacactaa atcagtaagt tggcagcatc acccataatt gtggtttcaa   2700
aatcggctcc gtcgatacta tgttatacgc caactttgaa aacaactttg aaaaagctgt   2760
tttctggtat ttaaggtttt agaatgcaag gaacagtgaa ttggagttcg tcttgttata   2820
attagcttct tggggtatct ttaaatactg tagaaaagag gaaggaaata ataaatggct   2880
aaaatgagaa tatcaccgga attgaaaaaa ctgatcgaaa aataccgctg cgtaaaagat   2940
acggaaggaa tgtctcctgc taaggtatat aagctggtgg gagaaaatga aaacctatat   3000
ttaaaaatga cggacagccg gtataaaggg accacctatg atgtggaacg ggaaaaggac   3060
atgatgctat ggctggaagg aaagctgcct gttccaaagg tcctgcactt tgaacggcat   3120
gatggctgga gcaatctgct catgagtgag gccgatggcg tcctttgctc ggaagagtat   3180
gaagatgaac aaagccctga aaagattatc gagctgtatg cggagtgcat caggctcttt   3240
cactccatcg acatatcgga ttgtccctat acgaatagct tagacagccg cttagccgaa   3300
ttggattact tactgaataa cgatctggcc gatgtggatt gcgaaaactg ggaagaagac   3360
actccattta aagatccgcg cgagctgtat gatttttaa agacggaaaa gcccgaagag   3420
gaacttgtct tttcccacgg cgacctggga gacagcaaca tctttgtgaa agatggcaaa   3480
gtaagtggct ttattgatct tgggagaagc ggcagggcgg acaagtggta tgacattgcc   3540
ttctgcgtcc ggtcgatcag ggaggatatc ggggaagaac agtatgtcga gctattttt   3600
gacttactgg ggatcaagcc tgattgggag aaaataaaat attatatttt actggatgaa   3660
ttgttttagt acctagatgt ggcgcaacga tgccggcgac aagcaggagc gcaccgactt   3720
cttccgcatc aagtgttttg gctctcaggc cgaggcccac ggcaagtatt tgggcaaggg   3780
gtcgctggta ttcgtgcagg gcaagattcg gaataccaag tacgagaagg acggccagac   3840
ggtctacggg accgacttca ttgccgataa ggtggattat ctggacacca aggcaccagg   3900
cgggtcaaat caggaataag ggcacattgc cccggcgtga gtcggggcaa tcccgcaagg   3960
agggtgaatg aatcggacgt ttgaccggaa ggcatacagg caagaactga tcgacgcggg   4020
gttttccgcc gaggatgccg aaaccatcgc aagccgcacc gtcatgcgtg cgccccgcga   4080
aaccttccag tccgtcggct cgatggtcca gcaagctacg gccaagatcg agcgcgacag   4140
cgtgcaactg gctccccctg ccctgcccgc gccatcggcc gccgtggagc gttcgcgtcg   4200
tctcgaacag gaggcggcag gtttggcgaa gtcgatgacc atcgacacgc gaggaactat   4260
gacgaccaag aagcgaaaaa ccgccggcga ggacctggca aaacaggtca gcgaggccaa   4320
gcaggccgcg ttgctgaaac acacgaagca gcagatcaag gaaatgcagc tttccttgtt   4380
```

-continued

```
cgatattgcg ccgtggccgg acacgatgcg agcgatgcca aacgacacgg cccgctctgc   4440
cctgttcacc acgcgcaaca agaaaatccc gcgcgaggcg ctgcaaaaca aggtcatttt   4500
ccacgtcaac aaggacgtga agatcaccta caccggcgtc gagctgcggg ccgacgatga   4560
cgaactggtg tggcagcagg tgttggagta cgcgaagcgc acccctatcg gcgagccgat   4620
caccttcacg ttctacgagc tttgccagga cctgggctgg tcgatcaatg gccggtatta   4680
cacgaaggcc gaggaatgcc tgtcgcgcct acaggcgacg gcgatgggct tcacgtccga   4740
ccgcgttggg cacctggaat cggtgtcgct gctgcaccgc ttccgcgtcc tggaccgtgg   4800
caagaaaacg tcccgttgcc aggtcctgat cgacgaggaa atcgtcgtgc tgtttgctgg   4860
cgaccactac acgaaattca tatgggagaa gtaccgcaag ctgtcgccga cggcccgacg   4920
gatgttcgac tatttcagct cgcaccggga gccgtacccg ctcaagctgg aaaccttccg   4980
cctcatgtgc ggatcggatt ccacccgcgt gaagaagtgg cgcgagcagg tcggcgaagc   5040
ctgcgaagag ttgcgaggca gcggcctggt ggaacacgcc tgggtcaatg atgacctggt   5100
gcattgcaaa cgctagggcc ttgtggggtc agttccggct gggggttcag cagccagcgc   5160
tttactggca tttcaggaac aagcgggcac tgctcgacgc acttgcttcg ctcagtatcg   5220
ctcgggacgc acggcgcgct ctacgaactg ccgataaaca gaggattaaa attgacaatt   5280
gtgattaagg ctcagattcg acggcttgga gcggccgacg tgcaggattt ccgcgagatc   5340
cgattgtcgg ccctgaagaa agctccagag atgttcgggt ccgtttacga gcacgaggag   5400
aaaaagccca tggaggcgtt cgctgaacgg ttgcgagatg ccgtggcatt cggcgcctac   5460
atcgacggcg agatcattgg gctgtcggtc ttcaaacagg aggacggccc caaggacgct   5520
cacaaggcgc atctgtccgg cgttttcgtg gagcccgaac agcgaggccg aggggtcgcc   5580
ggtatgctgc tgcgggcgtt gccggcgggt ttattgctcg tgatgatcgt ccgacagatt   5640
ccaacgggaa tctggtggat gcgcatcttc atcctcggcg cacttaatat ttcgctattc   5700
tggagcttgt tgtttatttc ggtctaccgc ctgccgggcg gggtcgcggc gacggtaggc   5760
gctgtgcagc cgctgatggt cgtgttcatc tctgccgctc tgctaggtag cccgatacga   5820
ttgatggcgg tcctgggggc tatttgcgga actgcgggcg tggcgctgtt ggtgttgaca   5880
ccaaacgcag cgctagatcc tgtcggcgtc gcagcgggcc tggcgggggc ggtttccatg   5940
gcgttcggaa ccgtgctgac ccgcaagtgg caacctcccg tgcctctgct cacctttacc   6000
gcctggcaac tggcggccgg aggacttctg ctcgttccag tagctttagt gtttgatccg   6060
ccaatcccga tgcctacagg aaccaatgtt ctcggcctgg cgtggctcgg cctgatcgga   6120
gcgggtttaa cctacttcct ttggttccgg gggatctcgc gactcgaacc tacagttgtt   6180
tccttactgg gctttctcag ccccagatct ggggtcgatc agccggggat gcatcaggcc   6240
gacagtcgga acttcgggtc cccgacctgt accattcggt gagcaatgga taggggagtt   6300
gatatcgtca acgttcactt ctaaagaaat agcgccactc agcttcctca gcggctttat   6360
ccagcgattt cctattatgt cggcatagtt ctcaagatcg acagcctgtc acggttaagc   6420
gagaaatgaa taagaaggct gataattcgg atctctgcga gggagatgat atttgatcac   6480
aggcagcaac gctctgtcat cgttacaatc aacatgctac cctccgcgag atcatccgtg   6540
tttcaaaccc ggcagcttag ttgccgttct tccgaatagc atcggtaaca tgagcaaagt   6600
ctgccgcctt acaacggctc tcccgctgac gccgtcccgg actgatgggc tgcctgtatc   6660
gagtggtgat tttgtgccga gctgccggtc ggggagctgt tggctggctg gtggcaggat   6720
atattgtggt gtaaacaaat tgacgcttag acaacttaat aacacattgc ggacgttttt   6780
```

-continued

```
aatgtactgg ccggccaaag cacatactta tcgatttaaa tttcatcgaa gagattaata   6840
tcgaataatc atatacatac tttaaataca taacaaattt taaatacata tatctggtat   6900
ataattaatt ttttaaagtc atgaagtatg tatcaaatac acatatggaa aaaattaact   6960
attcataatt taaaaaatag aaaagataca tctagtgaaa ttaggtgcat gtatcaaata   7020
cattaggaaa agggcatata tcttgatcta gataattaac gattttgatt tatgtataat   7080
ttccaaatga aggtttatat ctacttcaga aataacaata tacttttatc agaacattca   7140
acaaagcaac aaccaactag agtgaaaaat acacattgtt ctctagacat acaaaattga   7200
gaaaagaatc tcaaaattta gagaaacaaa tctgaatttc tagaagaaaa aaataattat   7260
gcactttgct attgctcgaa aaataaatga aagaaattag actttttttaa aagatgttag   7320
actagatata ctcaaaagct attaaaggag taatattctt cttacattaa gtattttagt   7380
tacagtcctg taattaaaga cacattttag attgtatcta aacttaaatg tatctagaat   7440
acatatattt gaatgcatca tatacatgta tccgacacac caattctcat aaaaaacgta   7500
atatcctaaa ctaatttatc cttcaagtca acttaagccc aatatacatt ttcatctcta   7560
aaggcccaag tggcacaaaa tgtcaggccc aattacgaag aaaagggctt gtaaaaccct   7620
aataaagtgg cactggcaga gcttacactc tcattccatc aacaaagaaa ccctaaaagc   7680
cgcagcgcca ctgatttctc tcctccaggc gaagatgcag atcttcgtga agaccttaac   7740
ggggaagacg atcaccctag aggttgagtc ttccgacacc atcgacaatg tcaaagccaa   7800
gatccaggac aaggaaggga ttcccccaga ccagcagcgt ttgattttcg ccggaaagca   7860
gcttgaggat ggtcgtactc ttgccgacta caacatccag aaggagtcaa ctctccatct   7920
cgtgctccgt ctccgtggtg gtagtttaaa catgattgaa caagatggat tgcacgcagg   7980
ttctccggcc gcttgggtgg agaggctatt cggctatgac tgggcacaac agacaatcgg   8040
ctgctctgat gccgccgtgt tccggctgtc agcgcagggg cgcccggttc tttttgtcaa   8100
gaccgacctg tccggtgccc tgaatgaact gcaggacgag gcagcgcggc tatcgtggct   8160
ggccacgacg ggcgttcctt gcgcagctgt gctcgacgtt gtcactgaag cgggaaggga   8220
ctggctgcta ttgggcgaag tgccggggca ggatctcctg tcatctcacc ttgctcctgc   8280
cgagaaagta tccatcatgg ctgatgcaat gcggcggctg catacgcttg atccggctac   8340
ctgcccattc gaccaccaag cgaaacatcg catcgagcga gcacgtactc ggatggaagc   8400
cggtcttgtc gatcaggatg atctggacga agagcatcag gggctcgcgc cagccgaact   8460
gttcgccagg ctcaaggcgc gcatgcccga cggcgaggat ctcgtcgtga cccatggcga   8520
tgcctgcttg ccgaatatca tggtggaaaa tggccgcttt tctggattca tcgactgtgg   8580
ccggctgggt gtggcggacc gctatcagga catagcgttg gctacccgtg atattgctga   8640
agagcttggc ggcgaatggg ctgaccgctt cctcgtgctt tacggtatcg ccgctcccga   8700
ttcgcagcgc atcgccttct atcgccttct tgacgagttc ttctgagttt aaacgatttt   8760
aatgtttagc aaatgtctta tcagttttct ctttttgtcg aacggtaatt tagagttttt   8820
tttgctatat ggattttcgt tttgatgta tgtgacaacc ctcgggattg ttgatttatt   8880
tcaaaactaa gagtttttgt cttattgttc tcgtctattt tggatatcaa tcttagtttt   8940
atatcttttc tagttctcta cgtgttaaat gttcaacaca ctagcaattt ggcctgccag   9000
cgtatggatt atggaactat caagtgtgtg ggatcgataa atatgcttct caggaatttg   9060
agattttta tcatgtcttt atgctcattc ccttgagtat aatatagtaa aaaaatagta   9120
```

```
aatttaagca ataatgttag gtgctatgtg tctgtcgaga ctattggccg gccatcgatg   9180
gtttcattgg tgacgtttcc ggccttgcta atggtaatgg tgctactggt gattttgctg   9240
gctctaattc ccaaatggct caagtcggtg acggtgataa ttcaccttta atgaataatt   9300
tccgtcaata tttaccttcc ctccctcaat cggttgaatg tcgccctttt gtctttggcc   9360
caatacgcaa accgcctctc cccgcgcgtt ggccgattca ttaatgcagc tggcacgaca   9420
ggtttcccga ctggaaagcg ggcagtgagc gcaacgcaat taatgtgagt tagctcactc   9480
attaggcacc ccaggcttta cactttatgc ttccggctcg tatgttgtgt ggaattgtga   9540
gcggataaca atttcacaca ggaaacagct atgaccatga ttacgccaag ctggcgcgcc   9600
cttgtaaaca ctggagtggg aggaatccac actccacact cccaatttag aaagtaaaca   9660
ctacctaaag gtatttacag tcaggatttt tttttccatg taacctcaaa tgcactatgc   9720
aataaaatat aaatataaat aaagcaagca gttactaagt ctttaggttg ttaggcagat   9780
gctaaggcct tgtcctgaat aagcccagca attcaaactt aagattacac tataaaaagg   9840
gggcgcaaag gcaaagaaag tggcacggca agtgcagcga aggaagcaaa ggagagcatg   9900
tcacactgag attacatgtc tgatatttgg ctccgcttct tccctttaaa cacctcgaaa   9960
taagcatcaa ggaagtggtc ttgtcatcat cttcttccag tacatcaatg gagaaacaac  10020
attcgaacac atggaaataa gaaaaatcat taaaattgac tactactgtt gcatattcat  10080
aatatgactg ctggcttttc ttctatctca gttttttca gagctcaact aagggcagtt  10140
tgatgctgtc attggatagc agtagcttga aaaactacag tactttagtg gttagtaaac  10200
acttattgct ataatttgga atttaggttc attttatccg atactcgaaa tacgctaatg  10260
ggaaaaatag tcaaaactca ggtaattttt tcatttctct ttttatgttt ctaaacacat  10320
caaaactctc tcttgatgtt taaaaaaatt tattaacttt taacttttat ttgtgtcctt  10380
tcttatttca tccatgatgt cgtaaaaccc actgttaatc aataaaaatt tctgaagata  10440
gaataatgaa ggatacaaaa aaatttacaa gccttttgta tatgatagtt gactatgtgt  10500
atcgggacaa tgttgtgagc attagattgg acaagttatg aatttttatc agtctagctc  10560
atacgcaaaa actttgaaaa actttgaaaa gaataagtta tccatataac acaaaatcac  10620
catttatact tagctcattt atattttta tggatatgaa tgtaaatttc tgcctttgga  10680
gagtaataat aatccaatat cgtcgacgtg gccgttgcag ttgccgagtc gatgcaaaaa  10740
gagcaacggc gatttgttga agagaagcaa cagcaactga ataataatat aacagcaaca  10800
acaacgttga ttcttcgaaa gagaaaagag tcaaatccgg caaaaaggcc aaggcaaaag  10860
cagccaccgt gtcggcgcac gaggcttttt attctaaatt gaaaaagaaa aattgggtaa  10920
ttaacttaac ttatcaagga taacattgtc atatcacaaa aaatatttta ttttgatgaa  10980
tagttacagt ttgtaaaata attaaatcaa ttaagaaaaa taagggcatt ttcattgtaa  11040
aataacgtaa ttttttagtg ttaggagtaa gtgtagcgtt tttaaattta aagaggcaag  11100
ctagaggaag atggagctgt caactttcaa gtaatgtatg catcaaggta agtgacagag  11160
ctaaggagaa atggacaagt actaatcatc gttataaaaa attaaacaga gcagcatttt  11220
gtcagttctg gccatatata tttttcaagg attgggactg ttagcaccgc tgtaatttta  11280
ttttcaagct cttctctgtc aaaacctatt ttactttcca aaatatctta ttccattttt  11340
ttagtttctt tctgattcaa gattttttt ttaaaaaaaa aaaatctgtt tcttccaaac  11400
aactccaatt acaatttttt tttataaatt tttgaattat taaatcatat atagttaact  11460
aaagagaatc atatatacaa actaaataga attaaaagtg gactcaaatg gctattatgt  11520
```

-continued

```
tattttttc taaattaaaa aaaaaagttt agaatcagag cctccttgta agccataaaa  11580
aaaaagaaaa gaaaagttta taatgcaaaa gtatttgtga gaaaaaaaaa aaacactttg  11640
atgtagttgc atgaatgtaa agagttagat agagaaatag agtgtataat tagatttatt  11700
tttttcttta aagtaatcgc aatataagag gggttaagaa tttcacagga gtgccactga  11760
ttcaactctt tttcaagaga attgatgttc tggaagaaaa ttatgactct atcattgcta  11820
ttagtttgtc ttgtaattca attattgccg acaagtatta actgtgatta tttttatttt  11880
aaaaattatt attattaatg tattgcaatt ttgagcctta taattgcaat tagtttgtct  11940
tgtaactaaa ttattgccga caaacactat catgctgaca aacaatgcat gcacgtcctc  12000
agtcacccac gtcctctact tgtgtgaatg tgtatataaa tatatctgga gcatattata  12060
aaaccagaag caaaagcaac tgaagttttg aatacggttc accagaagtt agaagatatc  12120
ttttctaatt tgaagaatat ggaaactcct tatccaggtt cttaggccat gttcagctga  12180
atgtcactta taatttttat tttaatatat gtatttatga atacaattgt tgttatgatt  12240
ttttcaggta agaacggatc cccgggtggt cagtccctta tgttacgtcc tgtagaaacc  12300
ccaacccgtg aaatcaaaaa actcgacggc ctgtgggcat tcagtctgga tcgcgaaaac  12360
tgtggaattg atcagcgttg gtgggaaagc gcgttacaag aaagccgggc aattgctgtg  12420
ccaggcagtt ttaacgatca gttcgccgat gcagatattc gtaattatgc gggcaacgtc  12480
tggtatcagc gcgaagtctt tataccgaaa ggttgggcag gccagcgtat cgtgctgcgt  12540
ttcgatgcgg tcactcatta cggcaaagtg tgggtcaata atcaggaagt gatggagcat  12600
cagggcggct atacgccatt tgaagccgat gtcacgccgt atgttattgc cgggaaaagt  12660
gtacgtatca ccgtttgtgt gaacaacgaa ctgaactggc agactatccc gccgggaatg  12720
gtgattaccg acgaaaacgg caagaaaaag cagtcttact tccatgattt ctttaactat  12780
gccggaatcc atcgcagcgt aatgctctac accacgccga acacctgggt ggacgatatc  12840
accgtggtga cgcatgtcgc gcaagactgt aaccacgcgt ctgttgactg gcaggtggtg  12900
gccaatggtg atgtcagcgt tgaactgcgt gatgcggatc aacaggtggt tgcaactgga  12960
caaggcacta gcgggacttt gcaagtggtg aatccgcacc tctggcaacc gggtgaaggt  13020
tatctctatg aactgtgcgt cacagccaaa agccagacag agtgtgatat ctacccgctt  13080
cgcgtcggca tccggtcagt ggcagtgaag ggcgaacagt tcctgattaa ccacaaaccg  13140
ttctacttta ctggctttgg tcgtcatgaa gatgcggact tgcgtggcaa aggattcgat  13200
aacgtgctga tggtgcacga ccacgcatta atggactgga ttggggccaa ctcctaccgt  13260
acctcgcatt acccttacgc tgaagagatg ctcgactggg cagatgaaca tggcatcgtg  13320
gtgattgatg aaactgctgc tgtcggcttt aacctctctt taggcattgg tttcgaagcg  13380
ggcaacaagc cgaaagaact gtacagcgaa gaggcagtca acggggaaac tcagcaagcg  13440
cacttacagg cgattaaaga gctgatagcg cgtgacaaaa accacccaag cgtggtgatg  13500
tggagtattg ccaacgaacc ggatacccgt ccgcaaggtg cacgggaata tttcgcgcca  13560
ctggcggaag caacgcgtaa actcgacccg acgcgtccga tcacctgcgt caatgtaatg  13620
ttctgcgacg ctcacaccga taccatcagc gatctctttg atgtgctgtg cctgaaccgt  13680
tattacggat ggtatgtcca aagcggcgat ttggaaacgg cagagaaggt actggaaaaa  13740
gaacttctgg cctggcagga gaaactgcat cagccgatta tcatcaccga atacggcgtg  13800
gatacgttag ccgggctgca ctcaatgtac accgacatgt ggagtgaaga gtatcagtgt  13860
```

-continued gcatggctgg atatgtatca ccgcgtcttt gatcgcgtca gcgccgtcgt cggtgaacag 13920
gtatggaatt tcgccgattt tgcgacctcg caaggcatat tgcgcgttgg cggtaacaag 13980
aaagggatct tcactcgcga ccgcaaaccg aagtcggcgg cttttctgct gcaaaaacgc 14040
tggactggca tgaacttcgg tgaaaaaccg cagcagggag gcaaacaatg aatcaacaac 14100
tctcctggcg caccatcgtc ggctacagcc tcgggaattg ctacgagctc gttgcctatt 14160
gttggttgtc gtgttgtctg gctgtgtctg ttgcccattg tggtggttat gtgttgcatc 14220
atggtctaaa aggatcatca atgtttttcg cttctgttcc tttctgtttc tcatttgtga 14280
ataataatgg tgtctttatg aacatccagt ttctggtttc ttttctgatt gcagtttgag 14340
tatttgtttt tgcttttgct tccgtctact acaccacttt gcaattactg tatcactcat 14400
gcattgttga tatactttag ccttcgatcc atcttctgtt tgatgattca aatggtattt 14460
atttaactca tacccaagtg aagcataaag ttagaggaga gttcatgttc cattacctgt 14520
ttgtttcatg agcaactcat cttaataaac ataagaaaaa ccataatgca atctgtgtag 14580
ctgatagact ttgatgacag acggactcat aagtaacaag aggaaacatg ataaacatgt 14640
acggaagtcg agctcgaatt cttaattaac aattcactgg ccgtcgtttt acaacgtcgt 14700
gactgggaaa accctggcgt tacccaactt aatcgccttg cagcacatcc ccctttcgcc 14760
agctggcgta atagcgaaga ggcccgcacc gatcgccctt cccaacagtt gcgcagcctg 14820
aatggcgccc gctcctttcg ctttcttccc ttcctttctc gccacgttcg ccggctttcc 14880
ccgtcaagct ctaaatcggg ggctcccttt agggttccga tttagtgctt tacggcacct 14940
cgaccccaaa aaacttgatt tgggtgatgg ttcacaaact atcagtgttt gacaggatat 15000
attggcgggt aaacctaaga gaaaagagcg tttattagaa taatcggata tttaaaaggg 15060
cgtgaaaagg tttatccgtt cgtccatttg tatgtgcatg ccaaccacag ggttccccag 15120
atctggcgcc ggccagcgag acgagcaaga ttggccgccg cccgaaacga tccgacagcg 15180
cgcccagcac aggtgcgcag gcaaattgca ccaacgcata cagcgccagc agaatgccat 15240
agtgggcggt gacgtcgttc gagtgaacca gatcgcgcag gaggcccggc agcaccggca 15300
taatcaggcc gatgccgaca gcgtcgagcg cgacagtgct cagaattacg atcaggggta 15360
tgttgggttt cacgtctggc ctccggacca gcctccgctg gtccgattga acgcgcggat 15420
tctttatcac tgataagttg gtggacatat tatgtttatc agtgataaag tgtcaagcat 15480
gacaaagttg cagccgaata cagtgatccg tgccgccctg gacctgttga acgaggtcgg 15540
cgtagacggt ctgacgacac gcaaactggc ggaacggttg ggggttcagc agccggcgct 15600
ttactggcac ttcaggaaca agcgggcgct gctcgacgca ctggccgaag ccatgctggc 15660
ggagaatcat acgcattcgg tgccgagagc cgacgacgac tggcgctcat ttctgatcgg 15720
gaatgcccgc agcttcaggc aggcgctgct cgcctaccgc gatggcgcgc gcatccatgc 15780
cggcacgcga ccgggcgcac cgcagatgga aacggccgac gcgcagcttc gcttcctctg 15840
cgaggcgggt ttttcggccg gggacgccgt caatgcgctg atgacaatca gctacttcac 15900
tgttggggcc gtgcttgagg agcaggccgg cgacagcgat gccggcgagc gcggcggcac 15960
cgttgaacag gctccgctct cgccgctgtt gcgggccgcg atagacgcct tcgacgaagc 16020
cggtccggac gcagcgttcg agcagggact cgcggtgatt gtcgatggat tggcgaaaag 16080
gaggctcgtt gtcaggaacg ttgaaggacc gagaaagggt gacgattgat caggaccgct 16140
gccggagcgc aacccactca ctacagcaga gccatgtaga caacatcccc tccccctttc 16200
caccgcgtca gacgcccgta gcagcccgct acgggctttt tcatgccctg ccctagcgtc 16260

-continued

```
caagcctcac ggccgcgctc ggcctctctg gcggccttct ggcgctcttc cgcttcctcg  16320

ctcactgact cgctgcgctc ggtcgttcgg ctgcggcgag cggtatcagc tcactcaaag  16380

gcggtaatac ggttatccac agaatcaggg gataacgcag gaaagaacat gtgagcaaaa  16440

ggccagcaaa aggccaggaa ccgtaaaaag gccgcgttgc tggcgttttt ccataggctc  16500

cgcccccctg acgagcatca caaaaatcga cgctcaagtc agaggtggcg aaacccgaca  16560

ggactataaa gataccaggc gtttccccct ggaagctccc tcgtgcgctc tcctgttccg  16620

accctgccgc ttaccggata cctgtccgcc tttctccctt cgggaagcgt ggcgcttttc  16680

cgctgcataa ccctgcttcg ggtcattat agcgattttt tcggtatatc catccttttt  16740

cgcacgatat acaggatttt gccaaagggt tcgtgtagac tttccttggt gtatccaacg  16800

gcgtcagccg ggcaggatag gtgaagtagg cccacccgcg agcgggtgtt ccttcttcac  16860

tgtcccttat tcgcacctgg cggtgctcaa cgggaatcct gctctgcgag gctggccggc  16920

taccgccggc gtaacagatg agggcaagcg gatggctgat gaaaccaagc caaccaggaa  16980

gggcagccca cctatcaagg tgtactgcct tccagacgaa cgaagagcga ttgaggaaaa  17040

ggcggcggcg gccggcatga gcctgtcggc ctacctgctg gccgtcggcc agggctacaa  17100

aatcacgggc gtcgtggact atgagcacgt ccgcgagctg gcccgcatca atggcgacct  17160

gggccgcctg ggcggcctgc tgaaactctg gctcaccgac gacccgcgca cggcgcggtt  17220

cggtgatgcc acgatcctcg ccctgctggc gaagatcgaa gagaagcagg acgagcttgg  17280

caaggtcatg atgggcgtgg tccgcccgag ggcagagcca tgactttttt agccgctaaa  17340

acggccgggg ggtgcgcgtg attgccaagc acgtccccat gcgctccatc aagaagagcg  17400

acttcgcgga gctggtgaag tacatcaccg acgagcaagg caagaccgag cgcctttgcg  17460

acgctca                                                            17467
```

<210> SEQ ID NO 2
<211> LENGTH: 17353
<212> TYPE: DNA
<213> ORGANISM: Artificial Sequence
<220> FEATURE:
<223> OTHER INFORMATION: plasmid

<400> SEQUENCE: 2

```
ccgggctggt tgccctcgcc gctgggctgg cggccgtcta tggccctgca aacgcgccag     60

aaacgccgtc gaagccgtgt gcgagacacc gcggccgccg gcgttgtgga tacctcgcgg    120

aaaacttggc cctcactgac agatgagggg cggacgttga cacttgaggg gccgactcac    180

ccggcgcggc gttgacagat gaggggcagg ctcgatttcg gccggcgacg tggagctggc    240

cagcctcgca aatcggcgaa aacgcctgat tttacgcgag tttcccacag atgatgtgga    300

caagcctggg gataagtgcc ctgcggtatt gacacttgag gggcgcgact actgacagat    360

gaggggcgcg atccttgaca cttgaggggc agagtgctga cagatgaggg gcgcacctat    420

tgacatttga ggggctgtcc acaggcagaa aatccagcat ttgcaagggt ttccgcccgt    480

ttttcggcca ccgctaacct gtcttttaac ctgcttttaa accaatattt ataaaccttg    540

tttttaacca gggctgcgcc ctgtgcgcgt gaccgcgcac gccgaagggg ggtgcccccc    600

cttctcgaac cctcccggcc cgctaacgcg ggcctcccat ccccccaggg gctgcgcccc    660

tcggccgcga acggcctcac cccaaaaatg gcagcgctgg cagtccttgc cattgccggg    720

atcggggcag taacgggatg ggcgatcagc ccgagcgcga cgcccggaag cattgacgtg    780
```

-continued

```
ccgcaggtgc tggcatcgac attcagcgac caggtgccgg gcagtgaggg cggcggcctg    840
ggtggcggcc tgcccttcac ttcggccgtc ggggcattca cggacttcat ggcggggccg    900
gcaattttta ccttgggcat tcttggcata gtggtcgcgg gtgccgtgct cgtgttcggg    960
ggtgcgataa acccagcgaa ccatttgagg tgataggtaa gattataccg aggtatgaaa   1020
acgagaattg gacctttaca gaattactct atgaagcgcc atatttaaaa agctaccaag   1080
acgaagagga tgaagaggat gaggaggcag attgccttga atatattgac aatactgata   1140
agataatata tcttttatat agaagatatc gccgtatgta aggatttcag ggggcaaggc   1200
ataggcagcg cgcttatcaa tatatctata gaatgggcaa agcataaaaa cttgcatgga   1260
ctaatgcttg aaacccagga caataacctt atagcttgta aattctatca taattgggta   1320
atgactccaa cttattgata gtgttttatg ttcagataat gcccgatgac tttgtcatgc   1380
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgccccagc gtcgccatag tgcgttcacc gaatacgtgc   1620
gcaacaaccg tcttccggag actgtcatac gcgtaaaaca gccagcgctg gcgcgattta   1680
gccccgacat agccccactg ttcgtccatt tccgcgcaga cgatgacgtc actgcccggc   1740
tgtatgcgcg aggttacata tgcggtgtga aataccgcac agatgcgtaa ggagaaaata   1800
ccgcatcagg cgctcttccg cttcctcgct cactgactcg ctgcgctcgg tcgttcggct   1860
gcggcgagcg gtatcagctc actcaaaggc ggtaatacgg ttatccacag aatcagggga   1920
taacgcagga aagaacatgt gagcaaaagg ccagcaaaag gccaggaacc gtaaaaaggc   1980
cgcgttgctg gcgtttttcc ataggctccg cccccctgac gagcatcaca aaaatcgacg   2040
ctcaagtcag aggtggcgaa acccgacagg actataaaga taccaggcgt ttccccctgg   2100
aagctccctc gtgcgctctc ctgttccgac cctgccgctt accggatacc tgtccgcctt   2160
tctcccttcg ggaagcgtgg cgctttctca tagctcacgc tgtaggtatc tcagttcggt   2220
gtaggtcgtt cgctccaagc tgggctgtgt gcacgaaccc cccgttcagc ccgaccgctg   2280
cgccttatcc ggtaactatc gtcttgagtc caacccggta agacacgact tatcgccact   2340
ggcagcagcc agttaccgac tgcggcctga gtttttaag tgacgtaaaa tcgtgttgag   2400
gccaacgccc ataatgcggg ctgttgcccg gcatccaacg ccattcatgg ccatatcaat   2460
gattttctgg tgcgtaccgg gttgagaagc ggtgtaagtg aactgcagtt gccatgtttt   2520
acggcagtga gagcagagat agcgctgatg tccggcggtg cttttgccgt tacgcaccac   2580
cccgtcagta gctgaacagg agggacagct gatagacaca gaagccactg gagcacctca   2640
aaaacaccat catacactaa atcagtaagt tggcagcatc acccataatt gtggtttcaa   2700
aatcggctcc gtcgatacta tgttatacgc caactttgaa aacaactttg aaaaagctgt   2760
tttctggtat ttaaggtttt agaatgcaag gaacagtgaa ttggagttcg tcttgttata   2820
attagcttct tggggtatct ttaaatactg tagaaaagag gaaggaaata ataaatggct   2880
aaaatgagaa tatcaccgga attgaaaaaa ctgatcgaaa aataccgctg cgtaaaagat   2940
acggaaggaa tgtctcctgc taaggtatat aagctggtgg gagaaaatga aaacctatat   3000
ttaaaaatga cggacagccg gtataaaggg accacctatg atgtggaacg ggaaaaggac   3060
atgatgctat ggctggaagg aaagctgcct gttccaaagg tcctgcactt tgaacggcat   3120
gatggctgga gcaatctgct catgagtgag gccgatggcg tcctttgctc ggaagagtat   3180
```

-continued

```
gaagatgaac aaagccctga aaagattatc gagctgtatg cggagtgcat caggctcttt   3240
cactccatcg acatatcgga ttgtccctat acgaatagct tagacagccg cttagccgaa   3300
ttggattact tactgaataa cgatctggcc gatgtggatt gcgaaaactg ggaagaagac   3360
actccattta aagatccgcg cgagctgtat gattttttaa agacggaaaa gcccgaagag   3420
gaacttgtct tttcccacgg cgacctggga gacagcaaca tctttgtgaa agatggcaaa   3480
gtaagtggct ttattgatct tgggagaagc ggcagggcgg acaagtggta tgacattgcc   3540
ttctgcgtcc ggtcgatcag ggaggatatc ggggaagaac agtatgtcga gctatttttt   3600
gacttactgg ggatcaagcc tgattgggag aaaataaaat attatatttt actggatgaa   3660
ttgttttagt acctagatgt ggcgcaacga tgccggcgac aagcaggagc gcaccgactt   3720
cttccgcatc aagtgttttg gctctcaggc cgaggcccac ggcaagtatt tgggcaaggg   3780
gtcgctggta ttcgtgcagg gcaagattcg gaataccaag tacgagaagg acggccagac   3840
ggtctacggg accgacttca ttgccgataa ggtggattat ctggacacca aggcaccagg   3900
cgggtcaaat caggaataag ggcacattgc cccggcgtga gtcggggcaa tcccgcaagg   3960
agggtgaatg aatcggacgt ttgaccggaa ggcatacagg caagaactga tcgacgcggg   4020
gttttccgcc gaggatgccg aaaccatcgc aagccgcacc gtcatgcgtg cgccccgcga   4080
aaccttccag tccgtcggct cgatggtcca gcaagctacg gccaagatcg agcgcgacag   4140
cgtgcaactg gctccccctg ccctgcccgc gccatcggcc gccgtggagc gttcgcgtcg   4200
tctcgaacag gaggcggcag gtttggcgaa gtcgatgacc atcgacacgc gaggaactat   4260
gacgaccaag aagcgaaaaa ccgccggcga ggacctggca aaacaggtca gcgaggccaa   4320
gcaggccgcg ttgctgaaac acacgaagca gcagatcaag gaaatgcagc tttccttgtt   4380
cgatattgcg ccgtggccgg acacgatgcg agcgatgcca aacgacacgg cccgctctgc   4440
cctgttcacc acgcgcaaca agaaaatccc gcgcgaggcg ctgcaaaaca aggtcatttt   4500
ccacgtcaac aaggacgtga agatcaccta caccggcgtc gagctgcggg ccgacgatga   4560
cgaactggtg tggcagcagg tgttggagta cgcgaagcgc acccctatcg gcgagccgat   4620
caccttcacg ttctacgagc tttgccagga cctgggctgg tcgatcaatg gccggtatta   4680
cacgaaggcc gaggaatgcc tgtcgcgcct acaggcgacg gcgatgggct tcacgtccga   4740
ccgcgttggg cacctggaat cggtgtcgct gctgcaccgc ttccgcgtcc tggaccgtgg   4800
caagaaaacg tcccgttgcc aggtcctgat cgacgaggaa atcgtcgtgc tgtttgctgg   4860
cgaccactac acgaaattca tatgggagaa gtaccgcaag ctgtcgccga cggcccgacg   4920
gatgttcgac tatttcagct cgcaccggga gccgtacccg ctcaagctgg aaaccttccg   4980
cctcatgtgc ggatcggatt ccacccgcgt gaagaagtgg cgcgagcagg tcggcgaagc   5040
ctgcgaagag ttgcgaggca gcggcctggt ggaacacgcc tgggtcaatg atgacctggt   5100
gcattgcaaa cgctagggcc ttgtggggtc agttccggct gggggttcag cagccagcgc   5160
tttactggca tttcaggaac aagcgggcac tgctcgacgc acttgcttcg ctcagtatcg   5220
ctcgggacgc acggcgcgct ctacgaactg ccgataaaca gaggattaaa attgacaatt   5280
gtgattaagg ctcagattcg acggcttgga gcggccgacg tgcaggattt ccgcgagatc   5340
cgattgtcgg ccctgaagaa agctccagag atgttcgggt ccgtttacga gcacgaggag   5400
aaaaagccca tggaggcgtt cgctgaacgg ttgcgagatg ccgtggcatt cggcgcctac   5460
atcgacggcg agatcattgg gctgtcggtc ttcaaacagg aggacggccc caaggacgct   5520
```

cacaaggcgc atctgtccgg cgttttcgtg gagcccgaac agcgaggccg aggggtcgcc 5580
ggtatgctgc tgcgggcgtt gccggcgggt ttattgctcg tgatgatcgt ccgacagatt 5640
ccaacgggaa tctggtggat gcgcatcttc atcctcggcg cacttaatat ttcgctattc 5700
tggagcttgt tgtttatttc ggtctaccgc ctgccgggcg ggtcgcggc gacggtaggc 5760 gctgtgcagc cgctgatggt cgtgttcatc tctgccgctc tgctaggtag cccgatacga 5820
ttgatggcgg tcctgggggc tatttgcgga actgcgggcg tggcgctgtt ggtgttgaca 5880
ccaaacgcag cgctagatcc tgtcggcgtc gcagcgggcc tggcgggggc ggtttccatg 5940
gcgttcggaa ccgtgctgac ccgcaagtgg caacctcccg tgcctctgct cacctttacc 6000
gcctggcaac tggcggccgg aggacttctg ctcgttccag tagctttagt gtttgatccg 6060
ccaatcccga tgcctacagg aaccaatgtt ctcggcctgg cgtggctcgg cctgatcgga 6120
gcgggtttaa cctacttcct ttggttccgg gggatctcgc gactcgaacc tacagttgtt 6180
tccttactgg gctttctcag ccccagatct ggggtcgatc agccggggat gcatcaggcc 6240
gacagtcgga acttcgggtc cccgacctgt accattcggt gagcaatgga taggggagtt 6300
gatatcgtca acgttcactt ctaaagaaat agcgccactc agcttcctca gcggctttat 6360
ccagcgattt cctattatgt cggcatagtt ctcaagatcg acagcctgtc acggttaagc 6420
gagaaatgaa taagaaggct gataattcgg atctctgcga gggagatgat atttgatcac 6480
aggcagcaac gctctgtcat cgttacaatc aacatgctac cctccgcgag atcatccgtg 6540
tttcaaaccc ggcagcttag ttgccgttct tccgaatagc atcggtaaca tgagcaaagt 6600
ctgccgcctt acaacggctc tcccgctgac gccgtcccgg actgatgggc tgcctgtatc 6660
gagtggtgat tttgtgccga gctgccggtc ggggagctgt tggctggctg gtggcaggat 6720
atattgtggt gtaaacaaat tgacgcttag acaacttaat aacacattgc ggacgttttt 6780
aatgtactgg ccggccaaag cacatactta tcgatttaaa tttcatcgaa gagattaata 6840
tcgaataatc atatacatac tttaaataca taacaaattt taaatacata tatctggtat 6900
ataattaatt ttttaaagtc atgaagtatg tatcaaatac acatatggaa aaaattaact 6960
attcataatt taaaaaatag aaaagataca tctagtgaaa ttaggtgcat gtatcaaata 7020
cattaggaaa agggcatata tcttgatcta gataattaac gattttgatt tatgtataat 7080
ttccaaatga aggtttatat ctacttcaga aataacaata tacttttatc agaacattca 7140
acaaagcaac aaccaactag agtgaaaaat acacattgtt ctctagacat acaaaattga 7200
gaaaagaatc tcaaaattta gagaaacaaa tctgaatttc tagaagaaaa aaataattat 7260
gcactttgct attgctcgaa aaataaatga aagaaattag actttttttaa aagatgttag 7320 actagatata ctcaaaagct attaaaggag taatattctt cttacattaa gtattttagt 7380
tacagtcctg taattaaaga cacattttag attgtatcta aacttaaatg tatctagaat 7440
acatatattt gaatgcatca tatacatgta tccgacacac caattctcat aaaaaacgta 7500
atatcctaaa ctaatttatc cttcaagtca acttaagccc aatatacatt ttcatctcta 7560
aaggcccaag tggcacaaaa tgtcaggccc aattacgaag aaaagggctt gtaaaaccct 7620
aataaagtgg cactggcaga gcttacactc tcattccatc aacaaagaaa ccctaaaagc 7680
cgcagcgcca ctgatttctc tcctccaggc gaagatgcag atcttcgtga agaccttaac 7740
ggggaagacg atcaccctag aggttgagtc ttccgacacc atcgacaatg tcaaagccaa 7800
gatccaggac aaggaaggga ttcccccaga ccagcagcgt ttgattttcg ccggaaagca 7860
gcttgaggat ggtcgtactc ttgccgacta caacatccag aaggagtcaa ctctccatct 7920

-continued

```
cgtgctccgt ctccgtggtg gtagtttaaa catgattgaa caagatggat tgcacgcagg   7980
ttctccggcc gcttgggtgg agaggctatt cggctatgac tgggcacaac agacaatcgg   8040
ctgctctgat gccgccgtgt tccggctgtc agcgcagggg cgcccggttc tttttgtcaa   8100
gaccgacctg tccggtgccc tgaatgaact gcaggacgag gcagcgcggc tatcgtggct   8160
ggccacgacg ggcgttcctt gcgcagctgt gctcgacgtt gtcactgaag cgggaaggga   8220
ctggctgcta ttgggcgaag tgccggggca ggatctcctg tcatctcacc ttgctcctgc   8280
cgagaaagta tccatcatgg ctgatgcaat gcggcggctg catacgcttg atccggctac   8340
ctgcccattc gaccaccaag cgaaacatcg catcgagcga gcacgtactc ggatggaagc   8400
cggtcttgtc gatcaggatg atctggacga agagcatcag gggctcgcgc cagccgaact   8460
gttcgccagg ctcaaggcgc gcatgcccga cggcgaggat ctcgtcgtga cccatggcga   8520
tgcctgcttg ccgaatatca tggtggaaaa tggccgcttt tctggattca tcgactgtgg   8580
ccggctgggt gtggcggacc gctatcagga catagcgttg gctacccgtg atattgctga   8640
agagcttggc ggcgaatggg ctgaccgctt cctcgtgctt tacggtatcg ccgctcccga   8700
ttcgcagcgc atcgccttct atcgccttct tgacgagttc ttctgagttt aaacgatttt   8760
aatgtttagc aaatgtctta tcagttttct ctttttgtcg aacggtaatt tagagttttt   8820
tttgctatat ggattttcgt tttgatgta tgtgacaacc ctcgggattg ttgatttatt    8880
tcaaaactaa gagtttttgt cttattgttc tcgtctattt tggatatcaa tcttagtttt   8940
atatcttttc tagttctcta cgtgttaaat gttcaacaca ctagcaattt ggcctgccag   9000
cgtatggatt atggaactat caagtgtgtg ggatcgataa atatgcttct caggaatttg   9060
agatttttta tcatgtcttt atgctcattc ccttgagtat aatatagtaa aaaaatagta   9120
aatttaagca ataatgttag gtgctatgtg tctgtcgaga ctattggccg gccatcgatg   9180
gtttcattgg tgacgtttcc ggccttgcta atggtaatgg tgctactggt gatttttgctg  9240
gctctaattc ccaaatggct caagtcggtg acggtgataa ttcaccttta atgaataatt   9300
tccgtcaata tttaccttcc ctccctcaat cggttgaatg tcgccctttt gtctttggcc   9360
caatacgcaa accgcctctc cccgcgcgtt ggccgattca ttaatgcagc tggcacgaca   9420
ggtttcccga ctggaaagcg ggcagtgagc gcaacgcaat taatgtgagt tagctcactc   9480
attaggcacc ccaggcttta cactttatgc ttccggctcg tatgttgtgt ggaattgtga   9540
gcggataaca atttcacaca ggaaacagct atgaccatga ttacgccaag ctggcgcgcc   9600
cttgtaaaca ctggagtggg aggaatccac actccacact cccaatttag aaagtaaaca   9660
ctacctaaag gtatttacag tcaggatttt tttttccatg taacctcaaa tgcactatgc   9720
aataaaatat aaatataaat aaagcaagca gttactaagt ctttaggttg ttaggcagat   9780
gctaaggcct tgtcctgaat aagcccagca attcaaactt aagattacac tataaaaagg   9840
gggcgcaaag gcaaagaaag tggcacggca agtgcagcga aggaagcaaa ggagagcatg   9900
tcacactgag attacatgtc tgatatttgg ctccgcttct tccctttaaa cacctcgaaa   9960
taagcatcaa ggaagtggtc ttgtcatcat cttcttccag tacatcaatg gagaaacaac  10020
attcgaacac atggaaataa gaaaaatcat taaaattgac tactactgtt gcatattcat  10080
aatatgactg ctggcttttc ttctatctca gtttttttca gagctcaact aagggcagtt  10140
tgatgctgtc attggatagc agtagcttga aaaactacag tactttagtg gttagtaaac  10200
acttattgct ataatttgga atttaggttc attttatccg atactcgaaa tacgctaatg  10260
```

```
ggaaaaatag tcaaaactca ggtaattttt tcatttctct ttttatgttt ctaaacacat  10320
caaaactctc tcttgatgtt taaaaaaatt tattaacttt taacttttat ttgtgtcctt  10380
tcttatttca tccatgatgt cgtaaaaccc actgttaatc aataaaaatt tctgaagata  10440
gaataatgaa ggatacaaaa aaatttacaa gccttttgta tatgatagtt gactatgtgt  10500
atcgggacaa tgttgtgagc attagattgg acaagttatg aatttttatc agtctagctc  10560
atacgcaaaa actttgaaaa actttgaaaa gaataagtta tccatataac acaaaatcac  10620
catttatact tagctcattt atattttta tggatatgaa tgtaaatttc tgcctttgga  10680
gagtaataat aatccaatat cgtcgacgtg gccgttgcag ttgccgagtc gatgcaaaaa  10740
gagcaacggc gatttgttga agagaagcaa cagcaactga ataataatat aacagcaaca  10800
acaacgttga ttcttcgaaa gagaaaagag tcaaatccgg caaaaaggcc aaggcaaaag  10860
cagccaccgt gtcggcgcac gaggcttttt attctaaatt gaaaaagaaa aattgggtaa  10920
ttaacttaac ttatcaagga taacattgtc atatcacaaa aaatatttta ttttgatgaa  10980
tagttacagt ttgtaaaata attaaatcaa ttaagaaaaa taagggcatt ttcattgtaa  11040
aataacgtaa ttttttagtg ttaggagtaa gtgtagcgtt tttaaattta aagaggcaag  11100
ctagaggaag atggagctgt caactttcaa gtaatgtatg catcaaggta agtgacagag  11160
ctaaggagaa atggacaagt actaatcatc gttataaaaa attaaacaga gcagcatttt  11220
gtcagttctg gccatatata tttttcaagg attgggactg ttagcaccgc tgtaatttta  11280
ttttcaagct cttctctgtc aaaacctatt ttactttcca aaatatctta ttccattttt  11340
ttagtttctt tctgattcaa gatttttttt ttaaaaaaaa aaaatctgtt tcttccaaac  11400
aactccaatt acaatttttt tttataaatt tttgaattat taaatcatat atagttaact  11460
aaagagaatc atatatacaa actaaataga attaaaagtg gactcaaatg gctattatgt  11520
tattttttc taaattaaaa aaaaaagttt agaatcagag cctccttgta agccataaaa  11580
aaaaagaaaa gaaaagttta taatgcaaaa gtatttgtga gaaaaaaaaa aaacactttg  11640
atgtagttgc atgaatgtaa agagttagat agagaaatag agtgtataat tagatttatt  11700
tttttcttta aagtaatcgc aatataagag gggttaagaa tttcacagga gtgccactga  11760
ttcaactctt tttcaagaga attgatgttc tggaagaaaa ttatgactct atcattgcta  11820
ttagtttgtc ttgtaattca attattgccg acaagtatta actgtgatta tttttatttt  11880
aaaaattatt attattaatg tattgcaatt ttgagcctta taattgcaat tagtttgtct  11940
tgtaactaaa ttattgccga caaacactat catgctgaca aacaatgcat gcacgtcctc  12000
agtcacccac gtcctctact tgtgtgaatg tgtatataaa tatatctgga gcatattata  12060
aaaccagaag caaaagcaac tgaagttttg aatacggttc accagaagtt agaagatatc  12120
ttttctaatt tgaagaatat gggatccccg ggtggtcagt cccttatgtt acgtcctgta  12180
gaaaccccaa cccgtgaaat caaaaaactc gacggcctgt gggcattcag tctggatcgc  12240
gaaaactgtg gaattgatca gcgttggtgg gaaagcgcgt tacaagaaag ccgggcaatt  12300
gctgtgccag gcagttttaa cgatcagttc gccgatgcag atattcgtaa ttatgcgggc  12360
aacgtctggt atcagcgcga agtctttata ccgaaaggtt gggcaggcca gcgtatcgtg  12420
ctgcgtttcg atgcggtcac tcattacggc aaagtgtggg tcaataatca ggaagtgatg  12480
gagcatcagg gcggctatac gccatttgaa gccgatgtca cgccgtatgt tattgccggg  12540
aaaagtgtac gtatcaccgt ttgtgtgaac aacgaactga actggcagac tatcccgccg  12600
ggaatggtga ttaccgacga aaacggcaag aaaaagcagt cttacttcca tgatttcttt  12660
```

```
aactatgccg gaatccatcg cagcgtaatg ctctacacca cgccgaacac ctgggtggac  12720
gatatcaccg tggtgacgca tgtcgcgcaa gactgtaacc acgcgtctgt tgactggcag  12780
gtggtggcca atggtgatgt cagcgttgaa ctgcgtgatg cggatcaaca ggtggttgca  12840
actggacaag gcactagcgg gactttgcaa gtggtgaatc cgcacctctg gcaaccgggt  12900
gaaggttatc tctatgaact gtgcgtcaca gccaaaagcc agacagagtg tgatatctac  12960
ccgcttcgcg tcggcatccg gtcagtggca gtgaagggcg aacagttcct gattaaccac  13020
aaaccgttct actttactgg ctttggtcgt catgaagatg cggacttgcg tggcaaagga  13080
ttcgataacg tgctgatggt gcacgaccac gcattaatgg actggattgg ggccaactcc  13140
taccgtacct cgcattaccc ttacgctgaa gagatgctcg actgggcaga tgaacatggc  13200
atcgtggtga ttgatgaaac tgctgctgtc ggctttaacc tctctttagg cattggtttc  13260
gaagcgggca acaagccgaa agaactgtac agcgaagagg cagtcaacgg ggaaactcag  13320
caagcgcact tacaggcgat taaagagctg atagcgcgtg acaaaaacca cccaagcgtg  13380
gtgatgtgga gtattgccaa cgaaccggat acccgtccgc aaggtgcacg ggaatatttc  13440
gcgccactgg cggaagcaac gcgtaaactc gacccgacgc gtccgatcac ctgcgtcaat  13500
gtaatgttct gcgacgctca caccgatacc atcagcgatc tctttgatgt gctgtgcctg  13560
aaccgttatt acggatggta tgtccaaagc ggcgatttgg aaacggcaga gaaggtactg  13620
gaaaaagaac ttctggcctg gcaggagaaa ctgcatcagc cgattatcat caccgaatac  13680
ggcgtggata cgttagccgg gctgcactca atgtacaccg acatgtggag tgaagagtat  13740
cagtgtgcat ggctggatat gtatcaccgc gtctttgatc gcgtcagcgc cgtcgtcggt  13800
gaacaggtat ggaatttcgc cgattttgcg acctcgcaag gcatattgcg cgttggcggt  13860
aacaagaaag ggatcttcac tcgcgaccgc aaaccgaagt cggcggcttt tctgctgcaa  13920
aaacgctgga ctggcatgaa cttcggtgaa aaaccgcagc agggaggcaa acaatgaatc  13980
aacaactctc ctggcgcacc atcgtcggct acagcctcgg gaattgctac gagctcgttg  14040
cctattgttg gttgtcgtgt tgtctggctg tgtctgttgc ccattgtggt ggttatgtgt  14100
tgcatcatgg tctaaaagga tcatcaatgt ttttcgcttc tgttcctttc tgtttctcat  14160
ttgtgaataa taatggtgtc tttatgaaca tccagtttct ggtttctttt ctgattgcag  14220
tttgagtatt tgtttttgct tttgcttccg tctactacac cactttgcaa ttactgtatc  14280
actcatgcat tgttgatata ctttagcctt cgatccatct tctgtttgat gattcaaatg  14340
gtatttattt aactcatacc caagtgaagc ataaagttag aggagagttc atgttccatt  14400
acctgtttgt ttcatgagca actcatctta ataaacataa gaaaaaccat aatgcaatct  14460
gtgtagctga tagactttga tgacagacgg actcataagt aacaagagga aacatgataa  14520
acatgtacgg aagtcgagct cgaattctta attaacaatt cactggccgt cgttttacaa  14580
cgtcgtgact gggaaaaccc tggcgttacc caacttaatc gccttgcagc acatccccct  14640
ttcgccagct ggcgtaatag cgaagaggcc cgcaccgatc gcccttccca acagttgcgc  14700
agcctgaatg gcgcccgctc ctttcgcttt cttcccttcc tttctcgcca cgttcgccgg  14760
ctttccccgt caagctctaa atcgggggct ccctttaggg ttccgattta gtgctttacg  14820
gcacctcgac cccaaaaaac ttgatttggg tgatggttca caaactatca gtgtttgaca  14880
ggatatattg gcgggtaaac ctaagagaaa agagcgttta ttagaataat cggatattta  14940
aaagggcgtg aaaaggttta tccgttcgtc catttgtatg tgcatgccaa ccacagggtt  15000
```

-continued

```
ccccagatct ggcgccggcc agcgagacga gcaagattgg ccgccgcccg aaacgatccg  15060
acagcgcgcc cagcacaggt gcgcaggcaa attgcaccaa cgcatacagc gccagcagaa  15120
tgccatagtg ggcggtgacg tcgttcgagt gaaccagatc gcgcaggagg cccggcagca  15180
ccggcataat caggccgatg ccgacagcgt cgagcgcgac agtgctcaga attacgatca  15240
ggggtatgtt gggtttcacg tctggcctcc ggaccagcct ccgctggtcc gattgaacgc  15300
gcggattctt tatcactgat aagttggtgg acatattatg tttatcagtg ataaagtgtc  15360
aagcatgaca aagttgcagc cgaatacagt gatccgtgcc gccctggacc tgttgaacga  15420
ggtcggcgta gacggtctga cgacacgcaa actggcggaa cggttggggg ttcagcagcc  15480
ggcgctttac tggcacttca ggaacaagcg ggcgctgctc gacgcactgg ccgaagccat  15540
gctggcggag aatcatacgc attcggtgcc gagagccgac gacgactggc gctcatttct  15600
gatcgggaat gcccgcagct tcaggcaggc gctgctcgcc taccgcgatg gcgcgcgcat  15660
ccatgccggc acgcgaccgg gcgcaccgca gatggaaacg gccgacgcgc agcttcgctt  15720
cctctgcgag gcgggttttt cggccgggga cgccgtcaat gcgctgatga caatcagcta  15780
cttcactgtt ggggccgtgc ttgaggagca ggccggcgac agcgatgccg gcgagcgcgg  15840
cggcaccgtt gaacaggctc cgctctcgcc gctgttgcgg gccgcgatag acgccttcga  15900
cgaagccggt ccggacgcag cgttcgagca gggactcgcg gtgattgtcg atggattggc  15960
gaaaaggagg ctcgttgtca ggaacgttga aggaccgaga aagggtgacg attgatcagg  16020
accgctgccg gagcgcaacc cactcactac agcagagcca tgtagacaac atcccctccc  16080
cctttccacc gcgtcagacg cccgtagcag cccgctacgg gctttttcat gccctgccct  16140
agcgtccaag cctcacggcc gcgctcggcc tctctggcgg ccttctggcg ctcttccgct  16200
tcctcgctca ctgactcgct gcgctcggtc gttcggctgc ggcgagcggt atcagctcac  16260
tcaaaggcgg taatacggtt atccacagaa tcaggggata acgcaggaaa gaacatgtga  16320
gcaaaaggcc agcaaaaggc caggaaccgt aaaaaggccg cgttgctggc gtttttccat  16380
aggctccgcc cccctgacga gcatcacaaa aatcgacgct caagtcagag gtggcgaaac  16440
ccgacaggac tataaagata ccaggcgttt ccccctggaa gctccctcgt gcgctctcct  16500
gttccgaccc tgccgcttac cggatacctg tccgcctttc tcccttcggg aagcgtggcg  16560
ctttccgct gcataaccct gcttcggggt cattatagcg atttttttcgg tatatccatc  16620
ctttttcgca cgatatacag gattttgcca aagggttcgt gtagactttc cttggtgtat  16680
ccaacggcgt cagccgggca ggataggtga agtaggccca cccgcgagcg ggtgttcctt  16740
cttcactgtc ccttattcgc acctggcggt gctcaacggg aatcctgctc tgcgaggctg  16800
gccggctacc gccggcgtaa cagatgaggg caagcggatg gctgatgaaa ccaagccaac  16860
caggaagggc agcccaccta tcaaggtgta ctgccttcca gacgaacgaa gagcgattga  16920
ggaaaaggcg gcggcggccg gcatgagcct gtcggcctac ctgctggccg tcggccaggg  16980
ctacaaaatc acgggcgtcg tggactatga gcacgtccgc gagctggccc gcatcaatgg  17040
cgacctgggc cgcctgggcg gcctgctgaa actctggctc accgacgacc cgcgcacggc  17100
gcggttcggt gatgccacga tcctcgccct gctggcgaag atcgaagaga agcaggacga  17160
gcttggcaag gtcatgatgg gcgtggtccg cccgagggca gagccatgac tttttttagcc  17220
gctaaaacgg ccggggggtg cgcgtgattg ccaagcacgt ccccatgcgc tccatcaaga  17280
agagcgactt cgcggagctg gtgaagtaca tcaccgacga gcaaggcaag accgagcgcc  17340
tttgcgacgc tca                                                     17353
```

<210> SEQ ID NO 3
<211> LENGTH: 17349
<212> TYPE: DNA
<213> ORGANISM: Artificial Sequence
<220> FEATURE:
<223> OTHER INFORMATION: plasmid

<400> SEQUENCE: 3
ccgggctggt tgccctcgcc gctgggctgg cggccgtcta tggccctgca aacgcgccag 60
aaacgccgtc gaagccgtgt gcgagacacc gcggccgccg gcgttgtgga tacctcgcgg 120
aaaacttggc cctcactgac agatgagggg cggacgttga cacttgaggg gccgactcac 180
ccggcgcggc gttgacagat gaggggcagg ctcgatttcg gccggcgacg tggagctggc 240
cagcctcgca aatcggcgaa aacgcctgat tttacgcgag tttcccacag atgatgtgga 300
caagcctggg gataagtgcc ctgcggtatt gacacttgag gggcgcgact actgacagat 360
gaggggcgcg atccttgaca cttgaggggc agagtgctga cagatgaggg gcgcacctat 420
tgacatttga ggggctgtcc acaggcagaa aatccagcat ttgcaagggt ttccgcccgt 480
ttttcggcca ccgctaacct gtcttttaac ctgcttttaa accaatattt ataaaccttg 540
tttttaacca gggctgcgcc ctgtgcgcgt gaccgcgcac gccgaagggg ggtgcccccc 600
cttctcgaac cctcccggcc cgctaacgcg ggcctcccat ccccccaggg gctgcgcccc 660
tcggccgcga acggcctcac cccaaaaatg gcagcgctgg cagtccttgc cattgccggg 720
atcggggcag taacgggatg ggcgatcagc ccgagcgcga cgcccggaag cattgacgtg 780
ccgcaggtgc tggcatcgac attcagcgac caggtgccgg gcagtgaggg cggcggcctg 840
ggtggcggcc tgcccttcac ttcggccgtc ggggcattca cggacttcat ggcggggccg 900
gcaattttta ccttgggcat tcttggcata gtggtcgcgg gtgccgtgct cgtgttcggg 960
ggtgcgataa acccagcgaa ccatttgagg tgataggtaa gattataccg aggtatgaaa 1020
acgagaattg gacctttaca gaattactct atgaagcgcc atatttaaaa agctaccaag 1080
acgaagagga tgaagaggat gaggaggcag attgccttga atatattgac aatactgata 1140
agataatata tcttttatat agaagatatc gccgtatgta aggatttcag ggggcaaggc 1200
ataggcagcg cgcttatcaa tatatctata gaatgggcaa agcataaaaa cttgcatgga 1260
ctaatgcttg aaacccagga caataacctt atagcttgta aattctatca taattgggta 1320
atgactccaa cttattgata gtgttttatg ttcagataat gcccgatgac tttgtcatgc 1380
agctccaccg attttgagaa cgacagcgac ttccgtccca gccgtgccag gtgctgcctc 1440
agattcaggt tatgccgctc aattcgctgc gtatatcgct tgctgattac gtgcagcttt 1500
cccttcaggc gggattcata cagcggccag ccatccgtca tccatatcac cacgtcaaag 1560
ggtgacagca ggctcataag acgccccagc gtcgccatag tgcgttcacc gaatacgtgc 1620
gcaacaaccg tcttccggag actgtcatac gcgtaaaaca gccagcgctg gcgcgattta 1680
gccccgacat agccccactg ttcgtccatt tccgcgcaga cgatgacgtc actgcccggc 1740
tgtatgcgcg aggttacata tgcggtgtga aataccgcac agatgcgtaa ggagaaaata 1800
ccgcatcagg cgctcttccg cttcctcgct cactgactcg ctgcgctcgg tcgttcggct 1860
gcggcgagcg gtatcagctc actcaaaggc ggtaatacgg ttatccacag aatcagggga 1920
taacgcagga aagaacatgt gagcaaaagg ccagcaaaag gccaggaacc gtaaaaaggc 1980
cgcgttgctg gcgtttttcc ataggctccg cccccctgac gagcatcaca aaaatcgacg 2040

-continued

```
ctcaagtcag aggtggcgaa acccgacagg actataaaga taccaggcgt ttccccctgg   2100
aagctccctc gtgcgctctc ctgttccgac cctgccgctt accggatacc tgtccgcctt   2160
tctcccttcg ggaagcgtgg cgctttctca tagctcacgc tgtaggtatc tcagttcggt   2220
gtaggtcgtt cgctccaagc tgggctgtgt gcacgaaccc cccgttcagc ccgaccgctg   2280
cgccttatcc ggtaactatc gtcttgagtc caacccggta agacacgact tatcgccact   2340
ggcagcagcc agttaccgac tgcggcctga gtttttaag tgacgtaaaa tcgtgttgag   2400
gccaacgccc ataatgcggg ctgttgcccg gcatccaacg ccattcatgg ccatatcaat   2460
gattttctgg tgcgtaccgg gttgagaagc ggtgtaagtg aactgcagtt gccatgtttt   2520
acggcagtga gagcagagat agcgctgatg tccggcggtg cttttgccgt tacgcaccac   2580
cccgtcagta gctgaacagg agggacagct gatagacaca gaagccactg gagcacctca   2640
aaaacaccat catacactaa atcagtaagt tggcagcatc acccataatt gtggtttcaa   2700
aatcggctcc gtcgatacta tgttatacgc caactttgaa aacaactttg aaaaagctgt   2760
tttctggtat ttaaggtttt agaatgcaag gaacagtgaa ttggagttcg tcttgttata   2820
attagcttct tggggtatct ttaaatactg tagaaaagag gaaggaaata ataaatggct   2880
aaaatgagaa tatcaccgga attgaaaaaa ctgatcgaaa aataccgctg cgtaaaagat   2940
acggaaggaa tgtctcctgc taaggtatat aagctggtgg gagaaaatga aaacctatat   3000
ttaaaaatga cggacagccg gtataaaggg accacctatg atgtggaacg ggaaaaggac   3060
atgatgctat ggctggaagg aaagctgcct gttccaaagg tcctgcactt tgaacggcat   3120
gatggctgga gcaatctgct catgagtgag gccgatggcg tcctttgctc ggaagagtat   3180
gaagatgaac aaagccctga aaagattatc gagctgtatg cggagtgcat caggctcttt   3240
cactccatcg acatatcgga ttgtccctat acgaatagct tagacagccg cttagccgaa   3300
ttggattact tactgaataa cgatctggcc gatgtggatt gcgaaaactg ggaagaagac   3360
actccattta aagatccgcg cgagctgtat gattttttaa agacggaaaa gcccgaagag   3420
gaacttgtct tttcccacgg cgacctggga gacagcaaca tctttgtgaa agatggcaaa   3480
gtaagtggct ttattgatct tgggagaagc ggcagggcgg acaagtggta tgacattgcc   3540
ttctgcgtcc ggtcgatcag ggaggatatc ggggaagaac agtatgtcga gctatttttt   3600
gacttactgg ggatcaagcc tgattgggag aaaataaaat attatatttt actggatgaa   3660
ttgttttagt acctagatgt ggcgcaacga tgccggcgac aagcaggagc gcaccgactt   3720
cttccgcatc aagtgttttg gctctcaggc cgaggcccac ggcaagtatt tgggcaaggg   3780
gtcgctggta ttcgtgcagg gcaagattcg gaataccaag tacgagaagg acggccagac   3840
ggtctacggg accgacttca ttgccgataa ggtggattat ctggacacca aggcaccagg   3900
cgggtcaaat caggaataag ggcacattgc cccggcgtga gtcggggcaa tcccgcaagg   3960
agggtgaatg aatcggacgt ttgaccggaa ggcatacagg caagaactga tcgacgcggg   4020
gttttccgcc gaggatgccg aaaccatcgc aagccgcacc gtcatgcgtg cgccccgcga   4080
aaccttccag tccgtcggct cgatggtcca gcaagctacg gccaagatcg agcgcgacag   4140
cgtgcaactg gctccccctg ccctgcccgc gccatcggcc gccgtggagc gttcgcgtcg   4200
tctcgaacag gaggcggcag gtttggcgaa gtcgatgacc atcgacacgc gaggaactat   4260
gacgaccaag aagcgaaaaa ccgccggcga ggacctggca aaacaggtca gcgaggccaa   4320
gcaggccgcg ttgctgaaac acacgaagca gcagatcaag gaaatgcagc tttccttgtt   4380
cgatattgcg ccgtggccgg acacgatgcg agcgatgcca aacgacacgg cccgctctgc   4440
```

-continued

```
cctgttcacc acgcgcaaca agaaaatccc gcgcgaggcg ctgcaaaaca aggtcatttt   4500
ccacgtcaac aaggacgtga agatcaccta caccggcgtc gagctgcggg ccgacgatga   4560
cgaactggtg tggcagcagg tgttggagta cgcgaagcgc acccctatcg gcgagccgat   4620
caccttcacg ttctacgagc tttgccagga cctgggctgg tcgatcaatg gccggtatta   4680
cacgaaggcc gaggaatgcc tgtcgcgcct acaggcgacg gcgatgggct tcacgtccga   4740
ccgcgttggg cacctggaat cggtgtcgct gctgcaccgc ttccgcgtcc tggaccgtgg   4800
caagaaaacg tcccgttgcc aggtcctgat cgacgaggaa atcgtcgtgc tgtttgctgg   4860
cgaccactac acgaaattca tatgggagaa gtaccgcaag ctgtcgccga cggcccgacg   4920
gatgttcgac tatttcagct cgcaccggga gccgtacccg ctcaagctgg aaaccttccg   4980
cctcatgtgc ggatcggatt ccacccgcgt gaagaagtgg cgcgagcagg tcggcgaagc   5040
ctgcgaagag ttgcgaggca gcggcctggt ggaacacgcc tgggtcaatg atgacctggt   5100
gcattgcaaa cgctagggcc ttgtggggtc agttccggct gggggttcag cagccagcgc   5160
tttactggca tttcaggaac aagcgggcac tgctcgacgc acttgcttcg ctcagtatcg   5220
ctcgggacgc acggcgcgct ctacgaactg ccgataaaca gaggattaaa attgacaatt   5280
gtgattaagg ctcagattcg acggcttgga gcggccgacg tgcaggattt ccgcgagatc   5340
cgattgtcgg ccctgaagaa agctccagag atgttcgggt ccgtttacga gcacgaggag   5400
aaaaagccca tggaggcgtt cgctgaacgg ttgcgagatg ccgtggcatt cggcgcctac   5460
atcgacggcg agatcattgg gctgtcggtc ttcaaacagg aggacggccc caaggacgct   5520
cacaaggcgc atctgtccgg cgttttcgtg gagcccgaac agcgaggccg aggggtcgcc   5580
ggtatgctgc tgcgggcgtt gccggcgggt ttattgctcg tgatgatcgt ccgacagatt   5640
ccaacgggaa tctggtggat gcgcatcttc atcctcggcg cacttaatat ttcgctattc   5700
tggagcttgt tgtttatttc ggtctaccgc ctgccgggcg gggtcgcggc gacggtaggc   5760
gctgtgcagc cgctgatggt cgtgttcatc tctgccgctc tgctaggtag cccgatacga   5820
ttgatggcgg tcctgggggc tatttgcgga actgcgggcg tggcgctgtt ggtgttgaca   5880
ccaaacgcag cgctagatcc tgtcggcgtc gcagcgggcc tggcgggggc ggtttccatg   5940
gcgttcggaa ccgtgctgac ccgcaagtgg caacctcccg tgcctctgct cacctttacc   6000
gcctggcaac tggcggccgg aggacttctg ctcgttccag tagctttagt gtttgatccg   6060
ccaatcccga tgcctacagg aaccaatgtt ctcggcctgg cgtggctcgg cctgatcgga   6120
gcgggtttaa cctacttcct ttggttccgg gggatctcgc gactcgaacc tacagttgtt   6180
tccttactgg gctttctcag ccccagatct ggggtcgatc agccggggat gcatcaggcc   6240
gacagtcgga acttcgggtc cccgacctgt accattcggt gagcaatgga taggggagtt   6300
gatatcgtca acgttcactt ctaaagaaat agcgccactc agcttcctca gcggctttat   6360
ccagcgattt cctattatgt cggcatagtt ctcaagatcg acagcctgtc acggttaagc   6420
gagaaatgaa taagaaggct gataattcgg atctctgcga gggagatgat atttgatcac   6480
aggcagcaac gctctgtcat cgttacaatc aacatgctac cctccgcgag atcatccgtg   6540
tttcaaaccc ggcagcttag ttgccgttct tccgaatagc atcggtaaca tgagcaaagt   6600
ctgccgcctt acaacggctc tcccgctgac gccgtcccgg actgatgggc tgcctgtatc   6660
gagtggtgat tttgtgccga gctgccggtc ggggagctgt tggctggctg gtggcaggat   6720
atattgtggt gtaaacaaat tgacgcttag acaacttaat aacacattgc ggacgttttt   6780
```

-continued

```
aatgtactgg ccggccaaag cacatactta tcgatttaaa tttcatcgaa gagattaata   6840
tcgaataatc atatacatac tttaaataca taacaaattt taaatacata tatctggtat   6900
ataattaatt ttttaaagtc atgaagtatg tatcaaatac acatatggaa aaaattaact   6960
attcataatt taaaaaatag aaaagataca tctagtgaaa ttaggtgcat gtatcaaata   7020
cattaggaaa agggcatata tcttgatcta gataattaac gattttgatt tatgtataat   7080
ttccaaatga aggtttatat ctacttcaga aataacaata tacttttatc agaacattca   7140
acaaagcaac aaccaactag agtgaaaaat acacattgtt ctctagacat acaaaattga   7200
gaaaagaatc tcaaaattta gagaaacaaa tctgaatttc tagaagaaaa aaataattat   7260
gcactttgct attgctcgaa aaataaatga aagaaattag actttttttaa aagatgttag   7320
actagatata ctcaaaagct attaaaggag taatattctt cttacattaa gtattttagt   7380
tacagtcctg taattaaaga cacattttag attgtatcta aacttaaatg tatctagaat   7440
acatatattt gaatgcatca tatacatgta tccgacacac caattctcat aaaaaacgta   7500
atatcctaaa ctaatttatc cttcaagtca acttaagccc aatatacatt ttcatctcta   7560
aaggcccaag tggcacaaaa tgtcaggccc aattacgaag aaaagggctt gtaaaaccct   7620
aataaagtgg cactggcaga gcttacactc tcattccatc aacaaagaaa ccctaaaagc   7680
cgcagcgcca ctgatttctc tcctccaggc gaagatgcag atcttcgtga agaccttaac   7740
ggggaagacg atcaccctag aggttgagtc ttccgacacc atcgacaatg tcaaagccaa   7800
gatccaggac aaggaaggga ttcccccaga ccagcagcgt ttgattttcg ccggaaagca   7860
gcttgaggat ggtcgtactc ttgccgacta caacatccag aaggagtcaa ctctccatct   7920
cgtgctccgt ctccgtggtg gtagtttaaa catgattgaa caagatggat tgcacgcagg   7980
ttctccggcc gcttgggtgg agaggctatt cggctatgac tgggcacaac agacaatcgg   8040
ctgctctgat gccgccgtgt tccggctgtc agcgcagggg cgcccggttc tttttgtcaa   8100
gaccgacctg tccggtgccc tgaatgaact gcaggacgag gcagcgcggc tatcgtggct   8160
ggccacgacg ggcgttcctt gcgcagctgt gctcgacgtt gtcactgaag cgggaaggga   8220
ctggctgcta ttgggcgaag tgccggggca ggatctcctg tcatctcacc ttgctcctgc   8280
cgagaaagta tccatcatgg ctgatgcaat gcggcggctg catacgcttg atccggctac   8340
ctgcccattc gaccaccaag cgaaacatcg catcgagcga gcacgtactc ggatggaagc   8400
cggtcttgtc gatcaggatg atctggacga agagcatcag gggctcgcgc cagccgaact   8460
gttcgccagg ctcaaggcgc gcatgcccga cggcgaggat ctcgtcgtga cccatggcga   8520
tgcctgcttg ccgaatatca tggtggaaaa tggccgcttt tctggattca tcgactgtgg   8580
ccggctgggt gtggcggacc gctatcagga catagcgttg gctacccgtg atattgctga   8640
agagcttggc ggcgaatggg ctgaccgctt cctcgtgctt tacggtatcg ccgctcccga   8700
ttcgcagcgc atcgccttct atcgccttct tgacgagttc ttctgagttt aaacgatttt   8760
aatgtttagc aaatgtctta tcagttttct ctttttgtcg aacggtaatt tagagttttt   8820
tttgctatat ggattttcgt tttgatgta tgtgacaacc ctcgggattg ttgatttatt   8880
tcaaaactaa gagtttttgt cttattgttc tcgtctattt tggatatcaa tcttagtttt   8940
atatcttttc tagttctcta cgtgttaaat gttcaacaca ctagcaattt ggcctgccag   9000
cgtatggatt atggaactat caagtgtgtg ggatcgataa atatgcttct caggaatttg   9060
agattttttta tcatgtcttt atgctcattc ccttgagtat aatatagtaa aaaaatagta   9120
aatttaagca ataatgttag gtgctatgtg tctgtcgaga ctattggccg gccatcgatg   9180
```

-continued

```
gtttcattgg tgacgtttcc ggccttgcta atggtaatgg tgctactggt gattttgctg   9240
gctctaattc ccaaatggct caagtcggtg acggtgataa ttcaccttta atgaataatt   9300
tccgtcaata tttaccttcc ctccctcaat cggttgaatg tcgccctttt gtctttggcc   9360
caatacgcaa accgcctctc cccgcgcgtt ggccgattca ttaatgcagc tggcacgaca   9420
ggtttcccga ctggaaagcg ggcagtgagc gcaacgcaat taatgtgagt tagctcactc   9480
attaggcacc ccaggcttta cactttatgc ttccggctcg tatgttgtgt ggaattgtga   9540
gcggataaca atttcacaca ggaaacagct atgaccatga ttacgccaag ctggcgcgcc   9600
cttgtaaaca ctggagtggg aggaatccac actccacact cccaatttag aaagtaaaca   9660
ctacctaaag gtatttacag tcaggatttt tttttccatg taacctcaaa tgcactatgc   9720
aataaaatat aaatataaat aaagcaagca gttactaagt ctttaggttg ttaggcagat   9780
gctaaggcct tgtcctgaat aagcccagca attcaaactt aagattacac tataaaaagg   9840
gggcgcaaag gcaaagaaag tggcacggca agtgcagcga aggaagcaaa ggagagcatg   9900
tcacactgag attacatgtc tgatatttgg ctccgcttct tccctttaaa cacctcgaaa   9960
taagcatcaa ggaagtggtc ttgtcatcat cttcttccag tacatcaatg gagaaacaac  10020
attcgaacac atggaaataa gaaaaatcat taaaattgac tactactgtt gcatattcat  10080
aatatgactg ctggcttttc ttctatctca gtttttttca gagctcaact aagggcagtt  10140
tgatgctgtc attggatagc agtagcttga aaaactacag tactttagtg gttagtaaac  10200
acttattgct ataatttgga atttaggttc attttatccg atactcgaaa tacgctaatg  10260
ggaaaaatag tcaaaactca ggtaattttt tcatttctct ttttatgttt ctaaacacat  10320
caaaactctc tcttgatgtt taaaaaaatt tattaacttt taacttttat ttgtgtcctt  10380
tcttatttca tccatgatgt cgtaaaaccc actgttaatc aataaaaatt tctgaagata  10440
gaataatgaa ggatacaaaa aaatttacaa gccttttgta tatgatagtt gactatgtgt  10500
atcgggacaa tgttgtgagc attagattgg acaagttatg aatttttatc agtctagctc  10560
atacgcaaaa actttgaaaa actttgaaaa gaataagtta tccatataac acaaaatcac  10620
catttatact tagctcattt atattttta tggatatgaa tgtaaatttc tgcctttgga  10680
gagtaataat aatccaatat cgtcgacgtg gccgttgcag ttgccgagtc gatgcaaaaa  10740
gagcaacggc gatttgttga agagaagcaa cagcaactga ataataatat aacagcaaca  10800
acaacgttga ttcttcgaaa gagaaaagag tcaaatccgg caaaaaggcc aaggcaaaag  10860
cagccaccgt gtcggcgcac gaggcttttt attctaaatt gaaaaagaaa aattgggtaa  10920
ttaacttaac ttatcaagga taacattgtc atatcacaaa aaatatttta ttttgatgaa  10980
tagttacagt ttgtaaaata attaaatcaa ttaagaaaaa taagggcatt ttcattgtaa  11040
aataacgtaa ttttttagtg ttaggagtaa gtgtagcgtt tttaaattta aagaggcaag  11100
ctagaggaag atggagctgt caactttcaa gtaatgtatg catcaaggta agtgacagag  11160
ctaaggagaa atggacaagt actaatcatc gttataaaaa attaaacaga gcagcatttt  11220
gtcagttctg gccatatata tttttcaagg attgggactg ttagcaccgc tgtaatttta  11280
ttttcaagct cttctctgtc aaaacctatt ttactttcca aaatatctta ttccattttt  11340
ttagtttctt tctgattcaa gatttttttt ttaaaaaaaa aaaatctgtt tcttccaaac  11400
aactccaatt acaatttttt tttataaatt tttgaattat taaatcatat atagttaact  11460
aaagagaatc atatatacaa actaaataga attaaaagtg gactcaaatg gctattatgt  11520
```

-continued

```
tattttttc taaattaaaa aaaaaagttt agaatcagag cctccttgta agccataaaa  11580
aaaaagaaaa gaaaagttta taatgcaaaa gtatttgtga gaaaaaaaaa aaacactttg  11640
atgtagttgc atgaatgtaa agagttagat agagaaatag agtgtataat tagatttatt  11700
tttttcttta aagtaatcgc aatataagag gggttaagaa tttcacagga gtgccactga  11760
ttcaactctt tttcaagaga attgatgttc tggaagaaaa ttatgactct atcattgcta  11820
ttagtttgtc ttgtaattca attattgccg acaagtatta actgtgatta tttttatttt  11880
aaaaattatt attattaatg tattgcaatt ttgagcctta taattgcaat tagtttgtct  11940
tgtaactaaa ttattgccga caaacactat catgctgaca aacaatgcat gcacgtcctc  12000
agtcacccac gtcctctact tgtgtgaatg tgtatataaa tatatctgga gcatattata  12060
aaaccagaag caaaagcaac tgaagttttg aatacggttc accagaagtt agaagatatc  12120
ttttctaatt tgaagaagga tccccgggtg gtcagtccct tatgttacgt cctgtagaaa  12180
ccccaacccg tgaaatcaaa aaactcgacg gcctgtgggc attcagtctg gatcgcgaaa  12240
actgtggaat tgatcagcgt tggtgggaaa gcgcgttaca agaaagccgg gcaattgctg  12300
tgccaggcag ttttaacgat cagttcgccg atgcagatat tcgtaattat gcgggcaacg  12360
tctggtatca gcgcgaagtc tttataccga aaggttgggc aggccagcgt atcgtgctgc  12420
gtttcgatgc ggtcactcat tacggcaaag tgtgggtcaa taatcaggaa gtgatggagc  12480
atcagggcgg ctatacgcca tttgaagccg atgtcacgcc gtatgttatt gccgggaaaa  12540
gtgtacgtat caccgtttgt gtgaacaacg aactgaactg gcagactatc ccgccgggaa  12600
tggtgattac cgacgaaaac ggcaagaaaa agcagtctta cttccatgat ttctttaact  12660
atgccggaat ccatcgcagc gtaatgctct acaccacgcc gaacacctgg gtggacgata  12720
tcaccgtggt gacgcatgtc gcgcaagact gtaaccacgc gtctgttgac tggcaggtgg  12780
tggccaatgg tgatgtcagc gttgaactgc gtgatgcgga tcaacaggtg gttgcaactg  12840
gacaaggcac tagcgggact ttgcaagtgg tgaatccgca cctctggcaa ccgggtgaag  12900
gttatctcta tgaactgtgc gtcacagcca aaagccagac agagtgtgat atctacccgc  12960
ttcgcgtcgg catccggtca gtggcagtga agggcgaaca gttcctgatt aaccacaaac  13020
cgttctactt tactggcttt ggtcgtcatg aagatgcgga cttgcgtggc aaaggattcg  13080
ataacgtgct gatggtgcac gaccacgcat taatggactg gattggggcc aactcctacc  13140
gtacctcgca ttacccttac gctgaagaga tgctcgactg ggcagatgaa catggcatcg  13200
tggtgattga tgaaactgct gctgtcggct ttaacctctc tttaggcatt ggtttcgaag  13260
cgggcaacaa gccgaaagaa ctgtacagcg aagaggcagt caacggggaa actcagcaag  13320
cgcacttaca ggcgattaaa gagctgatag cgcgtgacaa aaaccaccca agcgtggtga  13380
tgtggagtat tgccaacgaa ccggataccc gtccgcaagg tgcacgggaa tatttcgcgc  13440
cactggcgga agcaacgcgt aaactcgacc cgacgcgtcc gatcacctgc gtcaatgtaa  13500
tgttctgcga cgctcacacc gataccatca gcgatctctt tgatgtgctg tgcctgaacc  13560
gttattacgg atggtatgtc caaagcggcg atttggaaac ggcagagaag gtactggaaa  13620
aagaacttct ggcctggcag gagaaactgc atcagccgat tatcatcacc gaatacggcg  13680
tggatacgtt agccgggctg cactcaatgt acaccgacat gtggagtgaa gagtatcagt  13740
gtgcatggct ggatatgtat caccgcgtct ttgatcgcgt cagcgccgtc gtcggtgaac  13800
aggtatggaa tttcgccgat tttgcgacct cgcaaggcat attgcgcgtt ggcggtaaca  13860
agaaagggat cttcactcgc gaccgcaaac cgaagtcggc ggcttttctg ctgcaaaaac  13920
```

-continued

```
gctggactgg catgaacttc ggtgaaaaac cgcagcaggg aggcaaacaa tgaatcaaca  13980
actctcctgg cgcaccatcg tcggctacag cctcgggaat tgctacgagc tcgttgccta  14040
ttgttggttg tcgtgttgtc tggctgtgtc tgttgcccat tgtggtggtt atgtgttgca  14100
tcatggtcta aaaggatcat caatgttttt cgcttctgtt cctttctgtt tctcatttgt  14160
gaataataat ggtgtcttta tgaacatcca gtttctggtt tcttttctga ttgcagtttg  14220
agtatttgtt tttgcttttg cttccgtcta ctacaccact ttgcaattac tgtatcactc  14280
atgcattgtt gatatacttt agccttcgat ccatcttctg tttgatgatt caaatggtat  14340
ttatttaact catacccaag tgaagcataa agttagagga gagttcatgt tccattacct  14400
gtttgtttca tgagcaactc atcttaataa acataagaaa aaccataatg caatctgtgt  14460
agctgataga ctttgatgac agacggactc ataagtaaca agaggaaaca tgataaacat  14520
gtacggaagt cgagctcgaa ttcttaatta acaattcact ggccgtcgtt ttacaacgtc  14580
gtgactggga aaaccctggc gttacccaac ttaatcgcct tgcagcacat ccccctttcg  14640
ccagctggcg taatagcgaa gaggcccgca ccgatcgccc ttcccaacag ttgcgcagcc  14700
tgaatggcgc ccgctccttt cgctttcttc ccttcctttc tcgccacgtt cgccggcttt  14760
ccccgtcaag ctctaaatcg ggggctccct ttagggttcc gatttagtgc tttacggcac  14820
ctcgacccca aaaaacttga tttgggtgat ggttcacaaa ctatcagtgt ttgacaggat  14880
atattggcgg gtaaacctaa gagaaaagag cgtttattag aataatcgga tatttaaaag  14940
ggcgtgaaaa ggtttatccg ttcgtccatt tgtatgtgca tgccaaccac agggttcccc  15000
agatctggcg ccggccagcg agacgagcaa gattggccgc cgcccgaaac gatccgacag  15060
cgcgcccagc acaggtgcgc aggcaaattg caccaacgca tacagcgcca gcagaatgcc  15120
atagtgggcg gtgacgtcgt tcgagtgaac cagatcgcgc aggaggcccg gcagcaccgg  15180
cataatcagg ccgatgccga cagcgtcgag cgcgacagtg ctcagaatta cgatcagggg  15240
tatgttgggt ttcacgtctg gcctccggac cagcctccgc tggtccgatt gaacgcgcgg  15300
attctttatc actgataagt tggtggacat attatgttta tcagtgataa agtgtcaagc  15360
atgacaaagt tgcagccgaa tacagtgatc cgtgccgccc tggacctgtt gaacgaggtc  15420
ggcgtagacg gtctgacgac acgcaaactg gcggaacggt tgggggttca gcagccggcg  15480
ctttactggc acttcaggaa caagcgggcg ctgctcgacg cactggccga agccatgctg  15540
gcggagaatc atacgcattc ggtgccgaga gccgacgacg actggcgctc atttctgatc  15600
gggaatgccc gcagcttcag gcaggcgctg ctcgcctacc gcgatggcgc gcgcatccat  15660
gccggcacgc gaccgggcgc accgcagatg gaaacggccg acgcgcagct tcgcttcctc  15720
tgcgaggcgg gtttttcggc cggggacgcc gtcaatgcgc tgatgacaat cagctacttc  15780
actgttgggg ccgtgcttga ggagcaggcc ggcgacagcg atgccggcga gcgcggcggc  15840
accgttgaac aggctccgct ctcgccgctg ttgcgggccg cgatagacgc cttcgacgaa  15900
gccggtccgg acgcagcgtt cgagcaggga ctcgcggtga ttgtcgatgg attggcgaaa  15960
aggaggctcg ttgtcaggaa cgttgaagga ccgagaaagg gtgacgattg atcaggaccg  16020
ctgccggagc gcaacccact cactacagca gagccatgta gacaacatcc cctcccccctt  16080
tccaccgcgt cagacgcccg tagcagcccg ctacgggctt tttcatgccc tgccctagcg  16140
tccaagcctc acggccgcgc tcggcctctc tggcggcctt ctggcgctct tccgcttcct  16200
cgctcactga ctcgctgcgc tcggtcgttc ggctgcggcg agcggtatca gctcactcaa  16260
```

-continued

```
aggcggtaat acggttatcc acagaatcag gggataacgc aggaaagaac atgtgagcaa  16320

aaggccagca aaaggccagg aaccgtaaaa aggccgcgtt gctggcgttt ttccataggc  16380

tccgcccccc tgacgagcat cacaaaaatc gacgctcaag tcagaggtgg cgaaacccga  16440

caggactata aagataccag gcgtttcccc ctggaagctc cctcgtgcgc tctcctgttc  16500

cgaccctgcc gcttaccgga tacctgtccg cctttctccc ttcgggaagc gtggcgcttt  16560

tccgctgcat aaccctgctt cggggtcatt atagcgattt tttcggtata tccatccttt  16620

ttcgcacgat atacaggatt ttgccaaagg gttcgtgtag actttccttg gtgtatccaa  16680

cggcgtcagc cgggcaggat aggtgaagta ggcccacccg cgagcgggtg ttccttcttc  16740

actgtccctt attcgcacct ggcggtgctc aacgggaatc ctgctctgcg aggctggccg  16800

gctaccgccg gcgtaacaga tgagggcaag cggatggctg atgaaaccaa gccaaccagg  16860

aagggcagcc cacctatcaa ggtgtactgc cttccagacg aacgaagagc gattgaggaa  16920

aaggcggcgg cggccggcat gagcctgtcg gcctacctgc tggccgtcgg ccagggctac  16980

aaaatcacgg gcgtcgtgga ctatgagcac gtccgcgagc tggcccgcat caatggcgac  17040

ctgggccgcc tgggcggcct gctgaaactc tggctcaccg acgacccgcg cacggcgcgg  17100

ttcggtgatg ccacgatcct cgccctgctg gcgaagatcg aagagaagca ggacgagctt  17160

ggcaaggtca tgatgggcgt ggtccgcccg agggcagagc catgactttt ttagccgcta  17220

aaacggccgg ggggtgcgcg tgattgccaa gcacgtcccc atgcgctcca tcaagaagag  17280

cgacttcgcg gagctggtga agtacatcac cgacgagcaa ggcaagaccg agcgcctttg  17340

cgacgctca                                                          17349
```

```
<210> SEQ ID NO 4
<211> LENGTH: 16774
<212> TYPE: DNA
<213> ORGANISM: Artificial Sequence
<220> FEATURE:
<223> OTHER INFORMATION: plasmid

<400> SEQUENCE: 4

ccgggctggt tgccctcgcc gctgggctgg cggccgtcta tggccctgca aacgcgccag     60

aaacgccgtc gaagccgtgt gcgagacacc gcggccgccg gcgttgtgga tacctcgcgg    120

aaaacttggc cctcactgac agatgagggg cggacgttga cacttgaggg gccgactcac    180

ccggcgcggc gttgacagat gaggggcagg ctcgatttcg gccggcgacg tggagctggc    240

cagcctcgca aatcggcgaa aacgcctgat tttacgcgag tttcccacag atgatgtgga    300

caagcctggg gataagtgcc ctgcggtatt gacacttgag gggcgcgact actgacagat    360

gaggggcgcg atccttgaca cttgaggggc agagtgctga cagatgaggg gcgcacctat    420

tgacatttga ggggctgtcc acaggcagaa aatccagcat ttgcaagggt ttccgcccgt    480

ttttcggcca ccgctaacct gtcttttaac ctgcttttaa accaatattt ataaaccttg    540

tttttaacca gggctgcgcc ctgtgcgcgt gaccgcgcac gccgaagggg ggtgcccccc    600

cttctcgaac cctcccggcc cgctaacgcg ggcctcccat ccccccaggg gctgcgcccc    660

tcggccgcga acggcctcac cccaaaaatg gcagcgctgg cagtccttgc cattgccggg    720

atcggggcag taacgggatg ggcgatcagc ccgagcgcga cgcccggaag cattgacgtg    780

ccgcaggtgc tggcatcgac attcagcgac caggtgccgg gcagtgaggg cggcggcctg    840

ggtggcggcc tgcccttcac ttcggccgtc ggggcattca cggacttcat ggcggggccg    900

gcaattttta ccttgggcat tcttggcata gtggtcgcgg gtgccgtgct cgtgttcggg    960
```

```
ggtgcgataa acccagcgaa ccatttgagg tgataggtaa gattataccg aggtatgaaa   1020
acgagaattg gacctttaca gaattactct atgaagcgcc atatttaaaa agctaccaag   1080
acgaagagga tgaagaggat gaggaggcag attgccttga atatattgac aatactgata   1140
agataatata tcttttatat agaagatatc gccgtatgta aggatttcag gggcaaggc   1200
ataggcagcg cgcttatcaa tatatctata gaatgggcaa agcataaaaa cttgcatgga   1260
ctaatgcttg aaacccagga caataacctt atagcttgta aattctatca taattgggta   1320
atgactccaa cttattgata gtgttttatg ttcagataat gcccgatgac tttgtcatgc   1380
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgccccagc gtcgccatag tgcgttcacc gaatacgtgc   1620
gcaacaaccg tcttccggag actgtcatac gcgtaaaaca gccagcgctg gcgcgattta   1680
gccccgacat agccccactg ttcgtccatt tccgcgcaga cgatgacgtc actgcccggc   1740
tgtatgcgcg aggttacata tgcggtgtga aataccgcac agatgcgtaa ggagaaaata   1800
ccgcatcagg cgctcttccg cttcctcgct cactgactcg ctgcgctcgg tcgttcggct   1860
gcggcgagcg gtatcagctc actcaaaggc ggtaatacgg ttatccacag aatcagggga   1920
taacgcagga aagaacatgt gagcaaaagg ccagcaaaag gccaggaacc gtaaaaaggc   1980
cgcgttgctg gcgtttttcc ataggctccg cccccctgac gagcatcaca aaaatcgacg   2040
ctcaagtcag aggtggcgaa acccgacagg actataaaga taccaggcgt ttccccctgg   2100
aagctccctc gtgcgctctc ctgttccgac cctgccgctt accggatacc tgtccgcctt   2160
tctcccttcg ggaagcgtgg cgctttctca tagctcacgc tgtaggtatc tcagttcggt   2220
gtaggtcgtt cgctccaagc tgggctgtgt gcacgaaccc cccgttcagc ccgaccgctg   2280
cgccttatcc ggtaactatc gtcttgagtc caacccggta agacacgact tatcgccact   2340
ggcagcagcc agttaccgac tgcggcctga gtttttaag tgacgtaaaa tcgtgttgag   2400
gccaacgccc ataatgcggg ctgttgcccg gcatccaacg ccattcatgg ccatatcaat   2460
gattttctgg tgcgtaccgg gttgagaagc ggtgtaagtg aactgcagtt gccatgtttt   2520
acggcagtga gagcagagat agcgctgatg tccggcggtg cttttgccgt tacgcaccac   2580
cccgtcagta gctgaacagg agggacagct gatagacaca gaagccactg gagcacctca   2640
aaaacaccat catacactaa atcagtaagt tggcagcatc acccataatt gtggtttcaa   2700
aatcggctcc gtcgatacta tgttatacgc caactttgaa aacaactttg aaaaagctgt   2760
tttctggtat ttaaggtttt agaatgcaag gaacagtgaa ttggagttcg tcttgttata   2820
attagcttct tggggtatct ttaaatactg tagaaaagag gaaggaaata ataaatggct   2880
aaaatgagaa tatcaccgga attgaaaaaa ctgatcgaaa aataccgctg cgtaaaagat   2940
acggaaggaa tgtctcctgc taaggtatat aagctggtgg gagaaaatga aaacctatat   3000
ttaaaaatga cggacagccg gtataaaggg accacctatg atgtggaacg ggaaaaggac   3060
atgatgctat ggctggaagg aaagctgcct gttccaaagg tcctgcactt tgaacggcat   3120
gatggctgga gcaatctgct catgagtgag gccgatggcg tcctttgctc ggaagagtat   3180
gaagatgaac aaagccctga aaagattatc gagctgtatg cggagtgcat caggctcttt   3240
cactccatcg acatatcgga ttgtccctat acgaatagct tagacagccg cttagccgaa   3300
```

-continued

```
ttggattact tactgaataa cgatctggcc gatgtggatt gcgaaaactg ggaagaagac   3360
actccattta aagatccgcg cgagctgtat gattttttaa agacggaaaa gcccgaagag   3420
gaacttgtct tttcccacgg cgacctggga gacagcaaca tctttgtgaa agatggcaaa   3480
gtaagtggct ttattgatct tgggagaagc ggcagggcgg acaagtggta tgacattgcc   3540
ttctgcgtcc ggtcgatcag ggaggatatc ggggaagaac agtatgtcga gctatttttt   3600
gacttactgg ggatcaagcc tgattgggag aaaataaaat attatatttt actggatgaa   3660
ttgttttagt acctagatgt ggcgcaacga tgccggcgac aagcaggagc gcaccgactt   3720
cttccgcatc aagtgttttg gctctcaggc cgaggcccac ggcaagtatt tgggcaaggg   3780
gtcgctggta ttcgtgcagg gcaagattcg gaataccaag tacgagaagg acggccagac   3840
ggtctacggg accgacttca ttgccgataa ggtggattat ctggacacca aggcaccagg   3900
cgggtcaaat caggaataag ggcacattgc cccggcgtga gtcggggcaa tcccgcaagg   3960
agggtgaatg aatcggacgt ttgaccggaa ggcatacagg caagaactga tcgacgcggg   4020
gttttccgcc gaggatgccg aaaccatcgc aagccgcacc gtcatgcgtg cgccccgcga   4080
aaccttccag tccgtcggct cgatggtcca gcaagctacg gccaagatcg agcgcgacag   4140
cgtgcaactg gctccccctg ccctgcccgc gccatcggcc gccgtggagc gttcgcgtcg   4200
tctcgaacag gaggcggcag gtttggcgaa gtcgatgacc atcgacacgc gaggaactat   4260
gacgaccaag aagcgaaaaa ccgccggcga ggacctggca aaacaggtca gcgaggccaa   4320
gcaggccgcg ttgctgaaac acacgaagca gcagatcaag gaaatgcagc tttccttgtt   4380
cgatattgcg ccgtggccgg acacgatgcg agcgatgcca aacgacacgg cccgctctgc   4440
cctgttcacc acgcgcaaca agaaaatccc gcgcgaggcg ctgcaaaaca aggtcatttt   4500
ccacgtcaac aaggacgtga agatcaccta caccggcgtc gagctgcggg ccgacgatga   4560
cgaactggtg tggcagcagg tgttggagta cgcgaagcgc acccctatcg gcgagccgat   4620
caccttcacg ttctacgagc tttgccagga cctgggctgg tcgatcaatg gccggtatta   4680
cacgaaggcc gaggaatgcc tgtcgcgcct acaggcgacg gcgatgggct tcacgtccga   4740
ccgcgttggg cacctggaat cggtgtcgct gctgcaccgc ttccgcgtcc tggaccgtgg   4800
caagaaaacg tcccgttgcc aggtcctgat cgacgaggaa atcgtcgtgc tgtttgctgg   4860
cgaccactac acgaaattca tatgggagaa gtaccgcaag ctgtcgccga cggcccgacg   4920
gatgttcgac tatttcagct cgcaccggga gccgtacccg ctcaagctgg aaaccttccg   4980
cctcatgtgc ggatcggatt ccacccgcgt gaagaagtgg cgcgagcagg tcggcgaagc   5040
ctgcgaagag ttgcgaggca gcggcctggt ggaacacgcc tgggtcaatg atgacctggt   5100
gcattgcaaa cgctagggcc ttgtggggtc agttccggct gggggttcag cagccagcgc   5160
tttactggca tttcaggaac aagcgggcac tgctcgacgc acttgcttcg ctcagtatcg   5220
ctcgggacgc acggcgcgct ctacgaactg ccgataaaca gaggattaaa attgacaatt   5280
gtgattaagg ctcagattcg acggcttgga gcggccgacg tgcaggattt ccgcgagatc   5340
cgattgtcgg ccctgaagaa agctccagag atgttcgggt ccgtttacga gcacgaggag   5400
aaaaagccca tggaggcgtt cgctgaacgg ttgcgagatg ccgtggcatt cggcgcctac   5460
atcgacggcg agatcattgg gctgtcggtc ttcaaacagg aggacggccc caaggacgct   5520
cacaaggcgc atctgtccgg cgttttcgtg gagcccgaac agcgaggccg aggggtcgcc   5580
ggtatgctgc tgcgggcgtt gccggcgggt ttattgctcg tgatgatcgt ccgacagatt   5640
ccaacgggaa tctggtggat gcgcatcttc atcctcggcg cacttaatat ttcgctattc   5700
```

tggagcttgt tgtttatttc ggtctaccgc ctgccgggcg gggtcgcggc gacggtaggc 5760
gctgtgcagc cgctgatggt cgtgttcatc tctgccgctc tgctaggtag cccgatacga 5820
ttgatggcgg tcctgggggc tatttgcgga actgcgggcg tggcgctgtt ggtgttgaca 5880
ccaaacgcag cgctagatcc tgtcggcgtc gcagcgggcc tggcgggggc ggtttccatg 5940
gcgttcggaa ccgtgctgac ccgcaagtgg caacctcccg tgcctctgct cacctttacc 6000
gcctggcaac tggcggccgg aggacttctg ctcgttccag tagctttagt gtttgatccg 6060
ccaatcccga tgcctacagg aaccaatgtt ctcggcctgg cgtggctcgg cctgatcgga 6120
gcgggtttaa cctacttcct ttggttccgg gggatctcgc gactcgaacc tacagttgtt 6180
tccttactgg gctttctcag ccccagatct ggggtcgatc agccggggat gcatcaggcc 6240
gacagtcgga acttcgggtc cccgacctgt accattcggt gagcaatgga taggggagtt 6300
gatatcgtca acgttcactt ctaaagaaat agcgccactc agcttcctca gcggctttat 6360
ccagcgattt cctattatgt cggcatagtt ctcaagatcg acagcctgtc acggttaagc 6420
gagaaatgaa taagaaggct gataattcgg atctctgcga gggagatgat atttgatcac 6480
aggcagcaac gctctgtcat cgttacaatc aacatgctac cctccgcgag atcatccgtg 6540
tttcaaaccc ggcagcttag ttgccgttct tccgaatagc atcggtaaca tgagcaaagt 6600
ctgccgcctt acaacggctc tcccgctgac gccgtcccgg actgatgggc tgcctgtatc 6660
gagtggtgat tttgtgccga gctgccggtc ggggagctgt tggctggctg gtggcaggat 6720
atattgtggt gtaaacaaat tgacgcttag acaacttaat aacacattgc ggacgttttt 6780
aatgtactgg ccggccaaag cacatactta tcgatttaaa tttcatcgaa gagattaata 6840
tcgaataatc atatacatac tttaaataca taacaaattt taaatacata tatctggtat 6900
ataattaatt ttttaaagtc atgaagtatg tatcaaatac acatatggaa aaaattaact 6960
attcataatt taaaaaatag aaaagataca tctagtgaaa ttaggtgcat gtatcaaata 7020
cattaggaaa agggcatata tcttgatcta gataattaac gattttgatt tatgtataat 7080
ttccaaatga aggtttatat ctacttcaga aataacaata tacttttatc agaacattca 7140
acaaagcaac aaccaactag agtgaaaaat acacattgtt ctctagacat acaaaattga 7200
gaaaagaatc tcaaaattta gagaaacaaa tctgaatttc tagaagaaaa aaataattat 7260
gcactttgct attgctcgaa aaataaatga aagaaattag actttttaa aagatgttag 7320
actagatata ctcaaaagct attaaaggag taatattctt cttacattaa gtattttagt 7380
tacagtcctg taattaaaga cacattttag attgtatcta aacttaaatg tatctagaat 7440
acatatattt gaatgcatca tatacatgta tccgacacac caattctcat aaaaaacgta 7500
atatcctaaa ctaatttatc cttcaagtca acttaagccc aatatacatt ttcatctcta 7560
aaggcccaag tggcacaaaa tgtcaggccc aattacgaag aaaagggctt gtaaaaccct 7620
aataaagtgg cactggcaga gcttacactc tcattccatc aacaaagaaa ccctaaaagc 7680
cgcagcgcca ctgatttctc tcctccaggc gaagatgcag atcttcgtga agaccttaac 7740
ggggaagacg atcaccctag aggttgagtc ttccgacacc atcgacaatg tcaaagccaa 7800
gatccaggac aaggaaggga ttcccccaga ccagcagcgt ttgattttcg ccggaaagca 7860
gcttgaggat ggtcgtactc ttgccgacta caacatccag aaggagtcaa ctctccatct 7920
cgtgctccgt ctccgtggtg gtagtttaaa catgattgaa caagatggat tgcacgcagg 7980
ttctccggcc gcttgggtgg agaggctatt cggctatgac tgggcacaac agacaatcgg 8040

-continued

```
ctgctctgat gccgccgtgt tccggctgtc agcgcagggg cgcccggttc tttttgtcaa   8100
gaccgacctg tccggtgccc tgaatgaact gcaggacgag gcagcgcggc tatcgtggct   8160
ggccacgacg ggcgttcctt gcgcagctgt gctcgacgtt gtcactgaag cgggaaggga   8220
ctggctgcta ttgggcgaag tgccggggca ggatctcctg tcatctcacc ttgctcctgc   8280
cgagaaagta tccatcatgg ctgatgcaat gcggcggctg catacgcttg atccggctac   8340
ctgcccattc gaccaccaag cgaaacatcg catcgagcga gcacgtactc ggatggaagc   8400
cggtcttgtc gatcaggatg atctggacga agagcatcag gggctcgcgc cagccgaact   8460
gttcgccagg ctcaaggcgc gcatgcccga cggcgaggat ctcgtcgtga cccatggcga   8520
tgcctgcttg ccgaatatca tggtggaaaa tggccgcttt tctggattca tcgactgtgg   8580
ccggctgggt gtggcggacc gctatcagga catagcgttg gctacccgtg atattgctga   8640
agagcttggc ggcgaatggg ctgaccgctt cctcgtgctt tacggtatcg ccgctcccga   8700
ttcgcagcgc atcgccttct atcgccttct tgacgagttc ttctgagttt aaacgatttt   8760
aatgtttagc aaatgtctta tcagttttct ctttttgtcg aacggtaatt tagagttttt   8820
tttgctatat ggattttcgt tttgatgta tgtgacaacc ctcgggattg ttgatttatt   8880
tcaaaactaa gagtttttgt cttattgttc tcgtctattt tggatatcaa tcttagtttt   8940
atatcttttc tagttctcta cgtgttaaat gttcaacaca ctagcaattt ggcctgccag   9000
cgtatggatt atggaactat caagtgtgtg ggatcgataa atatgcttct caggaatttg   9060
agatttttta tcatgtcttt atgctcattc ccttgagtat aatatagtaa aaaaatagta   9120
aatttaagca ataatgttag gtgctatgtg tctgtcgaga ctattggccg gccatcgatg   9180
gtttcattgg tgacgtttcc ggccttgcta atggtaatgg tgctactggt gatttttgctg   9240
gctctaattc ccaaatggct caagtcggtg acggtgataa ttcaccttta atgaataatt   9300
tccgtcaata tttaccttcc ctccctcaat cggttgaatg tcgccctttt gtctttggcc   9360
caatacgcaa accgcctctc cccgcgcgtt ggccgattca ttaatgcagc tggcacgaca   9420
ggtttcccga ctggaaagcg ggcagtgagc gcaacgcaat taatgtgagt tagctcactc   9480
attaggcacc ccaggcttta cactttatgc ttccggctcg tatgttgtgt ggaattgtga   9540
gcggataaca atttcacaca ggaaacagct atgaccatga ttacgccaag ctggcgcgcc   9600
aacaaactcc gcatagtggt tagctaattc ttgcaaagaa ctcaaataac gtttatgtat   9660
tgtaaaatgt atttatttat tacactgatt taaatactat atttatattt attatagaac   9720
aatagattga aattaatttt cgttggataa atagaaccaa agagtgaaat aatcaaaagg   9780
gccatttgtg tgtctatttt ttaaacatta ggggtctttg tctatatcta aataaattat   9840
gactaaaaac atagggactg taaacgcacg aacattttcg caccgccatg ctctctcgaa   9900
acccatgctc atagaactac ttctattaaa tgctaaagaa gagtttaatt gtgataacta   9960
aaatgcttat ttacttctaa caagcgcgta aatcagttgg catagagttg ttttaactta  10020
accaaagtcc tcagttcgag acttgggagt acagttgtgt taaatacttg ttgggagagc  10080
tttggcgcct caatgatcct gcctgtctcg aatctaaatt agtcggggct caatgtagtc  10140
tttagatacc agatagttta atacaccaaa aataaataaa atacttattt actttagtta  10200
ttatttttca aataattaac tataatcgac tattttaaag ctttacaagg atagttagat  10260
ttgatgttga atagaaacag aattaagggt ttagtaaacc aaaaacatta cacgcctctc  10320
gtactgacat aaaagaaaaa ttataataat aacagaaaaa tataagaaat aaagaaggaa  10380
aagaaagata taaaaatgaa attaactttc agctgttaag taaaactatt acaaaatttc  10440
```

gttctttgct ctcataaaaa ggaagaaagc cagtccttcc aatgcactgt gttcggtagt 10500
ggtactaatt acttaatttg ttcgtctttc ttatttacaa ctatttattt tttggaccat 10560
atttcgcacg tgcaataatt taacaataca gagcccttaa tcttacctag ttattgtacg 10620
attaaacttg gaccgttgat ccattatctt taccatgcat gacttgttta tttgatacgt 10680
tggcactgtc ggctacttga tctatatgta tcgtcagttc gcttcttatt tattttttgg 10740
accactatgc ttgtggtctt cttatttatt tcctggaccc attgattcat actttatcta 10800
cacatgcagt tgaaccatat atagccgtta atcttacaat tatcagactt cagcggtaaa 10860
tctgttatct ttaccaagca attgtttggt aatggtattt atacctttct tttttttctt 10920
tttatctgat gacatggtat ttgattactt tgttcgtctt tcttgtttac tactatttat 10980
tttgtggacc atgtttcgca catgcaatga tttaacacta acagttaatc ttacctactt 11040
attgtatgat gaaatctgaa tggttgatcc attatctata gtataccacg cactattatt 11100
tggtaattgc atttattact ttatttgctc gtgtccttcg tatttagaat tatttatttt 11160
ttgaaccatg tatcgcacat gcactaactt aaccatatag agctgttgac cttccctact 11220
tattgtacga ttaaattaga accactgatc cattatcttt accatgcaca acgtgttact 11280
ttgccacgtt ggcaccgtag tgtcggctac ttgatctata tatatcagat caaaccagaa 11340
ataagaactc gctcaagcac aactacttac cttttgagtt ttgaatacgg ttcagtcgaa 11400
gccagcagaa atcttttgcc ttcctgattt gaagattatg ggaactcctt gcgcaggttt 11460
atacataggc catgcatttt caaataaatg tcatttataa ttcttatttt aataggtgta 11520
tttgtgatta agttttataa catgaatttt tcaggttata ccggatcccc gggtggtcag 11580
tcccttatgt tacgtcctgt agaaacccca acccgtgaaa tcaaaaaact cgacggcctg 11640
tgggcattca gtctggatcg cgaaaactgt ggaattgatc agcgttggtg ggaaagcgcg 11700
ttacaagaaa gccgggcaat tgctgtgcca ggcagtttta acgatcagtt cgccgatgca 11760
gatattcgta attatgcggg caacgtctgg tatcagcgcg aagtctttat accgaaaggt 11820
tgggcaggcc agcgtatcgt gctgcgtttc gatgcggtca ctcattacgg caaagtgtgg 11880
gtcaataatc aggaagtgat ggagcatcag ggcggctata cgccatttga agccgatgtc 11940
acgccgtatg ttattgccgg gaaaagtgta cgtatcaccg tttgtgtgaa caacgaactg 12000
aactggcaga ctatcccgcc gggaatggtg attaccgacg aaaacggcaa gaaaaagcag 12060
tcttacttcc atgatttctt taactatgcc ggaatccatc gcagcgtaat gctctacacc 12120
acgccgaaca cctgggtgga cgatatcacc gtggtgacgc atgtcgcgca agactgtaac 12180
cacgcgtctg ttgactggca ggtggtggcc aatggtgatg tcagcgttga actgcgtgat 12240
gcggatcaac aggtggttgc aactggacaa ggcactagcg ggactttgca agtggtgaat 12300
ccgcacctct ggcaaccggg tgaaggttat ctctatgaac tgtgcgtcac agccaaaagc 12360
cagacagagt gtgatatcta cccgcttcgc gtcggcatcc ggtcagtggc agtgaagggc 12420
gaacagttcc tgattaacca caaaccgttc tactttactg gctttggtcg tcatgaagat 12480
gcggacttgc gtggcaaagg attcgataac gtgctgatgg tgcacgacca cgcattaatg 12540
gactggattg gggccaactc ctaccgtacc tcgcattacc cttacgctga agagatgctc 12600
gactgggcag atgaacatgg catcgtggtg attgatgaaa ctgctgctgt cggctttaac 12660
ctctctttag gcattggttt cgaagcgggc aacaagccga aagaactgta cagcgaagag 12720
gcagtcaacg gggaaactca gcaagcgcac ttacaggcga ttaaagagct gatagcgcgt 12780

-continued

```
gacaaaaacc acccaagcgt ggtgatgtgg agtattgcca acgaaccgga tacccgtccg  12840
caaggtgcac gggaatattt cgcgccactg gcggaagcaa cgcgtaaact cgacccgacg  12900
cgtccgatca cctgcgtcaa tgtaatgttc tgcgacgctc acaccgatac catcagcgat  12960
ctctttgatg tgctgtgcct gaaccgttat tacggatggt atgtccaaag cggcgatttg  13020
gaaacggcag agaaggtact ggaaaaagaa cttctggcct ggcaggagaa actgcatcag  13080
ccgattatca tcaccgaata cggcgtggat acgttagccg ggctgcactc aatgtacacc  13140
gacatgtgga gtgaagagta tcagtgtgca tggctggata tgtatcaccg cgtctttgat  13200
cgcgtcagcg ccgtcgtcgg tgaacaggta tggaatttcg ccgattttgc gacctcgcaa  13260
ggcatattgc gcgttggcgg taacaagaaa gggatcttca ctcgcgaccg caaaccgaag  13320
tcggcggctt ttctgctgca aaaacgctgg actggcatga acttcggtga aaaaccgcag  13380
cagggaggca aacaatgaat caacaactct cctggcgcac catcgtcggc tacagcctcg  13440
ggaattgcta cgagctcgtt gcctattgtt ggttgtcgtg ttgtctggct gtgtctgttg  13500
cccattgtgg tggttatgtg ttgcatcatg gtctaaaagg atcatcaatg tttttcgctt  13560
ctgttccttt ctgtttctca tttgtgaata ataatggtgt ctttatgaac atccagtttc  13620
tggtttcttt tctgattgca gtttgagtat ttgtttttgc ttttgcttcc gtctactaca  13680
ccactttgca attactgtat cactcatgca ttgttgatat actttagcct tcgatccatc  13740
ttctgtttga tgattcaaat ggtatttatt taactcatac ccaagtgaag cataaagtta  13800
gaggagagtt catgttccat tacctgtttg tttcatgagc aactcatctt aataaacata  13860
agaaaaacca taatgcaatc tgtgtagctg atagactttg atgacagacg gactcataag  13920
taacaagagg aaacatgata aacatgtacg gaagtcgagc tcgaattctt aattaacaat  13980
tcactggccg tcgttttaca acgtcgtgac tgggaaaacc ctggcgttac ccaacttaat  14040
cgccttgcag cacatccccc tttcgccagc tggcgtaata gcgaagaggc ccgcaccgat  14100
cgcccttccc aacagttgcg cagcctgaat ggcgcccgct cctttcgctt tcttcccttc  14160
ctttctcgcc acgttcgccg gctttccccg tcaagctcta aatcgggggc tccctttagg  14220
gttccgattt agtgctttac ggcacctcga ccccaaaaaa cttgatttgg gtgatggttc  14280
acaaactatc agtgtttgac aggatatatt ggcgggtaaa cctaagagaa aagagcgttt  14340
attagaataa tcggatattt aaaagggcgt gaaaaggttt atccgttcgt ccatttgtat  14400
gtgcatgcca accacagggt tccccagatc tggcgccggc cagcgagacg agcaagattg  14460
gccgccgccc gaaacgatcc gacagcgcgc ccagcacagg tgcgcaggca aattgcacca  14520
acgcatacag cgccagcaga atgccatagt gggcggtgac gtcgttcgag tgaaccagat  14580
cgcgcaggag gcccggcagc accggcataa tcaggccgat gccgacagcg tcgagcgcga  14640
cagtgctcag aattacgatc aggggtatgt tgggtttcac gtctggcctc cggaccagcc  14700
tccgctggtc cgattgaacg cgcggattct ttatcactga taagttggtg gacatattat  14760
gtttatcagt gataaagtgt caagcatgac aaagttgcag ccgaatacag tgatccgtgc  14820
cgccctggac ctgttgaacg aggtcggcgt agacggtctg acgacacgca aactggcgga  14880
acggttgggg gttcagcagc cggcgcttta ctggcacttc aggaacaagc gggcgctgct  14940
cgacgcactg gccgaagcca tgctggcgga gaatcatacg cattcggtgc cgagagccga  15000
cgacgactgg cgctcatttc tgatcgggaa tgcccgcagc ttcaggcagg cgctgctcgc  15060
ctaccgcgat ggcgcgcgca tccatgccgg cacgcgaccg ggcgcaccgc agatggaaac  15120
ggccgacgcg cagcttcgct tcctctgcga ggcgggtttt tcggccgggg acgccgtcaa  15180
```

```
tgcgctgatg acaatcagct acttcactgt tggggccgtg cttgaggagc aggccggcga  15240

cagcgatgcc ggcgagcgcg gcggcaccgt tgaacaggct ccgctctcgc cgctgttgcg  15300

ggccgcgata gacgccttcg acgaagccgg tccggacgca gcgttcgagc agggactcgc  15360

ggtgattgtc gatggattgg cgaaaaggag gctcgttgtc aggaacgttg aaggaccgag  15420

aaagggtgac gattgatcag gaccgctgcc ggagcgcaac ccactcacta cagcagagcc  15480

atgtagacaa catcccctcc ccctttccac cgcgtcagac gcccgtagca gcccgctacg  15540

ggctttttca tgccctgccc tagcgtccaa gcctcacggc cgcgctcggc ctctctggcg  15600

gccttctggc gctcttccgc ttcctcgctc actgactcgc tgcgctcggt cgttcggctg  15660

cggcgagcgg tatcagctca ctcaaaggcg gtaatacggt tatccacaga atcaggggat  15720

aacgcaggaa agaacatgtg agcaaaaggc cagcaaaagg ccaggaaccg taaaaaggcc  15780

gcgttgctgg cgtttttcca taggctccgc ccccctgacg agcatcacaa aaatcgacgc  15840

tcaagtcaga ggtggcgaaa cccgacagga ctataaagat accaggcgtt tccccctgga  15900

agctccctcg tgcgctctcc tgttccgacc ctgccgctta ccggatacct gtccgccttt  15960

ctcccttcgg gaagcgtggc gcttttccgc tgcataaccc tgcttcgggg tcattatagc  16020

gatttttttcg gtatatccat cctttttcgc acgatataca ggattttgcc aaagggttcg  16080

tgtagacttt ccttggtgta tccaacggcg tcagccgggc aggataggtg aagtaggccc  16140

acccgcgagc gggtgttcct tcttcactgt cccttattcg cacctggcgg tgctcaacgg  16200

gaatcctgct ctgcgaggct ggccggctac cgccggcgta acagatgagg gcaagcggat  16260

ggctgatgaa accaagccaa ccaggaaggg cagcccacct atcaaggtgt actgccttcc  16320

agacgaacga agagcgattg aggaaaaggc ggcggcggcc ggcatgagcc tgtcggccta  16380

cctgctggcc gtcggccagg gctacaaaat cacgggcgtc gtggactatg agcacgtccg  16440

cgagctggcc cgcatcaatg gcgacctggg ccgcctgggc ggcctgctga aactctggct  16500

caccgacgac ccgcgcacgg cgcggttcgg tgatgccacg atcctcgccc tgctggcgaa  16560

gatcgaagag aagcaggacg agcttggcaa ggtcatgatg ggcgtggtcc gcccgagggc  16620

agagccatga ctttttttagc cgctaaaacg gccgggggggt gcgcgtgatt gccaagcacg  16680

tccccatgcg ctccatcaag aagagcgact tcgcggagct ggtgaagtac atcaccgacg  16740

agcaaggcaa gaccgagcgc ctttgcgacg ctca                              16774
```

<210> SEQ ID NO 5
<211> LENGTH: 16652
<212> TYPE: DNA
<213> ORGANISM: Artificial Sequence
<220> FEATURE:
<223> OTHER INFORMATION: plasmid

<400> SEQUENCE: 5

```
ccgggctggt tgccctcgcc gctgggctgg cggccgtcta tggccctgca aacgcgccag     60

aaacgccgtc gaagccgtgt gcgagacacc gcggccgccg gcgttgtgga tacctcgcgg    120

aaaacttggc cctcactgac agatgagggg cggacgttga cacttgaggg gccgactcac    180

ccggcgcggc gttgacagat gaggggcagg ctcgatttcg gccggcgacg tggagctggc    240

cagcctcgca aatcggcgaa aacgcctgat tttacgcgag tttcccacag atgatgtgga    300

caagcctggg gataagtgcc ctgcggtatt gacacttgag ggcgcgact actgacagat    360

gaggggcgcg atccttgaca cttgaggggc agagtgctga cagatgaggg gcgcacctat    420
```

-continued

```
tgacatttga ggggctgtcc acaggcagaa aatccagcat ttgcaagggt ttccgcccgt    480
ttttcggcca ccgctaacct gtcttttaac ctgcttttaa accaatattt ataaaccttg    540
tttttaacca gggctgcgcc ctgtgcgcgt gaccgcgcac gccgaagggg ggtgcccccc    600
cttctcgaac cctcccggcc cgctaacgcg ggcctcccat ccccccaggg gctgcgcccc    660
tcggccgcga acggcctcac cccaaaaatg gcagcgctgg cagtccttgc cattgccggg    720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840
ggtggcggcc tgcccttcac ttcggccgtc ggggcattca cggacttcat ggcggggccg    900
gcaattttta ccttgggcat tcttggcata gtggtcgcgg gtgccgtgct cgtgttcggg    960
ggtgcgataa acccagcgaa ccatttgagg tgataggtaa gattataccg aggtatgaaa   1020
acgagaattg gacctttaca gaattactct atgaagcgcc atatttaaaa agctaccaag   1080
acgaagagga tgaagaggat gaggaggcag attgccttga atatattgac aatactgata   1140
agataatata tcttttatat agaagatatc gccgtatgta aggatttcag ggggcaaggc   1200
ataggcagcg cgcttatcaa tatatctata gaatgggcaa agcataaaaa cttgcatgga   1260
ctaatgcttg aaacccagga caataacctt atagcttgta aattctatca taattgggta   1320
atgactccaa cttattgata gtgttttatg ttcagataat gcccgatgac tttgtcatgc   1380
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgccccagc gtcgccatag tgcgttcacc gaatacgtgc   1620
gcaacaaccg tcttccggag actgtcatac gcgtaaaaca gccagcgctg gcgcgattta   1680
gccccgacat agccccactg ttcgtccatt tccgcgcaga cgatgacgtc actgcccggc   1740
tgtatgcgcg aggttacata tgcggtgtga aataccgcac agatgcgtaa ggagaaaata   1800
ccgcatcagg cgctcttccg cttcctcgct cactgactcg ctgcgctcgg tcgttcggct   1860
gcggcgagcg gtatcagctc actcaaaggc ggtaatacgg ttatccacag aatcagggga   1920
taacgcagga aagaacatgt gagcaaaagg ccagcaaaag gccaggaacc gtaaaaaggc   1980
cgcgttgctg gcgtttttcc ataggctccg cccccctgac gagcatcaca aaaatcgacg   2040
ctcaagtcag aggtggcgaa acccgacagg actataaaga taccaggcgt ttccccctgg   2100
aagctccctc gtgcgctctc ctgttccgac cctgccgctt accggatacc tgtccgcctt   2160
tctcccttcg ggaagcgtgg cgctttctca tagctcacgc tgtaggtatc tcagttcggt   2220
gtaggtcgtt cgctccaagc tgggctgtgt gcacgaaccc cccgttcagc ccgaccgctg   2280
cgccttatcc ggtaactatc gtcttgagtc caacccggta agacacgact tatcgccact   2340
ggcagcagcc agttaccgac tgcggcctga gtttttaag tgacgtaaaa tcgtgttgag    2400
gccaacgccc ataatgcggg ctgttgcccg gcatccaacg ccattcatgg ccatatcaat   2460
gattttctgg tgcgtaccgg gttgagaagc ggtgtaagtg aactgcagtt gccatgtttt   2520
acggcagtga gagcagagat agcgctgatg tccggcggtg cttttgccgt tacgcaccac   2580
cccgtcagta gctgaacagg agggacagct gatagacaca gaagccactg gagcacctca   2640
aaaacaccat catacactaa atcagtaagt tggcagcatc acccataatt gtggtttcaa   2700
aatcggctcc gtcgatacta tgttatacgc caactttgaa aacaactttg aaaaagctgt   2760
tttctggtat ttaaggtttt agaatgcaag gaacagtgaa ttggagttcg tcttgttata   2820
```

-continued

```
attagcttct tggggtatct ttaaatactg tagaaaagag gaaggaaata ataaatggct   2880
aaaatgagaa tatcaccgga attgaaaaaa ctgatcgaaa aataccgctg cgtaaaagat   2940
acggaaggaa tgtctcctgc taaggtatat aagctggtgg gagaaaatga aaacctatat   3000
ttaaaaatga cggacagccg gtataaaggg accacctatg atgtggaacg ggaaaaggac   3060
atgatgctat ggctggaagg aaagctgcct gttccaaagg tcctgcactt tgaacggcat   3120
gatggctgga gcaatctgct catgagtgag gccgatggcg tcctttgctc ggaagagtat   3180
gaagatgaac aaagccctga aaagattatc gagctgtatg cggagtgcat caggctcttt   3240
cactccatcg acatatcgga ttgtccctat acgaatagct tagacagccg cttagccgaa   3300
ttggattact tactgaataa cgatctggcc gatgtggatt gcgaaaactg ggaagaagac   3360
actccattta aagatccgcg cgagctgtat gattttttaa agacggaaaa gcccgaagag   3420
gaacttgtct ttcccacggg cgacctggga gacagcaaca tctttgtgaa agatggcaaa   3480
gtaagtggct ttattgatct tgggagaagc ggcagggcgg acaagtggta tgacattgcc   3540
ttctgcgtcc ggtcgatcag ggaggatatc ggggaagaac agtatgtcga gctatttttt   3600
gacttactgg ggatcaagcc tgattgggag aaaataaaat attatatttt actggatgaa   3660
ttgttttagt acctagatgt ggcgcaacga tgccggcgac aagcaggagc gcaccgactt   3720
cttccgcatc aagtgttttg gctctcaggc cgaggcccac ggcaagtatt tgggcaaggg   3780
gtcgctggta ttcgtgcagg gcaagattcg gaataccaag tacgagaagg acggccagac   3840
ggtctacggg accgacttca ttgccgataa ggtggattat ctggacacca aggcaccagg   3900
cgggtcaaat caggaataag ggcacattgc cccggcgtga gtcggggcaa tcccgcaagg   3960
agggtgaatg aatcggacgt ttgaccggaa ggcatacagg caagaactga tcgacgcggg   4020
gttttccgcc gaggatgccg aaaccatcgc aagccgcacc gtcatgcgtg cgccccgcga   4080
aaccttccag tccgtcggct cgatggtcca gcaagctacg gccaagatcg agcgcgacag   4140
cgtgcaactg gctccccctg ccctgcccgc gccatcggcc gccgtggagc gttcgcgtcg   4200
tctcgaacag gaggcggcag gtttggcgaa gtcgatgacc atcgacacgc gaggaactat   4260
gacgaccaag aagcgaaaaa ccgccggcga ggacctggca aaacaggtca gcgaggccaa   4320
gcaggccgcg ttgctgaaac acacgaagca gcagatcaag gaaatgcagc tttccttgtt   4380
cgatattgcg ccgtggccgg acacgatgcg agcgatgcca aacgacacgg cccgctctgc   4440
cctgttcacc acgcgcaaca agaaaatccc gcgcgaggcg ctgcaaaaca aggtcatttt   4500
ccacgtcaac aaggacgtga agatcaccta caccggcgtc gagctgcggg ccgacgatga   4560
cgaactggtg tggcagcagg tgttggagta cgcgaagcgc acccctatcg gcgagccgat   4620
caccttcacg ttctacgagc tttgccagga cctgggctgg tcgatcaatg gccggtatta   4680
cacgaaggcc gaggaatgcc tgtcgcgcct acaggcgacg gcgatgggct tcacgtccga   4740
ccgcgttggg cacctggaat cggtgtcgct gctgcaccgc ttccgcgtcc tggaccgtgg   4800
caagaaaacg tcccgttgcc aggtcctgat cgacgaggaa atcgtcgtgc tgtttgctgg   4860
cgaccactac acgaaattca tatgggagaa gtaccgcaag ctgtcgccga cggcccgacg   4920
gatgttcgac tatttcagct cgcaccggga gccgtacccg ctcaagctgg aaaccttccg   4980
cctcatgtgc ggatcggatt ccacccgcgt gaagaagtgg cgcgagcagg tcggcgaagc   5040
ctgcgaagag ttgcgaggca gcggcctggt ggaacacgcc tgggtcaatg atgacctggt   5100
gcattgcaaa cgctagggcc ttgtggggtc agttccggct gggggttcag cagccagcgc   5160
```

-continued

```
tttactggca tttcaggaac aagcgggcac tgctcgacgc acttgcttcg ctcagtatcg   5220
ctcgggacgc acggcgcgct ctacgaactg ccgataaaca gaggattaaa attgacaatt   5280
gtgattaagg ctcagattcg acggcttgga gcggccgacg tgcaggattt ccgcgagatc   5340
cgattgtcgg ccctgaagaa agctccagag atgttcgggt ccgtttacga gcacgaggag   5400
aaaaagccca tggaggcgtt cgctgaacgg ttgcgagatg ccgtggcatt cggcgcctac   5460
atcgacggcg agatcattgg gctgtcggtc ttcaaacagg aggacggccc caaggacgct   5520
cacaaggcgc atctgtccgg cgttttcgtg gagcccgaac agcgaggccg aggggtcgcc   5580
ggtatgctgc tgcgggcgtt gccggcgggt ttattgctcg tgatgatcgt ccgacagatt   5640
ccaacgggaa tctggtggat gcgcatcttc atcctcggcg cacttaatat ttcgctattc   5700
tggagcttgt tgtttatttc ggtctaccgc ctgccgggcg gggtcgcggc gacggtaggc   5760
gctgtgcagc cgctgatggt cgtgttcatc tctgccgctc tgctaggtag cccgatacga   5820
ttgatggcgg tcctgggggc tatttgcgga actgcgggcg tggcgctgtt ggtgttgaca   5880
ccaaacgcag cgctagatcc tgtcggcgtc gcagcgggcc tggcgggggc ggtttccatg   5940
gcgttcggaa ccgtgctgac ccgcaagtgg caacctcccg tgcctctgct cacctttacc   6000
gcctggcaac tggcggccgg aggacttctg ctcgttccag tagctttagt gtttgatccg   6060
ccaatcccga tgcctacagg aaccaatgtt ctcggcctgg cgtggctcgg cctgatcgga   6120
gcgggtttaa cctacttcct ttggttccgg gggatctcgc gactcgaacc tacagttgtt   6180
tccttactgg gctttctcag ccccagatct ggggtcgatc agccggggat gcatcaggcc   6240
gacagtcgga acttcgggtc cccgacctgt accattcggt gagcaatgga taggggagtt   6300
gatatcgtca acgttcactt ctaaagaaat agcgccactc agcttcctca gcggctttat   6360
ccagcgattt cctattatgt cggcatagtt ctcaagatcg acagcctgtc acggttaagc   6420
gagaaatgaa taagaaggct gataattcgg atctctgcga gggagatgat atttgatcac   6480
aggcagcaac gctctgtcat cgttacaatc aacatgctac cctccgcgag atcatccgtg   6540
tttcaaaccc ggcagcttag ttgccgttct tccgaatagc atcggtaaca tgagcaaagt   6600
ctgccgcctt acaacggctc tcccgctgac gccgtcccgg actgatgggc tgcctgtatc   6660
gagtggtgat tttgtgccga gctgccggtc ggggagctgt tggctggctg gtggcaggat   6720
atattgtggt gtaaacaaat tgacgcttag acaacttaat aacacattgc ggacgttttt   6780
aatgtactgg ccggccaaag cacatactta tcgatttaaa tttcatcgaa gagattaata   6840
tcgaataatc atatacatac tttaaataca taacaaattt taaatacata tatctggtat   6900
ataattaatt ttttaaagtc atgaagtatg tatcaaatac acatatggaa aaaattaact   6960
attcataatt taaaaaatag aaaagataca tctagtgaaa ttaggtgcat gtatcaaata   7020
cattaggaaa agggcatata tcttgatcta gataattaac gattttgatt tatgtataat   7080
ttccaaatga aggtttatat ctacttcaga aataacaata tacttttatc agaacattca   7140
acaaagcaac aaccaactag agtgaaaaat acacattgtt ctctagacat acaaaattga   7200
gaaaagaatc tcaaaattta gagaaacaaa tctgaatttc tagaagaaaa aaataattat   7260
gcactttgct attgctcgaa aaataaatga aagaaattag actttttaa aagatgttag   7320
actagatata ctcaaaagct attaaaggag taatattctt cttacattaa gtattttagt   7380
tacagtcctg taattaaaga cacattttag attgtatcta aacttaaatg tatctagaat   7440
acatatattt gaatgcatca tatacatgta tccgacacac caattctcat aaaaaacgta   7500
atatcctaaa ctaatttatc cttcaagtca acttaagccc aatatacatt ttcatctcta   7560
```

-continued

```
aaggcccaag tggcacaaaa tgtcaggccc aattacgaag aaaagggctt gtaaaaccct   7620
aataaagtgg cactggcaga gcttacactc tcattccatc aacaaagaaa ccctaaaagc   7680
cgcagcgcca ctgatttctc tcctccaggc gaagatgcag atcttcgtga agaccttaac   7740
ggggaagacg atcaccctag aggttgagtc ttccgacacc atcgacaatg tcaaagccaa   7800
gatccaggac aaggaaggga ttcccccaga ccagcagcgt ttgattttcg ccggaaagca   7860
gcttgaggat ggtcgtactc ttgccgacta caacatccag aaggagtcaa ctctccatct   7920
cgtgctccgt ctccgtggtg gtagtttaaa catgattgaa caagatggat tgcacgcagg   7980
ttctccggcc gcttgggtgg agaggctatt cggctatgac tgggcacaac agacaatcgg   8040
ctgctctgat gccgccgtgt tccggctgtc agcgcagggg cgcccggttc tttttgtcaa   8100
gaccgacctg tccggtgccc tgaatgaact gcaggacgag gcagcgcggc tatcgtggct   8160
ggccacgacg ggcgttcctt gcgcagctgt gctcgacgtt gtcactgaag cgggaaggga   8220
ctggctgcta ttgggcgaag tgccggggca ggatctcctg tcatctcacc ttgctcctgc   8280
cgagaaagta tccatcatgg ctgatgcaat gcggcggctg catacgcttg atccggctac   8340
ctgcccattc gaccaccaag cgaaacatcg catcgagcga gcacgtactc ggatggaagc   8400
cggtcttgtc gatcaggatg atctggacga agagcatcag gggctcgcgc cagccgaact   8460
gttcgccagg ctcaaggcgc gcatgcccga cggcgaggat ctcgtcgtga cccatggcga   8520
tgcctgcttg ccgaatatca tggtggaaaa tggccgcttt tctggattca tcgactgtgg   8580
ccggctgggt gtggcggacc gctatcagga catagcgttg gctacccgtg atattgctga   8640
agagcttggc ggcgaatggg ctgaccgctt cctcgtgctt tacggtatcg ccgctcccga   8700
ttcgcagcgc atcgccttct atcgccttct tgacgagttc ttctgagttt aaacgatttt   8760
aatgtttagc aaatgtctta tcagttttct ctttttgtcg aacggtaatt tagagttttt   8820
tttgctatat ggattttcgt ttttgatgta tgtgacaacc ctcgggattg ttgatttatt   8880
tcaaaactaa gagtttttgt cttattgttc tcgtctattt tggatatcaa tcttagtttt   8940
atatcttttc tagttctcta cgtgttaaat gttcaacaca ctagcaattt ggcctgccag   9000
cgtatggatt atggaactat caagtgtgtg ggatcgataa atatgcttct caggaatttg   9060
agatttttta tcatgtcttt atgctcattc ccttgagtat aatatagtaa aaaaatagta   9120
aatttaagca ataatgttag gtgctatgtg tctgtcgaga ctattggccg gccatcgatg   9180
gtttcattgg tgacgtttcc ggccttgcta atggtaatgg tgctactggt gattttgctg   9240
gctctaattc ccaaatggct caagtcggtg acggtgataa ttcaccttta atgaataatt   9300
tccgtcaata tttaccttcc ctccctcaat cggttgaatg tcgccctttt gtctttggcc   9360
caatacgcaa accgcctctc cccgcgcgtt ggccgattca ttaatgcagc tggcacgaca   9420
ggtttcccga ctggaaagcg ggcagtgagc gcaacgcaat taatgtgagt tagctcactc   9480
attaggcacc ccaggcttta cactttatgc ttccggctcg tatgttgtgt ggaattgtga   9540
gcggataaca atttcacaca ggaaacagct atgaccatga ttacgccaag ctggcgcgcc   9600
aacaaactcc gcatagtggt tagctaattc ttgcaaagaa ctcaaataac gtttatgtat   9660
tgtaaaatgt atttatttat tacactgatt taaatactat atttatattt attatagaac   9720
aatagattga aattaatttt cgttggataa atagaaccaa agagtgaaat aatcaaaagg   9780
gccatttgtg tgtctatttt ttaaacatta ggggtctttg tctatatcta aataaattat   9840
gactaaaaac atagggactg taaacgcacg aacattttcg caccgccatg ctctctcgaa   9900
```

-continued

```
acccatgctc atagaactac ttctattaaa tgctaaagaa gagtttaatt gtgataacta   9960
aaatgcttat ttacttctaa caagcgcgta aatcagttgg catagagttg ttttaactta  10020
accaaagtcc tcagttcgag acttgggagt acagttgtgt taaatacttg ttgggagagc  10080
tttggcgcct caatgatcct gcctgtctcg aatctaaatt agtcggggct caatgtagtc  10140
tttagatacc agatagttta atacaccaaa aataaataaa atacttattt actttagtta  10200
ttatttttca aataattaac tataatcgac tattttaaag ctttacaagg atagttagat  10260
ttgatgttga atagaaacag aattaagggt ttagtaaacc aaaaacatta cacgcctctc  10320
gtactgacat aaaagaaaaa ttataataat aacagaaaaa tataagaaat aaagaaggaa  10380
aagaaagata taaaaatgaa attaactttc agctgttaag taaaactatt acaaaatttc  10440
gttctttgct ctcataaaaa ggaagaaagc cagtccttcc aatgcactgt gttcggtagt  10500
ggtactaatt acttaatttg ttcgtctttc ttatttacaa ctatttattt tttggaccat  10560
atttcgcacg tgcaataatt taacaataca gagcccttaa tcttacctag ttattgtacg  10620
attaaacttg gaccgttgat ccattatctt taccatgcat gacttgttta tttgatacgt  10680
tggcactgtc ggctacttga tctatatgta tcgtcagttc gcttcttatt tattttttgg  10740
accactatgc ttgtggtctt cttatttatt tcctggaccc attgattcat actttatcta  10800
cacatgcagt tgaaccatat atagccgtta atcttacaat tatcagactt cagcggtaaa  10860
tctgttatct ttaccaagca attgtttggt aatggtattt ataccttct tttttttctt  10920
tttatctgat gacatggtat ttgattactt tgttcgtctt tcttgtttac tactatttat  10980
tttgtggacc atgtttcgca catgcaatga tttaacacta acagttaatc ttacctactt  11040
attgtatgat gaaatctgaa tggttgatcc attatctata gtataccacg cactattatt  11100
tggtaattgc atttattact ttatttgctc gtgtccttcg tatttagaat tatttatttt  11160
ttgaaccatg tatcgcacat gcactaactt aaccatatag agctgttgac cttccctact  11220
tattgtacga ttaaattaga accactgatc cattatcttt accatgcaca acgtgttact  11280
ttgccacgtt ggcaccgtag tgtcggctac ttgatctata tatatcagat caaaccagaa  11340
ataagaactc gctcaagcac aactacttac cttttgagtt ttgaatacgg ttcagtcgaa  11400
gccagcagaa atcttttgcc ttcctgattt gaagattatg ggatccccgg gtggtcagtc  11460
ccttatgtta cgtcctgtag aaaccccaac ccgtgaaatc aaaaaactcg acggcctgtg  11520
ggcattcagt ctggatcgcg aaaactgtgg aattgatcag cgttggtggg aaagcgcgtt  11580
acaagaaagc cgggcaattg ctgtgccagg cagttttaac gatcagttcg ccgatgcaga  11640
tattcgtaat tatgcgggca acgtctggta tcagcgcgaa gtctttatac cgaaaggttg  11700
ggcaggccag cgtatcgtgc tgcgtttcga tgcggtcact cattacggca aagtgtgggt  11760
caataatcag gaagtgatgg agcatcaggg cggctatacg ccatttgaag ccgatgtcac  11820
gccgtatgtt attgccggga aaagtgtacg tatcaccgtt tgtgtgaaca acgaactgaa  11880
ctggcagact atcccgccgg gaatggtgat taccgacgaa aacggcaaga aaaagcagtc  11940
ttacttccat gatttcttta actatgccgg aatccatcgc agcgtaatgc tctacaccac  12000
gccgaacacc tgggtggacg atatcaccgt ggtgacgcat gtcgcgcaag actgtaacca  12060
cgcgtctgtt gactggcagg tggtggccaa tggtgatgtc agcgttgaac tgcgtgatgc  12120
ggatcaacag gtggttgcaa ctggacaagg cactagcggg actttgcaag tggtgaatcc  12180
gcacctctgg caaccgggtg aaggttatct ctatgaactg tgcgtcacag ccaaaagcca  12240
gacagagtgt gatatctacc cgcttcgcgt cggcatccgg tcagtggcag tgaagggcga  12300
```

-continued

```
acagttcctg attaaccaca aaccgttcta ctttactggc tttggtcgtc atgaagatgc  12360
ggacttgcgt ggcaaaggat tcgataacgt gctgatggtg cacgaccacg cattaatgga  12420
ctggattggg gccaactcct accgtacctc gcattaccct tacgctgaag agatgctcga  12480
ctgggcagat gaacatggca tcgtggtgat tgatgaaact gctgctgtcg gctttaacct  12540
ctctttaggc attggtttcg aagcgggcaa caagccgaaa gaactgtaca gcgaagaggc  12600
agtcaacggg gaaactcagc aagcgcactt acaggcgatt aaagagctga tagcgcgtga  12660
caaaaaccac ccaagcgtgg tgatgtggag tattgccaac gaaccggata cccgtccgca  12720
aggtgcacgg gaatatttcg cgccactggc ggaagcaacg cgtaaactcg acccgacgcg  12780
tccgatcacc tgcgtcaatg taatgttctg cgacgctcac accgatacca tcagcgatct  12840
ctttgatgtg ctgtgcctga accgttatta cggatggtat gtccaaagcg gcgatttgga  12900
aacggcagag aaggtactgg aaaaagaact tctggcctgg caggagaaac tgcatcagcc  12960
gattatcatc accgaatacg gcgtggatac gttagccggg ctgcactcaa tgtacaccga  13020
catgtggagt gaagagtatc agtgtgcatg gctggatatg tatcaccgcg tctttgatcg  13080
cgtcagcgcc gtcgtcggtg aacaggtatg gaatttcgcc gattttgcga cctcgcaagg  13140
catattgcgc gttggcggta acaagaaagg gatcttcact cgcgaccgca aaccgaagtc  13200
ggcggctttt ctgctgcaaa aacgctggac tggcatgaac ttcggtgaaa aaccgcagca  13260
gggaggcaaa caatgaatca acaactctcc tggcgcacca tcgtcggcta cagcctcggg  13320
aattgctacg agctcgttgc ctattgttgg ttgtcgtgtt gtctggctgt gtctgttgcc  13380
cattgtggtg gttatgtgtt gcatcatggt ctaaaaggat catcaatgtt tttcgcttct  13440
gttcctttct gtttctcatt tgtgaataat aatggtgtct ttatgaacat ccagtttctg  13500
gtttcttttc tgattgcagt ttgagtattt gtttttgctt ttgcttccgt ctactacacc  13560
actttgcaat tactgtatca ctcatgcatt gttgatatac tttagccttc gatccatctt  13620
ctgtttgatg attcaaatgg tatttattta actcataccc aagtgaagca taaagttaga  13680
ggagagttca tgttccatta cctgtttgtt tcatgagcaa ctcatcttaa taaacataag  13740
aaaaaccata atgcaatctg tgtagctgat agactttgat gacagacgga ctcataagta  13800
acaagaggaa acatgataaa catgtacgga agtcgagctc gaattcttaa ttaacaattc  13860
actggccgtc gttttacaac gtcgtgactg ggaaaaccct ggcgttaccc aacttaatcg  13920
ccttgcagca catcccccttt tcgccagctg gcgtaatagc gaagaggccc gcaccgatcg  13980
cccttcccaa cagttgcgca gcctgaatgg cgcccgctcc tttcgctttc ttcccttcct  14040
ttctcgccac gttcgccggc tttccccgtc aagctctaaa tcgggggctc cctttagggt  14100
tccgatttag tgctttacgg cacctcgacc ccaaaaaact tgatttgggt gatggttcac  14160
aaactatcag tgtttgacag gatatattgg cgggtaaacc taagagaaaa gagcgtttat  14220
tagaataatc ggatatttaa aagggcgtga aaaggtttat ccgttcgtcc atttgtatgt  14280
gcatgccaac cacagggttc cccagatctg gcgccggcca gcgagacgag caagattggc  14340
cgccgcccga aacgatccga cagcgcgccc agcacaggtg cgcaggcaaa ttgcaccaac  14400
gcatacagcg ccagcagaat gccatagtgg gcggtgacgt cgttcgagtg aaccagatcg  14460
cgcaggaggc ccggcagcac cggcataatc aggccgatgc cgacagcgtc gagcgcgaca  14520
gtgctcagaa ttacgatcag ggtatgttg ggtttcacgt ctggcctccg gaccagcctc  14580
cgctggtccg attgaacgcg cggattcttt atcactgata agttggtgga catattatgt  14640
```

-continued ttatcagtga taaagtgtca agcatgacaa agttgcagcc gaatacagtg atccgtgccg 14700
ccctggacct gttgaacgag gtcggcgtag acggtctgac gacacgcaaa ctggcggaac 14760
ggttgggggt tcagcagccg gcgctttact ggcacttcag gaacaagcgg gcgctgctcg 14820
acgcactggc cgaagccatg ctggcggaga atcatacgca ttcggtgccg agagccgacg 14880
acgactggcg ctcatttctg atcgggaatg cccgcagctt caggcaggcg ctgctcgcct 14940
accgcgatgg cgcgcgcatc catgccggca cgcgaccggg cgcaccgcag atggaaacgg 15000
ccgacgcgca gcttcgcttc ctctgcgagg cgggtttttc ggccggggac gccgtcaatg 15060
cgctgatgac aatcagctac ttcactgttg gggccgtgct tgaggagcag gccggcgaca 15120
gcgatgccgg cgagcgcggc ggcaccgttg aacaggctcc gctctcgccg ctgttgcggg 15180
ccgcgataga cgccttcgac gaagccggtc cggacgcagc gttcgagcag ggactcgcgg 15240
tgattgtcga tggattggcg aaaaggaggc tcgttgtcag gaacgttgaa ggaccgagaa 15300
agggtgacga ttgatcagga ccgctgccgg agcgcaaccc actcactaca gcagagccat 15360
gtagacaaca tcccctcccc ctttccaccg cgtcagacgc ccgtagcagc ccgctacggg 15420
ctttttcatg ccctgcccta gcgtccaagc ctcacggccg cgctcggcct ctctggcggc 15480
cttctggcgc tcttccgctt cctcgctcac tgactcgctg cgctcggtcg ttcggctgcg 15540
gcgagcggta tcagctcact caaaggcggt aatacggtta tccacagaat caggggataa 15600
cgcaggaaag aacatgtgag caaaaggcca gcaaaaggcc aggaaccgta aaaaggccgc 15660
gttgctggcg tttttccata ggctccgccc ccctgacgag catcacaaaa atcgacgctc 15720
aagtcagagg tggcgaaacc cgacaggact ataaagatac caggcgtttc cccctggaag 15780
ctccctcgtg cgctctcctg ttccgaccct gccgcttacc ggatacctgt ccgcctttct 15840
cccttcggga agcgtggcgc ttttccgctg cataaccctg cttcggggtc attatagcga 15900
ttttttcggt atatccatcc tttttcgcac gatatacagg attttgccaa agggttcgtg 15960
tagactttcc ttggtgtatc caacggcgtc agccgggcag gataggtgaa gtaggcccac 16020
ccgcgagcgg gtgttccttc ttcactgtcc cttattcgca cctggcggtg ctcaacggga 16080
atcctgctct gcgaggctgg ccggctaccg ccggcgtaac agatgagggc aagcggatgg 16140
ctgatgaaac caagccaacc aggaagggca gcccacctat caaggtgtac tgccttccag 16200
acgaacgaag agcgattgag gaaaaggcgg cggcggccgg catgagcctg tcggcctacc 16260
tgctggccgt cggccagggc tacaaaatca cgggcgtcgt ggactatgag cacgtccgcg 16320
agctggcccg catcaatggc gacctgggcc gcctgggcgg cctgctgaaa ctctggctca 16380
ccgacgaccc gcgcacggcg cggttcggtg atgccacgat cctcgccctg ctggcgaaga 16440
tcgaagagaa gcaggacgag cttggcaagg tcatgatggg cgtggtccgc ccgagggcag 16500
agccatgact tttttagccg ctaaaacggc cggggggtgc gcgtgattgc caagcacgtc 16560
cccatgcgct ccatcaagaa gagcgacttc gcggagctgg tgaagtacat caccgacgag 16620
caaggcaaga ccgagcgcct ttgcgacgct ca 16652

<210> SEQ ID NO 6
<211> LENGTH: 16653
<212> TYPE: DNA
<213> ORGANISM: Artificial Sequence
<220> FEATURE:
<223> OTHER INFORMATION: plasmid

<400> SEQUENCE: 6
ccgggctggt tgccctcgcc gctgggctgg cggccgtcta tggccctgca aacgcgccag 60

```
aaacgccgtc gaagccgtgt gcgagacacc gcggccgccg gcgttgtgga tacctcgcgg    120
aaaacttggc cctcactgac agatgagggg cggacgttga cacttgaggg gccgactcac    180
ccggcgcggc gttgacagat gaggggcagg ctcgatttcg gccggcgacg tggagctggc    240
cagcctcgca aatcggcgaa aacgcctgat tttacgcgag tttcccacag atgatgtgga    300
caagcctggg gataagtgcc ctgcggtatt gacacttgag ggcgcgact actgacagat    360
gaggggcgcg atccttgaca cttgaggggc agagtgctga cagatgaggg gcgcacctat    420
tgacatttga ggggctgtcc acaggcagaa aatccagcat ttgcaagggt ttccgcccgt    480
ttttcggcca ccgctaacct gtcttttaac ctgcttttaa accaatattt ataaaccttg    540
tttttaacca gggctgcgcc ctgtgcgcgt gaccgcgcac gccgaagggg ggtgcccccc    600
cttctcgaac cctcccggcc cgctaacgcg ggcctcccat ccccccaggg gctgcgcccc    660
tcggccgcga acggcctcac cccaaaaatg gcagcgctgg cagtccttgc cattgccggg    720
atcggggcag taacgggatg ggcgatcagc ccgagcgcga cgcccggaag cattgacgtg    780
ccgcaggtgc tggcatcgac attcagcgac caggtgccgg gcagtgaggg cggcggcctg    840
ggtggcggcc tgcccttcac ttcggccgtc ggggcattca cggacttcat ggcggggccg    900
gcaattttta ccttgggcat tcttggcata gtggtcgcgg gtgccgtgct cgtgttcggg    960
ggtgcgataa acccagcgaa ccatttgagg tgataggtaa gattataccg aggtatgaaa   1020
acgagaattg gacctttaca gaattactct atgaagcgcc atatttaaaa agctaccaag   1080
acgaagagga tgaagaggat gaggaggcag attgccttga atatattgac aatactgata   1140
agataatata tcttttatat agaagatatc gccgtatgta aggatttcag ggggcaaggc   1200
ataggcagcg cgcttatcaa tatatctata gaatgggcaa agcataaaaa cttgcatgga   1260
ctaatgcttg aaacccagga caataacctt atagcttgta aattctatca taattgggta   1320
atgactccaa cttattgata gtgttttatg ttcagataat gcccgatgac tttgtcatgc   1380
agctccaccg attttgagaa cgacagcgac ttccgtccca gccgtgccag gtgctgcctc   1440
agattcaggt tatgccgctc aattcgctgc gtatatcgct tgctgattac gtgcagcttt   1500
cccttcaggc gggattcata cagcggccag ccatccgtca tccatatcac cacgtcaaag   1560
ggtgacagca ggctcataag acgccccagc gtcgccatag tgcgttcacc gaatacgtgc   1620
gcaacaaccg tcttccggag actgtcatac gcgtaaaaca gccagcgctg gcgcgattta   1680
gccccgacat agccccactg ttcgtccatt tccgcgcaga cgatgacgtc actgcccggc   1740
tgtatgcgcg aggttacata tgcggtgtga aataccgcac agatgcgtaa ggagaaaata   1800
ccgcatcagg cgctcttccg cttcctcgct cactgactcg ctgcgctcgg tcgttcggct   1860
gcggcgagcg gtatcagctc actcaaaggc ggtaatacgg ttatccacag aatcagggga   1920
taacgcagga aagaacatgt gagcaaaagg ccagcaaaag gccaggaacc gtaaaaaggc   1980
cgcgttgctg gcgtttttcc ataggctccg cccccctgac gagcatcaca aaaatcgacg   2040
ctcaagtcag aggtggcgaa acccgacagg actataaaga taccaggcgt ttccccctgg   2100
aagctccctc gtgcgctctc ctgttccgac cctgccgctt accggatacc tgtccgcctt   2160
tctcccttcg ggaagcgtgg cgctttctca tagctcacgc tgtaggtatc tcagttcggt   2220
gtaggtcgtt cgctccaagc tgggctgtgt gcacgaaccc cccgttcagc ccgaccgctg   2280
cgccttatcc ggtaactatc gtcttgagtc caacccggta agacacgact tatcgccact   2340
ggcagcagcc agttaccgac tgcggcctga gttttttaag tgacgtaaaa tcgtgttgag   2400
```

-continued

```
gccaacgccc ataatgcggg ctgttgcccg gcatccaacg ccattcatgg ccatatcaat   2460
gattttctgg tgcgtaccgg gttgagaagc ggtgtaagtg aactgcagtt gccatgtttt   2520
acggcagtga gagcagagat agcgctgatg tccggcggtg cttttgccgt tacgcaccac   2580
cccgtcagta gctgaacagg agggacagct gatagacaca gaagccactg gagcacctca   2640
aaaacaccat catacactaa atcagtaagt tggcagcatc acccataatt gtggtttcaa   2700
aatcggctcc gtcgatacta tgttatacgc caactttgaa aacaactttg aaaaagctgt   2760
tttctggtat ttaaggtttt agaatgcaag gaacagtgaa ttggagttcg tcttgttata   2820
attagcttct tggggtatct ttaaatactg tagaaaagag gaaggaaata ataaatggct   2880
aaaatgagaa tatcaccgga attgaaaaaa ctgatcgaaa aataccgctg cgtaaaagat   2940
acggaaggaa tgtctcctgc taaggtatat aagctggtgg gagaaaatga aaacctatat   3000
ttaaaaatga cggacagccg gtataaaggg accacctatg atgtggaacg ggaaaaggac   3060
atgatgctat ggctggaagg aaagctgcct gttccaaagg tcctgcactt tgaacggcat   3120
gatggctgga gcaatctgct catgagtgag gccgatggcg tcctttgctc ggaagagtat   3180
gaagatgaac aaagccctga aaagattatc gagctgtatg cggagtgcat caggctcttt   3240
cactccatcg acatatcgga ttgtccctat acgaatagct tagacagccg cttagccgaa   3300
ttggattact tactgaataa cgatctggcc gatgtggatt gcgaaaactg ggaagaagac   3360
actccattta aagatccgcg cgagctgtat gatttttttaa agacggaaaa gcccgaagag   3420
gaacttgtct tttcccacgg cgacctggga gacagcaaca tctttgtgaa agatggcaaa   3480
gtaagtggct ttattgatct tgggagaagc ggcagggcgg acaagtggta tgacattgcc   3540
ttctgcgtcc ggtcgatcag ggaggatatc ggggaagaac agtatgtcga gctatttttt   3600
gacttactgg ggatcaagcc tgattgggag aaaataaaat attatatttt actggatgaa   3660
ttgttttagt acctagatgt ggcgcaacga tgccggcgac aagcaggagc gcaccgactt   3720
cttccgcatc aagtgttttg gctctcaggc cgaggcccac ggcaagtatt tgggcaaggg   3780
gtcgctggta ttcgtgcagg gcaagattcg gaataccaag tacgagaagg acggccagac   3840
ggtctacggg accgacttca ttgccgataa ggtggattat ctggacacca aggcaccagg   3900
cgggtcaaat caggaataag ggcacattgc cccggcgtga gtcggggcaa tcccgcaagg   3960
agggtgaatg aatcggacgt ttgaccggaa ggcatacagg caagaactga tcgacgcggg   4020
gttttccgcc gaggatgccg aaaccatcgc aagccgcacc gtcatgcgtg cgccccgcga   4080
aaccttccag tccgtcggct cgatggtcca gcaagctacg gccaagatcg agcgcgacag   4140
cgtgcaactg gctccccctg ccctgcccgc gccatcggcc gccgtggagc gttcgcgtcg   4200
tctcgaacag gaggcggcag gtttggcgaa gtcgatgacc atcgacacgc gaggaactat   4260
gacgaccaag aagcgaaaaa ccgccggcga ggacctggca aaacaggtca gcgaggccaa   4320
gcaggccgcg ttgctgaaac acacgaagca gcagatcaag gaaatgcagc tttccttgtt   4380
cgatattgcg ccgtggccgg acacgatgcg agcgatgcca aacgacacgg cccgctctgc   4440
cctgttcacc acgcgcaaca agaaaatccc gcgcgaggcg ctgcaaaaca aggtcatttt   4500
ccacgtcaac aaggacgtga agatcaccta caccggcgtc gagctgcggg ccgacgatga   4560
cgaactggtg tggcagcagg tgttggagta cgcgaagcgc acccctatcg gcgagccgat   4620
caccttcacg ttctacgagc tttgccagga cctgggctgg tcgatcaatg gccggtatta   4680
cacgaaggcc gaggaatgcc tgtcgcgcct acaggcgacg gcgatgggct tcacgtccga   4740
ccgcgttggg cacctggaat cggtgtcgct gctgcaccgc ttccgcgtcc tggaccgtgg   4800
```

-continued

```
caagaaaacg tcccgttgcc aggtcctgat cgacgaggaa atcgtcgtgc tgtttgctgg   4860
cgaccactac acgaaattca tatgggagaa gtaccgcaag ctgtcgccga cggcccgacg   4920
gatgttcgac tatttcagct cgcaccggga gccgtacccg ctcaagctgg aaaccttccg   4980
cctcatgtgc ggatcggatt ccacccgcgt gaagaagtgg cgcgagcagg tcggcgaagc   5040
ctgcgaagag ttgcgaggca gcggcctggt ggaacacgcc tgggtcaatg atgacctggt   5100
gcattgcaaa cgctagggcc ttgtggggtc agttccggct gggggttcag cagccagcgc   5160
tttactggca tttcaggaac aagcgggcac tgctcgacgc acttgcttcg ctcagtatcg   5220
ctcgggacgc acggcgcgct ctacgaactg ccgataaaca gaggattaaa attgacaatt   5280
gtgattaagg ctcagattcg acggcttgga gcggccgacg tgcaggattt ccgcgagatc   5340
cgattgtcgg ccctgaagaa agctccagag atgttcgggt ccgtttacga gcacgaggag   5400
aaaaagccca tggaggcgtt cgctgaacgg ttgcgagatg ccgtggcatt cggcgcctac   5460
atcgacggcg agatcattgg gctgtcggtc ttcaaacagg aggacggccc caaggacgct   5520
cacaaggcgc atctgtccgg cgttttcgtg gagcccgaac agcgaggccg aggggtcgcc   5580
ggtatgctgc tgcgggcgtt gccggcgggt ttattgctcg tgatgatcgt ccgacagatt   5640
ccaacgggaa tctggtggat gcgcatcttc atcctcggcg cacttaatat ttcgctattc   5700
tggagcttgt tgtttatttc ggtctaccgc ctgccgggcg gggtcgcggc gacggtaggc   5760
gctgtgcagc cgctgatggt cgtgttcatc tctgccgctc tgctaggtag cccgatacga   5820
ttgatggcgg tcctgggggc tatttgcgga actgcgggcg tggcgctgtt ggtgttgaca   5880
ccaaacgcag cgctagatcc tgtcggcgtc gcagcgggcc tggcgggggc ggtttccatg   5940
gcgttcggaa ccgtgctgac ccgcaagtgg caacctcccg tgcctctgct cacctttacc   6000
gcctggcaac tggcggccgg aggacttctg ctcgttccag tagctttagt gtttgatccg   6060
ccaatcccga tgcctacagg aaccaatgtt ctcggcctgg cgtggctcgg cctgatcgga   6120
gcgggtttaa cctacttcct ttggttccgg gggatctcgc gactcgaacc tacagttgtt   6180
tccttactgg gctttctcag ccccagatct ggggtcgatc agccggggat gcatcaggcc   6240
gacagtcgga acttcgggtc cccgacctgt accattcggt gagcaatgga taggggagtt   6300
gatatcgtca acgttcactt ctaaagaaat agcgccactc agcttcctca gcggctttat   6360
ccagcgattt cctattatgt cggcatagtt ctcaagatcg acagcctgtc acggttaagc   6420
gagaaatgaa taagaaggct gataattcgg atctctgcga gggagatgat atttgatcac   6480
aggcagcaac gctctgtcat cgttacaatc aacatgctac cctccgcgag atcatccgtg   6540
tttcaaaccc ggcagcttag ttgccgttct tccgaatagc atcggtaaca tgagcaaagt   6600
ctgccgcctt acaacggctc tcccgctgac gccgtcccgg actgatgggc tgcctgtatc   6660
gagtggtgat tttgtgccga gctgccggtc ggggagctgt tggctggctg gtggcaggat   6720
atattgtggt gtaaacaaat tgacgcttag acaacttaat aacacattgc ggacgttttt   6780
aatgtactgg ccggccaaag cacatactta tcgatttaaa tttcatcgaa gagattaata   6840
tcgaataatc atatacatac tttaaataca taacaaattt taaatacata tatctggtat   6900
ataattaatt ttttaaagtc atgaagtatg tatcaaatac acatatggaa aaaattaact   6960
attcataatt taaaaaatag aaaagataca tctagtgaaa ttaggtgcat gtatcaaata   7020
cattaggaaa agggcatata tcttgatcta gataattaac gattttgatt tatgtataat   7080
ttccaaatga aggtttatat ctacttcaga aataacaata tacttttatc agaacattca   7140
```

-continued

```
acaaagcaac aaccaactag agtgaaaaat acacattgtt ctctagacat acaaaattga   7200
gaaaagaatc tcaaaattta gagaaacaaa tctgaatttc tagaagaaaa aaataattat   7260
gcactttgct attgctcgaa aaataaatga aagaaattag actttttttaa aagatgttag   7320
actagatata ctcaaaagct attaaaggag taatattctt cttacattaa gtattttagt   7380
tacagtcctg taattaaaga cacattttag attgtatcta aacttaaatg tatctagaat   7440
acatatattt gaatgcatca tatacatgta tccgacacac caattctcat aaaaaacgta   7500
atatcctaaa ctaatttatc cttcaagtca acttaagccc aatatacatt ttcatctcta   7560
aaggcccaag tggcacaaaa tgtcaggccc aattacgaag aaaagggctt gtaaaaccct   7620
aataaagtgg cactggcaga gcttacactc tcattccatc aacaaagaaa ccctaaaagc   7680
cgcagcgcca ctgatttctc tcctccaggc gaagatgcag atcttcgtga agaccttaac   7740
ggggaagacg atcaccctag aggttgagtc ttccgacacc atcgacaatg tcaaagccaa   7800
gatccaggac aaggaaggga ttcccccaga ccagcagcgt ttgattttcg ccggaaagca   7860
gcttgaggat ggtcgtactc ttgccgacta caacatccag aaggagtcaa ctctccatct   7920
cgtgctccgt ctccgtggtg gtagtttaaa catgattgaa caagatggat tgcacgcagg   7980
ttctccggcc gcttgggtgg agaggctatt cggctatgac tgggcacaac agacaatcgg   8040
ctgctctgat gccgccgtgt tccggctgtc agcgcagggg cgcccggttc tttttgtcaa   8100
gaccgacctg tccggtgccc tgaatgaact gcaggacgag gcagcgcggc tatcgtggct   8160
ggccacgacg ggcgttcctt gcgcagctgt gctcgacgtt gtcactgaag cgggaaggga   8220
ctggctgcta ttgggcgaag tgccggggca ggatctcctg tcatctcacc ttgctcctgc   8280
cgagaaagta tccatcatgg ctgatgcaat gcggcggctg catacgcttg atccggctac   8340
ctgcccattc gaccaccaag cgaaacatcg catcgagcga gcacgtactc ggatggaagc   8400
cggtcttgtc gatcaggatg atctggacga agagcatcag gggctcgcgc cagccgaact   8460
gttcgccagg ctcaaggcgc gcatgcccga cggcgaggat ctcgtcgtga cccatggcga   8520
tgcctgcttg ccgaatatca tggtggaaaa tggccgcttt tctggattca tcgactgtgg   8580
ccggctgggt gtggcggacc gctatcagga catagcgttg gctacccgtg atattgctga   8640
agagcttggc ggcgaatggg ctgaccgctt cctcgtgctt tacggtatcg ccgctcccga   8700
ttcgcagcgc atcgccttct atcgccttct tgacgagttc ttctgagttt aaacgatttt   8760
aatgtttagc aaatgtctta tcagttttct ctttttgtcg aacggtaatt tagagttttt   8820
tttgctatat ggattttcgt ttttgatgta tgtgacaacc ctcgggattg ttgatttatt   8880
tcaaaactaa gagtttttgt cttattgttc tcgtctattt tggatatcaa tcttagtttt   8940
atatcttttc tagttctcta cgtgttaaat gttcaacaca ctagcaattt ggcctgccag   9000
cgtatggatt atggaactat caagtgtgtg ggatcgataa atatgcttct caggaatttg   9060
agatttttta tcatgtcttt atgctcattc ccttgagtat aatatagtaa aaaaatagta   9120
aatttaagca ataatgttag gtgctatgtg tctgtcgaga ctattggccg gccatcgatg   9180
gtttcattgg tgacgtttcc ggccttgcta atggtaatgg tgctactggt gattttgctg   9240
gctctaattc ccaaatggct caagtcggtg acggtgataa ttcaccttta atgaataatt   9300
tccgtcaata tttaccttcc ctccctcaat cggttgaatg tcgccctttt gtctttggcc   9360
caatacgcaa accgcctctc cccgcgcgtt ggccgattca ttaatgcagc tggcacgaca   9420
ggtttcccga ctggaaagcg ggcagtgagc gcaacgcaat taatgtgagt tagctcactc   9480
attaggcacc ccaggcttta cactttatgc ttccggctcg tatgttgtgt ggaattgtga   9540
```

-continued

```
gcggataaca atttcacaca ggaaacagct atgaccatga ttacgccaag ctggcgcgcc   9600
aacaaactcc gcatagtggt tagctaattc ttgcaaagaa ctcaaataac gtttatgtat   9660
tgtaaaatgt atttatttat tacactgatt taaatactat atttatattt attatagaac   9720
aatagattga aattaatttt cgttggataa atagaaccaa agagtgaaat aatcaaaagg   9780
gccatttgtg tgtctatttt ttaaacatta ggggtctttg tctatatcta aataaattat   9840
gactaaaaac atagggactg taaacgcacg aacattttcg caccgccatg ctctctcgaa   9900
acccatgctc atagaactac ttctattaaa tgctaaagaa gagtttaatt gtgataacta   9960
aaatgcttat ttacttctaa caagcgcgta aatcagttgg catagagttg ttttaactta  10020
accaaagtcc tcagttcgag acttgggagt acagttgtgt taaatacttg ttgggagagc  10080
tttggcgcct caatgatcct gcctgtctcg aatctaaatt agtcggggct caatgtagtc  10140
tttagatacc agatagttta atacaccaaa aataaataaa atacttattt actttagtta  10200
ttatttttca aataattaac tataatcgac tattttaaag ctttacaagg atagttagat  10260
ttgatgttga atagaaacag aattaagggt ttagtaaacc aaaaacatta cacgcctctc  10320
gtactgacat aaaagaaaaa ttataataat aacagaaaaa tataagaaat aaagaaggaa  10380
aagaaagata taaaaatgaa attaactttc agctgttaag taaaactatt acaaaatttc  10440
gttctttgct ctcataaaaa ggaagaaagc cagtccttcc aatgcactgt gttcggtagt  10500
ggtactaatt acttaatttg ttcgtctttc ttatttacaa ctatttattt tttggaccat  10560
atttcgcacg tgcaataatt taacaataca gagcccttaa tcttacctag ttattgtacg  10620
attaaacttg gaccgttgat ccattatctt taccatgcat gacttgttta tttgatacgt  10680
tggcactgtc ggctacttga tctatatgta tcgtcagttc gcttcttatt tattttttgg  10740
accactatgc ttgtggtctt cttatttatt tcctggaccc attgattcat actttatcta  10800
cacatgcagt tgaaccatat atagccgtta atcttacaat tatcagactt cagcggtaaa  10860
tctgttatct ttaccaagca attgtttggt aatggtattt atacctttct tttttttctt  10920
tttatctgat gacatggtat ttgattactt tgttcgtctt tcttgtttac tactatttat  10980
tttgtggacc atgtttcgca catgcaatga tttaacacta acagttaatc ttacctactt  11040
attgtatgat gaaatctgaa tggttgatcc attatctata gtataccacg cactattatt  11100
tggtaattgc atttattact ttatttgctc gtgtccttcg tatttagaat tatttatttt  11160
ttgaaccatg tatcgcacat gcactaactt aaccatatag agctgttgac cttccctact  11220
tattgtacga ttaaattaga accactgatc cattatcttt accatgcaca acgtgttact  11280
ttgccacgtt ggcaccgtag tgtcggctac ttgatctata tatatcagat caaaccagaa  11340
ataagaactc gctcaagcac aactacttac cttttgagtt ttgaatacgg ttcagtcgaa  11400
gccagcagaa atcttttgcc ttcctgattt gaagatggat ccccgggtgg tcagtccctt  11460
atgttacgtc ctgtagaaac cccaacccgt gaaatcaaaa aactcgacgg cctgtgggca  11520
ttcagtctgg atcgcgaaaa ctgtggaatt gatcagcgtt ggtgggaaag cgcgttacaa  11580
gaaagccggg caattgctgt gccaggcagt tttaacgatc agttcgccga tgcagatatt  11640
cgtaattatg cgggcaacgt ctggtatcag cgcgaagtct ttataccgaa aggttgggca  11700
ggccagcgta tcgtgctgcg tttcgatgcg gtcactcatt acggcaaagt gtgggtcaat  11760
aatcaggaag tgatggagca tcagggcggc tatacgccat ttgaagccga tgtcacgccg  11820
tatgttattg ccgggaaaag tgtacgtatc accgtttgtg tgaacaacga actgaactgg  11880
```

-continued

```
cagactatcc cgccgggaat ggtgattacc gacgaaaacg gcaagaaaaa gcagtcttac  11940
ttccatgatt tctttaacta tgccggaatc catcgcagcg taatgctcta caccacgccg  12000
aacacctggg tggacgatat caccgtggtg acgcatgtcg cgcaagactg taaccacgcg  12060
tctgttgact ggcaggtggt ggccaatggt gatgtcagcg ttgaactgcg tgatgcggat  12120
caacaggtgg ttgcaactgg acaaggcact agcgggactt tgcaagtggt gaatccgcac  12180
ctctggcaac cgggtgaagg ttatctctat gaactgtgcg tcacagccaa aagccagaca  12240
gagtgtgata tctacccgct tcgcgtcggc atccggtcag tggcagtgaa gggcgaacag  12300
ttcctgatta accacaaacc gttctacttt actggctttg gtcgtcatga agatgcggac  12360
ttgcgtggca aaggattcga taacgtgctg atggtgcacg accacgcatt aatggactgg  12420
attggggcca actcctaccg tacctcgcat tacccttacg ctgaagagat gctcgactgg  12480
gcagatgaac atggcatcgt ggtgattgat gaaactgctg ctgtcggctt taacctctct  12540
ttaggcattg gtttcgaagc gggcaacaag ccgaaagaac tgtacagcga agaggcagtc  12600
aacggggaaa ctcagcaagc gcacttacag gcgattaaag agctgatagc gcgtgacaaa  12660
aaccacccaa gcgtggtgat gtggagtatt gccaacgaac cggatacccg tccgcaaggt  12720
gcacgggaat atttcgcgcc actggcggaa gcaacgcgta aactcgaccc gacgcgtccg  12780
atcacctgcg tcaatgtaat gttctgcgac gctcacaccg ataccatcag cgatctcttt  12840
gatgtgctgt gcctgaaccg ttattacgga tggtatgtcc aaagcggcga tttggaaacg  12900
gcagagaagg tactggaaaa agaacttctg gcctggcagg agaaactgca tcagccgatt  12960
atcatcaccg aatacggcgt ggatacgtta gccgggctgc actcaatgta caccgacatg  13020
tggagtgaag agtatcagtg tgcatggctg gatatgtatc accgcgtctt tgatcgcgtc  13080
agcgccgtcg tcggtgaaca ggtatggaat ttcgccgatt ttgcgacctc gcaaggcata  13140
ttgcgcgttg gcggtaacaa gaaagggatc ttcactcgcg accgcaaacc gaagtcggcg  13200
gcttttctgc tgcaaaaacg ctggactggc atgaacttcg gtgaaaaacc gcagcaggga  13260
ggcaaacaat gaatcaacaa ctctcctggc gcaccatcgt cggctacagc ctcgggaatt  13320
gctacgagct cgttgcctat tgttggttgt cgtgttgtct ggctgtgtct gttgcccatt  13380
gtggtggtta tgtgttgcat catggtctaa aaggatcatc aatgtttttc gcttctgttc  13440
ctttctgttt ctcatttgtg aataataatg gtgtctttat gaacatccag tttctggttt  13500
cttttctgat tgcagtttga gtatttgttt ttgcttttgc ttccgtctac tacaccactt  13560
tgcaattact gtatcactca tgcattgttg atatacttta gccttcgatc catcttctgt  13620
ttgatgattc aaatggtatt tatttaactc atacccaagt gaagcataaa gttagaggag  13680
agttcatgtt ccattacctg tttgtttcat gagcaactca tcttaataaa cataagaaaa  13740
accataatgc aatctgtgta gctgatagac tttgatgaca gacggactca taagtaacaa  13800
gaggaaacat gataaacatg tacggaagtc gagctcgaat tcttaattaa caattcactg  13860
gccgtcgttt tacaacgtcg tgactgggaa aaccctggcg ttacccaact taatcgcctt  13920
gcagcacatc ccccctttcgc cagctggcgt aatagcgaag aggcccgcac cgatcgccct  13980
tcccaacagt tgcgcagcct gaatggcgcc cgctcctttc gctttcttcc cttcctttct  14040
cgccacgttc gccggctttc cccgtcaagc tctaaatcgg gggctccctt tagggttccg  14100
atttagtgct ttacggcacc tcgaccccaa aaaacttgat ttgggtgatg gttcacaaac  14160
tatcagtgtt tgacaggata tattggcggg taaacctaag agaaaagagc gtttattaga  14220
ataatcggat atttaaaagg gcgtgaaaag gtttatccgt tcgtccattt gtatgtgcat  14280
```

```
gccaaccaca gggttcccca gatctggcgc cggccagcga gacgagcaag attggccgcc  14340
gcccgaaacg atccgacagc gcgcccagca caggtgcgca ggcaaattgc accaacgcat  14400
acagcgccag cagaatgcca tagtgggcgg tgacgtcgtt cgagtgaacc agatcgcgca  14460
ggaggcccgg cagcaccggc ataatcaggc cgatgccgac agcgtcgagc gcgacagtgc  14520
tcagaattac gatcaggggt atgttgggtt tcacgtctgg cctccggacc agcctccgct  14580
ggtccgattg aacgcgcgga ttctttatca ctgataagtt ggtggacata ttatgtttat  14640
cagtgataaa gtgtcaagca tgacaaagtt gcagccgaat acagtgatcc gtgccgccct  14700
ggacctgttg aacgaggtcg gcgtagacgg tctgacgaca cgcaaactgg cggaacggtt  14760
gggggttcag cagccggcgc tttactggca cttcaggaac aagcgggcgc tgctcgacgc  14820
actggccgaa gccatgctgg cggagaatca tacgcattcg gtgccgagag ccgacgacga  14880
ctggcgctca tttctgatcg ggaatgcccg cagcttcagg caggcgctgc tcgcctaccg  14940
cgatggcgcg cgcatccatg ccggcacgcg accgggcgca ccgcagatgg aaacggccga  15000
cgcgcagctt cgcttcctct gcgaggcggg tttttcggcc ggggacgccg tcaatgcgct  15060
gatgacaatc agctacttca ctgttggggc cgtgcttgag gagcaggccg gcgacagcga  15120
tgccggcgag cgcggcggca ccgttgaaca ggctccgctc tcgccgctgt tgcgggccgc  15180
gatagacgcc ttcgacgaag ccggtccgga cgcagcgttc gagcagggac tcgcggtgat  15240
tgtcgatgga ttggcgaaaa ggaggctcgt tgtcaggaac gttgaaggac cgagaaaggg  15300
tgacgattga tcaggaccgc tgccggagcg caacccactc actacagcag agccatgtag  15360
acaacatccc ctcccccttt ccaccgcgtc agacgcccgt agcagcccgc tacgggcttt  15420
ttcatgccct gccctagcgt ccaagcctca cggccgcgct cggcctctct ggcggccttc  15480
tggcgctctt ccgcttcctc gctcactgac tcgctgcgct cggtcgttcg gctgcggcga  15540
gcggtatcag ctcactcaaa ggcggtaata cggttatcca cagaatcagg ggataacgca  15600
ggaaagaaca tgtgagcaaa aggccagcaa aaggccagga accgtaaaaa ggccgcgttg  15660
ctggcgtttt tccataggct ccgcccccct gacgagcatc acaaaaatcg acgctcaagt  15720
cagaggtggc gaaacccgac aggactataa agataccagg cgtttccccc tggaagctcc  15780
ctcgtgcgct ctcctgttcc gaccctgccg cttaccggat acctgtccgc ctttctccct  15840
tcgggaagcg tggcgctttt ccgctgcata accctgcttc ggggtcatta tagcgatttt  15900
ttcggtatat ccatcctttt tcgcacgata tacaggattt tgccaaaggg ttcgtgtaga  15960
ctttccttgg tgtatccaac ggcgtcagcc gggcaggata ggtgaagtag gcccacccgc  16020
gagcgggtgt tccttcttca ctgtccctta ttcgcacctg gcggtgctca acgggaatcc  16080
tgctctgcga ggctggccgg ctaccgccgg cgtaacagat gagggcaagc ggatggctga  16140
tgaaaccaag ccaaccagga agggcagccc acctatcaag gtgtactgcc ttccagacga  16200
acgaagagcg attgaggaaa aggcggcggc ggccggcatg agcctgtcgg cctacctgct  16260
ggccgtcggc cagggctaca aaatcacggg cgtcgtggac tatgagcacg tccgcgagct  16320
ggcccgcatc aatggcgacc tgggccgcct gggcggcctg ctgaaactct ggctcaccga  16380
cgacccgcgc acggcgcggt tcggtgatgc cacgatcctc gccctgctgg cgaagatcga  16440
agagaagcag gacgagcttg gcaaggtcat gatgggcgtg gtccgcccga gggcagagcc  16500
atgacttttt tagccgctaa aacggccggg gggtgcgcgt gattgccaag cacgtcccca  16560
tgcgctccat caagaagagc gacttcgcgg agctggtgaa gtacatcacc gacgagcaag  16620
```

gcaagaccga gcgcctttgc gacgctcagc tca 16653

<210> SEQ ID NO 7
<211> LENGTH: 17225
<212> TYPE: DNA
<213> ORGANISM: Artificial Sequence
<220> FEATURE:
<223> OTHER INFORMATION: plasmid

<400> SEQUENCE: 7
ccgggctggt tgccctcgcc gctgggctgg cggccgtcta tggccctgca aacgcgccag 60
aaacgccgtc gaagccgtgt gcgagacacc gcggccgccg gcgttgtgga tacctcgcgg 120
aaaacttggc cctcactgac agatgagggg cggacgttga cacttgaggg gccgactcac 180
ccggcgcggc gttgacagat gaggggcagg ctcgatttcg gccggcgacg tggagctggc 240
cagcctcgca aatcggcgaa aacgcctgat tttacgcgag tttcccacag atgatgtgga 300
caagcctggg gataagtgcc ctgcggtatt gacacttgag ggcgcgact actgacagat 360 gaggggcgcg atccttgaca cttgaggggc agagtgctga cagatgaggg gcgcacctat 420
tgacatttga ggggctgtcc acaggcagaa aatccagcat ttgcaagggt ttccgcccgt 480
ttttcggcca ccgctaacct gtcttttaac ctgcttttaa accaatattt ataaaccttg 540
tttttaacca gggctgcgcc ctgtgcgcgt gaccgcgcac gccgaagggg ggtgcccccc 600
cttctcgaac cctcccggcc cgctaacgcg ggcctcccat ccccccaggg gctgcgcccc 660
tcggccgcga acggcctcac cccaaaaatg gcagcgctgg cagtccttgc cattgccggg 720
atcggggcag taacgggatg ggcgatcagc ccgagcgcga cgcccggaag cattgacgtg 780
ccgcaggtgc tggcatcgac attcagcgac caggtgccgg gcagtgaggg cggcggcctg 840
ggtggcggcc tgcccttcac ttcggccgtc ggggcattca cggacttcat ggcggggccg 900
gcaattttta ccttgggcat tcttggcata gtggtcgcgg gtgccgtgct cgtgttcggg 960
ggtgcgataa acccagcgaa ccatttgagg tgataggtaa gattataccg aggtatgaaa 1020
acgagaattg gacctttaca gaattactct atgaagcgcc atatttaaaa agctaccaag 1080
acgaagagga tgaagaggat gaggaggcag attgccttga atatattgac aatactgata 1140
agataatata tcttttatat agaagatatc gccgtatgta aggatttcag ggggcaaggc 1200
ataggcagcg cgcttatcaa tatatctata gaatgggcaa agcataaaaa cttgcatgga 1260
ctaatgcttg aaacccagga caataacctt atagcttgta aattctatca taattgggta 1320
atgactccaa cttattgata gtgttttatg ttcagataat gcccgatgac tttgtcatgc 1380
agctccaccg attttgagaa cgacagcgac ttccgtccca gccgtgccag gtgctgcctc 1440
agattcaggt tatgccgctc aattcgctgc gtatatcgct tgctgattac gtgcagcttt 1500
cccttcaggc gggattcata cagcggccag ccatccgtca tccatatcac cacgtcaaag 1560
ggtgacagca ggctcataag acgccccagc gtcgccatag tgcgttcacc gaatacgtgc 1620
gcaacaaccg tcttccggag actgtcatac gcgtaaaaca gccagcgctg gcgcgattta 1680
gccccgacat agccccactg ttcgtccatt tccgcgcaga cgatgacgtc actgcccggc 1740
tgtatgcgcg aggttacata tgcggtgtga aataccgcac agatgcgtaa ggagaaaata 1800
ccgcatcagg cgctcttccg cttcctcgct cactgactcg ctgcgctcgg tcgttcggct 1860
gcggcgagcg gtatcagctc actcaaaggc ggtaatacgg ttatccacag aatcagggga 1920
taacgcagga aagaacatgt gagcaaaagg ccagcaaaag gccaggaacc gtaaaaaggc 1980
cgcgttgctg gcgtttttcc ataggctccg cccccctgac gagcatcaca aaaatcgacg 2040

```
ctcaagtcag aggtggcgaa acccgacagg actataaaga taccaggcgt ttccccctgg   2100
aagctccctc gtgcgctctc ctgttccgac cctgccgctt accggatacc tgtccgcctt   2160
tctcccttcg ggaagcgtgg cgctttctca tagctcacgc tgtaggtatc tcagttcggt   2220
gtaggtcgtt cgctccaagc tgggctgtgt gcacgaaccc cccgttcagc ccgaccgctg   2280
cgccttatcc ggtaactatc gtcttgagtc caacccggta agacacgact tatcgccact   2340
ggcagcagcc agttaccgac tgcggcctga gtttttaag tgacgtaaaa tcgtgttgag   2400
gccaacgccc ataatgcggg ctgttgcccg gcatccaacg ccattcatgg ccatatcaat   2460
gattttctgg tgcgtaccgg gttgagaagc ggtgtaagtg aactgcagtt gccatgtttt   2520
acggcagtga gagcagagat agcgctgatg tccggcggtg cttttgccgt tacgcaccac   2580
cccgtcagta gctgaacagg agggacagct gatagacaca gaagccactg gagcacctca   2640
aaaacaccat catacactaa atcagtaagt tggcagcatc acccataatt gtggtttcaa   2700
aatcggctcc gtcgatacta tgttatacgc caactttgaa aacaactttg aaaaagctgt   2760
tttctggtat ttaaggtttt agaatgcaag gaacagtgaa ttggagttcg tcttgttata   2820
attagcttct tggggtatct ttaaatactg tagaaaagag gaaggaaata ataaatggct   2880
aaaatgagaa tatcaccgga attgaaaaaa ctgatcgaaa aataccgctg cgtaaaagat   2940
acggaaggaa tgtctcctgc taaggtatat aagctggtgg gagaaaatga aaacctatat   3000
ttaaaaatga cggacagccg gtataaaggg accacctatg atgtggaacg ggaaaaggac   3060
atgatgctat ggctggaagg aaagctgcct gttccaaagg tcctgcactt tgaacggcat   3120
gatggctgga gcaatctgct catgagtgag gccgatggcg tcctttgctc ggaagagtat   3180
gaagatgaac aaagccctga aaagattatc gagctgtatg cggagtgcat caggctcttt   3240
cactccatcg acatatcgga ttgtccctat acgaatagct tagacagccg cttagccgaa   3300
ttggattact tactgaataa cgatctggcc gatgtggatt gcgaaaactg ggaagaagac   3360
actccattta aagatccgcg cgagctgtat gatttttaa agacggaaaa gcccgaagag   3420
gaacttgtct tttcccacgg cgacctggga gacagcaaca tctttgtgaa agatggcaaa   3480
gtaagtggct ttattgatct tgggagaagc ggcagggcgg acaagtggta tgacattgcc   3540
ttctgcgtcc ggtcgatcag ggaggatatc ggggaagaac agtatgtcga gctattttt   3600
gacttactgg ggatcaagcc tgattgggag aaaataaaat attatatttt actggatgaa   3660
ttgttttagt acctagatgt ggcgcaacga tgccggcgac aagcaggagc gcaccgactt   3720
cttccgcatc aagtgtttg gctctcaggc cgaggcccac ggcaagtatt tgggcaaggg   3780
gtcgctggta ttcgtgcagg gcaagattcg gaataccaag tacgagaagg acggccagac   3840
ggtctacggg accgacttca ttgccgataa ggtggattat ctggacacca aggcaccagg   3900
cgggtcaaat caggaataag ggcacattgc cccggcgtga gtcggggcaa tcccgcaagg   3960
agggtgaatg aatcggacgt ttgaccggaa ggcatacagg caagaactga tcgacgcggg   4020
gttttccgcc gaggatgccg aaaccatcgc aagccgcacc gtcatgcgtg cgccccgcga   4080
aaccttccag tccgtcggct cgatggtcca gcaagctacg gccaagatcg agcgcgacag   4140
cgtgcaactg gctccccctg ccctgcccgc gccatcggcc gccgtggagc gttcgcgtcg   4200
tctcgaacag gaggcggcag gtttggcgaa gtcgatgacc atcgacacgc gaggaactat   4260
gacgaccaag aagcgaaaaa ccgccggcga ggacctggca aaacaggtca gcgaggccaa   4320
gcaggccgcg ttgctgaaac acacgaagca gcagatcaag gaaatgcagc tttccttgtt   4380
```

-continued

```
cgatattgcg ccgtggccgg acacgatgcg agcgatgcca aacgacacgg cccgctctgc   4440
cctgttcacc acgcgcaaca agaaaatccc gcgcgaggcg ctgcaaaaca aggtcatttt   4500
ccacgtcaac aaggacgtga agatcaccta caccggcgtc gagctgcggg ccgacgatga   4560
cgaactggtg tggcagcagg tgttggagta cgcgaagcgc acccctatcg gcgagccgat   4620
caccttcacg ttctacgagc tttgccagga cctgggctgg tcgatcaatg gccggtatta   4680
cacgaaggcc gaggaatgcc tgtcgcgcct acaggcgacg gcgatgggct tcacgtccga   4740
ccgcgttggg cacctggaat cggtgtcgct gctgcaccgc ttccgcgtcc tggaccgtgg   4800
caagaaaacg tcccgttgcc aggtcctgat cgacgaggaa atcgtcgtgc tgtttgctgg   4860
cgaccactac acgaaattca tatgggagaa gtaccgcaag ctgtcgccga cggcccgacg   4920
gatgttcgac tatttcagct cgcaccggga gccgtacccg ctcaagctgg aaaccttccg   4980
cctcatgtgc ggatcggatt ccacccgcgt gaagaagtgg cgcgagcagg tcggcgaagc   5040
ctgcgaagag ttgcgaggca gcggcctggt ggaacacgcc tgggtcaatg atgacctggt   5100
gcattgcaaa cgctagggcc ttgtggggtc agttccggct gggggttcag cagccagcgc   5160
tttactggca tttcaggaac aagcgggcac tgctcgacgc acttgcttcg ctcagtatcg   5220
ctcgggacgc acggcgcgct ctacgaactg ccgataaaca gaggattaaa attgacaatt   5280
gtgattaagg ctcagattcg acggcttgga gcggccgacg tgcaggattt ccgcgagatc   5340
cgattgtcgg ccctgaagaa agctccagag atgttcgggt ccgtttacga gcacgaggag   5400
aaaaagccca tggaggcgtt cgctgaacgg ttgcgagatg ccgtggcatt cggcgcctac   5460
atcgacggcg agatcattgg gctgtcggtc ttcaaacagg aggacggccc caaggacgct   5520
cacaaggcgc atctgtccgg cgttttcgtg gagcccgaac agcgaggccg aggggtcgcc   5580
ggtatgctgc tgcgggcgtt gccggcgggt ttattgctcg tgatgatcgt ccgacagatt   5640
ccaacgggaa tctggtggat gcgcatcttc atcctcggcg cacttaatat ttcgctattc   5700
tggagcttgt tgtttatttc ggtctaccgc ctgccgggcg gggtcgcggc gacggtaggc   5760
gctgtgcagc cgctgatggt cgtgttcatc tctgccgctc tgctaggtag cccgatacga   5820
ttgatggcgg tcctgggggc tatttgcgga actgcgggcg tggcgctgtt ggtgttgaca   5880
ccaaacgcag cgctagatcc tgtcggcgtc gcagcgggcc tggcgggggc ggtttccatg   5940
gcgttcggaa ccgtgctgac ccgcaagtgg caacctcccg tgcctctgct cacctttacc   6000
gcctggcaac tggcggccgg aggacttctg ctcgttccag tagctttagt gtttgatccg   6060
ccaatcccga tgcctacagg aaccaatgtt ctcggcctgg cgtggctcgg cctgatcgga   6120
gcgggtttaa cctacttcct ttggttccgg gggatctcgc gactcgaacc tacagttgtt   6180
tccttactgg gctttctcag ccccagatct ggggtcgatc agccggggat gcatcaggcc   6240
gacagtcgga acttcgggtc cccgacctgt accattcggt gagcaatgga taggggagtt   6300
gatatcgtca acgttcactt ctaaagaaat agcgccactc agcttcctca gcggctttat   6360
ccagcgattt cctattatgt cggcatagtt ctcaagatcg acagcctgtc acggttaagc   6420
gagaaatgaa taagaaggct gataattcgg atctctgcga gggagatgat atttgatcac   6480
aggcagcaac gctctgtcat cgttacaatc aacatgctac cctccgcgag atcatccgtg   6540
tttcaaaccc ggcagcttag ttgccgttct tccgaatagc atcggtaaca tgagcaaagt   6600
ctgccgcctt acaacggctc tcccgctgac gccgtcccgg actgatgggc tgcctgtatc   6660
gagtggtgat tttgtgccga gctgccggtc ggggagctgt tggctggctg gtggcaggat   6720
atattgtggt gtaaacaaat tgacgcttag acaacttaat aacacattgc ggacgttttt   6780
```

```
aatgtactgg ccggccaaag cacatactta tcgatttaaa tttcatcgaa gagattaata   6840
tcgaataatc atatacatac tttaaataca taacaaattt taaatacata tatctggtat   6900
ataattaatt ttttaaagtc atgaagtatg tatcaaatac acatatggaa aaaattaact   6960
attcataatt taaaaaatag aaaagataca tctagtgaaa ttaggtgcat gtatcaaata   7020
cattaggaaa agggcatata tcttgatcta gataattaac gattttgatt tatgtataat   7080
ttccaaatga aggtttatat ctacttcaga aataacaata tacttttatc agaacattca   7140
acaaagcaac aaccaactag agtgaaaaat acacattgtt ctctagacat acaaaattga   7200
gaaaagaatc tcaaaattta gagaaacaaa tctgaatttc tagaagaaaa aaataattat   7260
gcactttgct attgctcgaa aaataaatga aagaaattag actttttttaa aagatgttag   7320
actagatata ctcaaaagct attaaaggag taatattctt cttacattaa gtattttagt   7380
tacagtcctg taattaaaga cacattttag attgtatcta aacttaaatg tatctagaat   7440
acatatattt gaatgcatca tatacatgta tccgacacac caattctcat aaaaaacgta   7500
atatcctaaa ctaatttatc cttcaagtca acttaagccc aatatacatt ttcatctcta   7560
aaggcccaag tggcacaaaa tgtcaggccc aattacgaag aaaagggctt gtaaaaccct   7620
aataaagtgg cactggcaga gcttacactc tcattccatc aacaaagaaa ccctaaaagc   7680
cgcagcgcca ctgatttctc tcctccaggc gaagatgcag atcttcgtga agaccttaac   7740
ggggaagacg atcaccctag aggttgagtc ttccgacacc atcgacaatg tcaaagccaa   7800
gatccaggac aaggaaggga ttcccccaga ccagcagcgt ttgattttcg ccggaaagca   7860
gcttgaggat ggtcgtactc ttgccgacta caacatccag aaggagtcaa ctctccatct   7920
cgtgctccgt ctccgtggtg gtagtttaaa catgattgaa caagatggat tgcacgcagg   7980
ttctccggcc gcttgggtgg agaggctatt cggctatgac tgggcacaac agacaatcgg   8040
ctgctctgat gccgccgtgt tccggctgtc agcgcagggg cgcccggttc tttttgtcaa   8100
gaccgacctg tccggtgccc tgaatgaact gcaggacgag gcagcgcggc tatcgtggct   8160
ggccacgacg ggcgttcctt gcgcagctgt gctcgacgtt gtcactgaag cgggaaggga   8220
ctggctgcta ttgggcgaag tgccggggca ggatctcctg tcatctcacc ttgctcctgc   8280
cgagaaagta tccatcatgg ctgatgcaat gcggcggctg catacgcttg atccggctac   8340
ctgcccattc gaccaccaag cgaaacatcg catcgagcga gcacgtactc ggatggaagc   8400
cggtcttgtc gatcaggatg atctggacga agagcatcag gggctcgcgc cagccgaact   8460
gttcgccagg ctcaaggcgc gcatgcccga cggcgaggat ctcgtcgtga cccatggcga   8520
tgcctgcttg ccgaatatca tggtggaaaa tggccgcttt tctggattca tcgactgtgg   8580
ccggctgggt gtggcggacc gctatcagga catagcgttg gctacccgtg atattgctga   8640
agagcttggc ggcgaatggg ctgaccgctt cctcgtgctt tacggtatcg ccgctcccga   8700
ttcgcagcgc atcgccttct atcgccttct tgacgagttc ttctgagttt aaacgatttt   8760
aatgtttagc aaatgtctta tcagttttct ctttttgtcg aacggtaatt tagagttttt   8820
tttgctatat ggattttcgt tttgatgta tgtgacaacc ctcgggattg ttgatttatt   8880
tcaaaactaa gagtttttgt cttattgttc tcgtctattt tggatatcaa tcttagtttt   8940
atatcttttc tagttctcta cgtgttaaat gttcaacaca ctagcaattt ggcctgccag   9000
cgtatggatt atggaactat caagtgtgtg ggatcgataa atatgcttct caggaatttg   9060
agatttttta tcatgtcttt atgctcattc ccttgagtat aatatagtaa aaaaatagta   9120
```

-continued

```
aatttaagca ataatgttag gtgctatgtg tctgtcgaga ctattggccg gccatcgatg   9180
gtttcattgg tgacgtttcc ggccttgcta atggtaatgg tgctactggt gattttgctg   9240
gctctaattc ccaaatggct caagtcggtg acggtgataa ttcaccttta atgaataatt   9300
tccgtcaata tttaccttcc ctccctcaat cggttgaatg tcgccctttt gtctttggcc   9360
caatacgcaa accgcctctc cccgcgcgtt ggccgattca ttaatgcagc tggcacgaca   9420
ggtttcccga ctggaaagcg ggcagtgagc gcaacgcaat taatgtgagt tagctcactc   9480
attaggcacc ccaggcttta cactttatgc ttccggctcg tatgttgtgt ggaattgtga   9540
gcggataaca atttcacaca ggaaacagct atgaccatga ttacgccaag ctggcgcgcc   9600
agcgagttgc ttgtttttga caaactgaag aacactttgt aagtagtatg tcaagtggta   9660
tctatttatt ggatgtacta tatacaaata ccaaatgaat gagtatcctc cttcgagatg   9720
tacaaaatta aagtactatc agagaagtgt agagttatag atccaaccat ccatccgtac   9780
atattttaat agttaccact aatttaaaaa agagattaga attcaatgct gaactgagtt   9840
tttgttaggt actgaatcaa tggcccaaac ttattttgat tttatacttt ttcatttcac   9900
catattgatc atttaatgat ttagtgttta gcaaaaacta agcttaacac caaatttatg   9960
tcattaaaaa aattgaagaa agtgcaattg tacgtggttt tattttgtgg gaatcatatg  10020
ttttaacagt gaaaaattct atgcgttgta ccaataaatt ccatcttaat cccacaaagg  10080
caaattcttg gggcaagttt gttattaatt caaaatttag aataatttta ttattagttc  10140
aatttttaat tactcttgta gggatggtaa aatagctcgg atcgtcacaa ctcatttaag  10200
atttgaccta agcttgcgag cttaggctta acccattaag tgaggccctg aatatgggcc  10260
taaattttgc aggccaataa tgtgccgtgt tgaggcattg aagccctgaa gcctgagctt  10320
agacttagcc tacttattac ccattttta aatttaaaat attaaaaaaa tataaaaata  10380
aaatatcatg gtatctgcat attaatgtta agtgaattat ggtttattat gaggttatga  10440
tgttattatt cgctaatgtt tatcggaatg tgacagtaat tgtgttattt tggtaatttt  10500
ttatgttgca cgcttaaaat tacatatata agttgtaaat ttttgcaaac tcactttact  10560
gggagtttta agtcgttttt cttttaaaat aaatgttgaa cattaaaaaa ttcaaaatga  10620
attcagaggc ccagcccaaa gccggcccaa aattggacaa gcgtatagag cactaggcaa  10680
gacttgacct agcccgtcca tttcccactt tttgttggag tagtggggtt aagtactctt  10740
tatcattaat ctttagcaac aacgacatca tatacaactg cgaatttcga taatacagta  10800
agtgtgtgtg tctatatatg tgtttatata tataatactt ttttagtgag gatattttta  10860
ctttgttaaa gtgagaatta ccattaaaat atttaaaaaa tataaatttt aatatattag  10920
cggttacttt ttttttttta gttactgcat tgaactctat atatatattt tttatttatt  10980
aatgacattc tcacattatt aaaatgaaga tatccccatt agtatatata tatattttct  11040
aatgaaagtt cctacacttt attaaagtat tgaaatgact tttaaaacat tgtaaatgaa  11100
ttttaaaaca aaaaaaaaaa taatggttca agagacataa ttttagagag aggatcggaa  11160
gcccacattt tcaatagaag ttttgacaca aaatcttaac cattaaattg taatcaacct  11220
aaaggtttaa agtgagctga caatcatgaa ttttcttatt ttaaaaacaa aaagaataat  11280
ggttgaagac atacaatttt aaacacaaat ttaaatataa ttttctaact attagattaa  11340
agtcttaata aagatgagtt aatggaaggt taagattgga agacatgaaa ttattaattt  11400
cattggcagt attgtctctt atacattgct ttggattgcg acacctaatg cgagaatgat  11460
gtggaattta ttaattaagt aacgctgatc ttgaatgatt ggtatggact ttagctgtgt  11520
```

acgatgttga gccatggggc ccagcaagct cccacgttat tctcgcaaat tgtactatag 11580
ctagctctta attaattttc aaaaaattat gccacgtgag ccattaaaaa atatttcaga 11640
aaagcgcggt tctggccaca ttttccaaat tattattatt attttttga aagaaaagac 11700 tattattgat attgcttatt actttcacta cgccccaca atgcgcccgc cttggcacag 11760
tcggctactg ctttatctat aaatacatgc atgtatgcta tatcaaacca gaagcaagaa 11820
ctcgcaaaag caactgaatt actctttaag ttttgattcc ggaagcagag atctttccag 11880
atatgaagaa tatggaaaca accagcgcag gtttttaggc cagctttact ttcatttgaa 11940
tatcattcat aattcttatt ttaatacatg catttgttaa tatattttta atataaaatt 12000
tacaggtaat gatggatccc cgggtggtca gtcccttatg ttacgtcctg tagaaacccc 12060
aacccgtgaa atcaaaaaac tcgacggcct gtgggcattc agtctggatc gcgaaaactg 12120
tggaattgat cagcgttggt gggaaagcgc gttacaagaa agccgggcaa ttgctgtgcc 12180
aggcagtttt aacgatcagt tcgccgatgc agatattcgt aattatgcgg gcaacgtctg 12240
gtatcagcgc gaagtcttta taccgaaagg ttgggcaggc cagcgtatcg tgctgcgttt 12300
cgatgcggtc actcattacg gcaaagtgtg ggtcaataat caggaagtga tggagcatca 12360
gggcggctat acgccatttg aagccgatgt cacgccgtat gttattgccg ggaaaagtgt 12420
acgtatcacc gtttgtgtga acaacgaact gaactggcag actatcccgc cgggaatggt 12480
gattaccgac gaaaacggca agaaaaagca gtcttacttc catgatttct ttaactatgc 12540
cggaatccat cgcagcgtaa tgctctacac cacgccgaac acctgggtgg acgatatcac 12600
cgtggtgacg catgtcgcgc aagactgtaa ccacgcgtct gttgactggc aggtggtggc 12660
caatggtgat gtcagcgttg aactgcgtga tgcggatcaa caggtggttg caactggaca 12720
aggcactagc gggactttgc aagtggtgaa tccgcacctc tggcaaccgg gtgaaggtta 12780
tctctatgaa ctgtgcgtca cagccaaaag ccagacagag tgtgatatct acccgcttcg 12840
cgtcggcatc cggtcagtgg cagtgaaggg cgaacagttc ctgattaacc acaaaccgtt 12900
ctactttact ggctttggtc gtcatgaaga tgcggacttg cgtggcaaag gattcgataa 12960
cgtgctgatg gtgcacgacc acgcattaat ggactggatt ggggccaact cctaccgtac 13020
ctcgcattac ccttacgctg aagagatgct cgactgggca gatgaacatg gcatcgtggt 13080
gattgatgaa actgctgctg tcggctttaa cctctcttta ggcattggtt tcgaagcggg 13140
caacaagccg aaagaactgt acagcgaaga ggcagtcaac ggggaaactc agcaagcgca 13200
cttacaggcg attaaagagc tgatagcgcg tgacaaaaac cacccaagcg tggtgatgtg 13260
gagtattgcc aacgaaccgg atacccgtcc gcaaggtgca cgggaatatt tcgcgccact 13320
ggcggaagca acgcgtaaac tcgacccgac gcgtccgatc acctgcgtca atgtaatgtt 13380
ctgcgacgct cacaccgata ccatcagcga tctctttgat gtgctgtgcc tgaaccgtta 13440
ttacggatgg tatgtccaaa gcggcgattt ggaaacggca gagaaggtac tggaaaaaga 13500
acttctggcc tggcaggaga aactgcatca gccgattatc atcaccgaat acggcgtgga 13560
tacgttagcc gggctgcact caatgtacac cgacatgtgg agtgaagagt atcagtgtgc 13620
atggctggat atgtatcacc gcgtctttga tcgcgtcagc gccgtcgtcg gtgaacaggt 13680
atggaatttc gccgattttg cgacctcgca aggcatattg cgcgttggcg gtaacaagaa 13740
agggatcttc actcgcgacc gcaaaccgaa gtcggcggct tttctgctgc aaaaacgctg 13800
gactggcatg aacttcggtg aaaaaccgca gcagggaggc aaacaatgaa tcaacaactc 13860

-continued

```
tcctggcgca ccatcgtcgg ctacagcctc gggaattgct acgagctcgt tgcctattgt  13920
tggttgtcgt gttgtctggc tgtgtctgtt gcccattgtg gtggttatgt gttgcatcat  13980
ggtctaaaag gatcatcaat gtttttcgct tctgttcctt tctgtttctc atttgtgaat  14040
aataatggtg tctttatgaa catccagttt ctggtttctt ttctgattgc agtttgagta  14100
tttgtttttg cttttgcttc cgtctactac accactttgc aattactgta tcactcatgc  14160
attgttgata tactttagcc ttcgatccat cttctgtttg atgattcaaa tggtatttat  14220
ttaactcata cccaagtgaa gcataaagtt agaggagagt tcatgttcca ttacctgttt  14280
gtttcatgag caactcatct taataaacat aagaaaaacc ataatgcaat ctgtgtagct  14340
gatagacttt gatgacagac ggactcataa gtaacaagag gaaacatgat aaacatgtac  14400
ggaagtcgag ctcgaattct taattaacaa ttcactggcc gtcgttttac aacgtcgtga  14460
ctgggaaaac cctggcgtta cccaacttaa tcgccttgca gcacatcccc ctttcgccag  14520
ctggcgtaat agcgaagagg cccgcaccga tcgcccttcc caacagttgc gcagcctgaa  14580
tggcgcccgc tcctttcgct ttcttccctt cctttctcgc cacgttcgcc ggctttcccc  14640
gtcaagctct aaatcggggg ctccctttag ggttccgatt tagtgcttta cggcacctcg  14700
accccaaaaa acttgatttg ggtgatggtt cacaaactat cagtgtttga caggatatat  14760
tggcgggtaa acctaagaga aaagagcgtt tattagaata atcggatatt taaaagggcg  14820
tgaaaaggtt tatccgttcg tccatttgta tgtgcatgcc aaccacaggg ttccccagat  14880
ctggcgccgg ccagcgagac gagcaagatt ggccgccgcc cgaaacgatc cgacagcgcg  14940
cccagcacag gtgcgcaggc aaattgcacc aacgcataca gcgccagcag aatgccatag  15000
tgggcggtga cgtcgttcga gtgaaccaga tcgcgcagga ggcccggcag caccggcata  15060
atcaggccga tgccgacagc gtcgagcgcg acagtgctca gaattacgat caggggtatg  15120
ttgggtttca cgtctggcct ccggaccagc ctccgctggt ccgattgaac gcgcggattc  15180
tttatcactg ataagttggt ggacatatta tgtttatcag tgataaagtg tcaagcatga  15240
caaagttgca gccgaataca gtgatccgtg ccgccctgga cctgttgaac gaggtcggcg  15300
tagacggtct gacgacacgc aaactggcgg aacggttggg ggttcagcag ccggcgcttt  15360
actggcactt caggaacaag cgggcgctgc tcgacgcact ggccgaagcc atgctggcgg  15420
agaatcatac gcattcggtg ccgagagccg acgacgactg gcgctcattt ctgatcggga  15480
atgcccgcag cttcaggcag gcgctgctcg cctaccgcga tggcgcgcgc atccatgccg  15540
gcacgcgacc gggcgcaccg cagatggaaa cggccgacgc gcagcttcgc ttcctctgcg  15600
aggcgggttt ttcggccggg gacgccgtca atgcgctgat gacaatcagc tacttcactg  15660
ttggggccgt gcttgaggag caggccggcg acagcgatgc cggcgagcgc ggcggcaccg  15720
ttgaacaggc tccgctctcg ccgctgttgc gggccgcgat agacgccttc gacgaagccg  15780
gtccggacgc agcgttcgag cagggactcg cggtgattgt cgatggattg gcgaaaagga  15840
ggctcgttgt caggaacgtt gaaggaccga gaaagggtga cgattgatca ggaccgctgc  15900
cggagcgcaa cccactcact acagcagagc catgtagaca acatcccctc cccctttcca  15960
ccgcgtcaga cgcccgtagc agcccgctac gggctttttc atgccctgcc ctagcgtcca  16020
agcctcacgg ccgcgctcgg cctctctggc ggccttctgg cgctcttccg cttcctcgct  16080
cactgactcg ctgcgctcgg tcgttcggct gcggcgagcg gtatcagctc actcaaaggc  16140
ggtaatacgg ttatccacag aatcagggga taacgcagga aagaacatgt gagcaaaagg  16200
ccagcaaaag gccaggaacc gtaaaaaggc cgcgttgctg gcgtttttcc ataggctccg  16260
```

-continued

```
ccccccctgac gagcatcaca aaaatcgacg ctcaagtcag aggtggcgaa acccgacagg  16320

actataaaga taccaggcgt ttccccctgg aagctccctc gtgcgctctc ctgttccgac  16380

cctgccgctt accggatacc tgtccgcctt tctcccttcg ggaagcgtgg cgctttttccg  16440

ctgcataacc ctgcttcggg gtcattatag cgatttttttc ggtatatcca tcctttttcg  16500

cacgatatac aggattttgc caaagggttc gtgtagactt tccttggtgt atccaacggc  16560

gtcagccggg caggataggt gaagtaggcc cacccgcgag cgggtgttcc ttcttcactg  16620

tcccttattc gcacctggcg gtgctcaacg ggaatcctgc tctgcgaggc tggccggcta  16680

ccgccggcgt aacagatgag ggcaagcgga tggctgatga aaccaagcca accaggaagg  16740

gcagcccacc tatcaaggtg tactgccttc cagacgaacg aagagcgatt gaggaaaagg  16800

cggcggcggc cggcatgagc ctgtcggcct acctgctggc cgtcggccag ggctacaaaa  16860

tcacgggcgt cgtggactat gagcacgtcc gcgagctggc ccgcatcaat ggcgacctgg  16920

gccgcctggg cggcctgctg aaactctggc tcaccgacga cccgcgcacg gcgcggttcg  16980

gtgatgccac gatcctcgcc ctgctggcga agatcgaaga gaagcaggac gagcttggca  17040

aggtcatgat gggcgtggtc cgcccgaggg cagagccatg actttttttag ccgctaaaac  17100

ggccgggggg tgcgcgtgat tgccaagcac gtccccatgc gctccatcaa gaagagcgac  17160

ttcgcggagc tggtgaagta catcaccgac gagcaaggca agaccgagcg cctttgcgac  17220

gctca                                                              17225
```

<210> SEQ ID NO 8
<211> LENGTH: 29
<212> TYPE: DNA
<213> ORGANISM: Citrus sinensis

<400> SEQUENCE: 8

```
cagttatgaa cccctaacat tactcatcc                                       29
```

<210> SEQ ID NO 9
<211> LENGTH: 27
<212> TYPE: DNA
<213> ORGANISM: Citrus sinensis

<400> SEQUENCE: 9

```
ctttagcaca aagagatctc gattctc                                         27
```

<210> SEQ ID NO 10
<211> LENGTH: 21
<212> TYPE: DNA
<213> ORGANISM: Artificial Sequence
<220> FEATURE:
<223> OTHER INFORMATION: synthesized

<400> SEQUENCE: 10

```
ggcgcgccag cgagttgctt g                                               21
```

<210> SEQ ID NO 11
<211> LENGTH: 26
<212> TYPE: DNA
<213> ORGANISM: Artificial Sequence
<220> FEATURE:
<223> OTHER INFORMATION: synthesized

<400> SEQUENCE: 11

```
ggatccatca ttacctgtaa atttta                                          26
```

<210> SEQ ID NO 12
<211> LENGTH: 28
<212> TYPE: DNA
<213> ORGANISM: Citrus clementina

<400> SEQUENCE: 12
cttgtaaaca ctggagtggg aggaatcc 28

<210> SEQ ID NO 13
<211> LENGTH: 27
<212> TYPE: DNA
<213> ORGANISM: Citrus clementina

<400> SEQUENCE: 13
ggcgtcaact tggtcaaagc tagactc 27

<210> SEQ ID NO 14
<211> LENGTH: 26
<212> TYPE: DNA
<213> ORGANISM: Artificial Sequence
<220> FEATURE:
<223> OTHER INFORMATION: synthesized

<400> SEQUENCE: 14
ggcgcgccct tgtaaacact ggagtg 26

<210> SEQ ID NO 15
<211> LENGTH: 26
<212> TYPE: DNA
<213> ORGANISM: Artificial Sequence
<220> FEATURE:
<223> OTHER INFORMATION: synthesized

<400> SEQUENCE: 15
gggatccgtt cttacctgaa aaaatc 26

<210> SEQ ID NO 16
<211> LENGTH: 28
<212> TYPE: DNA
<213> ORGANISM: Artificial Sequence
<220> FEATURE:
<223> OTHER INFORMATION: synthesized

<400> SEQUENCE: 16
ggatcccata ttcttcaaat tagaaaag 28

<210> SEQ ID NO 17
<211> LENGTH: 30
<212> TYPE: DNA
<213> ORGANISM: Artificial Sequence
<220> FEATURE:
<223> OTHER INFORMATION: synthesized

<400> SEQUENCE: 17
gggatccttc ttcaaattag aaaagatatc 30

<210> SEQ ID NO 18
<211> LENGTH: 19
<212> TYPE: DNA
<213> ORGANISM: Citrus clementina

<400> SEQUENCE: 18
aacaaactcc gcatagtgg 19

<210> SEQ ID NO 19
<211> LENGTH: 18
<212> TYPE: DNA
<213> ORGANISM: Citrus clementina

<400> SEQUENCE: 19
ccgaccaatc ggtataac 18

<210> SEQ ID NO 20
<211> LENGTH: 27
<212> TYPE: DNA
<213> ORGANISM: Artificial Sequence
<220> FEATURE:
<223> OTHER INFORMATION: synthesized

<400> SEQUENCE: 20
ggcgcgccaa caaactccgc atagtgg 27

<210> SEQ ID NO 21
<211> LENGTH: 25
<212> TYPE: DNA
<213> ORGANISM: Artificial Sequence
<220> FEATURE:
<223> OTHER INFORMATION: synthesized

<400> SEQUENCE: 21
ggatccggta taacctgaaa aattc 25

<210> SEQ ID NO 22
<211> LENGTH: 29
<212> TYPE: DNA
<213> ORGANISM: Artificial Sequence
<220> FEATURE:
<223> OTHER INFORMATION: synthesized

<400> SEQUENCE: 22
ggatcccata atcttcaaat caggaaggc 29

<210> SEQ ID NO 23
<211> LENGTH: 30
<212> TYPE: DNA
<213> ORGANISM: Artificial Sequence
<220> FEATURE:
<223> OTHER INFORMATION: synthesized

<400> SEQUENCE: 23
ggatccatct tcaaatcagg aaggcaaaag 30

<210> SEQ ID NO 24
<211> LENGTH: 3861
<212> TYPE: DNA
<213> ORGANISM: Citrus sinensis

<400> SEQUENCE: 24
cagttatgaa cccctaacat tactcatcca aatttttaat ccaacacaaa cacactctaa 60
atgcgaaaaa caattctaca aacttttgta tgtcatgcat aaactcttta tgcataacat 120
ctatatggtg cacttcaatg gactgatgtt gaatttccca atacttaaat ggttgtattt 180
agggctagtt tcataatact gtagttttta aaattattac agttggtcgt actatagaaa 240
taatcagctg taaaagaaat tagtgaaatg tttggtaaaa ttaactttaa aaagtactat 300
gaattttaaa agtagttgta tgtgtttagt aaatcttact gttaaactat tgtaagaata 360
taaattatta tattggacaa aatattaaat acaatttatt ggaacattca taaatatgta 420

-continued

```
cataaaatat ttgttattgt gtacatataa tatttgataa tcaaaataaa tattttatat    480
tattcgtttt attttttgtt ttgttatcaa tataattgat aataataatc taaagttaag    540
gattgtattt cctaattgat aaggataatt ttgaatgttt acaatatata taaggataaa    600
tatgaaattt tattaagtat aaaaatgatt caaaaaatga aaatttgaaa agctattcct    660
tccctacttt tcaaattcta ctgtaaaatg gagtgatttt aataaagtga tttctaaaaa    720
atttatcaaa caccaaaatt agcttttaac tttttaaaat tacttttgag cctcccaaaa    780
gcaatcctag tcaggaactt cattagcttg attagttaca aaattgagat ctaattatta    840
gaatattatt gaatttagta ggcagaagga tgccagcgag ttgcttgttt ttgacaaact    900
gaagaacact ttgtaagtag tatgtcaagt ggtatctatt tattggatgt actatataca    960
aataccaaat gaatgagtat cctccttcga gatgtacaaa attaaagtac tatcagagaa   1020
gtgtagagtt atagatccaa ccatccatcc gtacatattt taatagttac cactaattta   1080
aaaaagagat tagaattcaa tgctgaactg agtttttgtt aggtactgaa tcaatggccc   1140
aaacttattt tgattttata ctttttcatt tcaccatatt gatcatttaa tgatttagtg   1200
tttagcaaaa actaagctta acaccaaatt tatgtcatta aaaaaattga agaaagtgca   1260
attgtacgtg gttttatttt gtgggaatca tatgttttaa cagtgaaaaa ttctatgcgt   1320
tgtaccaata aattccatct taatcccaca aaggcaaatt cttggggcaa gtttgttatt   1380
aattcaaaat ttagaataat tttattatta gttcaatttt taattactct tgtagggatg   1440
gtaaaatagc tcggatcgtc acaactcatt taagatttga cctaagcttg cgagcttagg   1500
cttaacccat taagtgaggc cctgaatatg ggcctaaatt ttgcaggcca ataatgtgcc   1560
gtgttgaggc attgaagccc tgaagcctga gcttagactt agcctactta ttacccattt   1620
tttaaattta aaatattaaa aaaatataaa aataaaatat catggtatct gcatattaat   1680
gttaagtgaa ttatggttta ttatgaggtt atgatgttat tattcgctaa tgtttatcgg   1740
aatgtgacag taattgtgtt attttggtaa tttttttatgt tgcacgctta aaattacata   1800
tataagttgt aaatttttgc aaactcactt tactgggagt tttaagtcgt ttttctttta   1860
aaataaatgt tgaacattaa aaaattcaaa atgaattcag aggcccagcc caaagccggc   1920
ccaaaattgg acaagcgtat agagcactag gcaagacttg acctagcccg tccatttccc   1980
actttttgtt ggagtagtgg ggttaagtac tctttatcat taatctttag caacaacgac   2040
atcatataca actgcgaatt tcgataatac agtaagtgtg tgtgtctata tatgtgttta   2100
tatatataat acttttttag tgaggatatt tttactttgt taaagtgaga attaccatta   2160
aaatatttaa aaaatataaa ttttaatata ttagcggtta cttttttttt tttagttact   2220
gcattgaact ctatatatat atttttttatt tattaatgac attctcacat tattaaaatg   2280
aagatatccc cattagtata tatatatatt ttctaatgaa agttcctaca ctttattaaa   2340
gtattgaaat gacttttaaa acattgtaaa tgaattttaa aacaaaaaaa aaaataatgg   2400
ttcaagagac ataattttag agagaggatc ggaagcccac attttcaata gaagttttga   2460
cacaaaatct taaccattaa attgtaatca acctaaaggt ttaaagtgag ctgacaatca   2520
tgaattttct tattttaaaa acaaaaagaa taatggttga agacatacaa ttttaaacac   2580
aaatttaaat ataattttct aactattaga ttaaagtctt aataaagatg agttaatgga   2640
aggttaagat tggaagacat gaaattatta atttcattgg cagtattgtc tcttatacat   2700
tgctttggat tgcgacacct aatgcgagaa tgatgtggaa tttattaatt aagtaacgct   2760
gatcttgaat gattggtatg gactttagct gtgtacgatg ttgagccatg gggcccagca   2820
```

```
agctcccacg ttattctcgc aaattgtact atagctagct cttaattaat tttcaaaaaa   2880
ttatgccacg tgagccatta aaaaatattt cagaaaagcg cggttctggc cacattttcc   2940
aaattattat tattattttt ttgaaagaaa agactattat tgatattgct tattactttc   3000
actacgcccc cacaatgcgc ccgccttggc acagtcggct actgctttat ctataaatac   3060
atgcatgtat gctatatcaa accagaagca agaactcgca aaagcaactg aattactctt   3120
taagttttga ttccggaagc agagatcttt ccagatatga agaatatgga aacaaccagc   3180
gcaggttttt aggccagctt tactttcatt tgaatatcat tcataattct tattttaata   3240
catgcatttg ttaatatatt tttaatataa aatttacagg taatgatgat tggctggagg   3300
gttatgttgc tgccagtatt gttgatgata acattgcgaa tgatgtcaat ctcgatcttc   3360
ttactgtccc tcaatatggg agaaatattg atcaaaccgg ttaaatgcaa gcaatattac   3420
tcttttgtgt tatgcttatt taaataaaaa gatgggtact gttattacct atcaatgtgt   3480
gagtgtctgt ttactcagtt ctacttaata agatatcttg atatgtataa gagtttttct   3540
ttatttacta tctttgtgtg gtgtcttcct ggaaaaggta attactgaat aaaattgttg   3600
cgtctgttat aaagtgttga ttaaattagc ctgtccatat atatatgctt aattatgttc   3660
tctttttttt tttttcttta aattaacgaa ctccgcatgt tagttggcta attattgcgc   3720
tgctatagca agtgacttag atcgtctaaa gaatgtctat atttcctaaa tggcgtgtaa   3780
catcattata tgctaagcat cgatcttaaa tgttctatca gttctttgtt atatgagaat   3840
cgagatctct ttgtgctaaa g                                             3861
```

<210> SEQ ID NO 25
<211> LENGTH: 4817
<212> TYPE: DNA
<213> ORGANISM: Artificial Sequence
<220> FEATURE:
<223> OTHER INFORMATION: expression cassette

<400> SEQUENCE: 25

```
ggcgcgccag cgagttgctt gtttttgaca aactgaagaa cactttgtaa gtagtatgtc     60
aagtggtatc tatttattgg atgtactata tacaaatacc aaatgaatga gtatcctcct    120
tcgagatgta caaaattaaa gtactatcag agaagtgtag agttatagat ccaaccatcc    180
atccgtacat attttaatag ttaccactaa tttaaaaaag agattagaat tcaatgctga    240
actgagtttt tgttaggtac tgaatcaatg gcccaaactt attttgattt tatacttttt    300
catttcacca tattgatcat ttaatgattt agtgtttagc aaaaactaag cttaacacca    360
aatttatgtc attaaaaaaa ttgaagaaag tgcaattgta cgtggtttta ttttgtggga    420
atcatatgtt ttaacagtga aaaattctat gcgttgtacc aataaattcc atcttaatcc    480
cacaaaggca aattcttggg gcaagtttgt tattaattca aaatttagaa taattttatt    540
attagttcaa tttttaatta ctcttgtagg gatggtaaaa tagctcggat cgtcacaact    600
catttaagat ttgacctaag cttgcgagct taggcttaac ccattaagtg aggccctgaa    660
tatgggccta aattttgcag gccaataatg tgccgtgttg aggcattgaa gccctgaagc    720
ctgagcttag acttagccta cttattaccc atttttttaaa tttaaaatat taaaaaaata    780
taaaaataaa atatcatggt atctgcatat taatgttaag tgaattatgg tttattatga    840
ggttatgatg ttattattcg ctaatgttta tcggaatgtg acagtaattg tgttattttg    900
gtaatttttt atgttgcacg cttaaaatta catatataag ttgtaaattt ttgcaaactc    960
```

-continued

```
actttactgg gagttttaag tcgtttttct tttaaaataa atgttgaaca ttaaaaaatt   1020
caaaatgaat tcagaggccc agcccaaagc cggcccaaaa ttggacaagc gtatagagca   1080
ctaggcaaga cttgacctag cccgtccatt tcccactttt tgttggagta gtggggttaa   1140
gtactcttta tcattaatct ttagcaacaa cgacatcata tacaactgcg aatttcgata   1200
atacagtaag tgtgtgtgtc tatatatgtg tttatatata taatactttt ttagtgagga   1260
tatttttact ttgttaaagt gagaattacc attaaaatat ttaaaaaata taaattttaa   1320
tatattagcg gttacttttt tttttttagt tactgcattg aactctatat atatattttt   1380
tatttattaa tgacattctc acattattaa aatgaagata tccccattag tatatatata   1440
tattttctaa tgaaagttcc tacactttat taaagtattg aaatgacttt taaaacattg   1500
taaatgaatt ttaaaacaaa aaaaaaaata atggttcaag agacataatt ttagagagag   1560
gatcggaagc ccacatttc aatagaagtt ttgacacaaa atcttaacca ttaaattgta   1620
atcaacctaa aggtttaaag tgagctgaca atcatgaatt ttcttatttt aaaaacaaaa   1680
agaataatgg ttgaagacat acaattttaa acacaaattt aaatataatt ttctaactat   1740
tagattaaag tcttaataaa gatgagttaa tggaaggtta agattggaag acatgaaatt   1800
attaatttca ttggcagtat tgtctcttat acattgcttt ggattgcgac acctaatgcg   1860
agaatgatgt ggaatttatt aattaagtaa cgctgatctt gaatgattgg tatggacttt   1920
agctgtgtac gatgttgagc catggggccc agcaagctcc cacgttattc tcgcaaattg   1980
tactatagct agctcttaat taattttcaa aaaattatgc cacgtgagcc attaaaaaat   2040
atttcagaaa agcgcggttc tggccacatt ttccaaatta ttattattat tttttgaaa   2100
gaaaagacta ttattgatat tgcttattac tttcactacg cccccacaat gcgcccgcct   2160
tggcacagtc ggctactgct ttatctataa atacatgcat gtatgctata tcaaaccaga   2220
agcaagaact cgcaaaagca actgaattac tctttaagtt ttgattccgg aagcagagat   2280
ctttccagat atgaagaata tggaaacaac cagcgcaggt ttttaggcca gctttacttt   2340
catttgaata tcattcataa ttcttatttt aatacatgca tttgttaata tatttttaat   2400
ataaaattta caggtaatga tggatccccg ggtggtcagt cccttatgtt acgtcctgta   2460
gaaaccccaa cccgtgaaat caaaaaactc gacggcctgt gggcattcag tctggatcgc   2520
gaaaactgtg gaattgatca gcgttggtgg gaaagcgcgt tacaagaaag ccgggcaatt   2580
gctgtgccag gcagttttaa cgatcagttc gccgatgcag atattcgtaa ttatgcgggc   2640
aacgtctggt atcagcgcga agtctttata ccgaaaggtt gggcaggcca gcgtatcgtg   2700
ctgcgtttcg atgcggtcac tcattacggc aaagtgtggg tcaataatca ggaagtgatg   2760
gagcatcagg gcggctatac gccatttgaa gccgatgtca cgccgtatgt tattgccggg   2820
aaaagtgtac gtatcaccgt ttgtgtgaac aacgaactga actggcagac tatcccgccg   2880
ggaatggtga ttaccgacga aaacggcaag aaaaagcagt cttacttcca tgatttcttt   2940
aactatgccg gaatccatcg cagcgtaatg ctctacacca cgccgaacac ctgggtggac   3000
gatatcaccg tggtgacgca tgtcgcgcaa gactgtaacc acgcgtctgt tgactggcag   3060
gtggtggcca atggtgatgt cagcgttgaa ctgcgtgatg cggatcaaca ggtggttgca   3120
actggacaag gcactagcgg gactttgcaa gtggtgaatc cgcacctctg gcaaccgggt   3180
gaaggttatc tctatgaact gtgcgtcaca gccaaaagcc agacagagtg tgatatctac   3240
ccgcttcgcg tcggcatccg gtcagtggca gtgaagggcg aacagttcct gattaaccac   3300
aaaccgttct actttactgg ctttggtcgt catgaagatg cggacttgcg tggcaaagga   3360
```

ttcgataacg tgctgatggt gcacgaccac gcattaatgg actggattgg ggccaactcc 3420
taccgtacct cgcattaccc ttacgctgaa gagatgctcg actgggcaga tgaacatggc 3480
atcgtggtga ttgatgaaac tgctgctgtc ggctttaacc tctctttagg cattggtttc 3540
gaagcgggca acaagccgaa agaactgtac agcgaagagg cagtcaacgg ggaaactcag 3600
caagcgcact tacaggcgat taaagagctg atagcgcgtg acaaaaacca cccaagcgtg 3660
gtgatgtgga gtattgccaa cgaaccggat acccgtccgc aaggtgcacg ggaatatttc 3720
gcgccactgg cggaagcaac gcgtaaactc gacccgacgc gtccgatcac ctgcgtcaat 3780
gtaatgttct gcgacgctca caccgatacc atcagcgatc tctttgatgt gctgtgcctg 3840
aaccgttatt acggatggta tgtccaaagc ggcgatttgg aaacggcaga gaaggtactg 3900
gaaaaagaac ttctggcctg gcaggagaaa ctgcatcagc cgattatcat caccgaatac 3960
ggcgtggata cgttagccgg gctgcactca atgtacaccg acatgtggag tgaagagtat 4020
cagtgtgcat ggctggatat gtatcaccgc gtctttgatc gcgtcagcgc cgtcgtcggt 4080
gaacaggtat ggaatttcgc cgattttgcg acctcgcaag gcatattgcg cgttggcggt 4140
aacaagaaag ggatcttcac tcgcgaccgc aaaccgaagt cggcggcttt tctgctgcaa 4200
aaacgctgga ctggcatgaa cttcggtgaa aaaccgcagc agggaggcaa acaatgaatc 4260
aacaactctc ctggcgcacc atcgtcggct acagcctcgg gaattgctac gagctcgttg 4320
cctattgttg gttgtcgtgt tgtctggctg tgtctgttgc ccattgtggt ggttatgtgt 4380
tgcatcatgg tctaaaagga tcatcaatgt ttttcgcttc tgttcctttc tgtttctcat 4440
ttgtgaataa taatggtgtc tttatgaaca tccagtttct ggtttctttt ctgattgcag 4500
tttgagtatt tgtttttgct tttgcttccg tctactacac cactttgcaa ttactgtatc 4560
actcatgcat tgttgatata ctttagcctt cgatccatct tctgtttgat gattcaaatg 4620
gtatttattt aactcatacc caagtgaagc ataaagttag aggagagttc atgttccatt 4680
acctgtttgt ttcatgagca actcatctta ataaacataa gaaaaaccat aatgcaatct 4740
gtgtagctga tagactttga tgacagacgg actcataagt aacaagagga aacatgataa 4800
acatgtacgg aagtcga 4817

<210> SEQ ID NO 26
<211> LENGTH: 3144
<212> TYPE: DNA
<213> ORGANISM: Citrus clementina

<400> SEQUENCE: 26
cttgtaaaca ctggagtggg aggaatccac actccacact cccaatttag aaagtaaaca 60
ctacctaaag gtatttacag tcaggatttt tttttccatg taacctcaaa tgcactatgc 120
aataaaatat aaatataaat aaagcaagca gttactaagt ctttaggttg ttaggcagat 180
gctaaggcct tgtcctgaat aagcccagca attcaaactt aagattacac tataaaaagg 240
gggcgcaaag gcaaagaaag tggcacggca agtgcagcga aggaagcaaa ggagagcatg 300
tcacactgag attacatgtc tgatatttgg ctccgcttct tccctttaaa cacctcgaaa 360
taagcatcaa ggaagtggtc ttgtcatcat cttcttccag tacatcaatg gagaaacaac 420
attcgaacac atggaaataa gaaaaatcat taaaattgac tactactgtt gcatattcat 480
aatatgactg ctggcttttc ttctatctca gtttttttca gagctcaact aagggcagtt 540
tgatgctgtc attggatagc agtagcttga aaaactacag tactttagtg gttagtaaac 600

-continued

```
acttattgct ataatttgga atttaggttc attttatccg atactcgaaa tacgctaatg    660
ggaaaaatag tcaaaactca ggtaattttt tcatttctct ttttatgttt ctaaacacat    720
caaaactctc tcttgatgtt taaaaaaatt tattaacttt taacttttat ttgtgtcctt    780
tcttatttca tccatgatgt cgtaaaaccc actgttaatc aataaaaatt tctgaagata    840
gaataatgaa ggatacaaaa aaatttacaa gccttttgta tatgatagtt gactatgtgt    900
atcgggacaa tgttgtgagc attagattgg acaagttatg aatttttatc agtctagctc    960
atacgcaaaa actttgaaaa actttgaaaa gaataagtta tccatataac acaaaatcac   1020
catttatact tagctcattt atattttta tggatatgaa tgtaaatttc tgcctttgga   1080
gagtaataat aatccaatat cgtcgacgtg gccgttgcag ttgccgagtc gatgcaaaaa   1140
gagcaacggc gatttgttga agagaagcaa cagcaactga ataataatat aacagcaaca   1200
acaacgttga ttcttcgaaa gagaaaagag tcaaatccgg caaaaaggcc aaggcaaaag   1260
cagccaccgt gtcggcgcac gaggcttttt attctaaatt gaaaaagaaa aattgggtaa   1320
ttaacttaac ttatcaagga taacattgtc atatcacaaa aaatatttta ttttgatgaa   1380
tagttacagt ttgtaaaata attaaatcaa ttaagaaaaa taagggcatt ttcattgtaa   1440
aataacgtaa ttttttagtg ttaggagtaa gtgtagcgtt tttaaattta aagaggcaag   1500
ctagaggaag atggagctgt caactttcaa gtaatgtatg catcaaggta agtgacagag   1560
ctaaggagaa atggacaagt actaatcatc gttataaaaa attaaacaga gcagcatttt   1620
gtcagttctg gccatatata tttttcaagg attgggactg ttagcaccgc tgtaatttta   1680
ttttcaagct cttctctgtc aaaacctatt ttactttcca aaatatctta ttccattttt   1740
ttagtttctt tctgattcaa gatttttttt ttaaaaaaaa aaaatctgtt tcttccaaac   1800
aactccaatt acaatttttt tttataaatt tttgaattat taaatcatat atagttaact   1860
aaagagaatc atatatacaa actaaataga attaaaagtg gactcaaatg gctattatgt   1920
tattttttc taaattaaaa aaaaaagttt agaatcagag cctccttgta agccataaaa   1980
aaaaagaaaa gaaaagttta taatgcaaaa gtatttgtga gaaaaaaaaa aaacactttg   2040
atgtagttgc atgaatgtaa agagttagat agagaaatag agtgtataat tagatttatt   2100
tttttcttta aagtaatcgc aatataagag gggttaagaa tttcacagga gtgccactga   2160
ttcaactctt tttcaagaga attgatgttc tggaagaaaa ttatgactct atcattgcta   2220
ttagtttgtc ttgtaattca attattgccg acaagtatta actgtgatta tttttatttt   2280
aaaaattatt attattaatg tattgcaatt ttgagcctta taattgcaat tagtttgtct   2340
tgtaactaaa ttattgccga caaacactat catgctgaca aacaatgcat gcacgtcctc   2400
agtcacccac gtcctctact tgtgtgaatg tgtatataaa tatatctgga gcatattata   2460
aaaccagaag caaaagcaac tgaagttttg aatacggttc accagaagtt agaagatatc   2520
ttttctaatt tgaagaatat ggaaactcct tatccaggtt cttaggccat gttcagctga   2580
atgtcactta taatttttat tttaatatat gtatttatga atacaattgt tgttatgatt   2640
ttttcaggta agaacgaatg gtcagagggt aacccaataa ctatgtacag cattattaat   2700
gatgagagcg tgaatgacaa tctggatctt attgtcgtcc ctcaatacgg aagaaatctc   2760
gatcacactg gttaagtgct atcctactct ttcgtattat gttcaattaa ataaaatgat   2820
gggttattaa tacctgtcaa ttatgtgagt gtctctgttt ggtttagttc aacttataaa   2880
atctcttgaa atatacaaga gattttcttt atttacgttt gtgtaccgtg tcttcttgaa   2940
aaaagaaatt aataaaaaat atcattgtgt gatccttttc tttcccctac tgctgtagca   3000
```

tcaaatcctt agaattagat atcaagtggt attcgagccg tcaaatgatc cgtggcaaca 3060
cgcaacaaat caaatgctga atttcgcgaa gagattaaca aaatccttgc tagacacgag 3120
tctagctttg accaagttga cgcc 3144

<210> SEQ ID NO 27
<211> LENGTH: 5059
<212> TYPE: DNA
<213> ORGANISM: Artificial Sequence
<220> FEATURE:
<223> OTHER INFORMATION: expression cassette

<400> SEQUENCE: 27
ggcgcgccct tgtaaacact ggagtgggag gaatccacac tccacactcc caatttagaa 60
agtaaacact acctaaaggt atttacagtc aggatttttt tttccatgta acctcaaatg 120
cactatgcaa taaaatataa atataaataa agcaagcagt tactaagtct ttaggttgtt 180
aggcagatgc taaggccttg tcctgaataa gcccagcaat tcaaacttaa gattacacta 240
taaaaagggg gcgcaaaggc aaagaaagtg gcacggcaag tgcagcgaag gaagcaaagg 300
agagcatgtc acactgagat tacatgtctg atatttggct ccgcttcttc cctttaaaca 360
cctcgaaata agcatcaagg aagtggtctt gtcatcatct tcttccagta catcaatgga 420
gaaacaacat tcgaacacat ggaaataaga aaaatcatta aaattgacta ctactgttgc 480
atattcataa tatgactgct ggcttttctt ctatctcagt ttttttcaga gctcaactaa 540
gggcagtttg atgctgtcat tggatagcag tagcttgaaa aactacagta ctttagtggt 600
tagtaaacac ttattgctat aatttggaat ttaggttcat tttatccgat actcgaaata 660
cgctaatggg aaaaatagtc aaaactcagg taatttttc atttctcttt ttatgtttct 720
aaacacatca aaactctctc ttgatgttta aaaaaattta ttaactttta acttttattt 780
gtgtcctttc ttatttcatc catgatgtcg taaaacccac tgttaatcaa taaaaatttc 840
tgaagataga ataatgaagg atacaaaaaa atttacaagc cttttgtata tgatagttga 900
ctatgtgtat cgggacaatg ttgtgagcat tagattggac aagttatgaa tttttatcag 960
tctagctcat acgcaaaaac tttgaaaaac tttgaaaaga ataagttatc catataacac 1020
aaaatcacca tttatactta gctcatttat attttttatg gatatgaatg taaatttctg 1080
cctttggaga gtaataataa tccaatatcg tcgacgtggc cgttgcagtt gccgagtcga 1140
tgcaaaaaga gcaacggcga tttgttgaag agaagcaaca gcaactgaat aataatataa 1200
cagcaacaac aacgttgatt cttcgaaaga gaaaagagtc aaatccggca aaaaggccaa 1260
ggcaaaagca gccaccgtgt cggcgcacga ggctttttat tctaaattga aaaagaaaaa 1320
ttgggtaatt aacttaactt atcaaggata acattgtcat atcacaaaaa atattttatt 1380
ttgatgaata gttacagttt gtaaaataat taaatcaatt aagaaaaata agggcatttt 1440
cattgtaaaa taacgtaatt ttttagtgtt aggagtaagt gtagcgtttt taaatttaaa 1500
gaggcaagct agaggaagat ggagctgtca actttcaagt aatgtatgca tcaaggtaag 1560
tgacagagct aaggagaaat ggacaagtac taatcatcgt tataaaaaat taaacagagc 1620
agcattttgt cagttctggc catatatatt tttcaaggat tgggactgtt agcaccgctg 1680
taattttatt ttcaagctct tctctgtcaa aacctatttt actttccaaa atatcttatt 1740
ccattttttt agtttctttc tgattcaaga tttttttttt aaaaaaaaaa aatctgtttc 1800
ttccaaacaa ctccaattac aattttttt tataaatttt tgaattatta aatcatatat 1860

-continued agttaactaa agagaatcat atatacaaac taaatagaat taaaagtgga ctcaaatggc 1920
tattatgtta tttttttcta aattaaaaaa aaaagtttag aatcagagcc tccttgtaag 1980
ccataaaaaa aaagaaaaga aaagtttata atgcaaaagt atttgtgaga aaaaaaaaaa 2040
acactttgat gtagttgcat gaatgtaaag agttagatag agaaatagag tgtataatta 2100
gatttatttt tttctttaaa gtaatcgcaa tataagaggg gttaagaatt tcacaggagt 2160
gccactgatt caactctttt tcaagagaat tgatgttctg gaagaaaatt atgactctat 2220
cattgctatt agtttgtctt gtaattcaat tattgccgac aagtattaac tgtgattatt 2280
tttattttaa aaattattat tattaatgta ttgcaatttt gagccttata attgcaatta 2340
gtttgtcttg taactaaatt attgccgaca aacactatca tgctgacaaa caatgcatgc 2400
acgtcctcag tcacccacgt cctctacttg tgtgaatgtg tatataaata tatctggagc 2460
atattataaa accagaagca aaagcaactg aagttttgaa tacggttcac cagaagttag 2520
aagatatctt ttctaatttg aagaatatgg aaactcctta tccaggttct taggccatgt 2580
tcagctgaat gtcacttata atttttattt taatatatgt atttatgaat acaattgttg 2640
ttatgatttt ttcaggtaag aacggatccc cgggtggtca gtcccttatg ttacgtcctg 2700
tagaaacccc aacccgtgaa atcaaaaaac tcgacggcct gtgggcattc agtctggatc 2760
gcgaaaactg tggaattgat cagcgttggt gggaaagcgc gttacaagaa agccgggcaa 2820
ttgctgtgcc aggcagtttt aacgatcagt tcgccgatgc agatattcgt aattatgcgg 2880
gcaacgtctg gtatcagcgc gaagtcttta taccgaaagg ttgggcaggc cagcgtatcg 2940
tgctgcgttt cgatgcggtc actcattacg gcaaagtgtg ggtcaataat caggaagtga 3000
tggagcatca gggcggctat acgccatttg aagccgatgt cacgccgtat gttattgccg 3060
ggaaaagtgt acgtatcacc gtttgtgtga acaacgaact gaactggcag actatcccgc 3120
cgggaatggt gattaccgac gaaaacggca agaaaaagca gtcttacttc catgatttct 3180
ttaactatgc cggaatccat cgcagcgtaa tgctctacac cacgccgaac acctgggtgg 3240
acgatatcac cgtggtgacg catgtcgcgc aagactgtaa ccacgcgtct gttgactggc 3300
aggtggtggc caatggtgat gtcagcgttg aactgcgtga tgcggatcaa caggtggttg 3360
caactggaca aggcactagc gggactttgc aagtggtgaa tccgcacctc tggcaaccgg 3420
gtgaaggtta tctctatgaa ctgtgcgtca cagccaaaag ccagacagag tgtgatatct 3480
acccgcttcg cgtcggcatc cggtcagtgg cagtgaaggg cgaacagttc ctgattaacc 3540
acaaaccgtt ctactttact ggctttggtc gtcatgaaga tgcggacttg cgtggcaaag 3600
gattcgataa cgtgctgatg gtgcacgacc acgcattaat ggactggatt ggggccaact 3660
cctaccgtac ctcgcattac ccttacgctg aagagatgct cgactgggca gatgaacatg 3720
gcatcgtggt gattgatgaa actgctgctg tcggctttaa cctctcttta ggcattggtt 3780
tcgaagcggg caacaagccg aaagaactgt acagcgaaga ggcagtcaac ggggaaactc 3840
agcaagcgca cttacaggcg attaaagagc tgatagcgcg tgacaaaaac cacccaagcg 3900
tggtgatgtg gagtattgcc aacgaaccgg atacccgtcc gcaaggtgca cgggaatatt 3960
tcgcgccact ggcggaagca acgcgtaaac tcgacccgac gcgtccgatc acctgcgtca 4020
atgtaatgtt ctgcgacgct cacaccgata ccatcagcga tctctttgat gtgctgtgcc 4080
tgaaccgtta ttacggatgg tatgtccaaa gcggcgattt ggaaacggca gagaaggtac 4140
tggaaaaaga acttctggcc tggcaggaga aactgcatca gccgattatc atcaccgaat 4200
acggcgtgga tacgttagcc gggctgcact caatgtacac cgacatgtgg agtgaagagt 4260
atcagtgtgc atggctggat atgtatcacc gcgtctttga tcgcgtcagc gccgtcgtcg 4320
gtgaacaggt atggaatttc gccgattttg cgacctcgca aggcatattg cgcgttggcg 4380
gtaacaagaa agggatcttc actcgcgacc gcaaaccgaa gtcggcggct tttctgctgc 4440
aaaaacgctg gactggcatg aacttcggtg aaaaaccgca gcagggaggc aaacaatgaa 4500
tcaacaactc tcctggcgca ccatcgtcgg ctacagcctc gggaattgct acgagctcgt 4560
tgcctattgt tggttgtcgt gttgtctggc tgtgtctgtt gcccattgtg gtggttatgt 4620
gttgcatcat ggtctaaaag gatcatcaat gtttttcgct tctgttcctt tctgtttctc 4680
atttgtgaat aataatggtg tctttatgaa catccagttt ctggtttctt ttctgattgc 4740
agtttgagta tttgtttttg cttttgcttc cgtctactac accactttgc aattactgta 4800
tcactcatgc attgttgata tactttagcc ttcgatccat cttctgtttg atgattcaaa 4860
tggtatttat ttaactcata cccaagtgaa gcataaagtt agaggagagt tcatgttcca 4920
ttacctgttt gtttcatgag caactcatct taataaacat aagaaaaacc ataatgcaat 4980
ctgtgtagct gatagacttt gatgacagac ggactcataa gtaacaagag gaaacatgat 5040
aaacatgtac ggaagtcga 5059

<210> SEQ ID NO 28
<211> LENGTH: 4945
<212> TYPE: DNA
<213> ORGANISM: Artificial Sequence
<220> FEATURE:
<223> OTHER INFORMATION: expression cassette

<400> SEQUENCE: 28
ggcgcgccct tgtaaacact ggagtgggag gaatccacac tccacactcc caatttagaa 60
agtaaacact acctaaaggt atttacagtc aggatttttt tttccatgta acctcaaatg 120
cactatgcaa taaaatataa atataaataa agcaagcagt tactaagtct ttaggttgtt 180
aggcagatgc taaggccttg tcctgaataa gcccagcaat tcaaacttaa gattacacta 240
taaaaagggg gcgcaaaggc aaagaaagtg gcacggcaag tgcagcgaag gaagcaaagg 300
agagcatgtc acactgagat tacatgtctg atatttggct ccgcttcttc cctttaaaca 360
cctcgaaata agcatcaagg aagtggtctt gtcatcatct tcttccagta catcaatgga 420
gaaacaacat tcgaacacat ggaaataaga aaaatcatta aaattgacta ctactgttgc 480
atattcataa tatgactgct ggcttttctt ctatctcagt ttttttcaga gctcaactaa 540
gggcagtttg atgctgtcat tggatagcag tagcttgaaa aactacagta ctttagtggt 600
tagtaaacac ttattgctat aatttggaat ttaggttcat tttatccgat actcgaaata 660
cgctaatggg aaaaatagtc aaaactcagg taattttttc atttctcttt ttatgtttct 720
aaacacatca aaactctctc ttgatgttta aaaaaattta ttaactttta acttttattt 780
gtgtcctttc ttatttcatc catgatgtcg taaaacccac tgttaatcaa taaaaatttc 840
tgaagataga ataatgaagg atacaaaaaa atttacaagc cttttgtata tgatagttga 900
ctatgtgtat cgggacaatg ttgtgagcat tagattggac aagttatgaa tttttatcag 960
tctagctcat acgcaaaaac tttgaaaaac tttgaaaaga ataagttatc catataacac 1020
aaaatcacca tttatactta gctcatttat attttttatg gatatgaatg taaatttctg 1080
cctttggaga gtaataataa tccaatatcg tcgacgtggc cgttgcagtt gccgagtcga 1140
tgcaaaaaga gcaacggcga tttgttgaag agaagcaaca gcaactgaat aataatataa 1200

-continued

```
cagcaacaac aacgttgatt cttcgaaaga gaaaagagtc aaatccggca aaaaggccaa   1260
ggcaaaagca gccaccgtgt cggcgcacga ggctttttat tctaaattga aaaagaaaaa   1320
ttgggtaatt aacttaactt atcaaggata acattgtcat atcacaaaaa atattttatt   1380
ttgatgaata gttacagttt gtaaaataat taaatcaatt aagaaaaata agggcatttt   1440
cattgtaaaa taacgtaatt ttttagtgtt aggagtaagt gtagcgtttt taaatttaaa   1500
gaggcaagct agaggaagat ggagctgtca actttcaagt aatgtatgca tcaaggtaag   1560
tgacagagct aaggagaaat ggacaagtac taatcatcgt tataaaaaat taaacagagc   1620
agcattttgt cagttctggc catatatatt tttcaaggat tgggactgtt agcaccgctg   1680
taattttatt ttcaagctct tctctgtcaa aacctatttt actttccaaa atatcttatt   1740
ccattttttt agtttctttc tgattcaaga tttttttttt aaaaaaaaaa aatctgtttc   1800
ttccaaacaa ctccaattac aatttttttt tataaatttt tgaattatta aatcatatat   1860
agttaactaa agagaatcat atatacaaac taaatagaat taaaagtgga ctcaaatggc   1920
tattatgtta ttttttttcta aattaaaaaa aaaagtttag aatcagagcc tccttgtaag   1980
ccataaaaaa aaagaaaaga aaagtttata atgcaaaagt atttgtgaga aaaaaaaaaa   2040
acactttgat gtagttgcat gaatgtaaag agttagatag agaaatagag tgtataatta   2100
gatttatttt tttctttaaa gtaatcgcaa tataagaggg gttaagaatt tcacaggagt   2160
gccactgatt caactctttt tcaagagaat tgatgttctg gaagaaaatt atgactctat   2220
cattgctatt agtttgtctt gtaattcaat tattgccgac aagtattaac tgtgattatt   2280
tttattttaa aaattattat tattaatgta ttgcaatttt gagccttata attgcaatta   2340
gtttgtcttg taactaaatt attgccgaca aacactatca tgctgacaaa caatgcatgc   2400
acgtcctcag tcacccacgt cctctacttg tgtgaatgtg tatataaata tatctggagc   2460
atattataaa accagaagca aaagcaactg aagttttgaa tacggttcac cagaagttag   2520
aagatatctt ttctaatttg aagaatatgg gatccccggg tggtcagtcc cttatgttac   2580
gtcctgtaga aaccccaacc cgtgaaatca aaaaactcga cggcctgtgg gcattcagtc   2640
tggatcgcga aaactgtgga attgatcagc gttggtggga aagcgcgtta caagaaagcc   2700
gggcaattgc tgtgccaggc agttttaacg atcagttcgc cgatgcagat attcgtaatt   2760
atgcgggcaa cgtctggtat cagcgcgaag tctttatacc gaaaggttgg gcaggccagc   2820
gtatcgtgct gcgtttcgat gcggtcactc attacggcaa agtgtgggtc aataatcagg   2880
aagtgatgga gcatcagggc ggctatacgc catttgaagc cgatgtcacg ccgtatgtta   2940
ttgccgggaa aagtgtacgt atcaccgttt gtgtgaacaa cgaactgaac tggcagacta   3000
tcccgccggg aatggtgatt accgacgaaa acggcaagaa aaagcagtct tacttccatg   3060
atttctttaa ctatgccgga atccatcgca gcgtaatgct ctacaccacg ccgaacacct   3120
gggtggacga tatcaccgtg gtgacgcatg tcgcgcaaga ctgtaaccac gcgtctgttg   3180
actggcaggt ggtggccaat ggtgatgtca gcgttgaact gcgtgatgcg gatcaacagg   3240
tggttgcaac tggacaaggc actagcggga ctttgcaagt ggtgaatccg cacctctggc   3300
aaccgggtga aggttatctc tatgaactgt gcgtcacagc caaaagccag acagagtgtg   3360
atatctaccc gcttcgcgtc ggcatccggt cagtggcagt gaagggcgaa cagttcctga   3420
ttaaccacaa accgttctac tttactggct ttggtcgtca tgaagatgcg gacttgcgtg   3480
gcaaaggatt cgataacgtg ctgatggtgc acgaccacgc attaatggac tggattgggg   3540
ccaactccta ccgtacctcg cattaccctt acgctgaaga gatgctcgac tgggcagatg   3600
```

```
aacatggcat cgtggtgatt gatgaaactg ctgctgtcgg ctttaacctc tctttaggca   3660
ttggtttcga agcgggcaac aagccgaaag aactgtacag cgaagaggca gtcaacgggg   3720
aaactcagca agcgcactta caggcgatta aagagctgat agcgcgtgac aaaaaccacc   3780
caagcgtggt gatgtggagt attgccaacg aaccggatac ccgtccgcaa ggtgcacggg   3840
aatatttcgc gccactggcg gaagcaacgc gtaaactcga cccgacgcgt ccgatcacct   3900
gcgtcaatgt aatgttctgc gacgctcaca ccgataccat cagcgatctc tttgatgtgc   3960
tgtgcctgaa ccgttattac ggatggtatg tccaaagcgg cgatttggaa acggcagaga   4020
aggtactgga aaaagaactt ctggcctggc aggagaaact gcatcagccg attatcatca   4080
ccgaatacgg cgtggatacg ttagccgggc tgcactcaat gtacaccgac atgtggagtg   4140
aagagtatca gtgtgcatgg ctggatatgt atcaccgcgt ctttgatcgc gtcagcgccg   4200
tcgtcggtga acaggtatgg aatttcgccg attttgcgac ctcgcaaggc atattgcgcg   4260
ttggcggtaa caagaaaggg atcttcactc gcgaccgcaa accgaagtcg gcggcttttc   4320
tgctgcaaaa acgctggact ggcatgaact tcggtgaaaa accgcagcag ggaggcaaac   4380
aatgaatcaa caactctcct ggcgcaccat cgtcggctac agcctcggga attgctacga   4440
gctcgttgcc tattgttggt tgtcgtgttg tctggctgtg tctgttgccc attgtggtgg   4500
ttatgtgttg catcatggtc taaaaggatc atcaatgttt ttcgcttctg ttcctttctg   4560
tttctcattt gtgaataata atggtgtctt tatgaacatc cagtttctgg tttctttctt   4620
gattgcagtt tgagtatttg tttttgcttt tgcttccgtc tactacacca ctttgcaatt   4680
actgtatcac tcatgcattg ttgatatact ttagccttcg atccatcttc tgtttgatga   4740
ttcaaatggt atttatttaa ctcataccca agtgaagcat aaagttagag gagagttcat   4800
gttccattac ctgtttgttt catgagcaac tcatcttaat aaacataaga aaaaccataa   4860
tgcaatctgt gtagctgata gactttgatg acagacggac tcataagtaa caagaggaaa   4920
catgataaac atgtacggaa gtcga                                          4945
```

```
<210> SEQ ID NO 29
<211> LENGTH: 4941
<212> TYPE: DNA
<213> ORGANISM: Artificial Sequence
<220> FEATURE:
<223> OTHER INFORMATION: expression cassette

<400> SEQUENCE: 29
```

```
ggcgcgccct tgtaaacact ggagtgggag gaatccacac tccacactcc caatttagaa     60
agtaaacact acctaaaggt atttacagtc aggatttttt tttccatgta acctcaaatg    120
cactatgcaa taaaatataa atataaataa agcaagcagt tactaagtct ttaggttgtt    180
aggcagatgc taaggccttg tcctgaataa gcccagcaat tcaaacttaa gattacacta    240
taaaaagggg gcgcaaaggc aaagaaagtg gcacggcaag tgcagcgaag gaagcaaagg    300
agagcatgtc acactgagat tacatgtctg atatttggct ccgcttcttc cctttaaaca    360
cctcgaaata agcatcaagg aagtggtctt gtcatcatct tcttccagta catcaatgga    420
gaaacaacat tcgaacacat ggaaataaga aaaatcatta aaattgacta ctactgttgc    480
atattcataa tatgactgct ggcttttctt ctatctcagt ttttttcaga gctcaactaa    540
gggcagtttg atgctgtcat tggatagcag tagcttgaaa aactacagta ctttagtggt    600
tagtaaacac ttattgctat aatttggaat ttaggttcat tttatccgat actcgaaata    660
```

-continued

```
cgctaatggg aaaaatagtc aaaactcagg taattttttc atttctcttt ttatgtttct    720
aaacacatca aaactctctc ttgatgttta aaaaaattta ttaactttta acttttattt    780
gtgtcctttc ttatttcatc catgatgtcg taaaacccac tgttaatcaa taaaaatttc    840
tgaagataga ataatgaagg atacaaaaaa atttacaagc cttttgtata tgatagttga    900
ctatgtgtat cgggacaatg ttgtgagcat tagattggac aagttatgaa tttttatcag    960
tctagctcat acgcaaaaac tttgaaaaac tttgaaaaga ataagttatc catataacac   1020
aaaatcacca tttatactta gctcatttat attttttatg gatatgaatg taaatttctg   1080
cctttggaga gtaataataa tccaatatcg tcgacgtggc cgttgcagtt gccgagtcga   1140
tgcaaaaaga gcaacggcga tttgttgaag agaagcaaca gcaactgaat aataatataa   1200
cagcaacaac aacgttgatt cttcgaaaga gaaaagagtc aaatccggca aaaaggccaa   1260
ggcaaaagca gccaccgtgt cggcgcacga ggctttttat tctaaattga aaaagaaaaa   1320
ttgggtaatt aacttaactt atcaaggata acattgtcat atcacaaaaa atattttatt   1380
ttgatgaata gttacagttt gtaaaataat taaatcaatt aagaaaaata agggcatttt   1440
cattgtaaaa taacgtaatt ttttagtgtt aggagtaagt gtagcgtttt taaatttaaa   1500
gaggcaagct agaggaagat ggagctgtca actttcaagt aatgtatgca tcaaggtaag   1560
tgacagagct aaggagaaat ggacaagtac taatcatcgt tataaaaaat taaacagagc   1620
agcattttgt cagttctggc catatatatt tttcaaggat tgggactgtt agcaccgctg   1680
taattttatt ttcaagctct tctctgtcaa aacctatttt actttccaaa atatcttatt   1740
ccattttttt agtttctttc tgattcaaga tttttttttt aaaaaaaaaa aatctgtttc   1800
ttccaaacaa ctccaattac aatttttttt tataaatttt tgaattatta aatcatatat   1860
agttaactaa agagaatcat atatacaaac taaatagaat taaaagtgga ctcaaatggc   1920
tattatgtta tttttttcta aattaaaaaa aaaagtttag aatcagagcc tccttgtaag   1980
ccataaaaaa aaagaaaaga aaagtttata atgcaaaagt atttgtgaga aaaaaaaaaa   2040
acactttgat gtagttgcat gaatgtaaag agttagatag agaaatagag tgtataatta   2100
gatttatttt tttctttaaa gtaatcgcaa tataagaggg gttaagaatt tcacaggagt   2160
gccactgatt caactctttt tcaagagaat tgatgttctg gaagaaaatt atgactctat   2220
cattgctatt agtttgtctt gtaattcaat tattgccgac aagtattaac tgtgattatt   2280
tttattttaa aaattattat tattaatgta ttgcaatttt gagccttata attgcaatta   2340
gtttgtcttg taactaaatt attgccgaca aacactatca tgctgacaaa caatgcatgc   2400
acgtcctcag tcacccacgt cctctacttg tgtgaatgtg tatataaata tatctggagc   2460
atattataaa accagaagca aaagcaactg aagttttgaa tacggttcac cagaagttag   2520
aagatatctt ttctaatttg aagaaggatc cccgggtggt cagtccctta tgttacgtcc   2580
tgtagaaacc ccaacccgtg aaatcaaaaa actcgacggc ctgtgggcat tcagtctgga   2640
tcgcgaaaac tgtggaattg atcagcgttg gtgggaaagc gcgttacaag aaagccgggc   2700
aattgctgtg ccaggcagtt ttaacgatca gttcgccgat gcagatattc gtaattatgc   2760
gggcaacgtc tggtatcagc gcgaagtctt tataccgaaa ggttgggcag gccagcgtat   2820
cgtgctgcgt ttcgatgcgg tcactcatta cggcaaagtg tgggtcaata atcaggaagt   2880
gatggagcat cagggcggct atacgccatt tgaagccgat gtcacgccgt atgttattgc   2940
cgggaaaagt gtacgtatca ccgtttgtgt gaacaacgaa ctgaactggc agactatccc   3000
gccgggaatg gtgattaccg acgaaaacgg caagaaaaag cagtcttact tccatgattt   3060
```

ctttaactat gccggaatcc atcgcagcgt aatgctctac accacgccga acacctgggt 3120
ggacgatatc accgtggtga cgcatgtcgc gcaagactgt aaccacgcgt ctgttgactg 3180
gcaggtggtg gccaatggtg atgtcagcgt tgaactgcgt gatgcggatc aacaggtggt 3240
tgcaactgga caaggcacta gcgggacttt gcaagtggtg aatccgcacc tctggcaacc 3300
gggtgaaggt tatctctatg aactgtgcgt cacagccaaa agccagacag agtgtgatat 3360
ctacccgctt cgcgtcggca tccggtcagt ggcagtgaag ggcgaacagt tcctgattaa 3420
ccacaaaccg ttctacttta ctggctttgg tcgtcatgaa gatgcggact tgcgtggcaa 3480
aggattcgat aacgtgctga tggtgcacga ccacgcatta atggactgga ttggggccaa 3540
ctcctaccgt acctcgcatt acccttacgc tgaagagatg ctcgactggg cagatgaaca 3600
tggcatcgtg gtgattgatg aaactgctgc tgtcggcttt aacctctctt taggcattgg 3660
tttcgaagcg ggcaacaagc cgaaagaact gtacagcgaa gaggcagtca acggggaaac 3720
tcagcaagcg cacttacagg cgattaaaga gctgatagcg cgtgacaaaa accacccaag 3780
cgtggtgatg tggagtattg ccaacgaacc ggatacccgt ccgcaaggtg cacgggaata 3840
tttcgcgcca ctggcggaag caacgcgtaa actcgacccg acgcgtccga tcacctgcgt 3900
caatgtaatg ttctgcgacg ctcacaccga taccatcagc gatctctttg atgtgctgtg 3960
cctgaaccgt tattacggat ggtatgtcca aagcggcgat ttggaaacgg cagagaaggt 4020
actggaaaaa gaacttctgg cctggcagga gaaactgcat cagccgatta tcatcaccga 4080
atacggcgtg gatacgttag ccgggctgca ctcaatgtac accgacatgt ggagtgaaga 4140
gtatcagtgt gcatggctgg atatgtatca ccgcgtcttt gatcgcgtca gcgccgtcgt 4200
cggtgaacag gtatggaatt tcgccgattt tgcgacctcg caaggcatat tgcgcgttgg 4260
cggtaacaag aaagggatct tcactcgcga ccgcaaaccg aagtcggcgg cttttctgct 4320
gcaaaaacgc tggactggca tgaacttcgg tgaaaaaccg cagcagggag gcaaacaatg 4380
aatcaacaac tctcctggcg caccatcgtc ggctacagcc tcgggaattg ctacgagctc 4440
gttgcctatt gttggttgtc gtgttgtctg gctgtgtctg ttgcccattg tggtggttat 4500
gtgttgcatc atggtctaaa aggatcatca atgtttttcg cttctgttcc tttctgtttc 4560
tcatttgtga ataataatgg tgtctttatg aacatccagt ttctggtttc ttttctgatt 4620
gcagtttgag tatttgtttt tgcttttgct tccgtctact acaccacttt gcaattactg 4680
tatcactcat gcattgttga tatactttag ccttcgatcc atcttctgtt tgatgattca 4740
aatggtattt atttaactca tacccaagtg aagcataaag ttagaggaga gttcatgttc 4800
cattacctgt ttgtttcatg agcaactcat cttaataaac ataagaaaaa ccataatgca 4860
atctgtgtag ctgatagact ttgatgacag acggactcat aagtaacaag aggaaacatg 4920
ataaacatgt acggaagtcg a 4941

<210> SEQ ID NO 30
<211> LENGTH: 1972
<212> TYPE: DNA
<213> ORGANISM: Citrus clementina

<400> SEQUENCE: 30
aacaaactcc gcatagtggt tagctaattc ttgcaaagaa ctcaaataac gtttatgtat 60
tgtaaaatgt atttatttat tacactgatt taaatactat atttatattt attatagaac 120
aatagattga aattaatttt cgttggataa atagaaccaa agagtgaaat aatcaaaagg 180

```
gccatttgtg tgtctatttt ttaaacatta ggggtctttg tctatatcta aataaattat    240

gactaaaaac atagggactg taaacgcacg aacattttcg caccgccatg ctctctcgaa    300

acccatgctc atagaactac ttctattaaa tgctaaagaa gagtttaatt gtgataacta    360

aaatgcttat ttacttctaa caagcgcgta aatcagttgg catagagttg ttttaactta    420

accaaagtcc tcagttcgag acttgggagt acagttgtgt taaatacttg ttgggagagc    480

tttggcgcct caatgatcct gcctgtctcg aatctaaatt agtcggggct caatgtagtc    540

tttagatacc agatagttta atacaccaaa aataaataaa atacttattt actttagtta    600

ttatttttca aataattaac tataatcgac tattttaaag ctttacaagg atagttagat    660

ttgatgttga atagaaacag aattaagggt ttagtaaacc aaaaacatta cacgcctctc    720

gtactgacat aaaagaaaaa ttataataat aacagaaaaa tataagaaat aaagaaggaa    780

aagaaagata taaaaatgaa attaactttc agctgttaag taaaactatt acaaaatttc    840

gttctttgct ctcataaaaa ggaagaaagc cagtccttcc aatgcactgt gttcggtagt    900

ggtactaatt acttaatttg ttcgtctttc ttatttacaa ctatttattt tttggaccat    960

atttcgcacg tgcaataatt taacaataca gagcccttaa tcttacctag ttattgtacg   1020

attaaacttg gaccgttgat ccattatctt taccatgcat gacttgttta tttgatacgt   1080

tggcactgtc ggctacttga tctatatgta tcgtcagttc gcttcttatt tattttttgg   1140

accactatgc ttgtggtctt cttatttatt tcctggaccc attgattcat actttatcta   1200

cacatgcagt tgaaccatat atagccgtta atcttacaat tatcagactt cagcggtaaa   1260

tctgttatct ttaccaagca attgtttggt aatggtattt ataccttttct tttttttctt   1320

tttatctgat gacatggtat ttgattactt tgttcgtctt tcttgtttac tactatttat   1380

tttgtggacc atgtttcgca catgcaatga tttaacacta acagttaatc ttacctactt   1440

attgtatgat gaaatctgaa tggttgatcc attatctata gtataccacg cactattatt   1500

tggtaattgc atttattact ttatttgctc gtgtccttcg tatttagaat tatttatttt   1560

ttgaaccatg tatcgcacat gcactaactt aaccatatag agctgttgac cttccctact   1620

tattgtacga ttaaattaga accactgatc cattatcttt accatgcaca acgtgttact   1680

ttgccacgtt ggcaccgtag tgtcggctac ttgatctata tatatcagat caaaccagaa   1740

ataagaactc gctcaagcac aactacttac cttttgagtt ttgaatacgg ttcagtcgaa   1800

gccagcagaa atcttttgcc ttcctgattt gaagattatg ggaactcctt gcgcaggttt   1860

atacataggc catgcatttt caaataaatg tcatttataa ttcttatttt aataggtgta   1920

tttgtgatta agttttataa catgaatttt tcaggttata ccgattggtc gg           1972
```

<210> SEQ ID NO 31
<211> LENGTH: 4366
<212> TYPE: DNA
<213> ORGANISM: Artificial Sequence
<220> FEATURE:
<223> OTHER INFORMATION: expression cassette

<400> SEQUENCE: 31

```
ggcgcgccaa caaactccgc atagtggtta gctaattctt gcaaagaact caaataacgt     60

ttatgtattg taaaatgtat ttatttatta cactgattta aatactatat ttatatttat    120

tatagaacaa tagattgaaa ttaattttcg ttggataaat agaaccaaag agtgaaataa    180

tcaaaagggc catttgtgtg tctatttttt aaacattagg ggtctttgtc tatatctaaa    240

taaattatga ctaaaaacat agggactgta aacgcacgaa cattttcgca ccgccatgct    300
```

```
ctctcgaaac ccatgctcat agaactactt ctattaaatg ctaaagaaga gtttaattgt    360
gataactaaa atgcttattt acttctaaca agcgcgtaaa tcagttggca tagagttgtt    420
ttaacttaac caaagtcctc agttcgagac ttgggagtac agttgtgtta aatacttgtt    480
gggagagctt tggcgcctca atgatcctgc ctgtctcgaa tctaaattag tcggggctca    540
atgtagtctt tagataccag atagtttaat acaccaaaaa taaataaaat acttatttac    600
tttagttatt atttttcaaa taattaacta taatcgacta ttttaaagct ttacaaggat    660
agttagattt gatgttgaat agaaacagaa ttaagggttt agtaaaccaa aaacattaca    720
cgcctctcgt actgacataa aagaaaaatt ataataataa cagaaaaata taagaaataa    780
agaaggaaaa gaaagatata aaaatgaaat taactttcag ctgttaagta aaactattac    840
aaaatttcgt tctttgctct cataaaaagg aagaaagcca gtccttccaa tgcactgtgt    900
tcggtagtgg tactaattac ttaatttgtt cgtctttctt atttacaact atttattttt    960
tggaccatat ttcgcacgtg caataattta acaatacaga gcccttaatc ttacctagtt   1020
attgtacgat taaacttgga ccgttgatcc attatcttta ccatgcatga cttgtttatt   1080
tgatacgttg gcactgtcgg ctacttgatc tatatgtatc gtcagttcgc ttcttattta   1140
tttttggac cactatgctt gtggtcttct tatttatttc ctggacccat tgattcatac   1200
tttatctaca catgcagttg aaccatatat agccgttaat cttacaatta tcagacttca   1260
gcggtaaatc tgttatcttt accaagcaat tgtttggtaa tggtatttat acctttcttt   1320
tttttctttt tatctgatga catggtattt gattactttg ttcgtctttc ttgtttacta   1380
ctatttattt tgtggaccat gtttcgcaca tgcaatgatt taacactaac agttaatctt   1440
acctacttat tgtatgatga aatctgaatg gttgatccat tatctatagt ataccacgca   1500
ctattatttg gtaattgcat ttattacttt atttgctcgt gtccttcgta tttagaatta   1560
tttatttttt gaaccatgta tcgcacatgc actaacttaa ccatatagag ctgttgacct   1620
tccctactta ttgtacgatt aaattagaac cactgatcca ttatctttac catgcacaac   1680
gtgttacttt gccacgttgg caccgtagtg tcggctactt gatctatata tatcagatca   1740
aaccagaaat aagaactcgc tcaagcacaa ctacttacct tttgagtttt gaatacggtt   1800
cagtcgaagc cagcagaaat cttttgcctt cctgatttga agattatggg aactccttgc   1860
gcaggtttat acataggcca tgcattttca aataaatgtc atttataatt cttattttaa   1920
taggtgtatt tgtgattaag ttttataaca tgaatttttc aggttatacc ggatccccgg   1980
gtggtcagtc ccttatgtta cgtcctgtag aaaccccaac ccgtgaaatc aaaaaactcg   2040
acggcctgtg ggcattcagt ctggatcgcg aaaactgtgg aattgatcag cgttggtggg   2100
aaagcgcgtt acaagaaagc cgggcaattg ctgtgccagg cagttttaac gatcagttcg   2160
ccgatgcaga tattcgtaat tatgcgggca acgtctggta tcagcgcgaa gtctttatac   2220
cgaaaggttg ggcaggccag cgtatcgtgc tgcgtttcga tgcggtcact cattacggca   2280
aagtgtgggt caataatcag gaagtgatgg agcatcaggg cggctatacg ccatttgaag   2340
ccgatgtcac gccgtatgtt attgccggga aaagtgtacg tatcaccgtt tgtgtgaaca   2400
acgaactgaa ctggcagact atcccgccgg gaatggtgat taccgacgaa aacggcaaga   2460
aaaagcagtc ttacttccat gatttcttta actatgccgg aatccatcgc agcgtaatgc   2520
tctacaccac gccgaacacc tgggtggacg atatcaccgt ggtgacgcat gtcgcgcaag   2580
actgtaacca cgcgtctgtt gactggcagg tggtggccaa tggtgatgtc agcgttgaac   2640
```

```
tgcgtgatgc ggatcaacag gtggttgcaa ctggacaagg cactagcggg actttgcaag   2700

tggtgaatcc gcacctctgg caaccgggtg aaggttatct ctatgaactg tgcgtcacag   2760

ccaaaagcca gacagagtgt gatatctacc cgcttcgcgt cggcatccgg tcagtggcag   2820

tgaagggcga acagttcctg attaaccaca aaccgttcta ctttactggc tttggtcgtc   2880

atgaagatgc ggacttgcgt ggcaaaggat tcgataacgt gctgatggtg cacgaccacg   2940

cattaatgga ctggattggg gccaactcct accgtacctc gcattaccct tacgctgaag   3000

agatgctcga ctgggcagat gaacatggca tcgtggtgat tgatgaaact gctgctgtcg   3060

gctttaacct ctctttaggc attggtttcg aagcgggcaa caagccgaaa gaactgtaca   3120

gcgaagaggc agtcaacggg gaaactcagc aagcgcactt acaggcgatt aaagagctga   3180

tagcgcgtga caaaaaccac ccaagcgtgg tgatgtggag tattgccaac gaaccggata   3240

cccgtccgca aggtgcacgg gaatatttcg cgccactggc ggaagcaacg cgtaaactcg   3300

acccgacgcg tccgatcacc tgcgtcaatg taatgttctg cgacgctcac accgatacca   3360

tcagcgatct ctttgatgtg ctgtgcctga accgttatta cggatggtat gtccaaagcg   3420

gcgatttgga aacggcagag aaggtactgg aaaaagaact tctggcctgg caggagaaac   3480

tgcatcagcc gattatcatc accgaatacg gcgtggatac gttagccggg ctgcactcaa   3540

tgtacaccga catgtggagt gaagagtatc agtgtgcatg gctggatatg tatcaccgcg   3600

tctttgatcg cgtcagcgcc gtcgtcggtg aacaggtatg gaatttcgcc gattttgcga   3660

cctcgcaagg catattgcgc gttggcggta acaagaaagg gatcttcact cgcgaccgca   3720

aaccgaagtc ggcggctttt ctgctgcaaa aacgctggac tggcatgaac ttcggtgaaa   3780

aaccgcagca gggaggcaaa caatgaatca acaactctcc tggcgcacca tcgtcggcta   3840

cagcctcggg aattgctacg agctcgttgc ctattgttgg ttgtcgtgtt gtctggctgt   3900

gtctgttgcc cattgtggtg gttatgtgtt gcatcatggt ctaaaaggat catcaatgtt   3960

tttcgcttct gttcctttct gtttctcatt tgtgaataat aatggtgtct ttatgaacat   4020

ccagtttctg gtttcttttc tgattgcagt ttgagtattt gtttttgctt ttgcttccgt   4080

ctactacacc actttgcaat tactgtatca ctcatgcatt gttgatatac tttagccttc   4140

gatccatctt ctgtttgatg attcaaatgg tatttattta actcataccc aagtgaagca   4200

taaagttaga ggagagttca tgttccatta cctgtttgtt tcatgagcaa ctcatcttaa   4260

taaacataag aaaaaccata atgcaatctg tgtagctgat agactttgat gacagacgga   4320

ctcataagta acaagaggaa acatgataaa catgtacgga agtcga                  4366
```

<210> SEQ ID NO 32
<211> LENGTH: 4244
<212> TYPE: DNA
<213> ORGANISM: Artificial Sequence
<220> FEATURE:
<223> OTHER INFORMATION: expression cassette

<400> SEQUENCE: 32

```
ggcgcgccaa caaactccgc atagtggtta gctaattctt gcaaagaact caaataacgt     60

ttatgtattg taaaatgtat ttatttatta cactgattta aatactatat ttatatttat    120

tatagaacaa tagattgaaa ttaattttcg ttggataaat agaaccaaag agtgaaataa    180

tcaaaagggc catttgtgtg tctatttttt aaacattagg ggtctttgtc tatatctaaa    240

taaattatga ctaaaaacat agggactgta aacgcacgaa cattttcgca ccgccatgct    300

ctctcgaaac ccatgctcat agaactactt ctattaaatg ctaaagaaga gtttaattgt    360
```

-continued

```
gataactaaa atgcttattt acttctaaca agcgcgtaaa tcagttggca tagagttgtt     420
ttaacttaac caaagtcctc agttcgagac ttgggagtac agttgtgtta aatacttgtt     480
gggagagctt tggcgcctca atgatcctgc ctgtctcgaa tctaaattag tcggggctca     540
atgtagtctt tagataccag atagtttaat acaccaaaaa taaataaaat acttatttac     600
tttagttatt atttttcaaa taattaacta taatcgacta ttttaaagct ttacaaggat     660
agttagattt gatgttgaat agaaacagaa ttaagggttt agtaaaccaa aaacattaca     720
cgcctctcgt actgacataa aagaaaaatt ataataataa cagaaaaata taagaaataa     780
agaaggaaaa gaaagatata aaaatgaaat taactttcag ctgttaagta aaactattac     840
aaaatttcgt tctttgctct cataaaaagg aagaaagcca gtccttccaa tgcactgtgt     900
tcggtagtgg tactaattac ttaatttgtt cgtctttctt atttacaact atttattttt     960
tggaccatat ttcgcacgtg caataattta acaatacaga gcccttaatc ttacctagtt    1020
attgtacgat taaacttgga ccgttgatcc attatcttta ccatgcatga cttgtttatt    1080
tgatacgttg gcactgtcgg ctacttgatc tatatgtatc gtcagttcgc ttcttattta    1140
tttttggac cactatgctt gtggtcttct tatttatttc ctggacccat tgattcatac    1200
tttatctaca catgcagttg aaccatatat agccgttaat cttacaatta tcagacttca    1260
gcggtaaatc tgttatcttt accaagcaat tgtttggtaa tggtatttat acctttcttt    1320
tttttctttt tatctgatga catggtattt gattactttg ttcgtctttc ttgtttacta    1380
ctatttattt tgtggaccat gtttcgcaca tgcaatgatt taacactaac agttaatctt    1440
acctacttat tgtatgatga aatctgaatg gttgatccat tatctatagt ataccacgca    1500
ctattatttg gtaattgcat ttattacttt atttgctcgt gtccttcgta tttagaatta    1560
tttatttttt gaaccatgta tcgcacatgc actaacttaa ccatatagag ctgttgacct    1620
tccctactta ttgtacgatt aaattagaac cactgatcca ttatctttac catgcacaac    1680
gtgttacttt gccacgttgg caccgtagtg tcggctactt gatctatata tatcagatca    1740
aaccagaaat aagaactcgc tcaagcacaa ctacttacct tttgagtttt gaatacggtt    1800
cagtcgaagc cagcagaaat cttttgcctt cctgatttga agattatggg atccccgggt    1860
ggtcagtccc ttatgttacg tcctgtagaa accccaaccc gtgaaatcaa aaaactcgac    1920
ggcctgtggg cattcagtct ggatcgcgaa aactgtggaa ttgatcagcg ttggtgggaa    1980
agcgcgttac aagaaagccg ggcaattgct gtgccaggca gttttaacga tcagttcgcc    2040
gatgcagata ttcgtaatta tgcgggcaac gtctggtatc agcgcgaagt ctttataccg    2100
aaaggttggg caggccagcg tatcgtgctg cgtttcgatg cggtcactca ttacggcaaa    2160
gtgtgggtca ataatcagga agtgatggag catcagggcg gctatacgcc atttgaagcc    2220
gatgtcacgc cgtatgttat tgccgggaaa agtgtacgta tcaccgtttg tgtgaacaac    2280
gaactgaact ggcagactat cccgccggga atggtgatta ccgacgaaaa cggcaagaaa    2340
aagcagtctt acttccatga tttctttaac tatgccggaa tccatcgcag cgtaatgctc    2400
tacaccacgc cgaacacctg ggtggacgat atcaccgtgg tgacgcatgt cgcgcaagac    2460
tgtaaccacg cgtctgttga ctggcaggtg gtggccaatg gtgatgtcag cgttgaactg    2520
cgtgatgcgg atcaacaggt ggttgcaact ggacaaggca ctagcgggac tttgcaagtg    2580
gtgaatccgc acctctggca accgggtgaa ggttatctct atgaactgtg cgtcacagcc    2640
aaaagccaga cagagtgtga tatctacccg cttcgcgtcg gcatccggtc agtggcagtg    2700
```

aagggcgaac agttcctgat taaccacaaa ccgttctact ttactggctt tggtcgtcat 2760
gaagatgcgg acttgcgtgg caaaggattc gataacgtgc tgatggtgca cgaccacgca 2820
ttaatggact ggattggggc caactcctac cgtacctcgc attaccctta cgctgaagag 2880
atgctcgact gggcagatga acatggcatc gtggtgattg atgaaactgc tgctgtcggc 2940
tttaacctct ctttaggcat tggtttcgaa gcgggcaaca agccgaaaga actgtacagc 3000
gaagaggcag tcaacgggga aactcagcaa gcgcacttac aggcgattaa agagctgata 3060
gcgcgtgaca aaaaccaccc aagcgtggtg atgtggagta ttgccaacga accggatacc 3120
cgtccgcaag gtgcacggga atatttcgcg ccactggcgg aagcaacgcg taaactcgac 3180
ccgacgcgtc cgatcacctg cgtcaatgta atgttctgcg acgctcacac cgataccatc 3240
agcgatctct ttgatgtgct gtgcctgaac cgttattacg gatggtatgt ccaaagcggc 3300
gatttggaaa cggcagagaa ggtactggaa aaagaacttc tggcctggca ggagaaactg 3360
catcagccga ttatcatcac cgaatacggc gtggatacgt tagccgggct gcactcaatg 3420
tacaccgaca tgtggagtga agagtatcag tgtgcatggc tggatatgta tcaccgcgtc 3480
tttgatcgcg tcagcgccgt cgtcggtgaa caggtatgga atttcgccga ttttgcgacc 3540
tcgcaaggca tattgcgcgt tggcggtaac aagaaaggga tcttcactcg cgaccgcaaa 3600
ccgaagtcgg cggcttttct gctgcaaaaa cgctggactg gcatgaactt cggtgaaaaa 3660
ccgcagcagg gaggcaaaca atgaatcaac aactctcctg gcgcaccatc gtcggctaca 3720
gcctcgggaa ttgctacgag ctcgttgcct attgttggtt gtcgtgttgt ctggctgtgt 3780
ctgttgccca ttgtggtggt tatgtgttgc atcatggtct aaaaggatca tcaatgtttt 3840
tcgcttctgt tcctttctgt ttctcatttg tgaataataa tggtgtcttt atgaacatcc 3900
agtttctggt ttcttttctg attgcagttt gagtatttgt ttttgctttt gcttccgtct 3960
actacaccac tttgcaatta ctgtatcact catgcattgt tgatatactt tagccttcga 4020
tccatcttct gtttgatgat tcaaatggta tttatttaac tcatacccaa gtgaagcata 4080
aagttagagg agagttcatg ttccattacc tgtttgtttc atgagcaact catcttaata 4140
aacataagaa aaaccataat gcaatctgtg tagctgatag actttgatga cagacggact 4200
cataagtaac aagaggaaac atgataaaca tgtacggaag tcga 4244

<210> SEQ ID NO 33
<211> LENGTH: 4240
<212> TYPE: DNA
<213> ORGANISM: Artificial Sequence
<220> FEATURE:
<223> OTHER INFORMATION: expression cassette

<400> SEQUENCE: 33
ggcgcgccaa caaactccgc atagtggtta gctaattctt gcaaagaact caaataacgt 60
ttatgtattg taaaatgtat ttatttatta cactgattta aatactatat ttatatttat 120
tatagaacaa tagattgaaa ttaattttcg ttggataaat agaaccaaag agtgaaataa 180
tcaaaagggc catttgtgtg tctatttttt aaacattagg ggtctttgtc tatatctaaa 240
taaattatga ctaaaaacat agggactgta aacgcacgaa cattttcgca ccgccatgct 300
ctctcgaaac ccatgctcat agaactactt ctattaaatg ctaaagaaga gtttaattgt 360
gataactaaa atgcttattt acttctaaca agcgcgtaaa tcagttggca tagagttgtt 420
ttaacttaac caaagtcctc agttcgagac ttgggagtac agttgtgtta aatacttgtt 480
gggagagctt tggcgcctca atgatcctgc ctgtctcgaa tctaaattag tcggggctca 540

```
atgtagtctt tagataccag atagtttaat acaccaaaaa taaataaaat acttatttac    600
tttagttatt atttttcaaa taattaacta taatcgacta ttttaaagct ttacaaggat    660
agttagattt gatgttgaat agaaacagaa ttaagggttt agtaaaccaa aaacattaca    720
cgcctctcgt actgacataa aagaaaaatt ataataataa cagaaaaata taagaaataa    780
agaaggaaaa gaaagatata aaaatgaaat taactttcag ctgttaagta aaactattac    840
aaaatttcgt tctttgctct cataaaaagg aagaaagcca gtccttccaa tgcactgtgt    900
tcggtagtgg tactaattac ttaatttgtt cgtctttctt atttacaact atttattttt    960
tggaccatat ttcgcacgtg caataattta acaatacaga gcccttaatc ttacctagtt   1020
attgtacgat taaacttgga ccgttgatcc attatcttta ccatgcatga cttgtttatt   1080
tgatacgttg gcactgtcgg ctacttgatc tatatgtatc gtcagttcgc ttcttattta   1140
ttttttggac cactatgctt gtggtcttct tatttatttc ctggacccat tgattcatac   1200
tttatctaca catgcagttg aaccatatat agccgttaat cttacaatta tcagacttca   1260
gcggtaaatc tgttatcttt accaagcaat tgtttggtaa tggtatttat acctttcttt   1320
tttttctttt tatctgatga catggtattt gattactttg ttcgtctttc ttgtttacta   1380
ctatttattt tgtggaccat gtttcgcaca tgcaatgatt taacactaac agttaatctt   1440
acctacttat tgtatgatga aatctgaatg gttgatccat tatctatagt ataccacgca   1500
ctattatttg gtaattgcat ttattacttt atttgctcgt gtccttcgta tttagaatta   1560
tttatttttt gaaccatgta tcgcacatgc actaacttaa ccatatagag ctgttgacct   1620
tccctactta ttgtacgatt aaattagaac cactgatcca ttatctttac catgcacaac   1680
gtgttacttt gccacgttgg caccgtagtg tcggctactt gatctatata tatcagatca   1740
aaccagaaat aagaactcgc tcaagcacaa ctacttacct tttgagtttt gaatacggtt   1800
cagtcgaagc cagcagaaat cttttgcctt cctgatttga agatggatcc ccgggtggtc   1860
agtcccttat gttacgtcct gtagaaaccc caacccgtga aatcaaaaaa ctcgacggcc   1920
tgtgggcatt cagtctggat cgcgaaaact gtggaattga tcagcgttgg tgggaaagcg   1980
cgttacaaga aagccgggca attgctgtgc caggcagttt taacgatcag ttcgccgatg   2040
cagatattcg taattatgcg ggcaacgtct ggtatcagcg cgaagtcttt ataccgaaag   2100
gttgggcagg ccagcgtatc gtgctgcgtt tcgatgcggt cactcattac ggcaaagtgt   2160
gggtcaataa tcaggaagtg atggagcatc agggcggcta tacgccattt gaagccgatg   2220
tcacgccgta tgttattgcc gggaaaagtg tacgtatcac cgtttgtgtg aacaacgaac   2280
tgaactggca gactatcccg ccgggaatgg tgattaccga cgaaaacggc aagaaaaagc   2340
agtcttactt ccatgatttc tttaactatg ccggaatcca tcgcagcgta atgctctaca   2400
ccacgccgaa cacctgggtg gacgatatca ccgtggtgac gcatgtcgcg caagactgta   2460
accacgcgtc tgttgactgg caggtggtgg ccaatggtga tgtcagcgtt gaactgcgtg   2520
atgcggatca acaggtggtt gcaactggac aaggcactag cgggactttg caagtggtga   2580
atccgcacct ctggcaaccg ggtgaaggtt atctctatga actgtgcgtc acagccaaaa   2640
gccagacaga gtgtgatatc tacccgcttc gcgtcggcat ccggtcagtg gcagtgaagg   2700
gcgaacagtt cctgattaac cacaaaccgt tctactttac tggctttggt cgtcatgaag   2760
atgcggactt gcgtggcaaa ggattcgata acgtgctgat ggtgcacgac cacgcattaa   2820
tggactggat tggggccaac tcctaccgta cctcgcatta cccttacgct gaagagatgc   2880
```

-continued

```
tcgactgggc agatgaacat ggcatcgtgg tgattgatga aactgctgct gtcggcttta   2940

acctctcttt aggcattggt ttcgaagcgg gcaacaagcc gaaagaactg tacagcgaag   3000

aggcagtcaa cggggaaact cagcaagcgc acttacaggc gattaaagag ctgatagcgc   3060

gtgacaaaaa ccacccaagc gtggtgatgt ggagtattgc caacgaaccg gatacccgtc   3120

cgcaaggtgc acgggaatat ttcgcgccac tggcggaagc aacgcgtaaa ctcgacccga   3180

cgcgtccgat cacctgcgtc aatgtaatgt tctgcgacgc tcacaccgat accatcagcg   3240

atctctttga tgtgctgtgc ctgaaccgtt attacggatg gtatgtccaa agcggcgatt   3300

tggaaacggc agagaaggta ctggaaaaag aacttctggc ctggcaggag aaactgcatc   3360

agccgattat catcaccgaa tacggcgtgg atacgttagc cgggctgcac tcaatgtaca   3420

ccgacatgtg gagtgaagag tatcagtgtg catggctgga tatgtatcac cgcgtctttg   3480

atcgcgtcag cgccgtcgtc ggtgaacagg tatggaattt cgccgatttt gcgacctcgc   3540

aaggcatatt gcgcgttggc ggtaacaaga aagggatctt cactcgcgac cgcaaaccga   3600

agtcggcggc ttttctgctg caaaaacgct ggactggcat gaacttcggt gaaaaaccgc   3660

agcagggagg caaacaatga atcaacaact ctcctggcgc accatcgtcg gctacagcct   3720

cgggaattgc tacgagctcg ttgcctattg ttggttgtcg tgttgtctgg ctgtgtctgt   3780

tgcccattgt ggtggttatg tgttgcatca tggtctaaaa ggatcatcaa tgtttttcgc   3840

ttctgttcct ttctgtttct catttgtgaa taataatggt gtctttatga acatccagtt   3900

tctggtttct tttctgattg cagtttgagt atttgttttt gcttttgctt ccgtctacta   3960

caccactttg caattactgt atcactcatg cattgttgat atactttagc cttcgatcca   4020

tcttctgttt gatgattcaa atggtattta tttaactcat acccaagtga agcataaagt   4080

tagaggagag ttcatgttcc attacctgtt tgtttcatga gcaactcatc ttaataaaca   4140

taagaaaaac cataatgcaa tctgtgtagc tgatagactt tgatgacaga cggactcata   4200

agtaacaaga ggaaacatga taaacatgta cggaagtcga                         4240
```

<210> SEQ ID NO 34
<211> LENGTH: 181
<212> TYPE: DNA
<213> ORGANISM: Artificial Sequence
<220> FEATURE:
<223> OTHER INFORMATION: expression cassette partial sequence

<400> SEQUENCE: 34

```
atggaaacaa ccagcgcagg tttttaggcc agctttactt tcatttgaat atcattcata     60

attcttattt taatacatgc atttgttaat atatttttaa tataaaattt acaggtaatg    120

atggatcccc gggtggtcag tcccttatgt tacgtcctgt agaaacccca acccgtgaaa    180

t                                                                    181
```

<210> SEQ ID NO 35
<211> LENGTH: 20
<212> TYPE: PRT
<213> ORGANISM: Artificial Sequence
<220> FEATURE:
<223> OTHER INFORMATION: chimeric peptide

<400> SEQUENCE: 35

```
Met Glu Thr Thr Ser Ala Gly Asn Asp Gly Ser Pro Gly Gly Gln Ser
1               5                   10                  15

Leu Met Leu Arg
            20
```

<210> SEQ ID NO 36
<211> LENGTH: 165
<212> TYPE: DNA
<213> ORGANISM: Artificial Sequence
<220> FEATURE:
<223> OTHER INFORMATION: expression cassette partial sequence

<400> SEQUENCE: 36
ttctaatttg aagaatatgg aaactcctta tccaggttct taggccatgt tcagctgaat 60
gtcacttata atttttattt taatatatgt atttatgaat acaattgttg ttatgatttt 120
ttcaggtaag aacggatccc cgggtggtca gtcccttatg ttacg 165

<210> SEQ ID NO 37
<211> LENGTH: 20
<212> TYPE: PRT
<213> ORGANISM: Artificial Sequence
<220> FEATURE:
<223> OTHER INFORMATION: chimeric peptide

<400> SEQUENCE: 37

Met Glu Thr Pro Tyr Pro Gly Lys Asn Gly Ser Pro Gly Gly Gln Ser
1 5 10 15

Leu Met Leu Arg
20

<210> SEQ ID NO 38
<211> LENGTH: 51
<212> TYPE: DNA
<213> ORGANISM: Artificial Sequence
<220> FEATURE:
<223> OTHER INFORMATION: expression cassette partial sequence

<400> SEQUENCE: 38
ttctaatttg aagaatatgg gatccccggg tggtcagtcc cttatgttac g 51

<210> SEQ ID NO 39
<211> LENGTH: 12
<212> TYPE: PRT
<213> ORGANISM: Artificial Sequence
<220> FEATURE:
<223> OTHER INFORMATION: chimeric peptide

<400> SEQUENCE: 39

Met Gly Ser Pro Gly Gly Gln Ser Leu Met Leu Arg
1 5 10

<210> SEQ ID NO 40
<211> LENGTH: 47
<212> TYPE: DNA
<213> ORGANISM: Artificial Sequence
<220> FEATURE:
<223> OTHER INFORMATION: expression cassette partial sequence

<400> SEQUENCE: 40
ttctaatttg aagaaggatc cccgggtggt cagtccctta tgttacg 47

<210> SEQ ID NO 41
<211> LENGTH: 174
<212> TYPE: DNA
<213> ORGANISM: Artificial Sequence
<220> FEATURE:
<223> OTHER INFORMATION: expression cassette partial sequence

<400> SEQUENCE: 41

-continued

```
ttcctgattt gaagattatg ggaactcctt gcgcaggttt atacataggc catgcatttt     60

caaataaatg tcatttataa ttcttatttt aataggtgta tttgtgatta agttttataa    120

catgaatttt tcaggttata ccggatcccc gggtggtcag tcccttatgt tacg          174


<210> SEQ ID NO 42
<211> LENGTH: 20
<212> TYPE: PRT
<213> ORGANISM: Artificial Sequence
<220> FEATURE:
<223> OTHER INFORMATION: chimeric peptide

<400> SEQUENCE: 42

Met Gly Thr Pro Cys Ala Gly Tyr Thr Gly Ser Pro Gly Gly Gln Ser
1               5                   10                  15

Leu Met Leu Arg
            20


<210> SEQ ID NO 43
<211> LENGTH: 52
<212> TYPE: DNA
<213> ORGANISM: Artificial Sequence
<220> FEATURE:
<223> OTHER INFORMATION: expression cassette partial sequence

<400> SEQUENCE: 43

ttcctgattt gaagattatg ggatccccgg gtggtcagtc ccttatgtta cg             52


<210> SEQ ID NO 44
<211> LENGTH: 12
<212> TYPE: PRT
<213> ORGANISM: Artificial Sequence
<220> FEATURE:
<223> OTHER INFORMATION: chimeric peptide

<400> SEQUENCE: 44

Met Gly Ser Pro Gly Gly Gln Ser Leu Met Leu Arg
1               5                   10


<210> SEQ ID NO 45
<211> LENGTH: 48
<212> TYPE: DNA
<213> ORGANISM: Artificial Sequence
<220> FEATURE:
<223> OTHER INFORMATION: expression cassette partial sequence

<400> SEQUENCE: 45

ttcctgattt gaagatggat ccccgggtgg tcagtccctt atgttacg                 48
```

CITRUS DERIVED TRANSCRIPTION AND TRANSLATION REGULATORY ELEMENTS FOR TISSUE SPECIFIC EXPRESSION

BACKGROUND OF THE INVENTION

Sequence Listing

The Sequence Listing submitted via EFS-Web as ASCII compliant text file format (.txt) filed on Dec. 16, 2016, named "SequenceListing_ST25", (created on Dec. 15, 2016, 214 KB), is incorporated herein by reference. This Sequence Listing serves as paper copy of the Sequence Listing required by 37 C.F.R. § 1.821(c) and the Sequence Listing in computer-readable form (CRF) required by 37 C.F.R. § 1.821(e). A statement under 37 C.F.R. § 1.821(f) is not necessary.

FIELD OF THE INVENTION

This invention relates to transcription regulatory elements and translation regulatory elements obtained from *citrus* plants that are useful for tissue specific transcription of a heterologous polynucleotide and translation of a peptide or protein of interest. This invention also relates to expression cassettes containing these sequences operably linked to a heterologous polynucleotide sequence encoding a protein of interest, transgenic plants that contain these expression cassettes. These regulatory elements are active in dicots.

DESCRIPTION OF RELATED ART

Genetically altered plants are being used to solve various agricultural problems, environmental, pest infestation, low yield, etc. One method of generating genetically altered plants, one operably links a promoter with a polynucleotide encoding the gene of interest and introduces the heterologous DNA into a wild-type plant to generate the desired genetically altered plant. Of course, one may need to screen the transformed plants to select the genetically altered plant, and the genetically altered plant's progeny, for the desired trait/gene product.

A variety of different types or classes of promoters can be used in genetically altered plants. Promoters can be classified on the basis of characteristics, such as temporal or developmental range, levels of transgene expression, or tissue specificity. For example, a constitutive promoter continuously expresses a gene with minimal regulation. Therefore, promoters referred to as constitutive promoters are capable of transcribing operably linked polynucleotides efficiently and expressing those polynucleotides in multiple tissues.

Numerous promoters, which are active in plant cells, have been described in the literature. Non-exhaustive examples include the nopaline synthase (nos) promoter and octopine synthase (ocs) promoter which are carried on tumor-inducing plasmids of *Agrobacterium tumefaciens* (also known as *Rhizobium radiobacter*), and the caulimovirus promoters such as the Cauliflower Mosaic Virus (CaMV) 19S or 35S promoter (U.S. Pat. No. 5,352,605), CaMV 35S promoter with a duplicated enhancer (CaMVE35S, U.S. Pat. Nos. 5,164,316; 5,196,525; 5,322,938; 5,359,142; and 5,424,200), and the Figwort Mosaic Virus (FMV) 35S promoter (U.S. Pat. No. 5,378,619). These promoters and numerous others have been used in the creation of constructs for transgene expression (expression of heterologous DNA) in plants. Other useful promoters for expression of heterologous DNA are described, for example, in U.S. Pat. Nos. 5,391,725; 5,428,147; 5,447,858; 5,608,144; 5,614,399; 5,633,441; 6,232,526; and 5,633,435.

While previous work has provided a number of promoters useful to direct transcription in genetically altered plants, there is still a great need for novel promoters with beneficial expression characteristics. In particular, there is a need for promoters that are capable of directing expression of heterologous genes or polynucleotides in cells present in phloem tissue, root tissues, or fruit and/or abscission zones of the genetically altered plants.

A number of studies functionally characterized root hair promoters using promoter:reporter gene fusion constructs (cassettes or expression vectors). See, e.g., Kim, et al., *Plant Cell.* 18:2958-2970 (2006); Won, et al., *Plant Physiol.* 150:1459-1473 (2009); and Zhiming, et al., *Plant J.* February 11. doi:10.1111/j. (2011). However, these studies' goal was the elucidation of regulatory networks involved in root hair transcription, or the physiological role of the associated gene product, rather than identifying highly active promoters for driving heterologous DNA expression.

Non-limiting examples of phloem specific promoters are sucrose synthase-1 promoter (CsSUS1p and CsSUS1p-2; see Singer, et al., *Planta* 234:623-637 (2011)) and phloem protein-2 promoter (CsPP2; see Miyata, et al., *Plant Cell Report* 31(11):2005-2013 (2012)). Phloem-specific transgene expression in plants has been directed from promoters derived from plants (e.g., Okumoto, et al., *J. Exp. Bot.* 55(406):2155-2168 (2004); Tornero, et al., *Plant J.* 9(5):639-648 (1996); Zhao, et al., *Plant Cell Rep.* 23(4):224-230 (2004); Shi, et al., *J. Experi. Botany,* 45(274):623-631 (1994); and Gua, et al., *Transgenic Res.,* 13(6):559-566 (2004)), from bacteria (Schmulling, et al., *Plant Cell,* 1(7):665-670 (1989)), and viruses (Yin, et al., *Plant J.,* 12(5):1179-1188 (1997)). Fruit-specific transgene expression in plants (Fraser, et al., *Proc. Natl. Acad. Sci. USA,* 99(2):1092-1097 (2002); Davuluri, et al., *Nat. Biotechnol.* 23(7):890-895 (2005); Atkinson, et al., *Plant Mol. Bio.* 38(3):449-460 (1998); and Vanhaaren, et al., *Plant Mol. Bio.,* 21(4):625-640 (1993)) and abscission zone-specific transgene expression in plants (Koehler, et al., *Plant Mol. Bio.,* 31(3):595-606 (1996) and Hong, et al., *Plant Physiol.* 123(3):869-881 (2000)) have been directed from a variety of transcription control elements.

As more genetically altered plants are developed in response to diseases and the need to increase yield for food products, a need exists for transcription regulatory elements and translation regulatory elements capable of directing strong transgene expression specific to root tissue cells, phloem tissue cells, or fruit and/or abscission zone tissue cells, and the translation of the mRNA into a protein or peptide or RNA of interest. This invention is directed at promoters which direct high-level expression of heterologous DNA in cells present in these tissues in dicotyledonous plants and the methods of using the same. This invention is also directed at translation enhancing elements which direct high-level translation of mRNA into the protein or peptide of interest in cells present in these tissue in dicotyledonous plants and the methods of using the same.

BRIEF SUMMARY OF THE INVENTION

It is an object of this invention to have expression vectors and/or expression cassettes and genetically altered plants and parts thereof that contains these expression vectors and/or expression cassettes, whereby some of the expression vectors and/or cassettes are transcriptionally active in a tissue-specific manner, namely in phloem tissue cells, in root tissue cells, or fruit or abscission zone tissue cells, and express a polynucleotide of interest in the cells in a tissue-specific manner.

It is another object of this invention that some of the expression vectors and/or cassettes contain a 5' transcription regulatory element operably linked to the polynucleotide of interest (where the polynucleotide of interest can, optionally, contain a linker sequence prior to the sequence of product of interest). The 5' transcription regulatory element causes transcription of the polynucleotide of interest in phloem tissue cells, root tissue cells, and/or in fruit and abscission zone tissue cells. It is an optional object of this invention that the expression vectors and/or cassette contain a translation regulatory element located between and operably linked to the 5' transcription regulatory element and the polynucleotide of interest. It is another optional object of this invention that the expression vectors and/or cassettes contain an intron transcription regulatory element sequence located between and operably linked to the translation regulatory element and the polynucleotide of interest. Alternatively, if no translation regulatory element is present, the intron transcription regulatory element sequence located between and operably linked to the 5' transcription regulatory element and the polynucleotide of interest.

It is a further object of this invention to have methods of using these expression vectors and/or cassettes to express a heterologous polynucleotide of interest in a tissue-specific manner in a genetically altered plant or parts thereof by introducing one or more of the expression vectors or cassettes into at least one cell of a wild-type plant to generate at least one altered plant cell, selecting at least of one of the altered plant cells for expression of at least one polynucleotide of interest on the expression vector to obtain at least one genetically altered plant cell, and growing at least one of the genetically altered plant cells to obtain a genetically altered plant that expresses a polynucleotide of interest that is present on the expression vector or cassette. The expression of a polynucleotide of interest can be limited to phloem tissue cells, the root tissue cells, or the fruit and abscission zone tissue cells of the genetically altered plant.

It is another object of this invention to have expression vectors and/or cassettes that contain a promoter operably linked to a translation regulatory element which is operably linked to a polynucleotide of interest (where the polynucleotide of interest can, optionally, contain a linker sequence prior to the sequence of product of interest). The promoter used in these expression vectors and/or cassettes are different than the tissue-specific 5' transcription regulatory elements described in infra and the sequence listing attached hereto. It is an optional object of this invention that the expression vectors and/or cassettes contain an intron transcription regulatory element sequence located between and operably linked to the translation regulatory element and the polynucleotide of interest.

It is another object of this invention to have expression vectors and/or cassettes that contain a promoter operably linked an intron transcription regulatory element sequence which is operably linked to a polynucleotide of interest (where the polynucleotide of interest can, optionally, contain a linker sequence prior to the sequence of product of interest). The promoter used in these expression vectors and/or cassettes are different than the tissue-specific 5' transcription regulatory elements described in infra and the sequence listing attached hereto.

It is an object of this invention to have genetically altered plants and parts thereof containing these expression vectors and/or cassettes. It is another object of this invention to have genetically altered plants and parts thereof made using the methods described herein and containing the expression vectors and/or cassettes described herein. It is a further object of this invention that the genetically altered plants and parts thereof express the polynucleotide of interest in a many consist with the transcription and translation regulatory elements/sequences described herein.

BRIEF DESCRIPTION OF THE DRAWINGS

FIG. 1 shows a partial DNA sequence (SEQ ID NO: 34) and partial amino acid sequence (SEQ ID NO: 35) of the Small Cyclic Amphipathic Peptides (SCAmpPs) 396s-GUS translational fusion construct focusing on SCAmpPs 396s' first exon, intron, and partial second exon, a linker, and the initial sequences of *E. coli* β-glucuronidase gene (GUS).

FIG. 2A shows a partial DNA sequence (SEQ ID NO: 36) and partial amino acid sequence (SEQ ID NO: 37) for SCAmpPs 302z-GUS translational fusion construct. FIG. 2B shows a partial DNA sequence (SEQ ID NO: 38) and partial amino acid sequence (SEQ ID NO: 39) for SCAmpPs 302z No-Intron GUS fusion construct. FIG. 2C shows a partial DNA sequence (SEQ ID NO: 40) and partial amino acid sequence for SCAmpPs 302z No-Intron No-ATG fusion construct.

DETAILED DESCRIPTION OF THE INVENTION

Figures 3A, 3B, 3C:
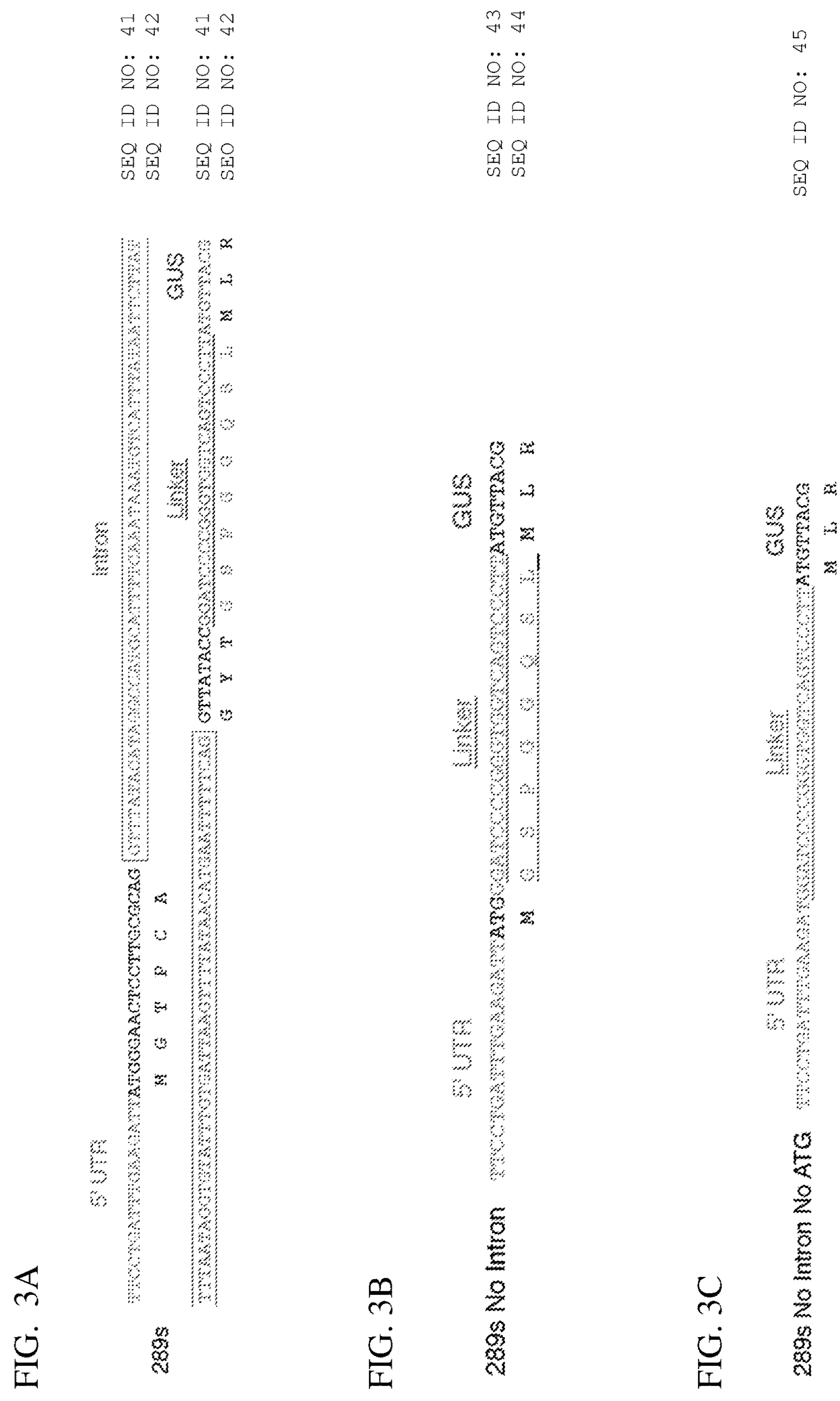
FIG. 3A shows a partial DNA sequence (SEQ ID NO: 41) and partial amino acid sequence (SEQ ID NO: 42) for SCAmpPs 289s-GUS translational fusion construct.
FIG. 3B shows a partial DNA sequence (SEQ ID NO: 43) and partial amino acid sequence (SEQ ID NO: 44) for SCAmpPs 289s No-Intron GUS fusion construct.
FIG. 3C shows a partial DNA sequence (SEQ ID NO: 45) and partial amino acid sequence for SCAmpPs 289s No-Intron No-ATG GUS fusion construct.

One of the goals of generating genetically altered plants is to produce plants with agronomically desirable characteristics or traits. Advances in genetic engineering have provided the requisite tools to transform plants to contain and express genes of interest. The gene of interest can then be expressed in a plant cell to exhibit the added characteristic or trait. In one approach, expression of a gene of interest in a plant cell or a plant tissue that does not normally express such a gene may confer a desirable phenotypic effect. In another approach, transcription of a gene of interest or part thereof in an antisense orientation or as short interfering RNA (siRNA) may produce a desirable effect by preventing or inhibiting expression of an endogenous gene.

The transcription regulatory elements and translation regulatory elements described herein are useful for selectively directing the expression of a heterologous polynucleotide in cells in either root tissue cells, fruit and/or abscission zone tissue cells, or phloem tissue cells and then translation of the mRNA in dicot plants. In particular, the "SCAmpPs 302z" regulatory elements are predominately active in root tissue cells; the "SCAmpPs 289s" regulatory elements are predominately active in fruit and/or abscission zone tissue cells; and the "SCAmpPs 396s" regulatory elements are predominately active in phloem tissue cells. Further, this invention include transcription regulatory elements having a nucleotide sequence that is at least 95%, or at least 96%, or at least 97%, or at least 98%, or at least 99% identical to the sequences described herein and which still are active predominantly in those specific tissue. And this invention include translation regulatory elements having a nucleotide sequence that is at least 95%, or at least 96%, or at least 97%, or at least 98%, or at least 99% identical to the elements described herein and which still are active predominantly in those specific tissue. For the purposes herein, "SCAmpPs" is an abbreviation for "Small Cyclic Amphipathic Peptides".

Thus, this invention covers expression cassettes containing either 302z, 289s, or 396s transcription regulatory element operably linked to a heterologous DNA encoding a product of interest. This invention also covers expression cassettes containing either 302z, 289s, or 396s transcription regulatory element operably linked to either 302z, 289s, or 396s translation regulatory element which is operably linked to a heterologous DNA encoding a product of interest. Each expression cassette can be part of an expression vector or exist without the expression vector.

SEQ ID NO: 1 contains the DNA sequence of SCAmpPs 302z-GUS in pBinPlusARS. In SEQ ID NO: 1, nt 1-618 is oriV, nt 1758-2351 is ColE1, nt 2875-3669 is NPTIII, nt 3968-5116 is TrfA RK2 transcriptional r, nt 6642-6788 is left border of T-DNA; nt 6795-7942 is Ubi3 fus prom; nt 7715-7942 ubiquitin monomer; nt 7715-8746 is UQ-NPTII fusion protein; nt 7952-8746 is nptII; nt 8747-9165 ubi3 terminator; nt 9593-9600 is AscI; nt 9601-12255 is 302Z PCR Product; nt 12085-12157 is Exon 1; nt 12158-12247 is Intron; nt 12248-12255 is Exon 2; 12256-12261 is BamHI; nt 12280-14091 is GUS; nt 14151-14651 is ubi 409 Term; and nt 14991-15015 is Right border T-DNA. In SEQ ID NO: 1, the SCAmpPs 302z 5' transcription regulatory element sequence is from nt 9601 to nt 12084, and the translation regulatory element sequence is from nt 12085 to nt 12141. The intron (nt 12158-12247) contains an intron transcription regulatory element. Any heterologous polynucleotide sequence encoding a product of interest can be operably linked to one or both of these regulatory elements, with or without an intervening linker, and placed into any expression vector. In SEQ ID NO: 1, SCAmpPs 302z-GUS in pBinPlusARS, the heterologous polynucleotide encodes GUS and is located from nt 12280 to nt 14091.

SEQ ID NO: 2 contains the DNA sequence of SCAmpPs 302z No-Intron-GUS in pBinPlusARS. In SEQ ID NO: 2, nt 1-618 is oriV; nt 1758-2351 is ColE1; nt 2875-3669 is NPTIII; nt 3968-5116 TrfA RK2 transcriptional r; nt 6642-6788 is Left border T-DNA; nt 6795-7942 is Ubi3 fus prom; nt 7715-7942 is Ubiquitin monomer; nt 7715-8746 is UQ-NPTII fusion protein; nt 7952-8746 is nptII; nt 8747-9165 is ubi3 Terminator; nt 9593-9600 is AscI; nt 9601-12142 is 302Z PCR Product; nt 12085-12142 is Exon1; nt 12139-13977 is GUS Fusion Protein; nt 12120-12147 is Complement Reverse Primer 302z No-Intron; nt 12141-12147 is BamHI; nt 12166-13977 is GUS, nt 14037-14537 is ubi 409 Term; nt 14877-14901 is Right border T-DNA; nt 16187 16565 is ColE1 ori; and nt 16694-16805 is RK2 oriT. In SEQ ID NO: 2, the SCAmpPs 302z 5' transcription regulatory sequence is from nt 9601 to nt 12084, and the translation regulatory element sequence is from nt 12085 to nt 12141. Any heterologous polynucleotide sequence encoding a product of interest can be operably linked to one or both of these regulatory elements, with or without an intervening linker, and placed into any expression vector. In SEQ ID NO: 2, SCAmpPs 302z No-Intron-GUS in pBinPlusARS, the heterologous polynucleotide encodes GUS and is located from nt 12166 to nt 13977.

SEQ ID NO: 3 contains the DNA sequence of SCAmpPs 302z No-ATG, No-Intron-GUS in pBinPlusARS. In SEQ ID NO: 3, nt 1-618 is oriV; nt 1758-2351 is ColE1; nt 2875-3669 is NPTIII; nt 3968-5116 is TrfA RK2 transcriptional r; nt 6642-6788 is Left border T-DNA; nt 6795-7942 Ubi3 fus prom; nt 7715-7942 is Ubiquitin monomer; nt 7715-8746 is UQ-NPTII fusion protein; nt 7952-8746 is nptII, nt 8747-9165 is ubi3 Terminator; nt 9593-9600 is AscI; nt 9601-12137 is 302Z PCR Product; nt 12085-1237 is Exon1; nt 12115-12144 is Complement Reverse Primer 302z No-Intron-No-ATG; nt 12138-12144 is BamHI; nt 12162-13973 is GUS; nt 14033-14533 in ubi 409 Term; nt 14873-14897 is Right border T-DNA; nt 16183-16561 is ColE1 ori; and nt 16690-16801 is RK2 oriT. In SEQ ID NO: 3, the SCAmpPs 302z 5' transcription regulatory element sequence is from nt 9601 to nt 12084, and the deactivated translation regulatory element sequence disabled by deletion of the SCAmpPs initiator ATG relative to SEQ ID NO: 2 is in SEQ ID NO: 3 from nt 12085 to nt 12137. Any heterologous polynucleotide sequence encoding a product of interest can be operably linked to one or both of these regulatory elements, with or without an intervening linker, and placed into any expression vector. In SEQ ID NO: 3, SCAmpPs 302z No-ATG, No-Intron-GUS in pBinPlusARS, the heterologous polynucleotide encodes GUS and is located from nt 12162 to nt 13973.

SEQ ID NO: 4 contains the DNA sequence of SCAmpPs 289s-GUS in pBinPlusARS. In SEQ ID NO: 4, nt 1-618 is oriV; nt 1758-2351 is ColE1; nt 2875-3669 is NPTIII; nt 3968-511 is TrfA RK2 transcriptional r; nt 6642-6788 is Left border T-DNA; nt 6795-7942 is Ubi3 fus prom; nt 7715-7942 is Ubiquitin monomer; nt 7715-8746 is UQ-NPTII fusion protein; nt 7952-8746 is nptII; nt 8747-9165 is ubi3 Terminator; nt 9593-9600 is AscI; nt 9601-11568 is 289s PCR Product; nt 11351-11456 is Exon1; nt 11457-11554 is Intron; nt 11555-11562 is Exon2; nt 11563-11568 is BamHI; nt 11587-13398 is GUS; nt 13458-13958 is ubi 409 Term; and nt 14298-14322 is Right border T-DNA. In SEQ ID NO: 4, the SCAmpPs 289s 5' transcription regulatory element sequence is from nt 9601 to nt 11350, and the translation regulatory element sequence is from nt 11351 to nt 11440. The intron (nt 11457-11554) contains an intron transcription regulatory element. Any heterologous polynucleotide sequence encoding a product of interest can be operably linked to one or both of these regulatory elements, with or without an intervening linker, and placed into any expression vector. In SEQ ID NO: 4, SCAmpPs 289s GUS in pBinPlusARS, the heterologous polynucleotide encodes GUS and is located from nt 11587 to nt 13398.

SEQ ID NO: 5 contains the DNA sequence of SCAmpPs 289s No-Intron-GUS in pBinPlusARS. In SEQ ID NO: 5, nt 1-618 is oriV; nt 1758-2351 is ColE1; nt 2875-3669 is NPTIII; nt 3968-5116 is TrfA RK2 transcriptional r; nt 6642-6788 is Left border T-DNA; nt 6795-7942 is Ubi3 fus prom; nt 7715-7942 is Ubiquitin monomer; nt 7715-8746 is UQ-NPTII fusion protein; nt 7952-8746 is nptII; nt 8747-9165 is ubi3 Terminator; nt 9593-9600 is AscI; nt 9593-9619 is Forward Primer; nt 9601-11446 is 289s PCR Product; nt 11351-11443 is Exon1; nt 11438-13276 is GUS Fusion Protein; nt 11418-11446 is C Reverse Primer; nt 11441-11446 is BamHI; nt 11465-13276 is GUS; nt 13336-13836 is ubi 409 Term; nt 14162-14297 is Right border T-DNA. In SEQ ID NO: 5, the SCAmpPs 289s 5' transcription regulatory element sequence is from nt 9601 to nt 11350, and the translation regulatory element sequence is from nt 11351 to nt 11440. Any heterologous polynucleotide sequence encoding a product of interest can be operably linked to one or both of these regulatory elements, with or without an intervening linker, and placed into any expression vector. In SEQ ID NO: 5, SCAmpPs 289s No-Intron-GUS in pBinPlusARS, the heterologous polynucleotide encodes GUS and is located from nt 11465 to nt 13276.

SEQ ID NO: 6 contains the DNA sequence of SCAmpPs 289s No-ATG, No-Intron-GUS in pBinPlusARS. In SEQ ID NO: 6, nt 1-oriV; nt 1758-2351 is ColE1; nt 2875-3669 is NPTIII; nt 3968-5116 is TrfA RK2 transcriptional r; nt 6642-6788 is Left border T-DNA; nt 6795-7942 is Ubi3 fus prom; nt 7715-7942 is Ubiquitin monomer; nt 7715-8746 is UQ-NPTII fusion protein; nt 7952-8746 is nptII; nt 8747-9165 is ubi3 Terminator; nt 9593-9600 is AscI; nt 9593-9619 is Forward Primer; nt 9601-11446 is 289s PCR Product; nt 11351-11436 is Exon1; nt 11413-11442 is Reverse Primer; nt 11437-11442 is BamHI; nt 11461-13272 is GUS; nt 113332-13832 is ubi 409 Term; and nt 14158-14293 is Right border T-DNA. In SEQ ID NO: 6, the SCAmpPs 289s 5' transcription regulatory element sequence is from nt 9601 to nt 11350, and the deactivated translation regulatory element sequence disabled by deletion of the SCAmpPs initiator ATG relative to SEQ ID NO: 5 is in SEQ ID NO: 6 from nt 11351 to nt 11436. Any heterologous polynucleotide sequence encoding a product of interest can be operably linked to one or both of these regulatory elements, with or without an intervening linker, and placed into any expression vector. In SEQ ID NO: 6, SCAmpPs 289s No-ATG No-Intron-GUS in pBinPlusARS, the heterologous polynucleotide encodes GUS and is located from nt 11461 to nt 13272.

SEQ ID NO: 7 contains the DNA sequence of SCAmpPs 396s-GUS in pBinPlusARS. In SEQ ID NO: 7, nt 1-618 is oriV; nt 1758-2351 is ColE1; nt 2875-3669 is NPTIII; nt 3968-5116 is TrfA RK2 transcriptional r; nt 6642-6788 is Left border T-DNA; nt 6795-7942 Ubi3 fus prom; nt 7715-7942 is Ubiquitin monomer; nt 7715-8746 is UQ-NPTII fusion protein; nt 7952-8746 is nptII; nt 8747-9165 is ubi3 Terminator; nt 9593-9600 is AscI; nt 9601-12019 is 396s PCR Product; nt 11823-11909 is Exon1; nt 11910-12004 is Intron; nt 12005-12013 is Exon2; nt 12014-12019 is BamHI; nt 12038-13849 is GUS; nt 13909-14409 ubi 409 Term; and nt 14749-14773 is Right border T-DNA. In SEQ ID NO: 7, the SCAmpPs 396s 5' transcription regulatory element sequence is from nt 9601 to nt 11822, and the translation regulatory element sequence is from nt 11823 to nt 11894. The intron (nt 11910-12004) contains an intron transcription regulatory element. Any heterologous polynucleotide sequence encoding a product of interest can be operably linked to one or both of these regulatory elements, with or without an intervening linker, and placed into any expression vector. In SEQ ID NO: 7, SCAmpPs 396s GUS in pBinPlusARS, the heterologous polynucleotide encodes GUS and is located from nt 12038 to nt 13849.

The transcription regulatory elements and the translation regulatory elements of this invention have a wide range of biotechnological applications, because they are an important tool for manipulating or regulating heterologous polynucleotide expression and translation within a cell type critical to plant growth (root and phloem) and/or fruit production (root, phloem, and fruit/abscission layer). Concerning root tissue and the 302z regulatory elements, root tissue cells are the majority of a plant's interface with its surrounding soil environment. Furthermore, some plants store food in their roots (i.e., carrots, etc.) Thus, numerous applications for the 302z transcription regulatory elements and translation regulatory elements exist, such as, but not limited to, expression of heterologous polynucleotide in genetically altered plant for which the product of interest (i) promotes colonization of beneficial rhizosphere-associated microbes, (ii) is a transporter, channel, or other protein that facilitates more efficient water and/or nutrient uptake (increase amount of water uptake and/or nutrient uptake) by the genetically altered plant compared to the amount that a non-genetically altered plant can uptake, (iii) increases efficiency of nitrogen fixation in leguminous crops compared to the nitrogen fixation efficiency of wild-type leguminous crop, (iv) is a protein useful in bioremediation (Wang, et al., *Nature Biotechnology,* 22:893-897 (2004)), (v) inhibits or reduces colonization by soil-borne pests such as parasitic nematodes (Huang, et al., *Proc. Natl. Acad. Sci. USA* 103(39):14302-14306 (2006)) compared to the colonization rate of soil-borne pests in wild-type plants, (vi) inhibits or reduces competition from neighboring plants by facilitating allelochemical production compared to the rate of competition in wild-type plants (Duke, S. O., *Trends in Biotechnology* 21(5):192-195 (2003); Baerson, et al., *Journal of Biological Chemistry,* 283:3231-3247 (2008)).

Ovule/fruit abscission zones are specialized cell layers subtending the ovule/fruit that respond to environmental/physiological conditions to trigger abscission. This process can be desirable, such as when excess fruit are shed early in the growing season to permit better fruit sizing, or to aid harvest when fruit are fully mature. It can also be undesirable commercially, resulting in excessive loss of developing fruits or pre-harvest drop as fruits mature. This pre-harvest drop is called "shattering" in crops such as grains. In some species tested, the 289s transcription regulatory elements and translation regulatory elements results in broader expression specific to entire fruits, permitting fruit-specific modification of numerous commercially valuable traits.

Thus, numerous applications for the 289s transcription regulatory elements and translation regulatory elements exist in specifically expressing and translating transgenes in the ovule/fruit abscission zone. Among the potential applications are (i) expression of genes to weaken abscission and reduce pre-harvest drop or shattering (e.g., genes to induce RNAi suppressing ethylene production); and (ii) inclusion of an additional inducible element to facilitate fruit drop following exogenous application of an inducer, which would permit elimination of cropping in street trees, or facilitate mechanical harvesting in crops like *citrus*. Innumerable applications exist for fruit-specific expression and translation of transgenes, among them are (i) modification of genes to increase accumulation of desirable "nutraceutical" or secondary metabolites compared the accumulation rate in a wild-type plant; (ii) suppression of genes that result in alternate bearing; (iii) enhancement of fruit cosmetics such as color, shape and size compared to the fruit cosmetics in wild-type plants; (iv) expression of genes to increase post-harvest fruit quality including resistance to post-harvest pathogens compared to the post-harvest fruit quality from wild-type plants; and (v) development of trap crops in which fruit-feeding pests are killed to suppress pests' populations affecting the commercial crop.

Concerning phloem tissue and the 396s transcription regulatory elements and translation regulatory elements, phloem cells transport photosynthetic products (i.e., sugars) from leaves to other parts of the plant (i.e., roots and fruit). Phloem-specific gene expression offers the potential for enhancing productivity through several mechanism including (i) expression of phloem pathogen (phytoplasmas and Liberibacters) inhibiting genes to suppress or reduce critical diseases like coconut lethal yellowing, sugarcane grassy shoot disease, witches broom disease in many crops, huanglongbing in *citrus*, and zebra chip in potatoes compared to the amount in wild-type plants; (ii) control flowering by suppression or overexpression of genes (FT, TFL1, etc.) involved in transition between vegetative and floral meristems; (iii) expression of phloem proteins associated with dwarfing in apples (Dw1 and Dw2); and (iv) expression of genes to enhance efficiency of phloem photosynthate transport (e.g., genes for sorbitol synthesis and utilization).

One embodiment of this invention is an expression cassette or vector containing at least one of the 5' transcription regulatory element sequences described herein (nt 9-2230 of SEQ ID NO: 25 for expression in phloem cells (396s); nt 1-2484 of SEQ ID NO: 26 for expression in root cells (302z); and nt 1-1750 of SEQ ID NO: 30 for expression in fruit cells and/or abscission zone cells (289s)), or containing at least one promoter sequence that is at least 95%, 96%, 97%, 98%, or 99% identical to these 5' transcription regulatory element, operably linked to a heterologous polynucleotide encoding a product of interest, and where the heterologous polynucleotide optionally contains a linker between the promoter sequence and the sequence of the product of interest.

Another embodiment of this invention is an expression cassette or vector containing at least one of the 5' transcription regulatory elements described above and at least one of the translation regulatory element sequences (nt 2231-2302 of SEQ ID NO: 25 for expression in phloem cells (396s); nt 2485-2541 of SEQ ID NO: 26 for expression in root cells (302z); and nt 1751-1840 of SEQ ID NO: 30 for expression in fruit cells and/or abscission zone cells (289s)), or at least one translation regulatory element that is at least 95%, 96%, 97%, 98%, or 99% identical thereof, operably linked to a heterologous polynucleotide encoding a product of interest, and where the heterologous polynucleotide optionally contains a linker between the translation regulatory element sequence and the sequence of the product of interest. In another embodiment, these translation regulatory elements may be, individually, operably linked to a heterologous 5' transcription regulatory element and/or heterologous intron transcription regulatory element. In an alternative embodiment, these translation regulatory elements may be, individually, operably linked to one of the intron transcription regulatory elements described herein and to a heterologous 5' transcription regulatory element.

Another embodiment of this invention is an expression cassette or vector containing at least one of the 5' transcription regulatory elements described above and at least one of the intron transcription regulatory elements described herein (nt 2319-2413 of SEQ ID NO: 25 for expression in phloem cells (396s); nt 2588-2647 of SEQ ID NO: 26 for expression in root cells (302z); and nt 1857-1954 of SEQ ID NO: 30 for expression in fruit cells and/or abscission zone cells (289s)), or at least one intron transcription regulatory element that is at least 95%, 96%, 97%, 98%, or 99% identical thereof, operably linked to a heterologous polynucleotide encoding a product of interest, and where the heterologous polynucleotide optionally contains a linker between the transcription regulatory intron sequence and the sequence of the product of interest. In another embodiment, these intron transcription regulatory elements may be, individually, operably linked to a heterologous 5' transcription regulatory element and/or to a heterologous translation regulatory element sequence.

Another embodiment of this invention is an expression cassette or vector containing at least one of the 5' transcription regulatory elements described above, at least one of the translation regulatory element sequences described above, and at least one of the intron transcription regulatory elements described above, operably linked to a heterologous polynucleotide encoding a product of interest, where the heterologous polynucleotide optionally contains a linker between the translation regulatory element sequence and the sequence of the product of interest. More particularly, this invention includes nt 9-2413 of SEQ ID NO: 25, or nt 1-2647 of SEQ ID NO: 26, or nt 1-1954 of SEQ ID NO: 31, operably linked to a heterologous polynucleotide encoding a product of interest, where the heterologous polynucleotide optionally contains a linker between these sequences and the sequence of the product of interest.

Another embodiment of this invention is one or more expression vectors or plasmids that contain one or more of these expression cassettes. Another embodiment of this invention is a genetically altered plant, parts thereof or progeny thereof, and/or a genetically altered plant cell that contains one or more of these expression cassettes or contains one or more these expression vectors containing one or more of these expression cassettes. The genetically altered plant, parts thereof, or progeny; or genetically altered plant cell will preferentially transcribe the heterologous polynucleotide and produce the product of interest in the genetically altered plant's cells in a tissue specific manner correlating to the transcription regulatory element and the translation regulatory element used (as described herein).

A "desired polynucleotide" is a "heterologous" polynucleotide to either the transcription regulatory element (i.e., the transcription regulatory element and the heterologous polynucleotide are not found, in nature, to be operably linked together), or the genetically altered plant (i.e., the heterologous polynucleotide is not normally present in the non-genetically altered plant (wild-type plant); or, the heterologous polynucleotide (or its product) is present in higher amount in the genetically altered plant compared to the non-genetically altered plant (wild-type plant), or, the heterologous polynucleotide is transcribed in the genetically altered plant's tissue (root, fruit/abscission layer, or phloem) in a higher amount compared to the amount transcribed in the non-genetically altered plant (wild-type plant)). Thus, the "desired polynucleotide" is also referred to as "heterologous polynucleotide" or "heterologous DNA" or "heterologous gene" or "heterologous gene polynucleotide" or "transcribable heterologous polynucleotide". In one embodiment of this invention, the polynucleotide sequences that encodes full-length or partial sequence of the SCAmpPs described herein are not considered "heterologous polynucleotides", but can be included in the expression cassette as described above (i.e., operably linked to its indicated transcription regulatory element at the SCAmpPs' 5' end and operably linked to the heterologous DNA at the SCAmpPs' 3' end) in order to increase the translational efficacy of the produced mRNA.

In the examples, below, the expression cassettes contain heterologous polynucleotide that encodes GUS (*E. coli* β-glucuronidase gene). However, one of ordinary skill in the art understands that one can substitute a polynucleotide sequence encoding a desired protein, siRNA, rRNA, or another product for GUS polynucleotide sequence in these expression cassettes (i.e., a heterologous polynucleotide). In fact, it is highly likely that one of ordinary skill in the art would want to exchange GUS' polynucleotide sequence for a heterologous polynucleotide sequence, and one of ordinary skill in the art would have the knowledge of how to construct such an expression cassette using information contained in the examples below or information that is well-known to one of ordinary skill in the art field.

In the examples below, a polynucleotide "linker" is between the SCAmpPs sequences and the heterologous polynucleotide (encodings GUS in the examples below, but can be any heterologous polynucleotide). This linker may help with the construction of the expression vector, may help with the transporting of the product encoded by the heterologous polynucleotide to the correct area of the cell (and/or exporting the product from the cell), and/or may help with proper alignment of the heterologous polynucleotide so that it is operably linked to the promoter sequences (e.g., correct codon reading frame). One of ordinary skill in the art is aware that a linker is optional. Further, one of ordinary skill in the art is aware that one can use linkers having different sequences than the linkers used in the examples below.

One of ordinary skill in the art has the knowledge to insert the transcription regulatory elements and/or the translation regulatory elements and/or the intron transcription regulatory elements described herein operably linked to a heterologous polynucleotide into a different expression vector than the plasmids described herein. Also, one of ordinary skill in the art has the knowledge to insert the transcription regulatory elements described herein, optionally operably linked to the translation regulatory elements describe herein, and optionally operably linked to the intron transcription regulatory elements described herein, operably linked to a heterologous polynucleotide into a different expression vector than the plasmids described herein. Further one of ordinary skill in the art has the knowledge of how to transform the desired plant or plant cell with the new expression vector and generate a genetically altered plant containing the expression vector containing the desired expression cassette.

Because this invention involves production of genetically altered plants and involves recombinant DNA techniques, the following definitions are provided to assist in describing this invention. The terms "isolated", "purified", or "biologically pure" as used herein, refer to material that is substantially or essentially free from components that normally accompany the material in its native state or when the material is produced. In an exemplary embodiment, purity and homogeneity are determined using analytical chemistry techniques such as polyacrylamide gel electrophoresis or high performance liquid chromatography. A nucleic acid or particular bacteria that are the predominant species present in a preparation is substantially purified. In an exemplary embodiment, the term "purified" denotes that a nucleic acid or protein that gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Exemplary analogs include, without limitation, phosphorothioates, phosphoramidates, methyl phosphonates, chiral-methyl phosphonates, 2-O-methyl ribonucleotides, and peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The terms "identical" or percent "identity", in the context of two or more nucleic acids or polypeptide sequences, refer to two or more sequences or subsequences that are the same or have a specified percentage of amino acid residues or nucleotides that are the same (e.g., 80%, 85% identity, 90% identity, 99%, or 100% identity), when compared and aligned for maximum correspondence over a designated region as measured using a sequence comparison algorithm or by manual alignment and visual inspection. The higher the percentage of identity two sequences have, the better that they will anneal under highly stringent conditions.

The phrase "high percent identical" or "high percent identity", in the context of two polynucleotides or polypeptides, refers to two or more sequences or subsequences that have at least about 80%, identity, at least about 81%, 82%, 83%, 84%, 85%, 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In an exemplary embodiment, a high percent identity exists over a region of the sequences that is at least about 50 residues in length. In another exemplary embodiment, a high percent identity exists over a region of the sequences that is at least about 100 residues in length. In still another exemplary embodiment, a high percent identity exists over a region of the sequences that is at least about 150 residues or more in length. In one exemplary embodiment, the sequences are high percent identical over the entire length of the nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well-known in the art. Optimal alignment of sequences for comparison can be conducted, e.g., by the local homology algorithm of Smith &

Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al. (eds.), *Current Protocols in Molecular Biology,* 1995 supplement).

The term “recombinant” when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells may express genes/polynucleotides that are not found within the native (non-recombinant or wild-type) form of the cell or express native genes in an otherwise abnormal amount—over-expressed, under-expressed or not expressed at all—compared to the non-recombinant or wild-type cell or organism. In particular, one can alter the genomic DNA of a wild-type plant by molecular biology techniques that are well-known to one of ordinary skill in the art and generate a recombinant plant.

The terms “transgenic”, “transformed”, “transformation”, and “transfection” are similar in meaning to “recombinant”. “Transformation”, “transgenic”, and “transfection” refer to the transfer of a polynucleotide into a host organism or into a cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subjected for a period of time to one or more conditions which require the transcription of some or all of the transferred polynucleotide in order for the transgenic organism or cell to live and/or grow. Polynucleotides that are transformed into a cell but are not integrated into the host’s chromosome remain as an expression vector within the cell. One may need to grow the cell under certain growth or environmental conditions in order for the expression vector to remain in the cell or the cell’s progeny. Further, for expression to occur the organism or cell may need to be kept under certain conditions. Genetically altered organisms or cells containing the recombinant polynucleotide can be referred to as “transgenic” or “transformed” organisms or cells or simply as “transformants”, as well as recombinant organisms or cells.

A genetically altered organism is any organism with any changes to its genetic material, whether in the nucleus or cytoplasm (organelle). As such, a genetically altered organism can be a recombinant or transformed organism. A genetically altered organism can also be an organism that was subjected to one or more mutagens or the progeny of an organism that was subjected to one or more mutagens and has mutations in its DNA caused by the one or more mutagens, as compared to the wild-type organism (i.e, organism not subjected to the mutagens). Also, an organism that has been bred to incorporate a mutation into its genetic material is a genetically altered organism. For the purposes of this invention, the organism is a plant.

As used herein, the term “promoter” and “5' transcription regulatory element” refer to a polynucleotide that, in its native state, is located upstream or 5' to a translation start codon of an open reading frame (or protein-coding region) and that is involved in recognition and binding of RNA polymerase and other proteins (trans-acting transcription factors) to initiate transcription. A “plant promoter” is a native or non-native promoter that is functional in plant cells. The promoters (5' transcription regulatory element) described herein are predominately functional in cells of specific tissue and thus are considered “tissue-specific”. A plant promoter can be used as a 5' regulatory element for modulating expression of a particular desired polynucleotide (heterologous polynucleotide) operably linked thereto. When operably linked to a transcribeable heterologous polynucleotide, a promoter typically causes the transcribable heterologous polynucleotide to be transcribed in a manner that is similar to that of which the promoter is normally associated. This heterologous polynucleotide of interest, when transcribed, provides a desirable characteristic associated with plant morphology, physiology, growth and development, yield, nutritional enhancement, disease or pest resistance, or environmental or chemical tolerance. Furthermore, the term “transcription regulatory element” includes promoter sequences and cis-acting elements sequences (e.g., terminators and enhancers) which are involved with transcription of the gene of interest.

The term “vector” refers to DNA, RNA, a protein, or polypeptide that was be introduced into a host cell or organism. The polynucleotides, protein, and polypeptide which are to be introduced into a host can be therapeutic or prophylactic in nature; can encode or be an antigen; can be regulatory in nature; etc. There are various types of vectors including virus, plasmid, bacteriophages, cosmids, and bacteria.

An expression vector is nucleic acid capable of replicating in a selected host cell or organism. An expression vector can replicate as an autonomous structure, or alternatively can integrate, in whole or in part, into the host cell chromosomes or the nucleic acids of an organelle, or it is used as a shuttle for delivering foreign DNA to cells, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector (including genes of interest) are transcribed and translated into a polypeptide or protein within the cell, organelle or organism; or any suitable construct known in the art, which comprises an “expression cassette”. In contrast, as described in the examples herein, a “cassette” is a polynucleotide containing a section of an expression vector. The use of the cassettes assists in the assembly of the expression vectors. An expression vector is a replicon, such as plasmid, phage, virus, chimeric virus, or cosmid, and which contains the desired polynucleotide sequence operably linked to the expression control sequence(s).

A heterologous polynucleotide sequence is operably linked to one or more transcription regulatory elements (e.g., promoter, terminator and, optionally, enhancer) such that the transcription regulatory elements control and regulate the transcription and/or translation of that heterologous polynucleotide sequence. An expression cassette can have the heterologous polynucleotide operably linked to one or more transcription regulatory elements (5' transcription regulatory element and/or intron transcription regulatory element) and/or one or more translation regulatory elements. As used herein, the term “operably linked” refers to a first polynucleotide, such as a promoter, connected with a second transcribable heterologous polynucleotide, such as a gene of interest, where the polynucleotides are arranged such that the first polynucleotide affects the transcription of the second polynucleotide. In some embodiments, the two polynucleotide molecules are part of a single contiguous polynucleotide. In other embodiments, the two polynucleotides are adjacent. For example, a promoter is operably linked to a gene of interest if the promoter regulates or mediates transcription of the gene of interest in a cell. Similarly a terminator is operably linked to the polynucleotide of interest if the terminator regulates or mediates transcription of the polynucleotide of interest, and in particular, the termination of transcription. Constructs of the present invention would typically contain a promoter operably linked to a transcribable heterologous polynucleotide operably linked to a terminator.

Exemplary heterologous polynucleotide for incorporation into constructs of the present invention include, for example, desired polynucleotides from a species other than the target plant's species, or even desired polynucleotides that originate with or are present in the same plant species, but are incorporated into the genetically altered plant cells by genetic engineering methods rather than classical reproduction or breeding techniques or by a combination of genetic engineering methods followed by breeding techniques. Heterologous polynucleotides refer to any polynucleotide molecule that is introduced into a recipient cell and is transcribed at levels that differ from the wild-type cell. A heterologous polynucleotide can include a polynucleotide that is already present in the plant cell, polynucleotide from another plant, polynucleotide from a different organism, or a polynucleotide generated externally, such as a polynucleotide containing an antisense message of a gene, or a polynucleotide encoding an artificial or modified version of a gene.

As used herein, "gene of interest" refers to any heterologous polynucleotide encoding a "product of interest" that, upon transcription and, optionally, translation, imparts a desirable characteristic associated with plant morphology, physiology, growth and development, yield, nutritional enhancement, disease or pest resistance, or environmental or chemical tolerance. The expression of a gene of interest is desirable in order to confer an important trait to the genetically altered plant cell, plant, parts thereof and/or progeny. A gene of interest that provides a beneficial agronomic trait to crop plants includes, but is not limited to, polynucleotides that encode herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121,436; 6,316,407, and 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985,605 and 6,171,640), biopolymers (U.S. Pat. Nos. 5,958,745 and 6,946,588), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700). For the purposes of this invention, plant "nutrients" include minerals and organic compounds that plants need.

Alternatively, a heterologous polynucleotide can affect the plant's phenotype by encoding a non-translated RNA that causes targeted inhibition of expression of an endogenous gene, for example, by antisense and inhibitory RNA, or RNA interference-mediated mechanisms. The non-translated RNA could also be a catalytic RNA molecule (i.e., a ribozyme) engineered to cleave a desired endogenous RNA product. For the purposes of this invention, the gene of interest includes within its definition a non-translated RNA because such a non-translated RNA affects the characteristics of the genetically altered plant cell, plant, parts thereof, and/or progeny containing the construct described herein. Thus, any heterologous polynucleotide that encodes a protein or RNA that expresses a phenotype or morphology change of interest is useful for the practice of the present invention.

Transformation and generation of genetically altered monocotyledonous and dicotyledonous plant cells is well known in the art. See, e.g., Weising, et al., *Ann. Rev. Genet.* 22:421-477 (1988); U.S. Pat. No. 5,679,558; *Agrobacterium* Protocols, ed: Gartland, Humana Press Inc. (1995); and Wang, et al. *Acta Hort.* 461:401-408 (1998). The choice of method varies with the type of plant to be transformed, the particular application and/or the desired result. The appropriate transformation technique is readily chosen by the skilled practitioner.

Exemplary transformation/transfection methods available to those skilled in the art include, but are not limited to: direct uptake of foreign DNA constructs (see, e.g., EP 295959); techniques of electroporation (see, e.g., Fromm et al., *Nature* 319:791 (1986)); and high-velocity ballistic bombardment with metal particles coated with the nucleic acid constructs (see, e.g., Kline, et al., *Nature* 327:70 (1987) and U.S. Pat. No. 4,945,050). Specific methods to transform heterologous genes into commercially important crops (to make genetically altered plants) are published for rapeseed (De Block, et al., *Plant Physiol.* 91:694-701 (1989)); sunflower (Everett, et al., *Bio/Technology* 5:1201 (1987)); soybean (McCabe, et al., *Bio/Technology* 6:923 (1988), Hinchee, et al., *Bio/Technology* 6:915 (1988), Chee, et al., *Plant Physiol.* 91:1212-1218 (1989), and Christou, et al., *Proc. Natl. Acad. Sci USA* 86:7500-7504 (1989)); rice (Hiei, et al., *Plant J.* 6:271-282 (1994)), and corn (Gordon-Kamm, et al., *Plant Cell* 2:603-618 (1990), and Fromm, et al., *Biotechnology* 8:833-839 (1990)). Other known methods are disclosed in U.S. Pat. Nos. 5,597,945; 5,589,615; 5,750,871; 5,268,526; 5,262,316; and 5,569,831.

One exemplary method includes employing *Agrobacterium tumefaciens* (*Rhizobium radiobacter*) or *Agrobacterium rhizogenes* as the transforming agent to transfer heterologous DNA into the plant. *Agrobacterium tumefaciens*-meditated transformation techniques are well described in the scientific literature. See, e.g., Horsch, et al. *Science* 233:496-498 (1984), and Fraley, et al. *Proc. Natl. Acad. Sci. USA* 80:4803 (1983). Typically, a plant cell, an explant, a meristem or a seed is infected with *Agrobacterium tumefaciens* transformed with the expression vector/construct which contains the heterologous nucleic acid operably linked to a promoter. Under appropriate conditions known in the art, the transformed plant cells are grown to form shoots, roots, and develop further into genetically altered plants. In some embodiments, the heterologous nucleic acid can be introduced into plant cells, by means of the Ti plasmid of

*Agrobacterium tumefaciens*. The Ti plasmid is transmitted to plant cells upon infection by *Agrobacterium tumefaciens*, and is stably integrated into the plant genome. See, e.g., Horsch, et al. (1984), and Fraley, et al. (1983).

Transformed plant cells which are derived by any of the above transformation techniques can be cultured to regenerate a whole plant which possesses the desired transformed phenotype. Such regeneration techniques rely on manipulation of certain phytohormones in a tissue culture growth media, typically relying on a biocide and/or herbicide marker which has been introduced together with the desired nucleotide sequences. Plant regeneration from cultured protoplasts is described in Evans et al., *Protoplasts Isolation and Culture*, in *Handbook of Plant Cell Culture*, pp. 124-176, MacMillan Publishing Company, New York, 1983; and Binding, *Regeneration of Plants*, in *Plant Protoplasts*, pp. 21-73, CRC Press, Boca Raton, 1985. Regeneration can also be obtained from plant callus, explants, organs, or parts thereof. Such regeneration techniques are described generally in Klee, et al., *Ann. Rev. of Plant Phys.* 38:467-486 (1987).

Once a genetically altered plant has been generated, one can breed it with a wild-type plant and screen for heterozygous F1 generation plants containing the genetic change present in the parent genetically altered plant. Then F2 generation plants can be generated which are homozygous for the genetic alteration. These heterozygous F1 generation plants and homozygous F2 plants, progeny of the original genetically altered plant, are considered genetically altered plants, having the altered genomic material from the genetically altered parent plant.

Many techniques involving molecular biology discussed herein are well-known to one of ordinary skill in the art and are described in, e.g., Green and Sambrook, *Molecular Cloning, A Laboratory Manual* 4th ed. 2012, Cold Spring Harbor Laboratory; Ausubel et al. (eds.), *Current Protocols in Molecular Biology,* 1994—current, John Wiley & Sons; and Kriegler, Gene *Transfer and Expression: A Laboratory Manual* (1993). Unless otherwise noted, technical terms are used according to conventional usage. Definitions of common terms in molecular biology maybe found in e.g., Benjamin Lewin, *Genes IX*, Oxford University Press, 2007 (ISBN 0763740632); Krebs, et al. (eds.), *The Encyclopedia of Molecular Biology*, Blackwell Science Ltd., 1994 (ISBN 0-632-02182-9); and Robert A. Meyers (ed.), *Molecular Biology and Biotechnology: a Comprehensive Desk Reference*, VCH Publishers, Inc., 1995 (ISBN 1-56081-569-8).

The term "plant" includes whole plants, plant organs, progeny of whole plants or plant organs, embryos, somatic embryos, embryo-like structures, protocorms, protocorm-like bodies (PLBs), and suspensions of plant cells. Plant organs/parts comprise, e.g., shoot vegetative organs/structures (e.g., leaves, stems and tubers), roots, flowers and floral organs/structures (e.g., bracts, sepals, petals, stamens, carpels, anthers and ovules), seed (including embryo, endosperm, and seed coat) and fruit (the mature ovary), plant tissue (e.g., vascular tissue, ground tissue, and the like) and cells (e.g., guard cells, egg cells, trichomes and the like). The class of plants that can be used in the method of the invention is generally as broad as the class of higher and lower plants amenable to the molecular biology and plant breeding techniques described herein, specifically dicotyledonous (dicots) plants. It includes plants of a variety of ploidy levels, including aneuploid, polyploid, diploid, haploid and hemizygous. The genetically altered plants described herein can be dicot plants, and more particularly, dicot crops, such as apple, pear, peach, plum, orange, lemon, lime, grapefruit, pomegranate, olive, peanut, cotton, tobacco, cucumber, carrot, potato, celery, tomato, legume (beans), raspberry, blackberry, blackberry, strawberry, blueberry, etc. Also, the genetically altered plants (or plants with altered genomic DNA) can be horticultural plants such as rose, marigold, primrose, dogwood, pansy, geranium, etc. Other plants include, but are not limited to, grasses, oak, walnut, pecan, poplar, etc. The genetically altered plants described herein can also be gymnosperms, such as but not limited to cycads, conifers (redwoods, sequoias, pines, fir and hemlock), and ginkgo.

The terms "approximately" and "about" refer to a quantity, level, value or amount that varies by as much as 30%, or in another embodiment by as much as 20%, and in a third embodiment by as much as 10% to a reference quantity, level, value or amount. As used herein, the singular form "a", "an", and "the" include plural references unless the context clearly dictates otherwise. For example, the term "a bacterium" includes both a single bacterium and a plurality of bacteria.

Having now generally described this invention, the same will be better understood by reference to certain specific examples and the accompanying drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

Example 1. SCAmpPs 396s Transcription Regulatory Elements and Translation Regulatory Element Sequences Isolation and Heterologous Gene of Interest Construction Highly expressed tissue-specific SCAmpPs genes were identified by their over-representation in EST libraries prepared from specific *citrus* plant tissues. See Belknap, et al., *BMC Genomics* 16:303 (2015). SCAmpPs genes were identified on the *Citrus clementina* (assembly v1.0) (Wu, et al., *Nat. Biotechnol.* 32(7):656-62 (2014)) and *Citrus sinensis* (assembly v1.0) (Xu, et al., *Nat. Genet.* 45(1):59-66 (2013)) assemblies by Pustell matrix analysis (Pustell, et al., *Nucleic Acids Res.* 14(1):479-88 (1986)) of individual down-loaded chromosomes (MacVector11.1) using the SCAmpPs precursor peptide consensus sequence (see, Belknap, et al. (2015)). Individual SCAmpPs coding domains and flanking regions were then used in BLAST searches of the NCBI *citrus* EST database to identify related ESTs.

SCAmpPs genes were amplified from *Citrus* genomic DNA using synthetic oligonucleotide primers. For the 396s promoter, the complete phloem-specific SCAmpPs 396 gene was amplified from Carrizo citrange (*Citrus sinensis* 'Washington' sweet orange X *Poncirus trifoliata*) DNA using forward primer 5'-CAGTTATGAACCCCTAACATTACTCATCC-3' (SEQ ID NO: 8) and reverse primer 5'-CTTTAGCACAAAGAGATCTCGATTCTC-3' (SEQ ID NO: 9). PCR amplification was performed for 30 cycles using Phusion 2× High Fidelity Master Mix with HF buffer at manufacturer's suggested annealing temperatures and conditions (New England Biolabs, Inc., Ipswich, Mass.). The generated amplicon was 3861 bp (SEQ ID NO: 24) which was cloned into the pCR-Blunt vector and sequenced. The sequence included the SCAmpPs 396s gene with 2209 bp of 5' sequence (promoter; 5' transcription regulatory element, nt 872-3096 of SEQ ID NO: 24), exon 1 (the translation regulatory element, nt 3097-3168 of SEQ ID NO: 24), intron (intron transcription regulatory element, nt 3184-3278 of SEQ ID NO: 24), exon 2, and 234 bp of 3' sequence (polyadenylation signal, nucleotides 3629-3861 of SEQ ID NO: 24). See, Belknap, et al. (2015).

Because of the potential for translation regulatory element associated with the SCAmpPs initiation codon (translation enhancer) and/or the intron containing transcription enhancer activity (intron transcription regulation), the SCAmpPs 396s gene (up to and including second exon sequences) was operably linked to the GUS marker gene as a translational fusion via a linker to produce SEQ ID NO: 25. See, also, FIG. 1. This fusion was constructed employing a previously described binary vector containing the bul409s polyubiquitin promoter translationally fused to GUS in the pBINPLUS/ARS binary transformation vector (Rockhold, et al., *American J. Potato Res.* 85:219-26 (2008); Belknap, et al., *Biotech.* 44:739-750 (2008)). The bul409s-GUS transgene and the polyubiquitin regulation sequences are flanked by unique AscI (5') and BamHI (3') restriction enzyme sites. The SCAmpPs 396s GUS fusion cassette (SEQ ID NO: 25) has the complete SCAmpPs 396s first exon, intron, and partial second exon operably linked to GUS via a linker. The following PCR primers were designed to introduce AscI and BamHI sites 5' to the SCAmpPs 396s gene and within the second exon (contained in SEQ ID NO: 24), respectively: forward primer 5'-GGCGCGCCAGCGAGTTGCTTG-3' (SEQ ID NO: 10) and reverse primer 5'-GGATCCATCATTACCTGTAAATTTTA-3' (SEQ ID NO: 11). These primers were used to amplify a 2427 bp AscI-BamHI flanked fragment containing 2221 bp of SCAmpPs 396s 5' sequence (5' transcription regulatory element, nt 9-2230 of SEQ ID NO: 25) and the first exon, intron and a portion of the second exon (of which the translation regulatory element is at nt 2231-2302 of SEQ ID NO: 25 and the intron transcription regulatory element is at nt 2319-2413 of SEQ ID NO: 25). When this fragment replaces the AscI-BamHI polyubiquitin fragment in the bul409s-GUS pBINPLUS/ARS binary vector, the junction shown in FIG. 1 (DNA in SEQ ID NO: 34, amino acid in SEQ ID NO: 35) results, which includes a linker between SCAmpPs 396 sequences and GUS sequences; the linker is nt 2422-2445 of SEQ ID NO: 25. GUS' cds is nt 2446-4257 of SEQ ID NO: 25. This SCAmpPs 396s-GUS pBINPLUS/ARS plasmid has the DNA sequence of SEQ ID NO: 7. This SCAmpPs 396s-GUS pBINPLUS/ARS plasmid is then transformed into *Agrobacterium* for transformation of plants. *Agrobacterium* GV3101 is used for plant transformation. Cells are grown to a turbidity of $OD_{600}$ 0.5-0.7 and prepared as electrocompetent using the protocol in *Methods in Molecular Biology*, Vol. 49*: Plant Gene Transfer and Expression Protocols*. H. Jones (ed.) Humana Press, Totowa, N.J.

Example 2. SCAmpPs 302z Transcription Regulatory Elements and Translation Regulatory Element Sequences Isolation and Heterologous Gene of Interest Construction Similar to the isolation of SCAmpPs 396s gene sequence in Example 1 above, the SCAmpPs 302z gene sequence was amplified from *Citrus clementina* genomic DNA employing forward primer 5'-CTTGTAAACACTGGAGTGGGAGGAATCC-3' (SEQ ID NO: 12) and reverse primer 5'-GGCGTCAACTTGGTCAAAGCTAGACTC-3' (SEQ ID NO: 13). PCR amplification was performed for 30 cycles using Phusion 2× High Fidelity Master Mix with HF buffer at manufacturer's suggested annealing temperatures and conditions (New England Biolabs, Inc., Ipswich, Mass.). The amplicon was a 3144 bp polynucleotide (SEQ ID NO: 26) which was cloned into the pCR-Blunt vector and sequenced. The sequence included the SCAmpPs 302z gene with 2484 bp of 5' sequence (5' transcription regulatory element, nt 1-2484 of SEQ ID NO: 26), exon 1, intron, exon 2, and intron sequences (translation regulatory element, nt 2485-2975 of SEQ ID NO: 26, and the intron transcription regulatory element, nt 2588-2647 of SEQ ID NO: 26), and 170 bp of 3' sequence (polyadenylation signal, nt 2976-3144 of SEQ ID NO: 26).

Because of the potential for translation regulatory sequences associated with the SCAmpPs initiation codon (translation enhancer) and/or intron containing transcription enhancer activity (intron transcription regulation), the SCAmpPs 302z gene (up to and including some second exon sequences) was joined to the GUS marker gene as a translational fusion; but in the following three different fusion cassettes: 302z GUS (FIG. 2A), 302z No-Intron GUS (FIG. 2B), and 302z No-Intron No-ATG GUS (FIG. 2C). These fusions were constructed employing the binary vector containing the bul409s polyubiquitin promoter translationally fused to GUS in the pBINPLUS/ARS binary transformation vector (Rockhold, et al. (2008); Belknap, et al. (2008)). The bul409s-GUS transgene and the polyubiquitin regulation sequences are flanked by unique AscI (5') and BamHI (3') restriction enzyme sites. These three transgenes cassettes have identical promoter and 5' UTR sequences.

The SCAmpPs 302z GUS fusion cassette (SEQ ID NO: 27) has the complete SCAmpPs 302z first exon, intron, and partial second exon operably linked to GUS via a linker (FIG. 2A). The following PCR primers were designed to introduce AscI and BamHI sites 5' to the SCAmpPs 302z gene and within the second exon (contained in the amplicon having SEQ ID NO: 26), respectively: forward primer 5'-GGCGCGCCCTTGTAAACACTGGAGTG-3' (SEQ ID NO: 14) and reverse primer 5'-GGGATCCGTTCTTACCTGAAAAAATC-3' (SEQ ID NO: 15). These primers were used to amplify a 2669 bp AscI-BamHI flanked fragment containing 2466 bp of SCAmpPs 302z 5' sequence (5' transcription regulatory element, nt 28-2492 of SEQ ID NO: 27) and 170 bp of the first exon, intron and a portion of the second exon (of which the translation regulatory element is at nt 2493-2549 of SEQ ID NO: 27 and the intron transcription regulatory element is at nt 2566-2655 of SEQ ID NO: 27). When this fragment replaces the AscI-BamHI polyubiquitin fragment in the bul409s-GUS pBINPLUS/ARS binary vector, the junction shown in FIG. 2A results (DNA sequence in SEQ ID NO: 36 and amino acid sequence in SEQ ID NO: 37), which contains a linker between the SCAmpPs 302z sequences and GUS sequences; the linker is nt 2664-2687 of SEQ ID NO: 27. GUS' cds is nt 2688-4499 of SEQ ID NO: 27. This SCAmpPs 302z-GUS pBINPLUS/ARS plasmid has the DNA sequence of SEQ ID NO: 1. This SCAmpPs 302z-GUS pBINPLUS/ARS plasmid is then cloned into *Agrobacterium* for transformation of plants. *Agrobacterium* GV3101 is used for plant transformation. Cells are grown to a turbidity of $OD_{600}$ 0.5-0.7 and prepared as electrocompetent as described above.

In the SCAmpPs 302z No-Intron GUS cassette (SEQ ID NO: 28), SCAmpPs 302z ATG initiation codon is operably linked to GUS via a linker and thus GUS will be translated using the SCAmpPs 302z ATG initiation codon, but the SCAmpPs 302z intron sequences are absent (FIG. 2B). The following PCR primers were designed to introduce AscI and BamHI sites 5' to the SCAmpPs 302z gene and after the ATG codon (contained in the amplicon having SEQ ID NO: 26), respectively: forward primer 5'-GGCGCGCCCTTG-TAAACACTGGAGTG-3' (SEQ ID NO: 14) and reverse primer 5'-GGATCCCATATTCTTCAAATTAGAAAAG-3' (SEQ ID NO: 16). These primers were used to amplify a 2555 bp AscI-BamHI flanked fragment containing 2483 bp of SCAmpPs 302z 5' sequence (5' transcription regulatory element, nt 9-2492 of SEQ ID NO: 28) and 56 bp of SCAmpPs 302z exon 1 (translation regulatory element, nt 2493-2549 of SEQ ID NO: 28). When this fragment replaces the AscI-BamHI polyubiquitin fragment in the bul409s-GUS pBINPLUS/ARS binary vector, the junction shown in FIG. 2B results (DNA sequence in SEQ ID NO: 38 and amino acid sequence in SEQ ID NO: 39), which contains a linker between the SCAmpPs 302z sequences and GUS sequences; the linker is nt 2550-2574 of SEQ ID NO: 28. GUS' cds is nt 2574-4385 of SEQ ID NO: 28. This SCAmpPs 302z No-Intron GUS pBINPLUS/ARS plasmid has the DNA sequence of SEQ ID NO: 2. This SCAmpPs 302z No-Intron GUS pBINPLUS/ARS plasmid is then cloned into *Agrobacterium* for transformation of plants. *Agrobacterium* GV3101 is used for plant transformation. Cells are grown to a turbidity of $OD_{600}$ 0.5-0.7 and prepared as electrocompetent as described above.

In the SCAmpPs 302z No-Intron No-ATG GUS cassette (SEQ ID NO: 29), the SCAmpPs 302z initiation codon is absent, so translation will be initiated at the GUS ATG which is operably linked to SCAmpPs 5' sequences via a linker (FIG. 2C). The following PCR primers were designed to introduce AscI and BamHI sites 5' to the SCAmpPs 302z gene and prior to the SCAmpPs 302z ATG codon (contained in the amplicon having SEQ ID NO: 26), respectively: forward primer 5'-GGCGCGCCCTTGTAAACACTG-GAGTG-3' (SEQ ID NO: 14) and reverse primer 5'-GGGATCCTTCTTCAAATTAGAAAAGATATC-3' (SEQ ID NO: 17). These primers were used to amplify a 2551 bp AscI-BamHI flanked fragment containing 2483 bp of SCAmpPs 302z 5' sequence (5' transcription regulatory element, nt 9-2492 of SEQ ID NO: 29) and 52 bp of SCAmpPs 302z exon 1 (3' deleted translation regulatory element, nt 2493-2545 of SEQ ID NO: 29). When this fragment replaces the AscI-BamHI polyubiquitin fragment in the bul409s-GUS pBINPLUS/ARS binary vector, the junction shown in FIG. 2C results (DNA sequence in SEQ ID NO: 40 and amino acid sequence (MLR)), which contains a linker between the SCAmpPs 302z sequences and GUS sequences; the linker is nt 2546-2569 of SEQ ID NO: 29. GUS' cds is nt 2570-4381 of SEQ ID NO: 29. This SCAmpPs 302z No-Intron No-ATG GUS pBINPLUS/ARS plasmid has the DNA sequence of SEQ ID NO: 3. This SCAmpPs 302z No-Intron No-ATG GUS pBINPLUS/ARS plasmid is then cloned into *Agrobacterium* for transformation of plants. *Agrobacterium* GV3101 is used for plant transformation. Cells are grown to a turbidity of $OD_{600}$ 0.5-0.7 and prepared as electrocompetent using the method described above.

These latter two cassettes, when compared to the 302z GUS fusion cassette, allow evaluation of potential regulatory effects of removing the 302z SCAmpPs intron (transcriptional effects) and the 302z SCAmpPs initiation codon (translational effects).

Example 3. SCAmpPs 289s Transcription Regulatory Elements and Translation Regulatory Element Sequences Isolation and Heterologous Gene of Interest Construction Similar to the root-specific SCAmpPs 302z sequences described above, fruit and/or abscission zone SCAmpPs 289s genomic sequence was amplified from *Citrus clementina* genomic DNA employing the primers: forward primer 5'-AACAAACTCCGCATAGTGG-3' (SEQ ID NO: 18) and reverse primer 5'-CCGACCAATCGGTATAAC-3' (SEQ ID NO: 19). PCR amplification was performed for 30 cycles using Phusion 2× High Fidelity Master Mix with HF buffer at manufacturer's suggested annealing temperatures and conditions (New England Biolabs, Inc., Ipswich, Mass.). The amplicon was a 1972 bp polynucleotide (SEQ ID NO: 30) which was cloned into the pCR-Blunt vector and sequenced. The sequence included the SCAmpPs 289s gene with 1734 bp of 5' sequence (5' transcription regulatory element, nt 1-1753 of SEQ ID NO: 30), exon 1, the complete intron and part of exon 2 (translation regulatory element, nt 1754-1972 of SEQ ID NO: 30 and intron transcription regulatory element, nt 1857-1954 of SEQ ID NO: 30).

Because of the potential for regulatory sequences associated with the SCAmpPs initiation codon (translation enhancer) and/or the intron (transcriptional regulation), the SCAmpPs 289s gene (up to and including second exon sequences) was joined to the GUS marker gene as a translational fusion, but in the following three different fusion cassettes: 289s GUS (FIG. 3A), 289s No-Intron GUS (FIG. 3B), and 289s No-Intron No-ATG GUS (FIG. 3C). These fusions were constructed employing the binary vector containing the bul409s polyubiquitin promoter translationally fused to GUS in the pBINPLUS/ARS binary transformation vector (Rockhold, et al. (2008); Belknap, et al. (2008)). The bul409s-GUS transgene and the polyubiquitin regulation sequences are flanked by unique AscI (5') and BamHI (3') restriction enzyme sites. These three transgenes cassettes have identical promoter and 5' UTR sequences.

The SCAmpPs 289s GUS fusion cassette (SEQ ID NO: 31) has the complete SCAmpPs 289s first exon, intron, and partial second exon operably linked to GUS via a linker (FIG. 3A). The following PCR primers were designed to introduce AscI and BamHI sites 5' to the SCAmpPs 289s gene and within the second exon (contained in the amplicon having SEQ ID NO: 30), respectively: forward primer 5'-GGCGCGCCAACAAACTCCGCATAGTGG-3' (SEQ ID NO: 20) and reverse primer 5'-GGATCCGGTATAAC-CTGAAAAATTC-3' (SEQ ID NO: 21). These primers were used to amplify a 1976 bp AscI-BamHI polynucleotide containing 1749 bp of SCAmpPs 289s 5' sequence (5' transcription regulatory sequence, nt 9-1758 of SEQ ID NO: 31) and 212 bp of the first exon, intron, and a portion of the second exon (translation regulatory element, nt 1759-1848 of SEQ ID NO: 31, and intron transcription regulatory element, nt 1865-1962 of SEQ ID NO: 31). When this fragment replaces the AscI-BamHI polyubiquitin fragment in the bul409s-GUS pBINPLUS/ARS binary vector, the junction shown in FIG. 3A results (DNA sequence in SEQ ID NO: 41 and amino acid sequence in SEQ ID NO: 42), which contains a linker between the SCAmpPs 289s sequences and GUS sequences; the linker is nt 1971-1994 of SEQ ID NO: 31. GUS' cds is nt 1995-3806 of SEQ ID NO: 31. This SCAmpPs 289s GUS pBINPLUS/ARS plasmid has the DNA sequence of SEQ ID NO: 4. This SCAmpPs 289s GUS pBINPLUS/ARS plasmid is then cloned into *Agrobacterium* for transformation of plants. *Agrobacterium* GV3101 is used for plant transformation. Cells were grown to a turbidity of $OD_{600}$ 0.5-0.7 and prepared as electrocompetent using the protocol described above.

In the SCAmpPs 289s No-Intron GUS cassette (SEQ ID NO: 32), SCAmpPs 289s ATG initiation codon is operably linked to GUS via a linker and thus GUS will be translated using the SCAmpPs 289s ATG initiation codon, but the SCAmpPs 289s intron sequences are absent (FIG. 3B). The following PCR primers were designed to introduce AscI and BamHI sites 5' to the SCAmpPs 289s gene and after the ATG codon (contained in the amplicon having SEQ ID NO: 30), respectively: forward primer 5'-GGCGCGC-CAACAAACTCCGCATAGTGG-3' (SEQ ID NO: 20) and reverse primer 5'-GGATCCCATAATCTTCAAATCAG-GAAGGC-3' (SEQ ID NO: 22). These primers were used to amplify a 1854 bp polynucleotide of SCAmpPs 289s 5' sequence (5' transcription regulatory element, nt 9-1758 of SEQ ID NO: 32) and 90 bp of SCAmpPs 289s exon 1 (translation regulatory element, nt 1759-1848 of SEQ ID NO: 32). When this fragment replaces the AscI-BamHI polyubiquitin fragment in the bul409s-GUS pBINPLUS/ARS binary vector, the junction shown in FIG. 3B results (DNA sequence in SEQ ID NO: 43 and amino acid sequence in SEQ ID NO: 44), which contains a linker between the SCAmpPs 289S sequences and GUS sequences; the linker is nt 1849-1872 of SEQ ID NO: 32. GUS' cds is nt 1873-3684 of SEQ ID NO: 32. This SCAmpPs 289s No-Intron GUS pBINPLUS/ARS plasmid has the DNA sequence of SEQ ID NO: 5. This SCAmpPs 289s No-Intron GUS pBINPLUS/ARS plasmid is then cloned into *Agrobacterium* for transformation of plants. *Agrobacterium* GV3101 was used for plant transformation. Cells were grown to a turbidity of $OD_{600}$ 0.5-0.7 and prepared as electrocompetent using the protocol described above.

In the SCAmpPs 289s No-Intron No-ATG GUS cassette (SEQ ID NO: 33), the SCAmpPs 289s initiation codon is absent, so translation will be initiated at the GUS ATG which is operably linked to SCAmpPs 289s 5' sequences via a linker (FIG. 3C). The following PCR primers were designed to introduce AscI and BamHI sites 5' to the SCAmpPs 289s gene and prior to the SCAmpPs 289s ATG codon (contained in the amplicon having SEQ ID NO: 30), respectively: forward primer 5'-GGCGCGCCAACAAACTCCG-CATAGTGG-3' (SEQ ID NO: 20) and reverse primer 5'-GGATCCATCTTCAAATCAGGAAGGCAAAAG-3' (SEQ ID NO: 23). These primers were used to amplify a 1850 bp polynucleotide of SCAmpPs 289s 5' sequence (5' transcription regulatory element, nt 9-1758 of SEQ ID NO: 33) and 85 bp of SCAmpPs 289s exon 1 (3' translation regulatory element, nt 1759-1844 of SEQ ID NO: 33). When this fragment replaces the AscI-BamHI polyubiquitin fragment in the bul409s-GUS pBINPLUS/ARS binary vector, the junction shown in FIG. 3C results (DNA sequence in SEQ ID NO: 45 and amino acid sequence (MLR)), which contains a linker between the SCAmpPs 289S sequences and GUS ATG codon; the linker is nt 1845-1868 of SEQ ID NO: 33. GUS' cds is nt 1869-3680 of SEQ ID NO: 33. This SCAmpPs 289s No-Intron No-ATG GUS pBINPLUS/ARS plasmid has the DNA sequence of SEQ ID NO: 6. This SCAmpPs 289s No-Intron No-ATG GUS pBINPLUS/ARS plasmid is then cloned into *Agrobacterium* for transformation of plants. *Agrobacterium* GV3101 was used for plant transformation. Cells were grown to a turbidity of $OD_{600}$ 0.5-0.7 and prepared as electrocompetent using the protocol described above.

These latter two fusion cassettes, SCAmpPs 289s No-Intron GUS and SCAmpPs 289s No-Intron No-ATG GUS, when compared to the original SCAmpPs 289s GUS fusion cassette, allow evaluation of potential regulatory effects of removing the intron (transcriptional effects) and the SCAmpPs 289s initiation codon (translational effects).

Example 4. Transformation of the SCAmpS GUS Constructs into *Arabidopsis* and Assessment of GUS Expression Each of the above *Agrobacterium* constructs are used to transform *Arabidopsis* using the following protocol. *Arabidopsis* floral dip method (Clough and Bent, 1998, *Plant J.* 16:735-743) is modified by adding 0.01% Silwet L-77 (Lehle Seeds, Round Rock, Tex.) to the infiltration media. Primary transformants are selected on MS media (Sigma Aldrich, St. Louis, Mo.), 1% sucrose, 0.7% agar with 20 μg/ml hygromycin or 50 μg/ml kanamycin as needed for 10 days prior to cultivation in soil. Approximately four pots, each containing four plants four weeks of age, are floral dipped into solution containing the *Agrobacterium*. After dipping, the plants are maintained at room temperature in high humidity overnight after which they are taken to the greenhouse. In the greenhouse the plants are maintained at 24° C. 16/8 hour light dark cycle until senescence, approximately three weeks later. Seeds are harvested and dried from three to five days at 30° C. Seeds are 10% bleach sterilized, rinsed thoroughly, and plated on MS media and antibiotic. Seeds are placed in 4° C. to synchronize seed germination for three days and then transferred to a 24° C. incubator. The day of transfer to the 24° C. incubator is considered day 0.

To assess the expression of GUS in the transformed *Arabidopsis* plants, each plant is subjected to vacuum infiltration for 5 minutes with 1 mM of 5-bromo-4-chloro-3-indolyl-glucuronic acid (X-Gluc) and incubated 20 minutes for 2 hours at 37° C. to detect GUS activity (Jefferson, 1987, *Plant Mol. Biol. Rep.* 5:387-405). GUS activity is graded as “weak” (i) if, when the plant or plant part is viewed against a white background, silique is translucent, or it is possible to see outline of seeds; or (ii) if when viewed under loupe and backlit, one can see color in silique. GUS activity is graded as “strong” if, when the plant or plant part is viewed against a white background, silique is nearly opaque; and if the outline of the seeds are not visible or obscured. A negative result is no GUS activity.

For 396s GUS fusion cassette, the transformed plants expressed GUS as follows. Of the 13 396s GUS transformed *Arabidopsis* plants that contained the constructed as determined by antibiotic resistance, eight plants express GUS in the phloem. Four plants have weak phloem expression, four plants have strong expression, and five plants are negative for GUS activity from an overnight stain at 37° C. Of the strong expression lines, all four plants also process wound response capacity. Wound response capacity is determined by GUS staining at both cut and crushed areas of the harvested plant material.

For the three fusion cassettes, 302z GUS, 302z No-Intron GUS, and 302z No-Intron No-ATG GUS, the transformed 7-10 day old seedling express GUS as follows. Of the ten 302z GUS transformed *Arabidopsis* plants, 9 plants have strong GUS expression in the roots after 4 hours in stain at 37° C.; all nine plants have moderate GUS expression in the roots at 1 hour in stain at 37° C.; and all nine plants have weak GUS expression in the roots after 10 minutes in stain at 37° C. All functional lines show root specific expression at 10 minutes and 1 hour staining. At 4 hour stains, 6 of the 10 plants are so intense as to ‘leak’ up in the stem. One line is nonfunctional. Of the ten 302z No-Intron GUS transformed *Arabidopsis* plants, seven plants are functional. All 7 plants have strong GUS expression in the roots after 4 hours in stain at 37° C.; seven plants have moderate GUS expression in the roots at 1 hours in stain at 37° C.; and all seven plants have weak GUS expression in the roots after 10 minutes in stain at 37° C. All functional lines show root specific expression at 10 minutes and 1 hour staining. At 4 hour stains, all seven lines are so intense as to 'leak' up in the stem. Four lines are nonfunctional. The results are comparable to 302z. Of the ten 302z No-Intron No-ATG GUS transformed *Arabidopsis* plants, all ten plants are functional. 7-10 day old seedling express GUS as follows. All ten plants have moderate GUS expression in the roots after 4 hours in stain at 37° C.; have weak to moderate GUS expression in the roots at 1 hours in stain at 37° C.; and have very weak GUS expression in the roots after 10 minutes in stain at 37° C. All functional lines show root specific expression at 10 minutes and 1 hour staining. At 4 hour stains, only the strongest 4 lines are intense enough as to 'leak' up in the stem. These lines appear approximately ¼ the strength of 302z.

Six weak old mature plants from three 302z plants show GUS expression predominately in the roots of the whole plant stain after 4 hours at 37° C. Weak and intermittent GUS expression is observed in the abscission zone of the siliques.

For the three fusion cassettes, 289s GUS, 289s No-Intron GUS, and 289s No-Intron No-ATG GUS, the aerial portion of transformed 6 week old mature plants are collected and express GUS as follows. Of the forty-five 289s GUS transformed *Arabidopsis* plants, nine plants express GUS in abscission zone only, eighteen plants have weak expression, sixteen plants have strong expression, and two plants are negative for GUS activity from an overnight stain at 37° C. Of the forty-seven 289s No-Intron GUS transformed *Arabidopsis* plants, four plants express GUS in abscission zone only, nineteen plants have weak expression, twenty-four plants have strong expression, and zero plants are negative for GUS activity from an overnight stain at 37° C. Of the forty-eight 289s No-Intron No-ATG GUS transformed *Arabidopsis* plants, sixteen plants express GUS in abscission zone only, twenty-one plants have weak expression, two plants have strong expression, and eight plants are negative for GUS activity from an overnight stain at 37° C.

For the three fusion cassettes, 289s GUS, 289s No-Intron GUS, and 289s No-Intron No-ATG GUS, the transformed 7-10 day old seedling express GUS as follows. Of the ten 289s GUS transformed *Arabidopsis* plants, all plants have weak to moderate GUS expression in the leaves and petioles after 4 hours in stain at 37° C.; all ten plants have very weak GUS expression in the leaves and petioles at 1 hour in stain at 37° C.; and all ten plants have no visible GUS expression after 10 minutes in stain at 37° C. All functional lines show leaves and petioles expression at 4 hours and 1 hour staining but no root expression is visible. Of the ten 289s No-Intron GUS transformed *Arabidopsis* plants, all plants have weak to moderate GUS expression in the leaves and petioles after 4 hours in stain at 37° C.; three plants have very weak GUS expression in the leaves and petioles at 1 hour in stain at 37° C.; and ten plants have no visible GUS expression after 10 minutes in stain at 37° C. Seven lines show leaves and petioles expression at 4 hours and 1 hour staining but no root expression, while the three strongest lines show root expression. Of the ten 289s No-Intron No-ATG GUS transformed *Arabidopsis* plants, only five plants have weak to moderate GUS expression in the leaves and petioles after 4 hours in stain at 37° C.; three plants have very weak GUS expression in the leaves and petioles at 1 hour in stain at 37° C.; and all ten plants have no visible GUS expression after 10 minutes in stain at 37° C. Seven lines show leaves and petioles expression at 4 hours and 1 hour staining but no root expression, while the three strongest plants show root expression.

289s GUS whole mature (6 week old) plant stains show strongest expression in the abscission zone of the siliques. Moderate staining is also observed in the anthers and stamen of all flowers. Weak staining is observed at the junction of the petiole to the stock of the plant and is the junction zone of the aerial leaf to the stock. Patchy weak staining is observed on some leaves. Not wishing to be bound to any hypothesis, that weak staining may have occurred because of powdery mildew infection promoter activation. No staining is observed in the roots, seed, petals, or stock of the plant.

289s No-Intron GUS whole mature (6 week old) plant stains have the same pattern overall of expression as the 289s GUS. However, the expression pattern is leaky in some plants. GUS staining bleeds down the stocks of the florets and appears to include the petals. The most obvious difference is the moderate GUS expression in the roots.

Example 5. Transformation of the SCAmpPs GUS Constructs into Tomato and Assessment of GUS Expression Each of the above *Agrobacterium* constructs are used to transform tomato plants using the following protocol which is based on the protocols in Orzaez, et al., *Plant Physiology,* 140(1):3-11 (2006) and Spolaore, et al., *J. Experimental Botany* 52, 845-8503 (2001). One colony of *A. tumefaciens* carrying one of the above SCAmpPs GUS cassettes is selected and grown overnight in 5 ml of YEB media plus selective antibiotics at 28° C. Then each culture is transferred to 50 mL of induction media plus antibiotics and grown again overnight at 28° C. The bacteria are recovered by centrifugation, resuspend in infiltration media, and incubated at room temperature with gentle agitation (20 rpm) for a minimum of 2 hours. The bacteria culture is injected in the tomato fruit using a 1 ml syringe with a 0.5×16 mm needle. The needle is introduced 3 mm to 4 mm in depth into the fruit tissue through the stylar apex, and the infiltration solution is injected gently into the fruit until some drops of infiltration solution begin to show running off the hydathodes at the tip of the sepals. For tomato leaf agroinfiltration, the needle is removed from the fruit and introduced into the intercellular spaces for injection of the bacteria. For stable tomato transformation, one uses explants from cotyledons cultured for 1 day on the media with zeatin 2 mg/L, IAA 0.1 mg/L, carefully submerged in the *Agrobacterium* inoculum (OD600=0.2) for 20 minutes, then co-cultured with the *Agrobacterium* for 3 days on the same media, followed by a transfer to the same media with 500 mg/L cefotaxin for 3 days and then by a transfer to the same media with 100 mg/L kanamycin and 500 mg/L carabenillin for 6-8 weeks. See, Sun, et al., *Plant Cell Physiol.* 47(3):426-431 (2006), and Qiu, et al., *Scientia Horticulturae* 112:172-175 (2007). To assess for GUS expression, the assay describe supra is used. See, Jefferson, 1987. GUS activity is determined using the grading scale described supra.

The two fusion constructs, 289s GUS and 289s No-Intron GUS, are evaluated by transient expression and X-gluc staining tomato fruit tissue. The transgenes within the binary pBinPLUS-ARS vector are transformed into the *Agrobacterium* as above, followed by direct injection into intact tomato fruits. Introduction of either construct resulted in intense staining when the fruit is exposed to X-gluc, indicating efficient expression in this tissue. The effect of inclusion on tissue specificity of the intron is apparent in these experiments. When the intron is present, expression in the tomato fruit is limited to seed mucosal coat of green fruit, removal of the intron allows expression throughout the green fruit.

These two promoter element-GUS fusions are also stably transformed into tomato. The 289s GUS construct (containing the intron) express GUS in only mature fruits, while transgenic tomato fruit containing 289s No-Intron GUS construct (no intron) express GUS in both green and mature fruit, indicating intron-dependent transcriptional control. Expression of both these promoters (5' transcription regulatory element and intron transcription regulatory element) is limited to the tomato fruits (no observed expression in stems, leaves or roots).

Example 6. Transformation of the SCAmpPs GUS Constructs into *Citrus* and Assessment of GUS Expression Each of the above *Agrobacterium* constructs were used to transform *citrus* plants using the following protocol. Seeds are removed from mature *citrus* fruits and treated with pectinase for one hour. Next, the seeds are strained and then treated with 10% 8-hydroxyquinoline sulfate (Q8) for 30 minutes followed by air drying in a lab fume hood overnight. Store the seeds in a labeled Ziploc bag at 4° C. until ready to use. The outer seed coat is removed for more uniform germination and should be used within a few days. Surface sterilize peeled seeds by soaking in ETOH in a sterile mason jar or beaker for 10 minutes with stirring and then rinse the sterilized screens with sterile deionized water in the laminar flow hood. The seeds are then soaked and stirred in a 10% bleach solution for 10 minutes, and then rinse 2 or 3 times with sterile deionized water. Seeds are now ready for aseptic planting. The seeds are aseptically placed on the surface of 1×MS media with Gel rite (Sigma Aldrich, St. Louis, Mo.) in tall Magenta vessels. Autoclaving forceps, in addition to ETOH sterilization, is recommended between plantings. The Magenta vessel trays are labeled and wrapped in black plastic bags and placed in the dark for 14-21 days at 27° C. Once seedlings have germinated and reached the top of the magenta vessels, the plastic bags are removed, and the tray is placed in light at 27° C. for 4-7 days before aseptically cutting the epicotyls for co-culture with the transformed *Agrobacterium* described above.

A single colony of each of the above described *Agrobacterium* are inoculated into 50 ml YEP media (1 L contains 10 g yeast extract (ThermoFisher Scientific, Waltham, Mass.) 20 g peptone (United States Biological, Salem Mass.), 10 mL 100×AA stock of each adenine (6 g/L), tryptophan (8 g/L) and uracil (2 g/L)), 50 μl of 100 mg/ml kanamycin, and 50 μl of 100 μM acetosyringone (Sigma Aldrich, St. Louis, Mo.) and are grown overnight at 28° C. on a shaker at 225 rpm. Cell density is measured at 600 nm, and the culture is adjusted as needed to get an absorbance of 0.4 to 0.6 for sweet orange cultivars and 0.6 to 0.8 for trifoliate rootstock cultivars. Next, the cells are spun at 6,000 RPM for 10 minutes, supernatant is decanted, and the cells are re-suspend in LB broth with acetosyringone. The seedling epicotyls are cut into 0.5 cm to 1 cm segments with distal and proximal ends cut with at least 45 degree angles so that each angle will be in the opposite direction of the other. The epicotyls segments should have angle cuts at each end that will maximize the exposure of the cambium after the epicotyls is placed on the co-culture media. The epictoyl segments are placed in the *Agrobacterium* solution for 20 minutes, then removed and blotted on sterile filter paper. The explants are plated onto CM1 co-culture media ((MS with sucrose) 30 g/L, agar 8 g/L, NAA 1 mg/L, BAP 1 mg/L). 25-30 explants are placed per plate, with angled cut surfaces facing upwards. Plates are placed in the dark at 24° C. for 3 days. One plate of epicotyls segments for each construct is not soaked in solution on CM1 co-culture media as a control. These explants are placed onto MSB1 media with and without antibiotics to test the fidelity of the media and the regeneration of the epicotyl segments. After three days of culture at 24° C., the explants are triple rinsed in sterile water. 200 explants are place in a petri dish and soaked in sterile water before removing water with a pipette, and repeated twice. 250 mg/L cefotaxime and 250 mg/L vancomycin are added to the sterile water to control *Agrobacterium* overgrowth. After explants are rinsed and blotted on sterile filter paper, half of the explants are plated with cut surfaces facing upwards into MSB1+antibiotics, while the other half are plated into MSB1 without antibiotics. The plates are placed in a dark growth chamber at 27° C. for 2-3 weeks after which the cultures are moved to 16 hours of light and 8 hours of dark at 27° C. Within one month of epicotyl explants being on MSB1+antibiotic selection and antibiotic suppression of *Agrobacterium*, explants are transferred onto fresh MSB1+antibiotics. Shoots greater than 1 cm are cut and micrografted onto Carrizo seedling rootstocks. Micrografts of scion cultivars (Hamlin, Valencia) are micro grafted onto trifoliate hybrid rootstocks (Carrizo) and micrografts of rootstock cultivars (Carrizo) are micro grafted onto Volkameria or Cleopatra. Micrografts are done onto etiolated seedlings in soil and covered with clear Ziploc bag. Micrografts are placed into a light incubator at 27° C., 30% RH, 16 hours daylight for 1 week. After 7 days, the micrografts are watered with ¼ MS Basal salt mixture (Sigma Aldrich, St. Louis, Mo.) and placed in the greenhouse and acclimated. Over the next 1-2 weeks, the Ziploc bag is opened then removed completely.

For SCAmpPs 396s GUS fusion construct, the transformed *citrus* plants expressed GUS in leaf and stem secondary phloem tissue, as detected by X-gluc staining of intact transgenic *citrus* plants. The expected rapid staining of stem vascular regions is observed and in leaves staining is observed in the midrib of fully developed leaves.

The 302z GUS fusion construct (containing ATG and intron) has been evaluated by X-gluc staining of transgenic *citrus* plant tissue. Rapid and intense staining of root tissues is observed, with limited staining of other plant tissues. This staining pattern indicates that specificity of the promoter observed in *Arabidopsis* is maintained in *citrus*.

The 289s GUS fusion construct and the 289s No-Intron GUS fusion construct have been evaluated by transient expression and X-gluc staining of *citrus* fruit tissue. The transgenes within the binary pBinPLUS-ARS vector are transformed into the *Agrobacterium* as described above, followed by direct injection into intact *citrus* fruits. Introduction of either construct result in intense staining when the fruit is exposed to X-gluc, indicating efficient expression in this tissue.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We, the inventors, claim as follows:

1. An expression cassette comprising a 5' tissue specific transcription regulatory element operably linked to a heterologous polynucleotide of interest, wherein said 5' transcription regulatory element comprises nucleotides 1-2484 of SEQ ID NO. 26.

2. The expression cassette of claim 1, further comprising an intron transcription regulatory element comprising nucleotides 2588-2647 of SEQ ID NO: 26; wherein the 5' end of sail intron transcription regulatory element is operably linked to the 3' end of said 5' transcription regulatory element and the 3' end of said intron transcription regulatory element is operably linked to the 5' of said heterologous polynucleotide of interest.

3. The expression cassette of claim 1, further comprising a translation regulatory element, wherein said translation regulatory element comprises nucleotides 2485-2541 of SEQ ID NO: 26; wherein the 5' end of said translation regulatory element is operably linked to the 3' end of said 5' transcription regulatory element and the 3' end of said translation regulatory element is operably linked to the 5' of said heterologous polynucleotide of interest.

4. The expression cassette of claim 3, further comprising an intron transcription regulatory element comprising nucleotides 2588-2647 of SEQ ID NO: 26; wherein the 5' end of said intron transcription regulatory element is operably linked to the 3' end of said translation regulatory element and the 3' end of said intron transcription regulatory element is operably linked to the 5' end of said heterologous polynucleotide of interest.

5. The expression cassette of claim 4, wherein the sequence of said 5' transcription regulatory element, said translation regulatory element, and said intron transcription regulatory element comprises nucleotides 1-2647 of SEQ ID NO: 26.

6. The expression cassette of claim 5, further comprising a linker polynucleotide, wherein the 5' end of said linker polynucleotide is operably linked to the 3' end of said intron transcription regulatory element and the 3' end of said linker polynucleotide is operably linked to the 5' end of said heterologous polynucleotide of interest.

7. The expression cassette of claim 1, wherein said heterologous polynucleotide of interest encodes a protein of interest or a RNA of interest.

8. A genetically altered plant comprising the expression cassette of claim 1.

9. A genetically altered cell of said genetically altered plant of claim 8, wherein said cell comprises the expression cassette.

10. A genetically altered seed of said genetically altered plant of claim 8, wherein said seed comprises the expression cassette.

11. A genetically altered pollen of said genetically altered plant of claim 8, wherein pollen comprises the expression cassette.

12. A genetically altered germplasm of said genetically altered plant of claim 8, wherein said germplasm comprises the expression cassette.

13. A method for expressing a heterologous polynucleotide of interest in a plant, said method comprising (a) providing an expression vector comprising a 5' transcription regulatory element operably linked to a heterologous polynucleotide sequence of interest, wherein said 5' transcription regulatory element comprises nucleotides 1-2484 of SEQ ID NO: 26, (b) introducing said expression vector into at least one plant cell to generate at least one altered plant cell, and (c) growing at least one of said genetically altered plant cell to obtain a genetically altered plant that expresses said heterologous polynucleotide of interest.

14. The method of claim 13, wherein said expression vector further comprises an intron transcription regulatory element comprising nucleotides 2588-2647 of SEQ ID NO: 26; wherein the 5' end of said intron transcription regulatory element is operably linked to the 3' end of said 5' transcription regulatory element and the 3' end of said intron transcription regulatory element is operably linked to the 5' of said heterologous polynucleotide of interest.

15. The method of claim 13, wherein said expression vector further comprises a translation regulatory element, wherein said translation regulatory element comprises nucleotides 2485-2541 of SEQ ID NO: 26; wherein the 5' end of said translation regulatory element is operably linked to the 3' end of said 5' transcription regulatory element and the 3' end of said translation regulatory element is operably linked to said 5' of said heterologous polynucleotide of interest.

16. The method of claim 15, wherein said expression vector further comprises an intron transcription regulatory element comprising nucleotides 2588-2647 of SEQ ID NO: 26; wherein the 5' end of said intron transcription regulatory element is operably linked to the 3' end of said translation regulatory element and the 3' end of said intron transcription regulatory element is operably linked to the 5' end of said heterologous polynucleotide of interest.

17. The method of claim 16, wherein the sequence of said 5' transcription regulatory element, said translation regulatory element, and said intron transcription regulatory element comprises nucleotides 1-2647 of SEQ ID NO: 26.

18. The method of claim 17, wherein said expression vector further comprises a linker polynucleotide, wherein the 5' end of said linker polynucleotide is operably linked to the 3' end of said intron transcription regulatory element and the 3' end of said linker polynucleotide is operably linked to the 5' end of said heterologous polynucleotide of interest.

19. The method of claim 13, wherein said heterologous polynucleotide of interest encodes a protein of interest or a RNA of interest.

20. The method of claim 13, wherein said introducing said expression vector into at least one plant cell occurs via breeding with a genetically altered plant that contains said expression vector or transfecting said expression vector into a plant cell.

* * * * *